(12) United States Patent
Novek

(10) Patent No.: US 11,542,219 B2
(45) Date of Patent: Jan. 3, 2023

(54) PROCESSES PRODUCING ALKALI HYDROXIDES, ALKALI CARBONATES, ALKALI BICARBONATES, AND/OR ALKALINE EARTH SULFATES

(71) Applicant: INNOVATOR ENERGY, LLC, Houston, TX (US)

(72) Inventor: Ethan J. Novek, Houston, TX (US)

(73) Assignee: INNOVATOR ENERGY, LLC, Houston, TX (US)

(*) Notice: Subject to any disclaimer, the term of this patent is extended or adjusted under 35 U.S.C. 154(b) by 0 days.

(21) Appl. No.: 17/744,161

(22) Filed: May 13, 2022

(65) Prior Publication Data
US 2022/0274907 A1 Sep. 1, 2022

Related U.S. Application Data

(63) Continuation of application No. 17/732,808, filed on Apr. 29, 2022, which is a continuation-in-part of (Continued)

(51) Int. Cl.
 *C01F 11/02* (2006.01)
 *C01F 11/04* (2006.01)
 (Continued)

(52) U.S. Cl.
 CPC ............ *C07C 51/02* (2013.01); *C01F 11/02* (2013.01); *C01F 11/04* (2013.01); *C01F 11/06* (2013.01); *C07C 51/47* (2013.01)

(58) Field of Classification Search
 None
 See application file for complete search history.

(56) References Cited

U.S. PATENT DOCUMENTS

| 3,883,639 A | 5/1975 | Cronkright, Jr. et al. |
| 3,919,394 A | 11/1975 | Selmeczi et al. |

(Continued)

OTHER PUBLICATIONS

International Search Report and Written Opinion dated Aug. 3, 2022 issued in PCT/US2022/029198.

*Primary Examiner* — Daniel Berns
(74) *Attorney, Agent, or Firm* — Hunton Andrews Kurth LLP

(57) ABSTRACT

The present application pertains to methods for making alkali hydroxide, or alkali carbonates, or alkali bicarbonates, or alkaline—earth sulfates. In one embodiment, a material comprising an alkaline earth is converted to an alkaline earth sulfite or bisulfite and reacted with an alkali sulfate to form an alkaline earth sulfate and alkali sulfite or bisulfite. The alkali sulfite or bisulfite is converted into an alkali hydroxide, or an alkali carbonate, or an alkali bicarbonate. In another embodiment, ammonium carbonate or ammonium bicarbonate is reacted with an alkali sulfate, to form ammonium sulfate and an alkali carbonate or alkali bicarbonate. A material comprising an alkaline earth is converted to an alkaline earth sulfite or bisulfite and reacted with the ammonium sulfate to form an alkaline earth sulfate and ammonium sulfite or ammonium bisulfite. The ammonium sulfite or bisulfite is regenerated into ammonia, or ammonium hydroxide, or ammonium carbonate, or ammonium bicarbonate.

7 Claims, 18 Drawing Sheets

Related U.S. Application Data application No. 17/590,483, filed on Feb. 1, 2022, which is a continuation of application No. 17/243,714, filed on Apr. 29, 2021, now Pat. No. 11,236,033, which is a continuation-in-part of application No. 16/944,850, filed on Jul. 31, 2020, now Pat. No. 11,034,619, application No. 17/744,161, which is a continuation of application No. 17/590,483, filed on Feb. 1, 2022.

(60) Provisional application No. 63/188,275, filed on May 13, 2021, provisional application No. 63/179,822, filed on Apr. 26, 2021, provisional application No. 63/163,993, filed on Mar. 22, 2021, provisional application No. 63/157,847, filed on Mar. 8, 2021, provisional application No. 63/153,461, filed on Feb. 25, 2021, provisional application No. 63/147,286, filed on Feb. 9, 2021, provisional application No. 63/042,397, filed on Jun. 22, 2020, provisional application No. 62/895,557, filed on Sep. 4, 2019, provisional application No. 62/890,254, filed on Aug. 22, 2019.

(51) Int. Cl.
*C01F 11/06* (2006.01)
*C07C 51/02* (2006.01)
*C07C 51/47* (2006.01)

(56) References Cited

U.S. PATENT DOCUMENTS

| | | |
|---|---|---|
| 4,331,640 A | 5/1982 | Morita et al. |
| 4,937,056 A | 6/1990 | Kirk et al. |
| 11,174,169 B2 | 11/2021 | Novek |
| 11,236,033 B2 | 2/2022 | Novek |
| 2005/0049433 A1* | 3/2005 | Fan .................... C07C 51/42 562/513 |
| 2008/0025891 A1 | 1/2008 | Roche |
| 2021/0061706 A1 | 3/2021 | Novek |

\* cited by examiner

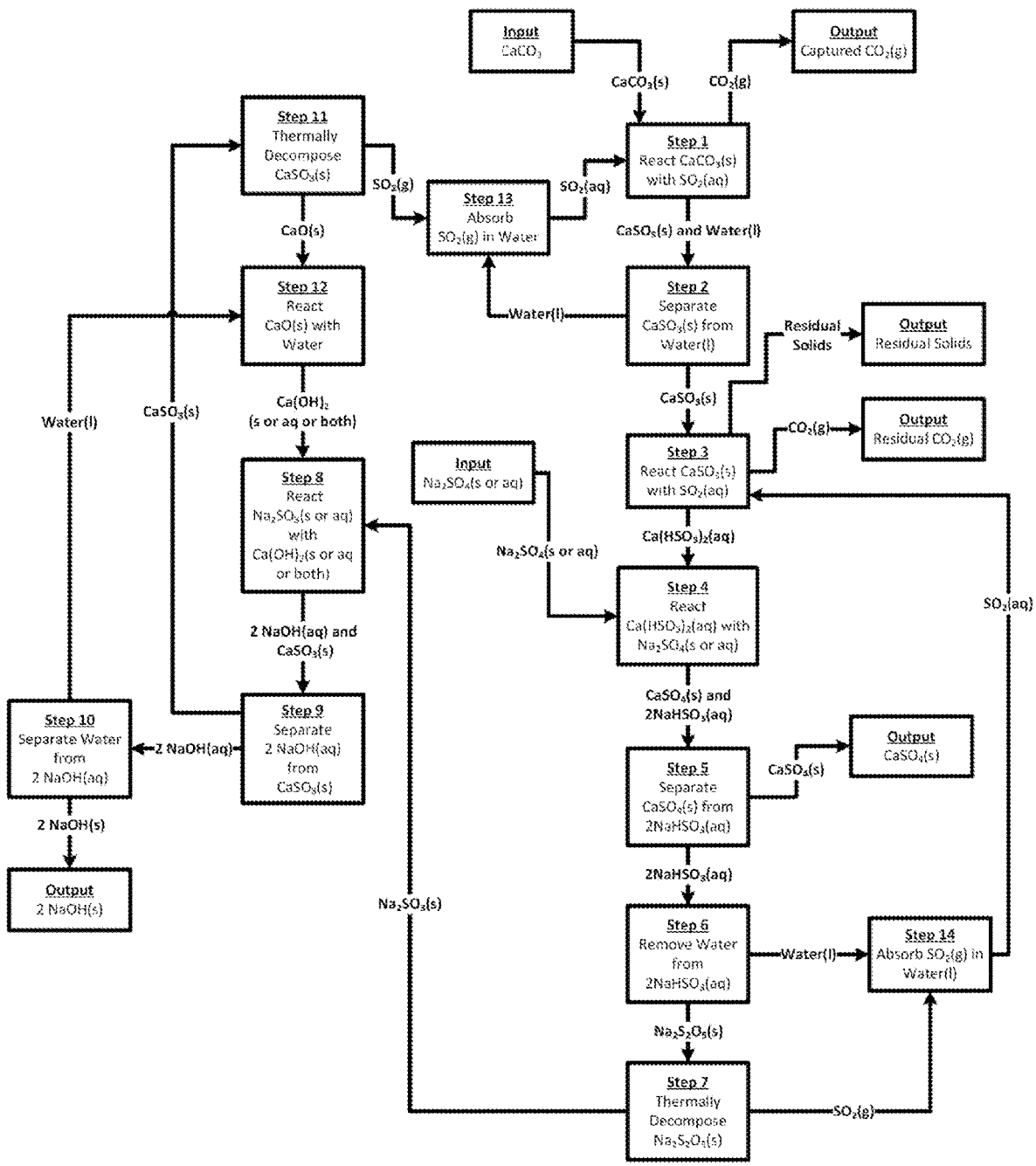
Figure 1A (Above)

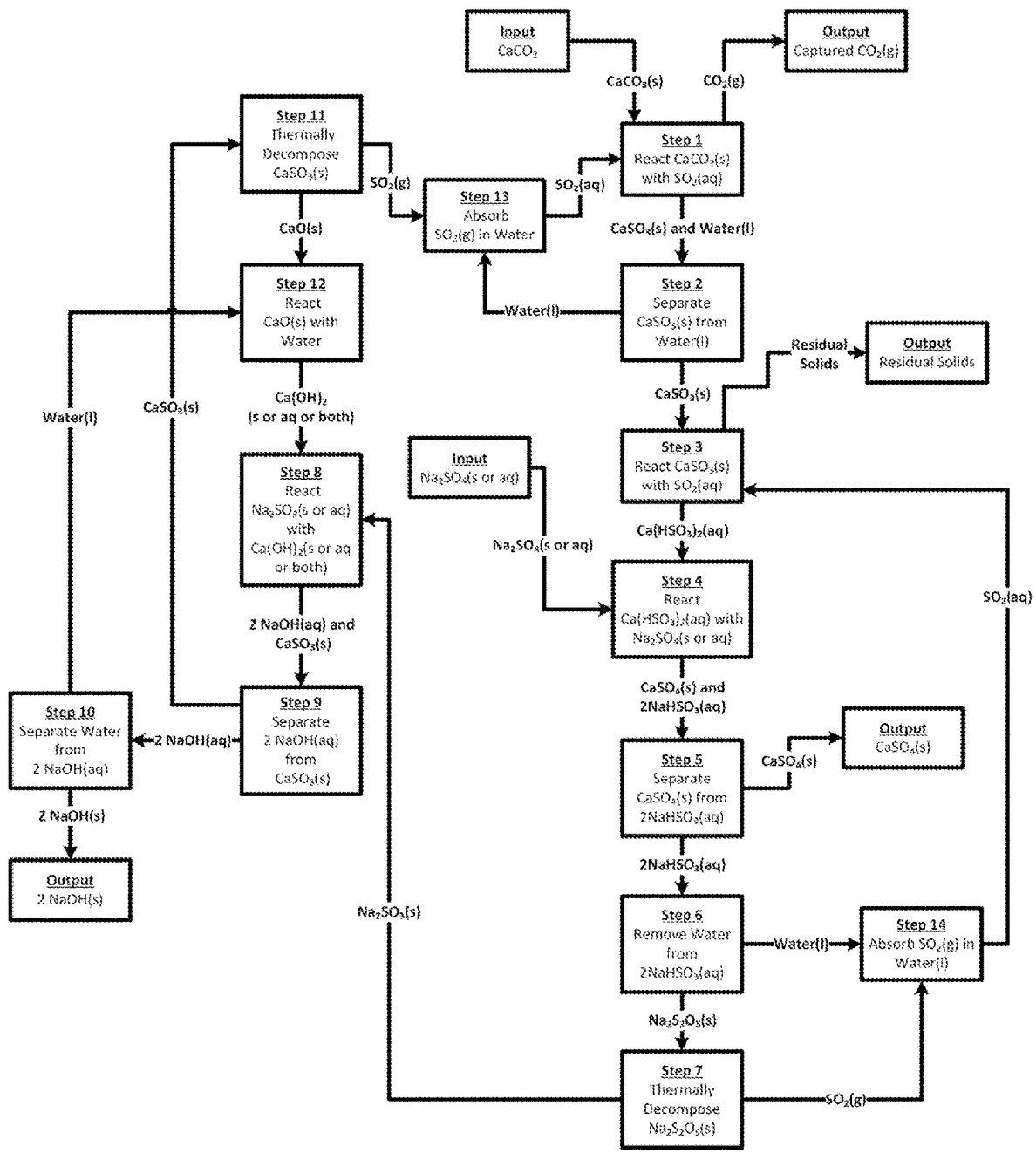
Figure 1B (Above)

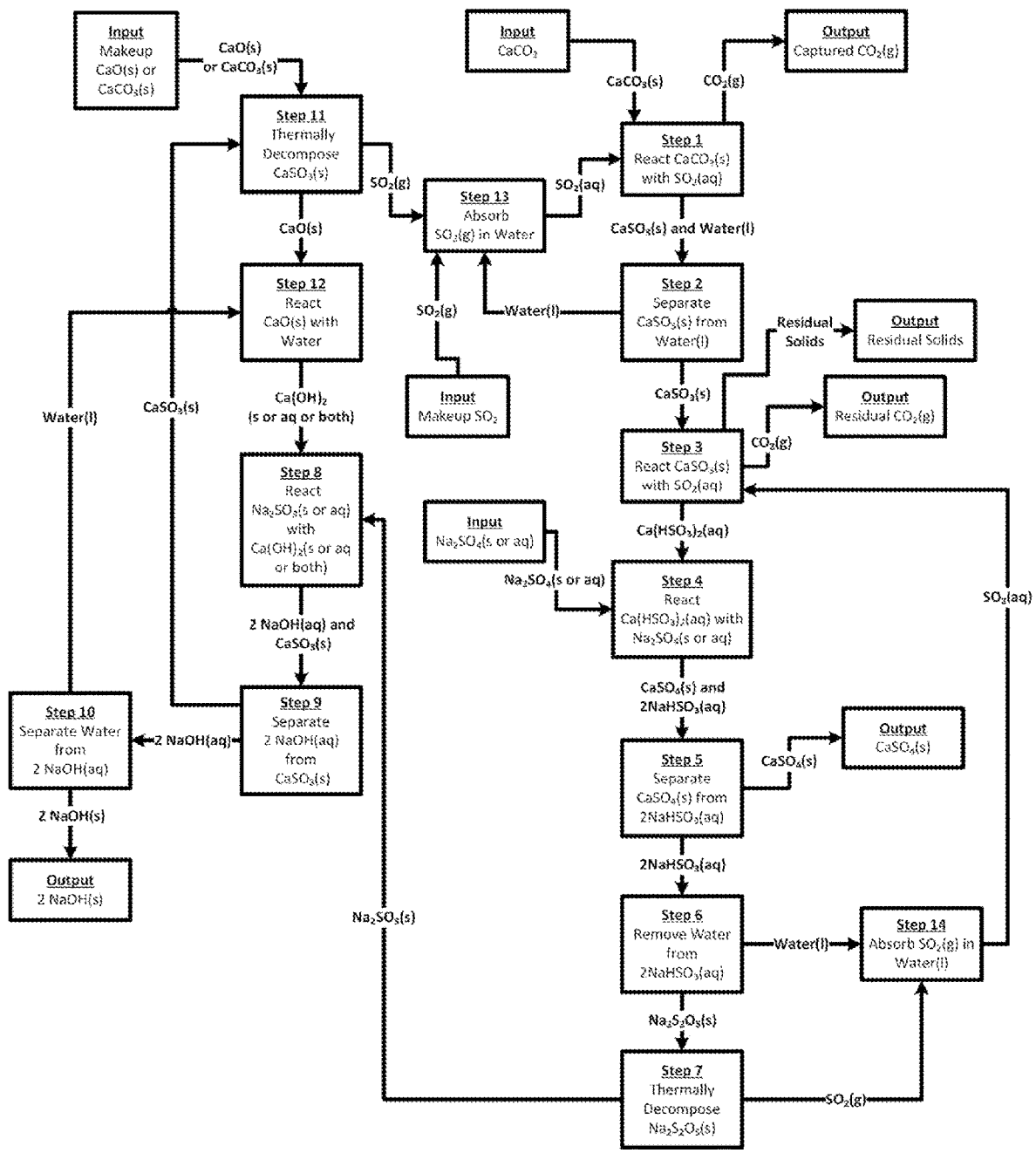
Figure 1C (Above)

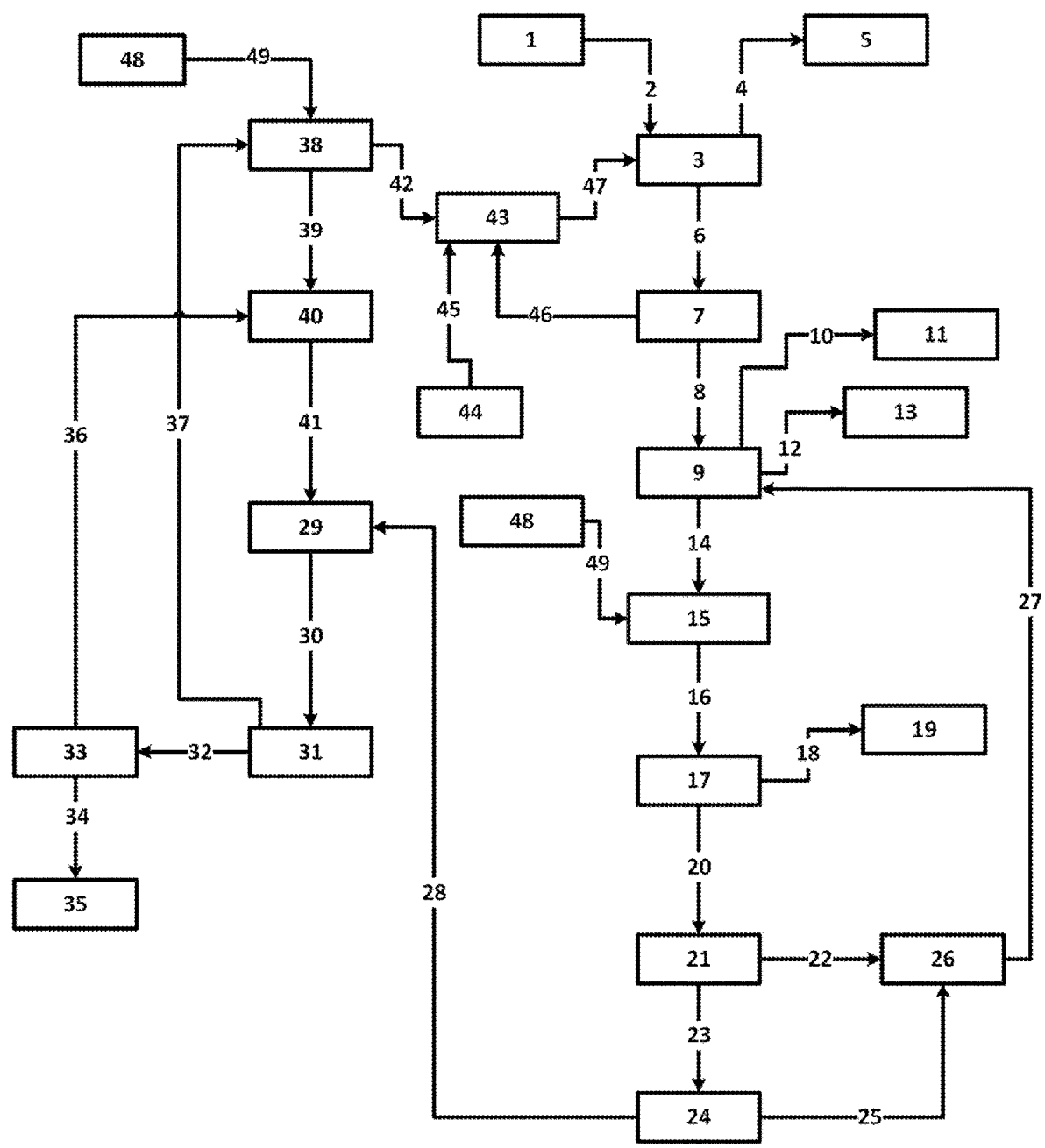
Figure 1D (Above)

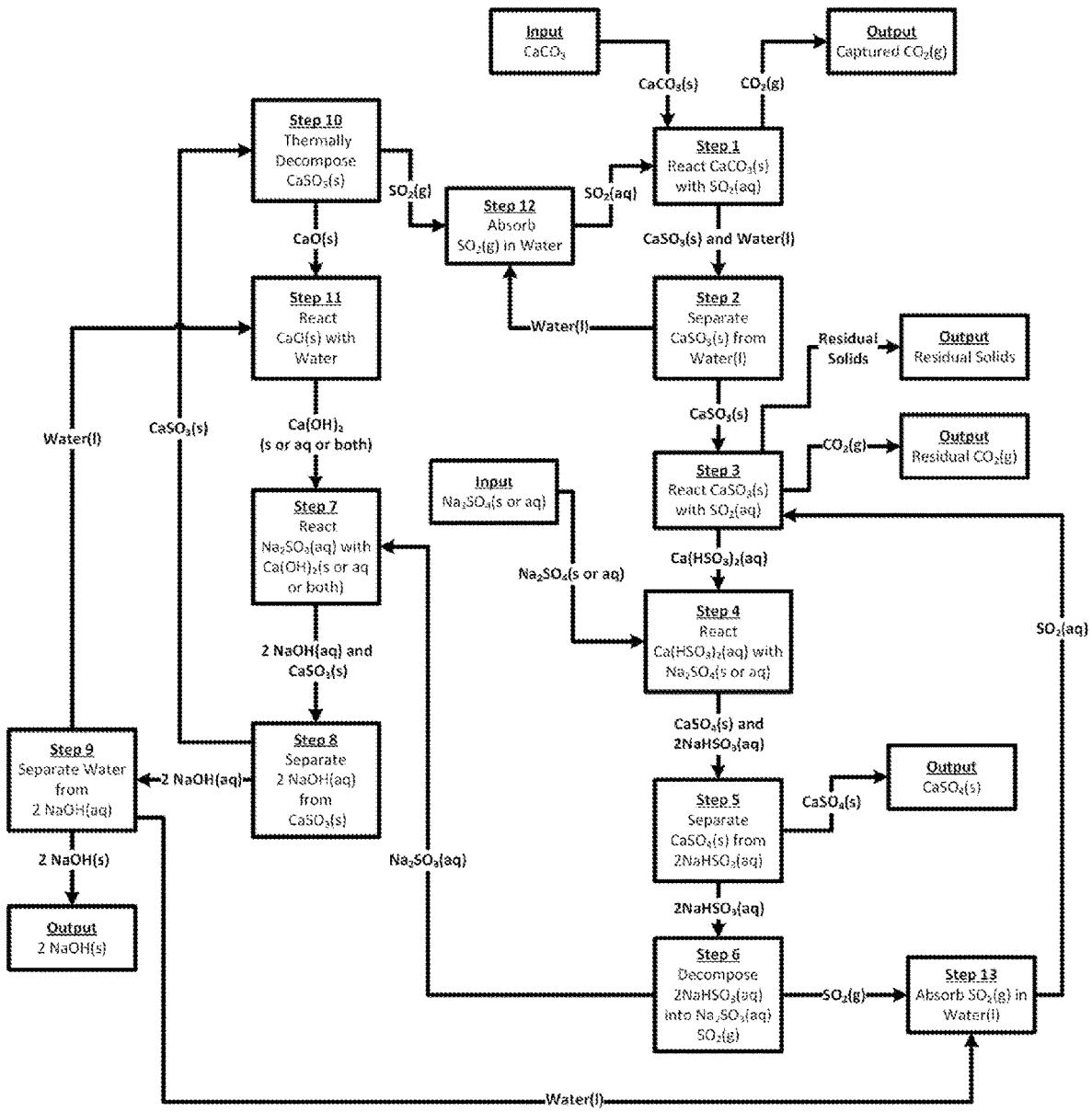
Figure 1E (Above)

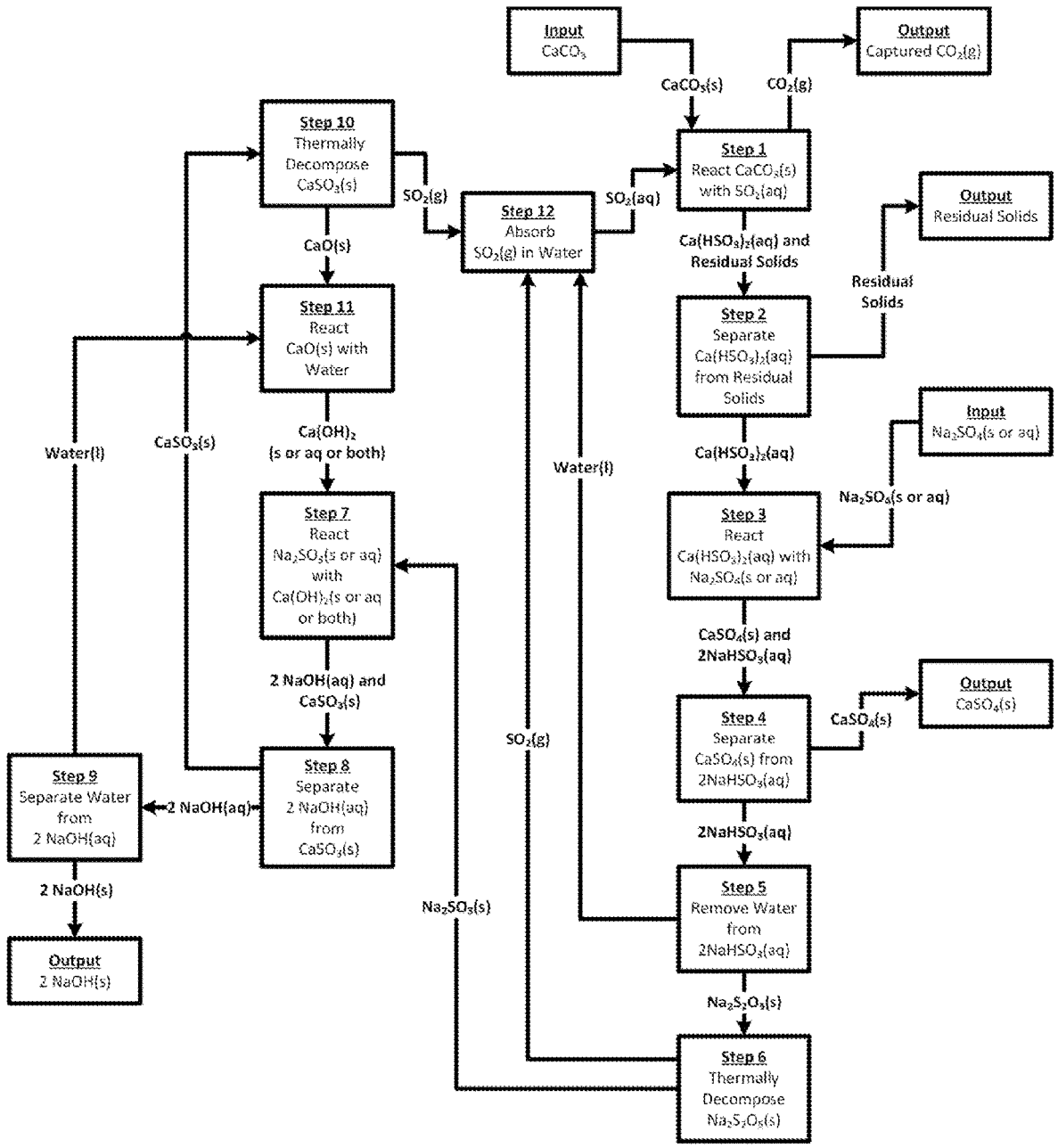
Figure 2A (Above)

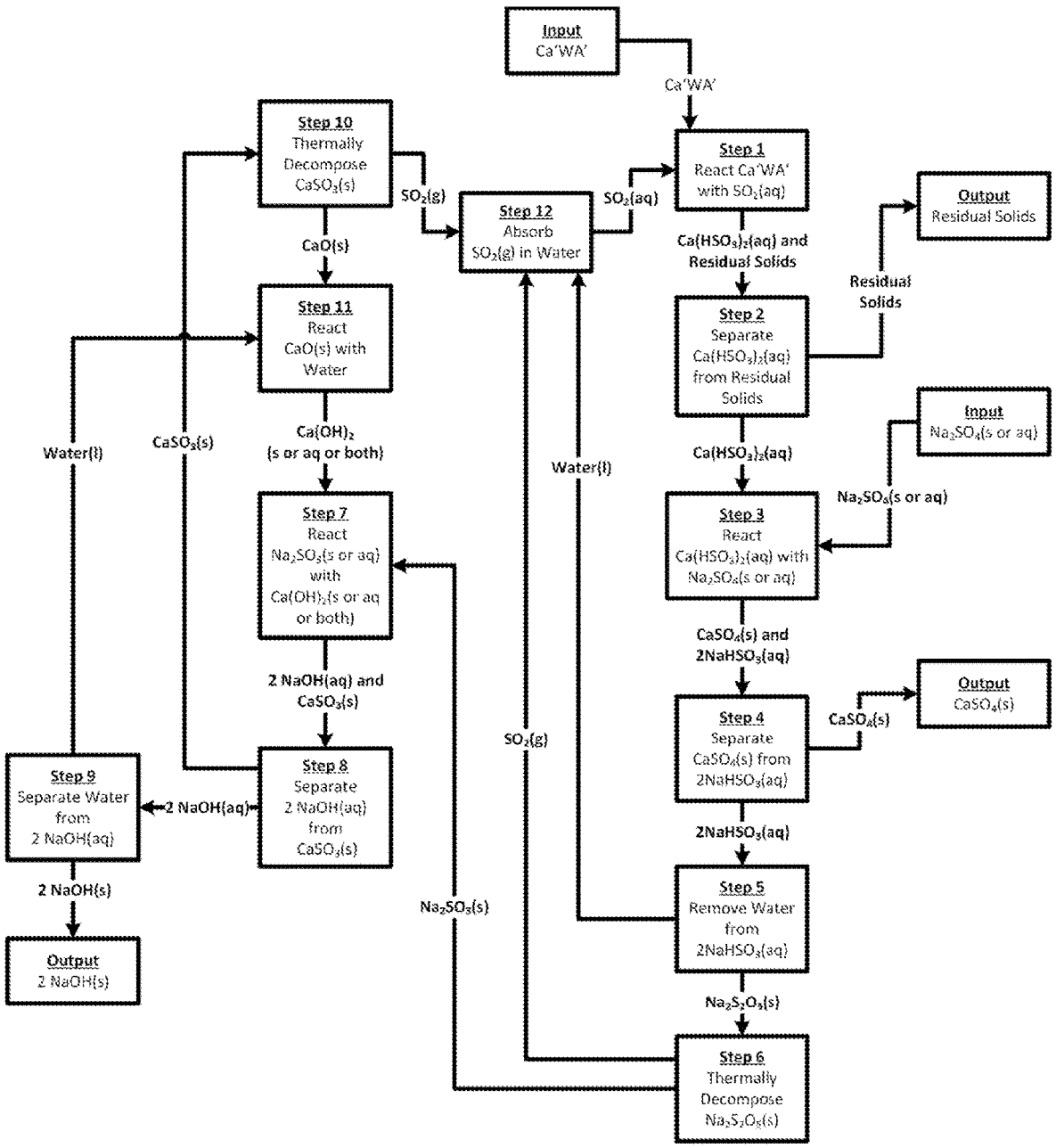
Figure 2B (Above)

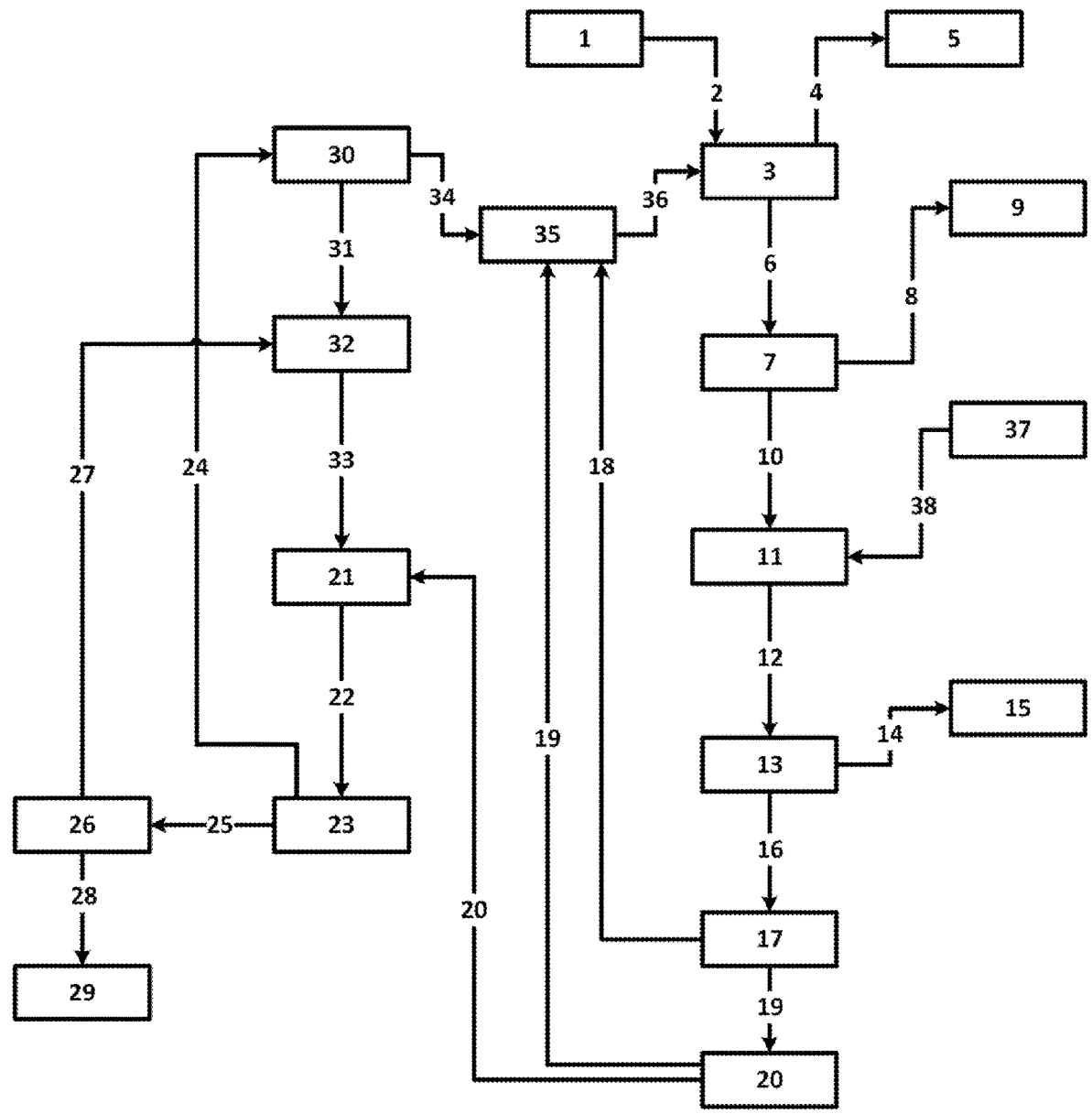
Figure 2C (Above)

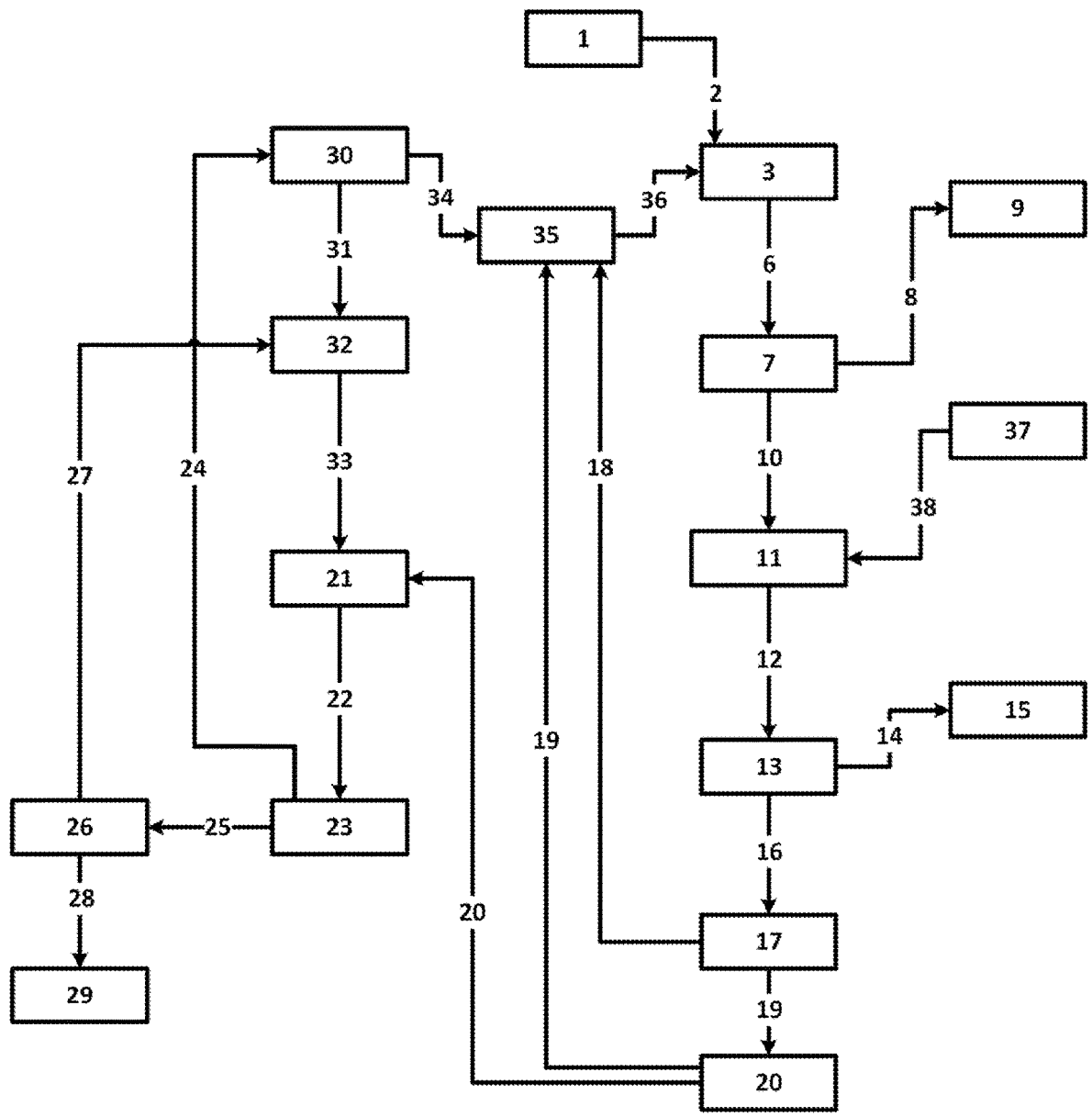
Figure 2D (Above)

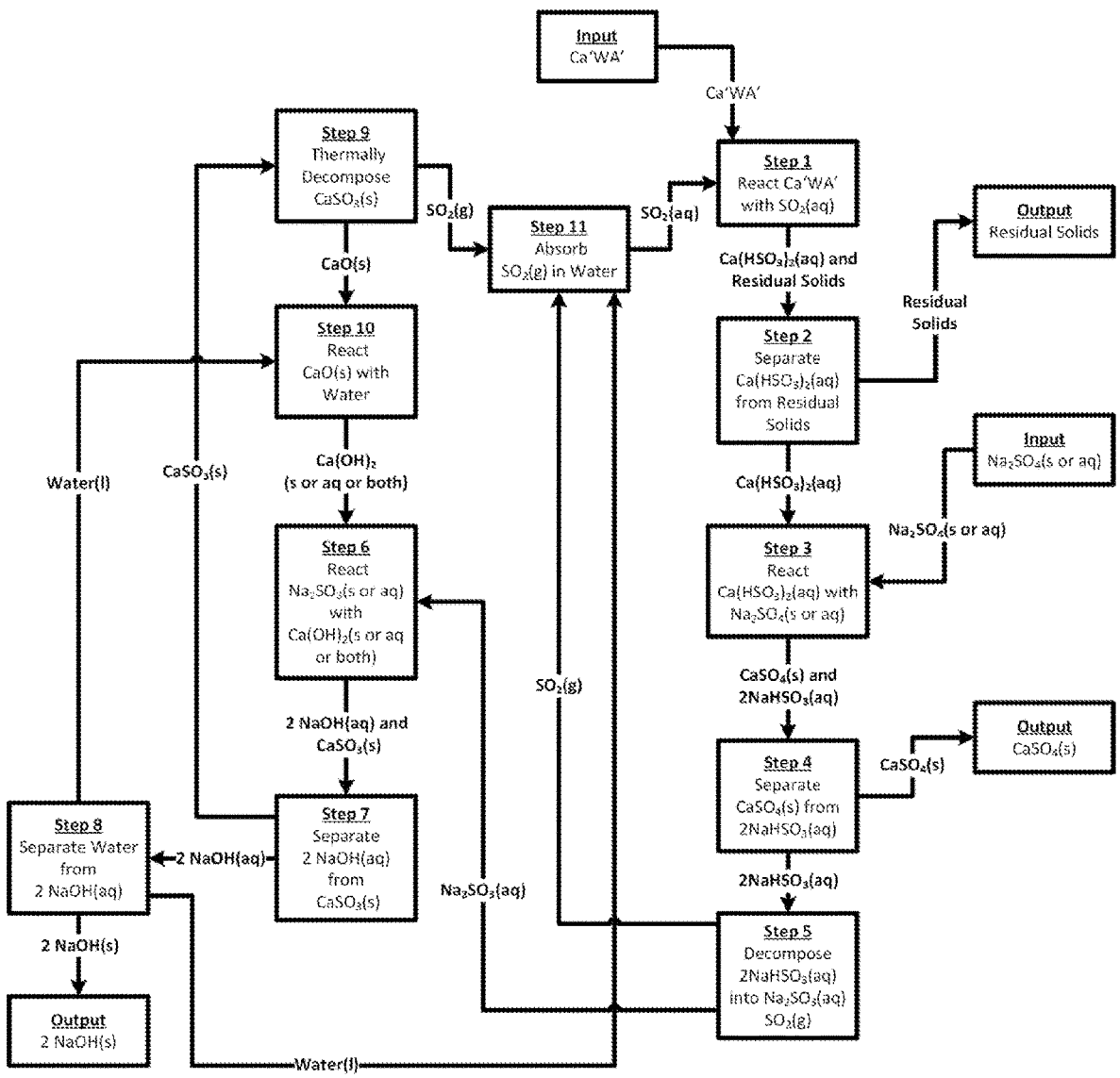
Figure 2E (Above)

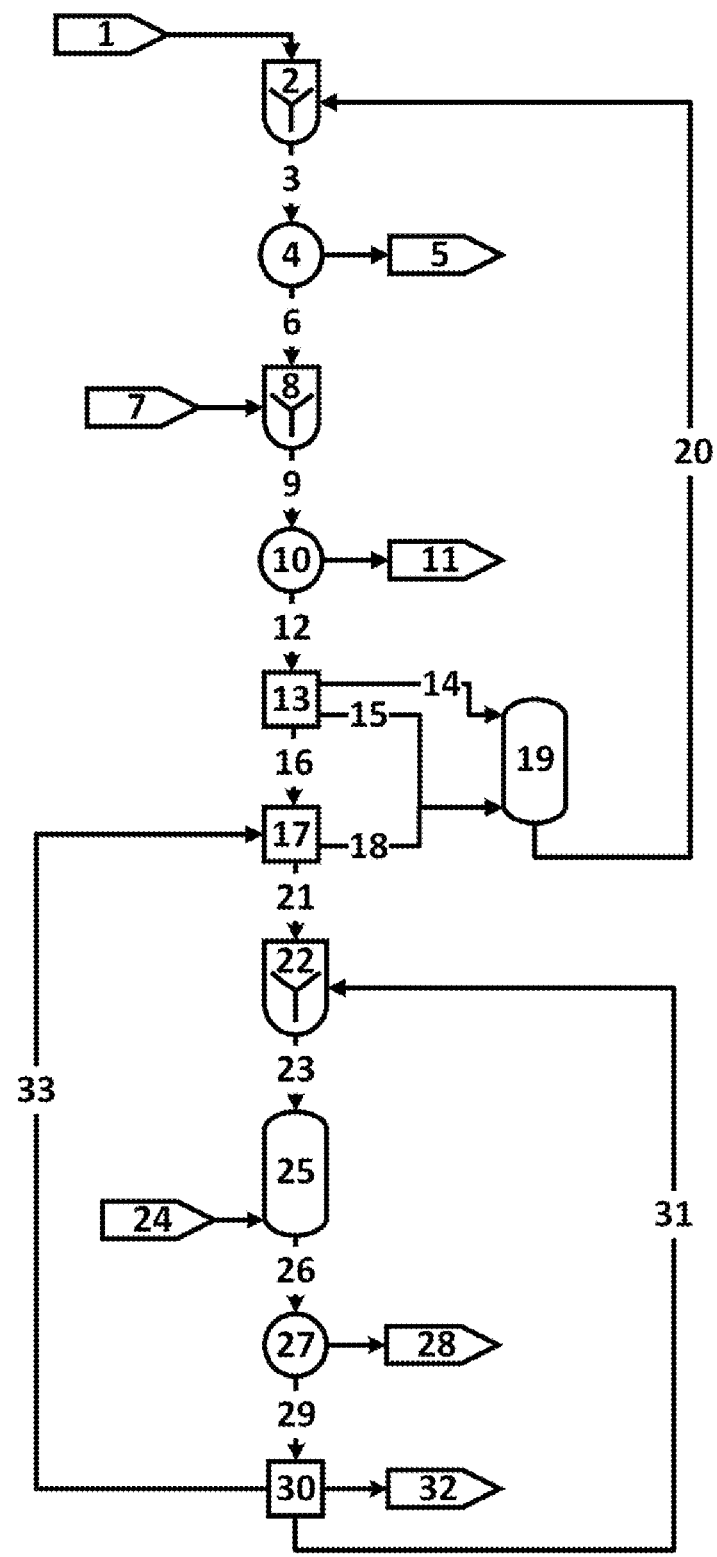
Figure 3 (Above)

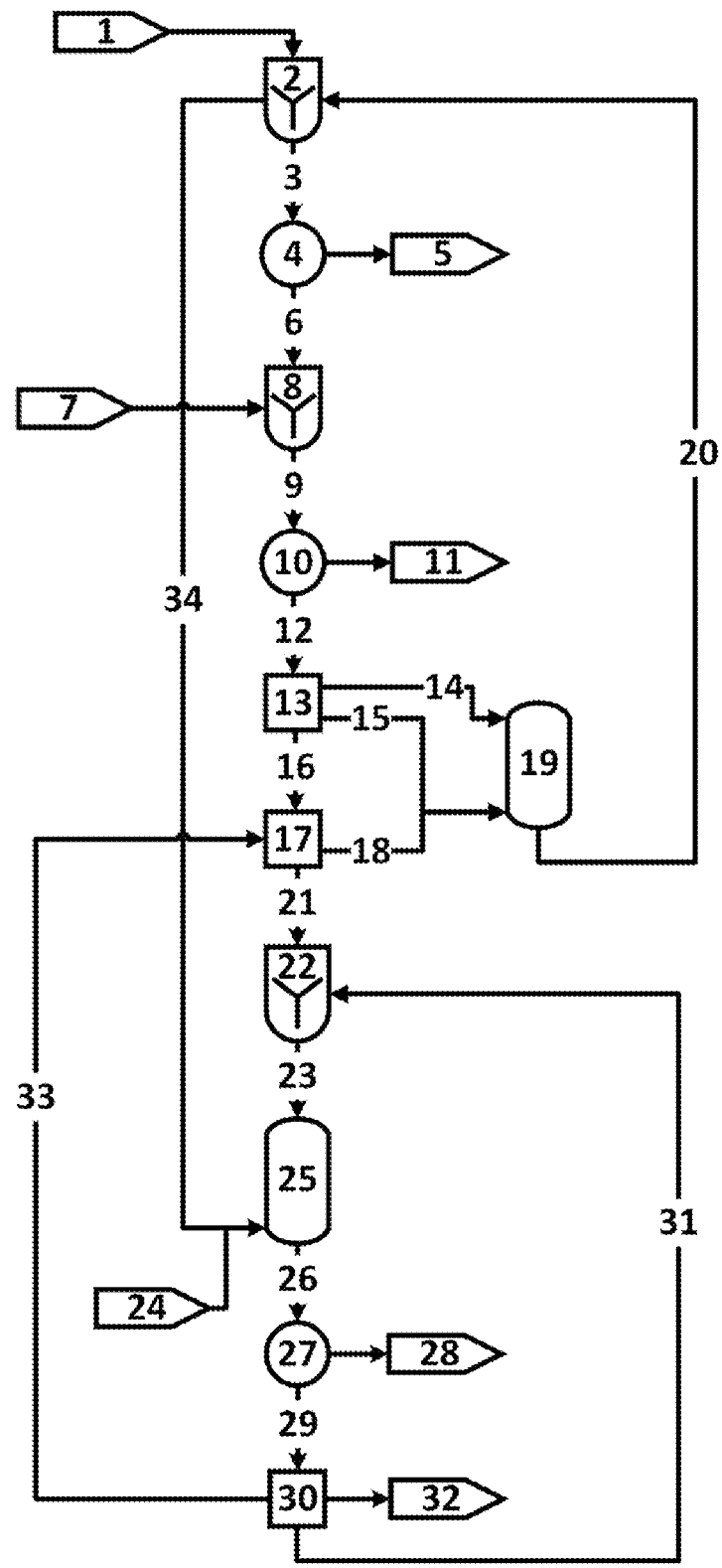
Figure 4 (Above)

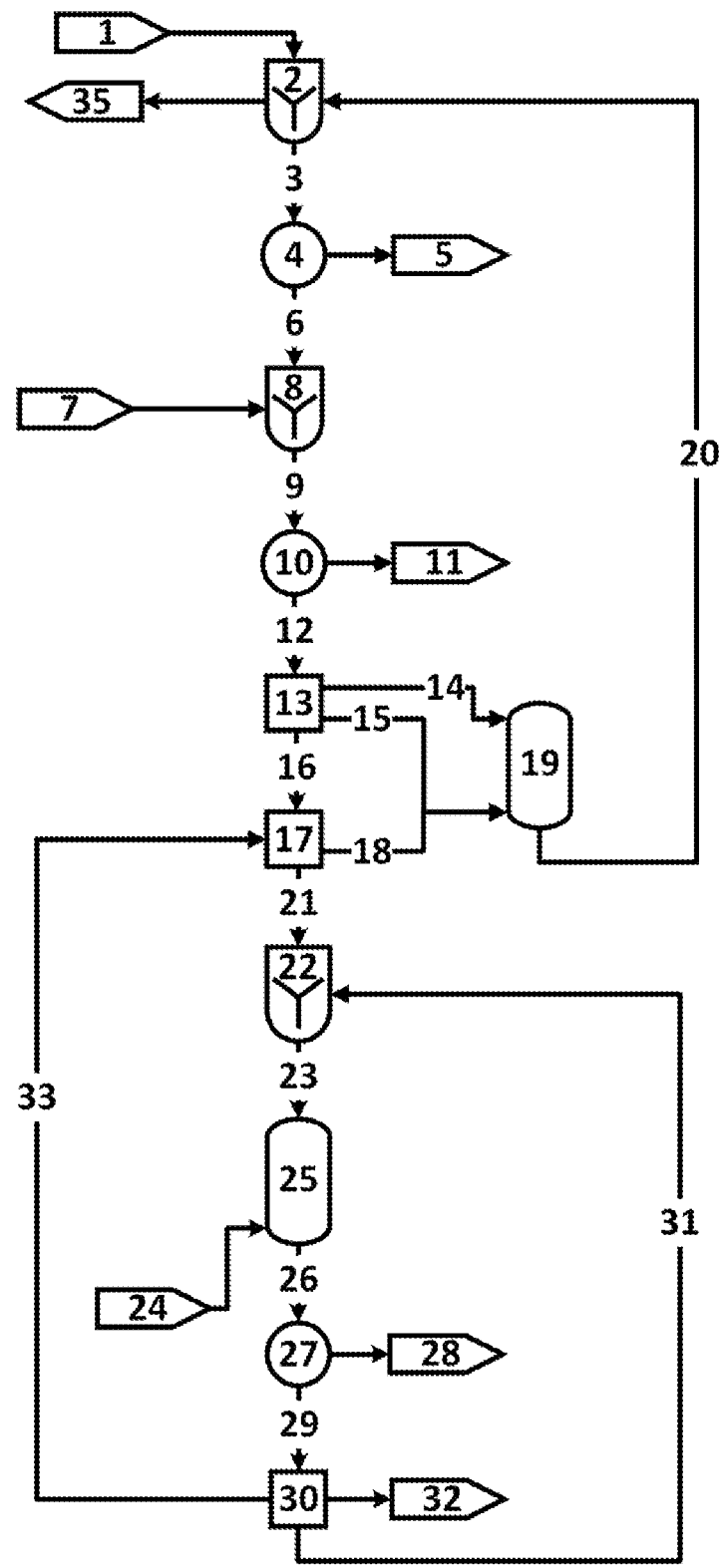
Figure 5 (Above)

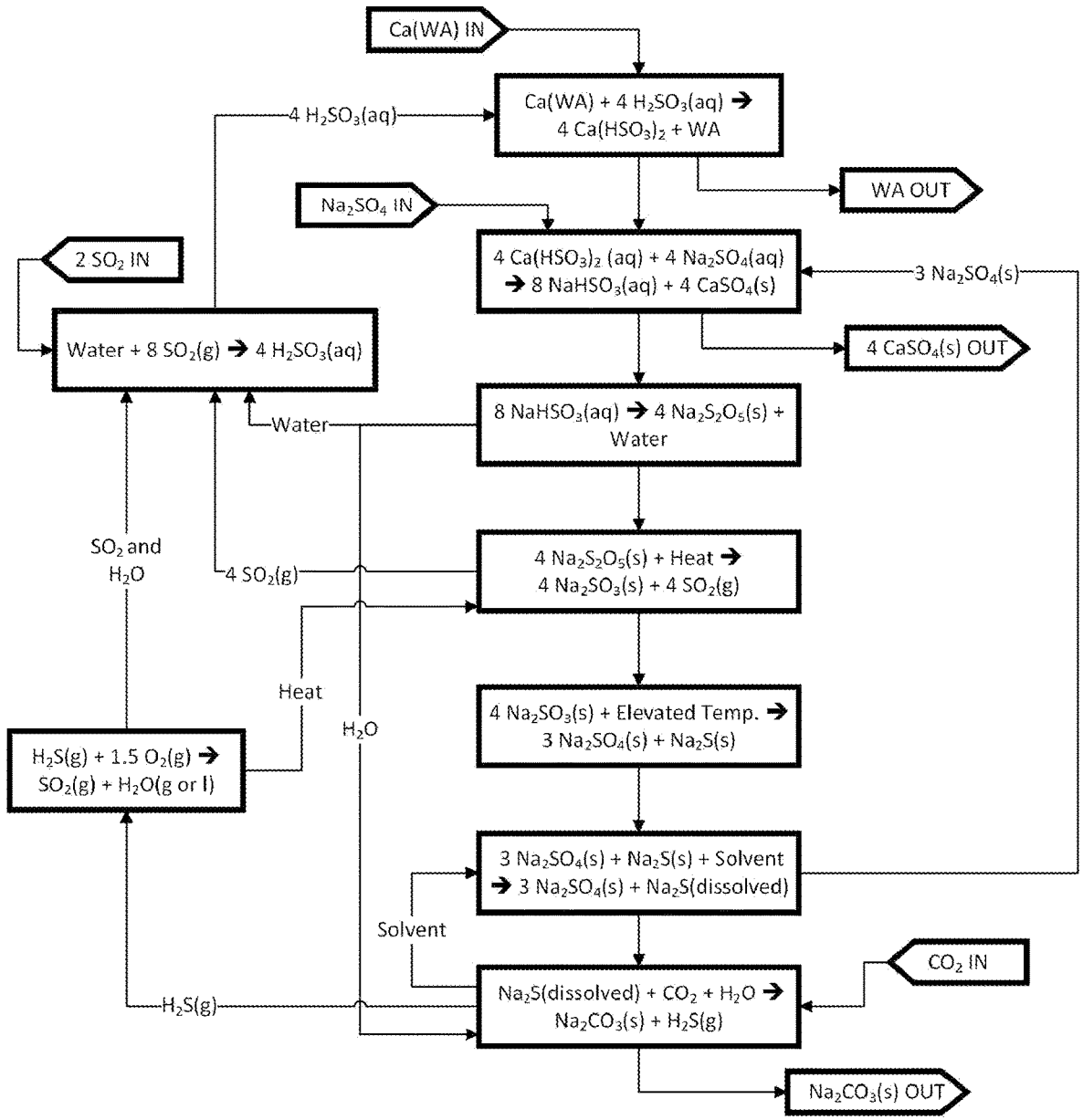
Figure 6 (Above)

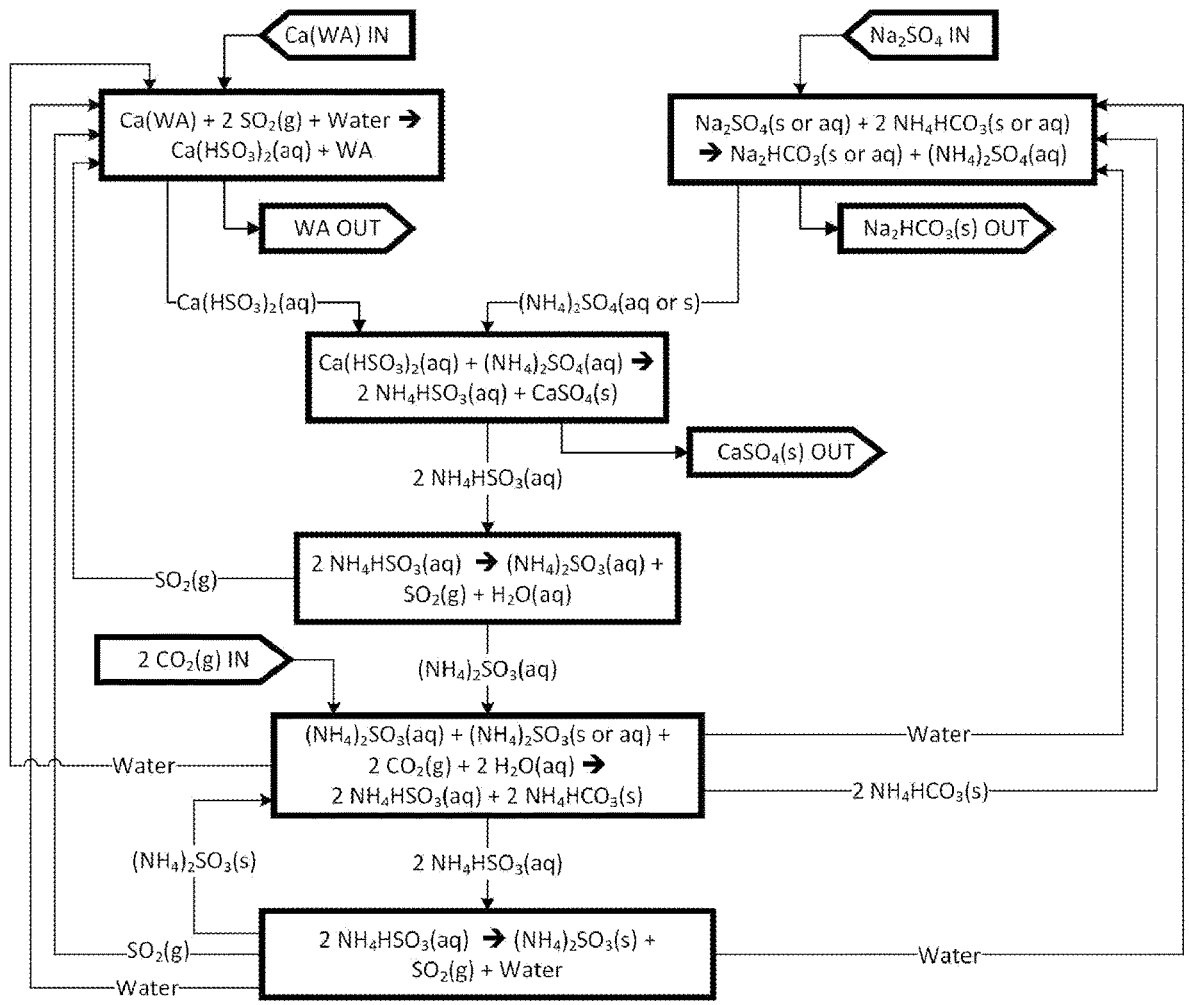
Figure 7A (Above)

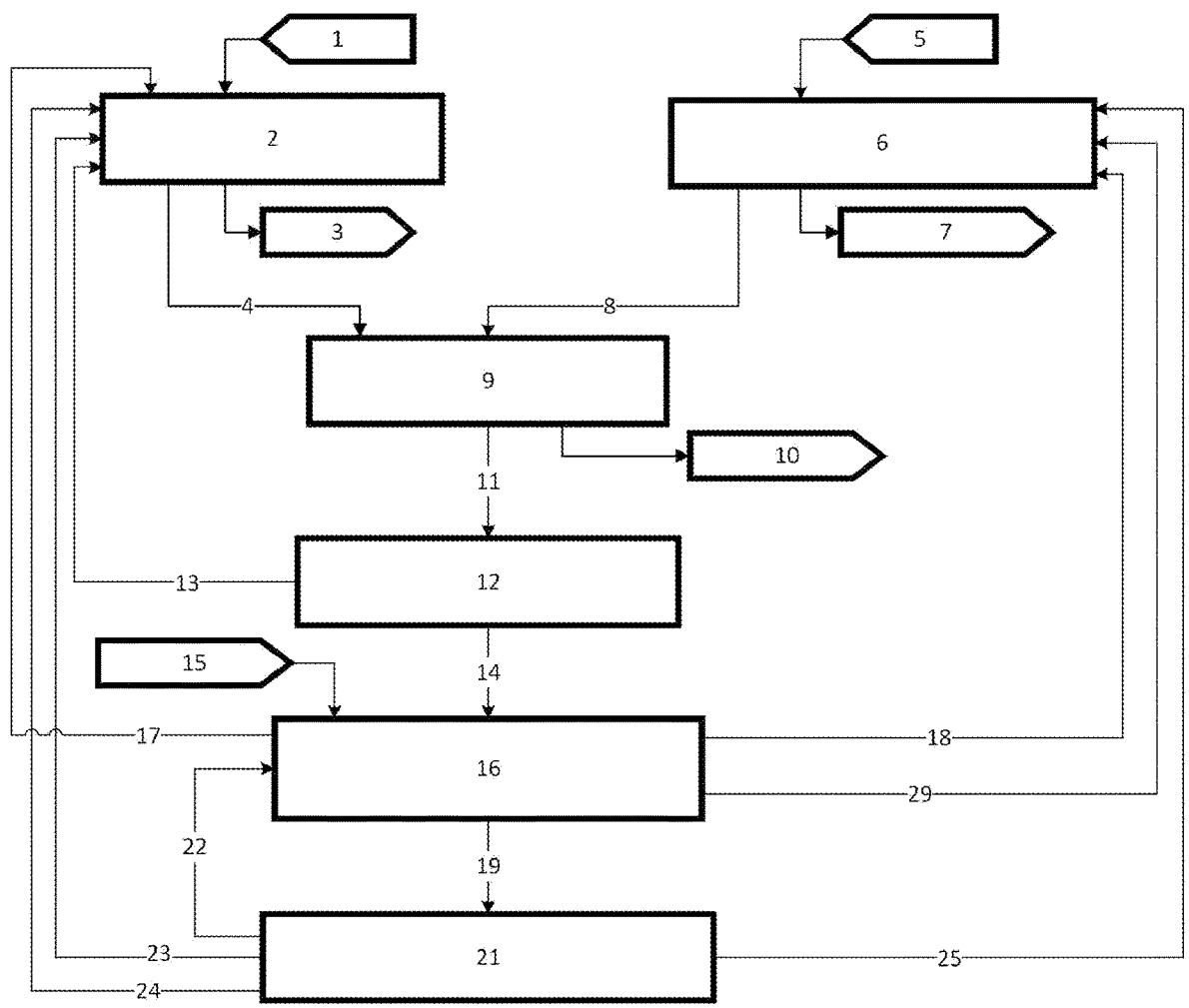
Figure 7B (Above)

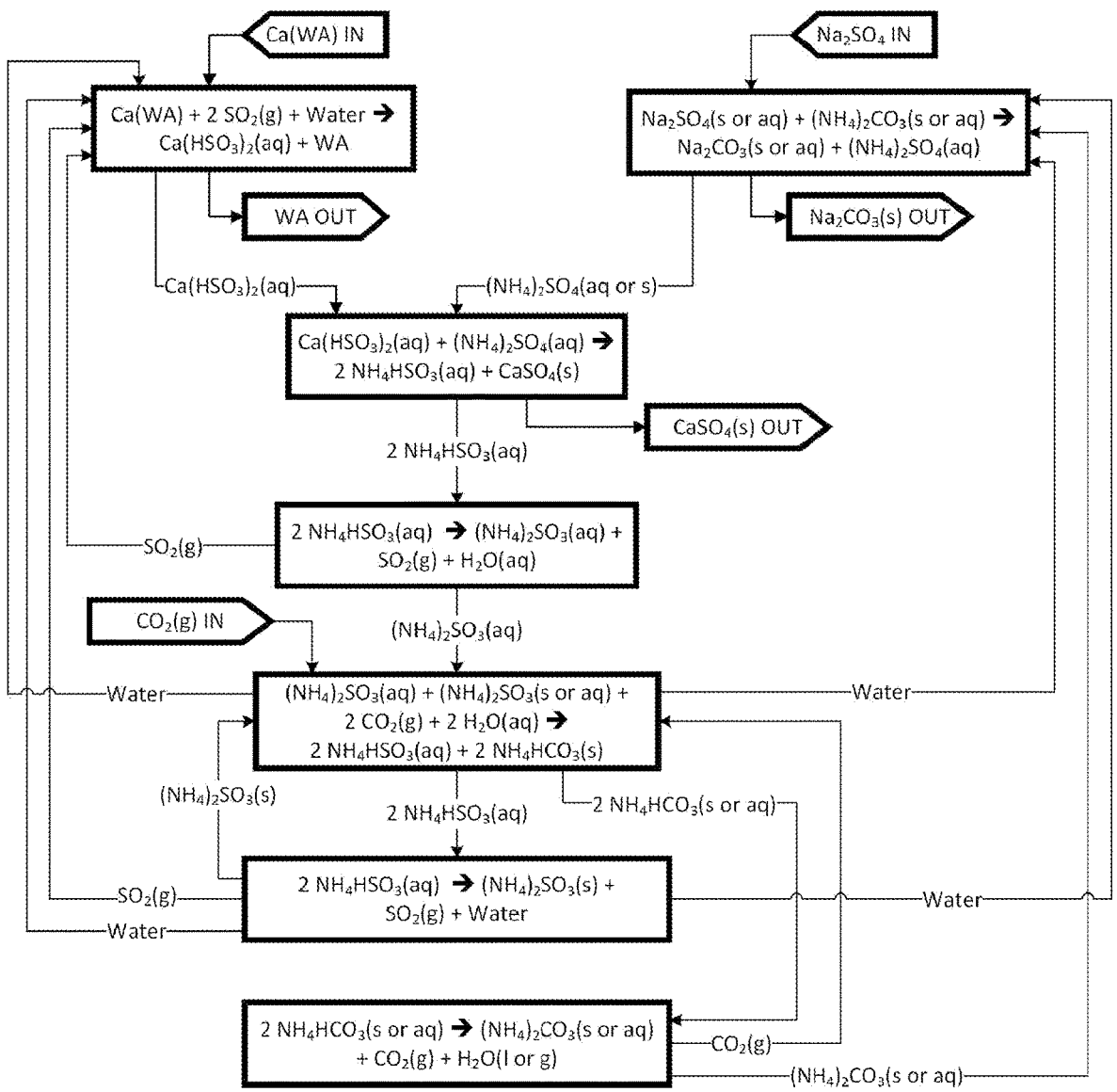
Figure 8A (Above)

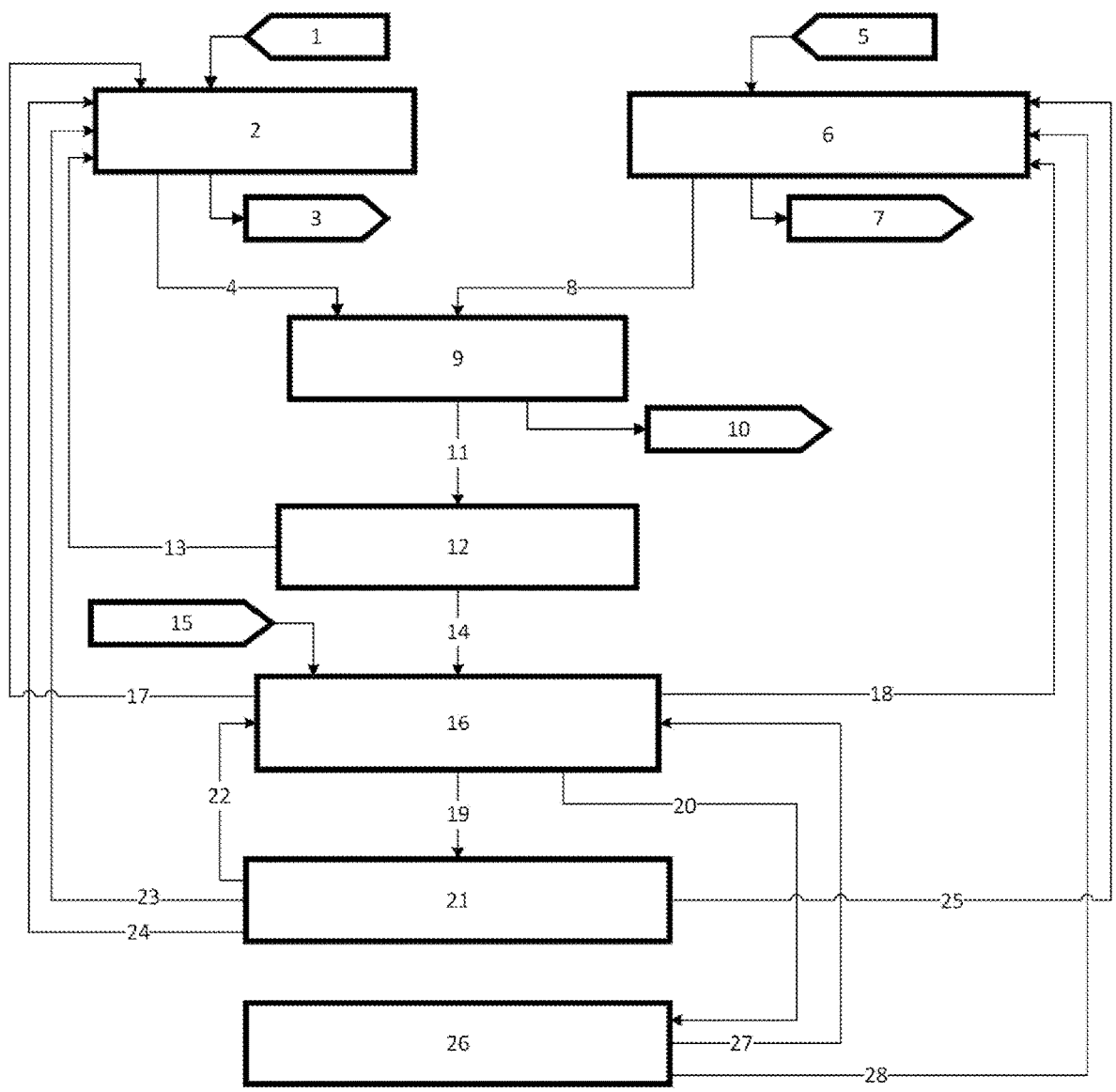
Figure 8B (Above)

PROCESSES PRODUCING ALKALI HYDROXIDES, ALKALI CARBONATES, ALKALI BICARBONATES, AND/OR ALKALINE EARTH SULFATES

CROSS-REFERENCE TO RELATED APPLICATIONS

For PCT purposes the present application claims priority to U.S. Provisional Application No. 63/188,275 filed May 13, 2021 which application is incorporated herein by reference. The present application also claims priority to U.S. application Ser. No. 17/590,483 filed Feb. 1, 2022 and U.S. application Ser. No. 17/732,808 filed Apr. 29, 2022.

For U.S. purposes the present application is a continuation-in-part of U.S. application Ser. No. 17/732,808 filed Apr. 29, 2022 which application is a continuation-in-part of U.S. application Ser. No. 17/590,483 filed Feb. 1, 2022 which application is a continuation of U.S. application Ser. No. 17/243,714 filed Apr. 29, 2021 issued as U.S. Pat. No. 11,236,033 which application is a continuation-in-part of U.S. application Ser. No. 16/944,850 filed Jul. 31, 2020 issued as U.S. Pat. No. 11,034,619 which application claims priority from U.S. Provisional Application No. 62/895,557 filed Sep. 4, 2019 and U.S. Provisional Application No. 63/042,397 filed Jun. 22, 2020 and U.S. Provisional Application No. 62/890,254 filed Aug. 22, 2019. The present application also claims priority to U.S. Provisional Application No. 63/188,275 filed May 13, 2021.

The above described continuation which is U.S. application Ser. No. 17/590,483 filed Feb. 1, 2022 also claims priority to U.S. Provisional Application No. 63/147,286 filed Feb. 9, 2021; U.S. Provisional Application No. 63/153,461 filed Feb. 25, 2021; U.S. Provisional Application No. 63/157,847 filed Mar. 8, 2021; U.S. Provisional Application No. 63/163,993 filed Mar. 22, 2021; and U.S. Provisional Application No. 63/179,822 filed Apr. 26, 2021. All of the above applications are incorporated herein by reference.

BACKGROUND OF THE INVENTION

Sodium hydroxide production is generally produced using the chlor-alkali process, which is energy intensive, requires rare metal anodes and cathodes, and produces hydrochloric acid, which has a limited market and cannot be discharged into the environment. Commercial applications of hydrochloric acid often involve employing hydrochloric acid in a reaction with a carbonate salt, which may result in the release of $CO_2$ and may counter any $CO_2$ emissions reduction benefit. Additionally, if hydrochloric acid is released into the environment, it will react with carbonate or bicarbonate salts present in the environment, emitting carbon dioxide and acidifying water bodies, such as the ocean. There is a significant need for a low energy consumption, low $CO_2$ emissions, environmentally friendly process for producing sodium hydroxide.

SUMMARY OF THE INVENTION

Some embodiments of the present invention may pertain to low carbon emissions, or low energy consumption, or carbon negative production of sodium hydroxide, or sodium carbonate, or sodium bicarbonate, or sodium sulfite, or sodium bisulfite, or gypsum, or alkaline-earth sulfate, or alkali hydroxide, or alkali carbonate, or alkali bicarbonate, or alkali sulfite. Some embodiments of the present invention may enable ultra-low CO2 emissions production of sodium hydroxide with calcium sulfate as the side product. Calcium sulfate comprises a solid, is minimally soluble in water, is non-toxic, is not dangerous for the environment, and has a multi-billion metric ton per year market in gypsum wallboard, concrete aggregates, fireproofing, plaster, building materials, and other applications. Some embodiments of the present invention may be capable of scaling to greater than 1 billion ton per year $CO_2$ emissions reduction, or carbon removal, or a combination thereof. Additionally some embodiments may lower the required cost and energy consumption of alkali hydroxides, alkali carbonates, and alkali bicarbonates. Some embodiments may be employ equipment comprising abundant and recyclable materials.

Advantages of some embodiments include lower energy consumption, lower cost, or lower $CO_2$ emissions, CO2 emissions negative outputs, or application in carbon dioxide removal, or no strong acid products, or abundant materials, or global scalability.

BRIEF FIGURE DESCRIPTIONS

FIG. 1A: Process for Producing Sodium Hydroxide, Calcium Sulfate, and Captured Carbon Dioxide with Inputs Comprising Calcium Carbonate and Sodium Sulfate and Intermediates Comprising Sulfur Dioxide and Alkaline Earth Intermediates FIG. 1B: Process for Producing Sodium Hydroxide, Calcium Sulfate, and Captured Carbon Dioxide with Inputs Comprising Calcium Carbonate and Sodium Sulfate and Intermediates Comprising Sulfur Dioxide and Alkaline Earth Intermediates FIG. 1C: Process for Producing Sodium Hydroxide, Calcium Sulfate, and Captured Carbon Dioxide with Inputs Comprising Calcium Carbonate and Sodium Sulfate and Intermediates Comprising Sulfur Dioxide and Alkaline Earth Intermediates FIG. 1D: Process for Producing Alkali Hydroxide, Alkaline Earth Sulfate, and Weak Acid Derivative with Inputs Comprising Alkaline Earth Cation—Weak Acid Anion salt and Alkali Sulfate and Intermediates Comprising Sulfur Dioxide, Alkaline Earth Oxides, and Alkaline Earth Hydroxides FIG. 1E: Process for Producing Alkali Hydroxide, Alkaline Earth Sulfate, and Weak Acid Derivative with Inputs Comprising Alkaline Earth Cation—Weak Acid Anion salt and Alkali Sulfate and Intermediates Comprising Sulfur Dioxide, Alkaline Earth Oxides, and Alkaline Earth Hydroxides FIG. 2A: Process for Producing Sodium Hydroxide, Calcium Sulfate, and Captured Carbon Dioxide with Inputs Comprising Calcium Carbonate and Sodium Sulfate and Intermediates Comprising Sulfur Dioxide and Intermediates Comprising Sulfur Dioxide, Alkaline Earth Oxides, and Alkaline Earth Hydroxides FIG. 2B: Process for Producing Sodium Hydroxide, Calcium Sulfate, and Captured Carbon Dioxide with Inputs Comprising Calcium—Weak Acid Anion and Sodium Sulfate and Intermediates Comprising Sulfur Dioxide, Alkaline Earth Oxides, and Alkaline Earth Hydroxides FIG. 2C: Process for Producing Alkali Hydroxide, Alkaline Earth Sulfate, and Weak Acid Derivative with Inputs Comprising Alkaline Earth Cation—Weak Acid Anion salt and Alkali Sulfate and Intermediates Comprising Sulfur Dioxide, Alkaline Earth Oxides, and Alkaline Earth Hydroxides FIG. 2D: Process for Producing Alkali Hydroxide, Alkaline Earth Sulfate, and Weak Acid Derivative with Inputs Comprising Alkaline Earth Cation—Weak Acid Anion salt and Alkali Sulfate and Intermediates Comprising Sulfur Dioxide, Alkaline Earth Oxides, and Alkaline Earth Hydroxides FIG. 2E: Process for Producing Alkali Hydroxide, Alkaline Earth Sulfate, and Weak Acid Derivative with Inputs Comprising Alkaline Earth Cation—Weak Acid Anion salt and Alkali Sulfate and Intermediates Comprising Sulfur Dioxide, Alkaline Earth Oxides, and Alkaline Earth Hydroxides FIG. 3: Process for Producing Sodium Carbonate or Sodium Bicarbonate from Sodium Sulfate FIG. 4: Process for Producing Sodium Carbonate or Sodium Bicarbonate from Sodium Sulfate FIG. 5: Process for Producing Sodium Carbonate or Sodium Bicarbonate from Sodium Sulfate FIG. 6: Process for Producing Sodium Carbonate and Alkaline Earth Sulfate from Sodium Sulfate Employing the Thermal Transformation of Sodium Sulfite FIG. 7A: Process for Producing Sodium Carbonate or Sodium Bicarbonate from Sodium Sulfate and Calcium—Weak Acid Input using an Ammonia Intermediate FIG. 7B: Process for Producing Alkali Carbonate or Alkali Bicarbonate from Alkali Sulfate and Alkaline Earth—Weak Acid Input using an Ammonia Intermediate FIG. 8A: Process for Producing Sodium Carbonate or Sodium Bicarbonate from Sodium Sulfate and Calcium—Weak Acid Input using an Ammonia Intermediate FIG. 8B: Process for Producing Alkali Carbonate or Alkali Bicarbonate from Alkali Sulfate and Alkaline Earth—Weak Acid Input using an Ammonia Intermediate

DETAILED DESCRIPTION OF THE INVENTION

The present invention may pertain to a process or system for the production of an alkali hydroxide, or alkali carbonate, or alkali carbonate, or alkaline earth sulfate, or captured carbon dioxide, or aggregate, or silicon dioxide, or any combination thereof. Some embodiments may employ ammonia or ammonium intermediate reactants or intermediates. The present invention may pertain to a process or system for the production of alkali bisulfite, or alkali metabisulfite, or alkali sulfite, or alkaline earth sulfate, or captured carbon dioxide, or silicon dioxide, or aggregate, or weak acid, or any combination thereof from alkali sulfate and alkaline earth carbonate, or alkaline earth silicate, or alkaline earth—weak acid anion, or any combination thereof. The present invention may pertain to a process or system for the production of sodium bisulfite, or sodium metabisulfite, or sodium sulfite, or calcium sulfate, or captured carbon dioxide, or silicon dioxide, or aggregate, or any combination thereof from sodium sulfate and calcium carbonate, or calcium silicate, or calcium—weak acid anion, or any combination thereof. Some embodiments may comprise producing an alkali hydroxide using inputs comprising an alkaline earth cation—weak acid anion salt, or an alkali sulfate, or water, or any combination thereof. Some embodiments may comprise producing an alkali carbonate or alkali bicarbonate or alkali sesquicarbonate using inputs comprising an alkaline earth cation—weak acid anion salt, or an alkali sulfate, or water, or carbon dioxide, or any combination thereof. Some embodiments may employ intermediates comprising sulfur dioxide, or calcium, or water, or any combination thereof. In some embodiments, one or more intermediates may comprise inputs or outputs.

EXAMPLE CHEMISTRY

Example 1: Production of Sodium Hydroxide and Weak Acid or Weak Acid Anion Derivative (1) $CaCO_3 + SO_2(aq) \rightarrow CaSO_3(s) + CO_2(g)$
(2) $CaSO_3(s) + H_2O(aq) + SO_2(aq) \rightarrow Ca(HSO_3)_2(aq)$
(3) $Ca(HSO_3)_2(aq) + Na_2SO_4(aq\ or\ s) \rightarrow 2NaHSO_3(aq) + CaSO_4(s)$
(4) $2NaHSO_3(aq) \rightarrow Na_2SO_3(aq) + SO_2(g)$
(6) $Na_2SO_3(aq) + Ca(OH)_2(s\ or\ aq\ or\ suspension) \rightarrow 2NaOH(aq) + CaSO_3(s)$
   Note: In some embodiments, CaO(s) may be reacted with $Na_2SO_3(aq)$.
   Note: $CaSO_3(s)$ may be separated from 2NaOH(aq) using a solid-liquid separation.
(7) $CaSO_3(s) + Heat \rightarrow CaO(s) + SO_2(g)$
(8) $2NaOH(aq) \rightarrow 2NaOH(s) + Water(solvent)$
   Note: In some embodiments, it may be desirable for 2NaOH to remain at an aqueous phase. For example, NaOH may be sold or transferred or used at an aqueous phase
(9) $CaO(s) + H_2O\ (l\ or\ g) \rightarrow Ca(OH)_2(s\ or\ aq\ or\ suspension)$
(10) $SO_2(g) + Water(solvent) \rightarrow SO_2(aq)$ Or (1) $CaCO_3 + SO_2\ (aq) \rightarrow CaSO_3(s) + CO_2(g)$
(2) $CaSO_3(s) + H_2O(aq) + SO_2(aq) \rightarrow Ca(HSO_3)_2(aq)$
(3) $Ca(HSO_3)_2(aq) + Na_2SO_4(aq\ or\ s) \rightarrow 2NaHSO_3(aq) + CaSO_4(s)$
(4) May Comprise one or more or any combination of the following:
   $2NaHSO_3(aq) \rightarrow Na_2S_2O_5(s) + H_2O(l\ or\ g) + Water(solvent)$
   $2NaHSO_3(aq) \rightarrow Na_2S_2O_5(s) + Water(solvent)$
(5) $Na_2S_2O_5(s) + Heat \rightarrow Na_2SO_3(s) + SO_2(g)$
(6) $Na_2SO_3(s\ or\ aq) + Ca(OH)_2(s\ or\ aq\ or\ suspension) \rightarrow 2NaOH(aq) + CaSO_3(s)$
(7) $CaSO_3(s) + Heat \rightarrow CaO(s) + SO_2(g)$
(8) $2NaOH(aq) \rightarrow 2NaOH(s) + Water(solvent)$
(9) $CaO(s) + H_2O\ (l\ or\ g) \rightarrow Ca(OH)_2(s\ or\ aq\ or\ suspension)$
(10) $SO_2(g) + Water(solvent) \rightarrow SO_2(aq)$ Example 2: Production of Sodium Hydroxide and Weak Acid or Weak Acid Anion Derivative (1) $CaCO_3 + 2\ SO_2(aq) + H_2O(aq) \rightarrow Ca(HSO_3)_2(aq) + CO_2(g)$
(2) $Ca(HSO_3)_2(aq) + Na_2SO_4(aq\ or\ s) \rightarrow 2NaHSO_3(aq) + CaSO_4(s)$
(3) $2NaHSO_3(aq) \rightarrow Na_2SO_3(aq) + SO_2(g)$
(4) $Na_2SO_3(s\ or\ aq) + Ca(OH)_2(s\ or\ aq\ or\ suspension) \rightarrow 2NaOH(aq) + CaSO_3(s)$
(5) $CaSO_3(s) + Heat \rightarrow CaO(s) + SO_2(g)$
(6) $2NaOH(aq) \rightarrow 2NaOH(s) + Water(solvent)$
(7) $2SO_2(g) + Water(solvent) \rightarrow 2SO_2(aq)$
(8) $CaO(s) + H_2O\ (l\ or\ g) \rightarrow Ca(OH)_2(s\ or\ aq\ or\ suspension)$ Or (1) $CaCO_3 + 2\ SO_2(aq) + H_2O(aq) \rightarrow Ca(HSO_3)_2(aq) + CO_2(g)$
(2) $Ca(HSO_3)_2(aq) + Na_2SO_4(aq\ or\ s) \rightarrow 2NaHSO_3(aq) + CaSO_4(s)$
(3) $2NaHSO_3(aq) \rightarrow Na_2S_2O_5(s) + Water(solvent)$
(4) $Na_2S_2O_5(s) + Heat \rightarrow Na_2SO_3(s) + SO_2(g)$ (5) $Na_2SO_3$(s or aq)+$Ca(OH)_2$(s or aq or suspension)→2NaOH(aq)+$CaSO_3$(s)
(6) $CaSO_3$(s)+Heat→CaO(s)+$SO_2$(g)
(7) 2NaOH(aq)→2NaOH(s)+Water(solvent)
(8) 2$SO_2$(g)+Water(solvent)→2$SO_2$(aq)
(9) CaO(s)+$H_2O$ (l or g)→$Ca(OH)_2$(s or aq or suspension)

Example 3: Production of Sodium Hydroxide and Weak Acid or Weak Acid Anion Derivative (1) Calcium Silicate(s)+2$SO_2$(aq)+$H_2O$(aq)→$Ca(HSO_3)_2$(aq)+Silicon Dioxide(s)
(2) $Ca(HSO_3)_2$(aq)+$Na_2SO_4$(aq or s)→2$NaHSO_3$(aq)+$CaSO_4$(s)
(3) 2$NaHSO_3$(aq)→$Na_2SO_3$(aq)+$SO_2$(g)
(4) $Na_2SO_3$(s or aq)+$Ca(OH)_2$(s or aq or suspension)→2NaOH(aq)+$CaSO_3$(s)
(5) $CaSO_3$(s)+Heat→CaO(s)+$SO_2$(g)
(6) 2NaOH(aq)→2NaOH(s)+Water(solvent)
(7) 2$SO_2$(g)+Water(solvent)→2 $SO_2$(aq)
(8) CaO(s)+$H_2O$ (l or g)→$Ca(OH)_2$(s or aq or suspension)
Or
(1) Calcium Silicate(s)+2$SO_2$(aq)+$H_2O$(aq)→$Ca(HSO_3)_2$(aq)+Silicon Dioxide(s)
(2) $Ca(HSO_3)_2$(aq)+$Na_2SO_4$(aq or s)→2$NaHSO_3$(aq)+$CaSO_4$(s)
(3) 2$NaHSO_3$(aq)→$Na_2S_2O_5$(s)+Water(solvent)
(4) $Na_2S_2O_5$(s)+Heat→$Na_2SO_3$(s)+$SO_2$(g)
(5) $Na_2SO_3$(s or aq)+$Ca(OH)_2$(s or aq or suspension)→2NaOH(aq)+$CaSO_3$(s)
(6) $CaSO_3$(s)+Heat→CaO(s)+$SO_2$(g)
(7) 2NaOH(aq)→2NaOH(s)+Water(solvent)
(8) 2$SO_2$(g)+Water(solvent)→2 $SO_2$(aq)
(9) CaO(s)+$H_2O$ (l or g)→$Ca(OH)_2$(s or aq or suspension)

Example 4: Production of Sodium Hydroxide and Weak Acid or Weak Acid Anion Derivative (1) Calcium(Weak Acid Anion)+2$SO_2$(aq)+$H_2O$(aq)→$Ca(HSO_3)_2$(aq)+Weak Acid(s or aqueous or gas or liquid)
(2) $Ca(HSO_3)_2$(aq)+$Na_2SO_4$(aq or s)→2$NaHSO_3$(aq)+$CaSO_4$(s)
(3) 2$NaHSO_3$(aq)→$Na_2SO_3$(aq)+$SO_2$(g)
(4) $Na_2SO_3$(s or aq)+$Ca(OH)_2$(s or aq or suspension)→2NaOH(aq)+$CaSO_3$(s)
(5) $CaSO_3$(s)+Heat→CaO(s)+$SO_2$(g)
(6) 2NaOH(aq)→2NaOH(s)+Water(solvent)
(7) 2$SO_2$(g)+Water(solvent)→2 $SO_2$(aq)
(8) CaO(s)+$H_2O$ (l or g)→$Ca(OH)_2$(s or aq or suspension)
Or
(1) Calcium(Weak Acid Anion)+2$SO_2$(aq)+$H_2O$(aq)→$Ca(HSO_3)_2$(aq)+Weak Acid(s or aqueous or gas or liquid)
(2) $Ca(HSO_3)_2$(aq)+$Na_2SO_4$(aq or s)→2$NaHSO_3$(aq)+$CaSO_4$(s)
(3) 2$NaHSO_3$(aq)→$Na_2S_2O_5$(s)+Water(solvent)
(4) $Na_2S_2O_5$(s)+Heat→$Na_2SO_3$(s)+$SO_2$(g)
(5) $Na_2SO_3$(s or aq)+$Ca(OH)_2$(s or aq or suspension)→2NaOH(aq)+$CaSO_3$(s)
(6) $CaSO_3$(s)+Heat→CaO(s)+$SO_2$(g)
(7) 2NaOH(aq)→2NaOH(s)+Water(solvent)
(8) 2$SO_2$(g)+Water(solvent)→2 $SO_2$(aq)
(9) CaO(s)+$H_2O$ (l or g)→$Ca(OH)_2$(s or aq or suspension)

Example 5: Production of Sodium Hydroxide and Weak Acid or Weak Acid Anion Derivative (1) Calcium(Weak Acid Anion)+2$SO_2$(aq)+$H_2O$(aq)→$Ca(HSO_3)_2$(aq)+Weak Acid(s or aqueous or gas or liquid)
(2) $Ca(HSO_3)_2$(aq)+$Na_2SO_4$(aq or s)→2$NaHSO_3$(aq)+$CaSO_4$(s)
(3) 2$NaHSO_3$(aq)→$Na_2SO_3$(aq)+$SO_2$(g)
(4) $Na_2SO_3$(s or aq)+$Ca(OH)_2$(s or aq or suspension)→2NaOH(aq)+$CaSO_3$(s)
(5) $CaSO_3$(s)+Heat→CaO(s)+$SO_2$(g)
(6) One or more or any combination of the following:
2NaOH(aq)→2NaOH(s)+Water(solvent)
2NaOH(aq)
2NaOH(aq) or 2NaOH(s) added to seawater or body of water
(7) 2$SO_2$(g)+Water(solvent)→2 $SO_2$(aq)
(8) CaO(s)+$H_2O$ (l or g)→$Ca(OH)_2$(s or aq or suspension)
Or
(1) Calcium(Weak Acid Anion)+2$SO_2$(aq)+$H_2O$(aq)→$Ca(HSO_3)_2$(aq)+Weak Acid(s or aqueous or gas or liquid)
(2) $Ca(HSO_3)_2$(aq)+$Na_2SO_4$(aq or s)→2$NaHSO_3$(aq)+$CaSO_4$(s)
(3) 2$NaHSO_3$(aq)→$Na_2S_2O_5$(s)+Water(solvent)
Note: $NaHSO_3$(aq) may generally exist at an aqueous phase. Upon precipitation or crystallization, $NaHSO_3$(aq) precipitates or crystalizes as $Na_2S_2O_5$(s). $Na_2S_2O_5$(s) may be considered anhydrous.
(4) $Na_2S_2O_5$(s)+Heat→$Na_2SO_3$(s)+$SO_2$(g)
(5) $Na_2SO_3$(s or aq)+$Ca(OH)_2$(s or aq or suspension)→2NaOH(aq)+$CaSO_3$(s)
(6) $CaSO_3$(s)+Heat→CaO(s)+$SO_2$(g)
(7) One or more or any combination of the following:
2NaOH(aq)→2NaOH(s)+Water(solvent)
2NaOH(aq)
2NaOH(aq) or 2NaOH(s) added to seawater or body of water
(8) 2$SO_2$(g)+Water(solvent)→2 $SO_2$(aq)
(9) CaO(s)+$H_2O$ (l or g)→$Ca(OH)_2$(s or aq or suspension)

Example 6: Production of Sodium Hydroxide and Weak Acid or Weak Acid Anion Derivative (1) Calcium(Weak Acid Anion)+2$SO_2$(aq)+$H_2O$(aq)→$Ca(HSO_3)_2$(aq)+Weak Acid(s or aqueous or gas or liquid)
(2) $Ca(HSO_3)_2$(aq)+$Na_2SO_4$(aq or s)→2$NaHSO_3$(aq)+$CaSO_4$(s)
(3) 2$NaHSO_3$(aq)→$Na_2SO_3$(aq)+$H_2O$(aq)+$SO_2$(g)
(4) $Na_2SO_3$(s or aq)+$Ca(OH)_2$(s or aq or suspension)→2NaOH(aq)+$CaSO_3$(s)
(5) $CaSO_3$(s)+Heat→CaO(s)+$SO_2$(g)
(6) One or more or any combination of the following:
2NaOH(aq)→2NaOH(s)+Water(solvent)
2NaOH(aq)
2NaOH(aq) or 2NaOH(s) added to seawater or body of water
(7) 2$SO_2$(g)+Water(solvent)→2 $SO_2$(aq)
(8) CaO(s)+$H_2O$ (l or g)→$Ca(OH)_2$(s or aq or suspension)

Example 7: Production of Sodium Carbonate or Sodium Bicarbonate (1) One or more or any combination of the following:
$CaCO_3$+2 $SO_2$(aq)+$H_2O$(aq)→$Ca(HSO_3)_2$(aq)+$CO_2$(g)
CaS+2$SO_2$(aq)+$H_2O$(aq)→$Ca(HSO_3)_2$(aq)+$H_2S$(g)
Calcium Silicate(s)+2$SO_2$(aq)+$H_2O$(aq)→$Ca(HSO_3)_2$(aq)+Silicon Dioxide(s)
Calcium(Weak Acid Anion)+2$SO_2$(aq)+$H_2O$(aq) $Ca(HSO_3)_2$(aq)+Weak Acid(s or aqueous or gas or liquid)

(2) $Ca(HSO_3)_2(aq)+Na_2SO_4(aq\ or\ s) \rightarrow 2NaHSO_3(aq)+CaSO_4(s)$ (3) $NaHSO_3(aq) \rightarrow NaHSO_3(aq)+Water(solvent)$ Note: In some embodiments, residual sodium bicarbonate or sodium carbonate or sodium—carbon dioxide may be present in solution. In some embodiments, residual sodium bicarbonate or sodium carbonate or sodium-carbon dioxide may decompose and/or form carbon dioxide gas. Said carbon dioxide gas may be recirculated and/or employed in '(6)'.

(4) $2NaHSO_3(aq) \rightarrow Na_2SO_3(aq)+H_2O(aq)+SO_2(g)$ (5) $Na_2SO_3(aq)+CO_2(g)+2H_2O(aq) \rightarrow NaHSO_3(aq)+NaHCO_3(aq\ or\ s)$ Note: In some embodiments, the aqueous solution may be concentrated, or cooled, or both to promote the further precipitation of sodium bicarbonate or further separation of sodium bicarbonate. For example, in some embodiments, an aqueous solution comprising 2 $NaHSO_3(aq)+2NaHCO_3(aq)$ may be concentrated using, for example, mechanical vapor compression distillation, or distillation, or desorption, and the precipitation of $2NaHCO_3(s)$ may be facilitated due to, for example, the concentrating beyond solubility limits and/or lower temperature and/or extraction and/or other separation system or method.

(6) Remaining $NaHSO_3(aq)$ in '(5)' may be transferred to '(3)'

Or (1) One or more or any combination of the following:

$CaCO_3+2\ SO_2(aq)+H_2O(aq) \rightarrow Ca(HSO_3)_2(aq)+CO_2(g)$ $CaS+2SO_2(aq)+H_2O(aq) \rightarrow Ca(HSO_3)_2(aq)+H_2S(g)$ Calcium Silicate(s)+$2SO_2(aq)+H_2O(aq) \rightarrow Ca(HSO_3)_2(aq)$+Silicon Dioxide(s)

Calcium(Weak Acid Anion)+$2SO_2(aq)+H_2O(aq) \rightarrow Ca(HSO_3)_2(aq)$+Weak Acid(s or aqueous or gas or liquid)

(2) $Ca(HSO_3)_2(aq)+Na_2SO_4(aq\ or\ s) \rightarrow 2NaHSO_3(aq)+CaSO_4(s)$ (3) $2NaHSO_3(aq) \rightarrow Na_2S_2O_5(s)+Water(solvent)$ Note: In some embodiments, residual sodium bicarbonate or sodium carbonate or sodium—carbon dioxide may be present in solution. In some embodiments, residual sodium bicarbonate or sodium carbonate or sodium-carbon dioxide may decompose and/or form carbon dioxide gas. Said carbon dioxide gas may be recirculated and/or employed in '(6)'.

(4) $Na_2S_2O_5(s)+Heat \rightarrow Na_2SO_3(s)+SO_2(g)$ (5) $Na_2SO_3(s)+Water\ (Solvent) \rightarrow Na_2SO_3(aq)$ (6) $Na_2SO_3(aq)+CO_2(g)+2H_2O(aq) \rightarrow NaHSO_3(aq)+NaHCO_3(aq\ or\ s)$ Note: In some embodiments, the aqueous solution may be concentrated, or cooled, or both to promote the further precipitation of sodium bicarbonate or further separation of sodium bicarbonate. For example, in some embodiments, an aqueous solution comprising 2 $NaHSO_3(aq)+2NaHCO_3(aq)$ may be concentrated using, for example, mechanical vapor compression distillation, or distillation, or desorption, and the precipitation of $2NaHCO_3(s)$ may be facilitated due to, for example, the concentrating beyond solubility limits and/or lower temperature and/or extraction and/or other separation system or method.

(7) Remaining $NaHSO_3(aq)$ in '(6)' may be transferred to '(3)'

Example 8: Production of Sodium Carbonate or Sodium Bicarbonate (1) One or more or any combination of the following:

$CaCO_3+2\ SO_2(aq)+H_2O(aq) \rightarrow Ca(HSO_3)_2(aq)+CO_2(g)$

Calcium Silicate(s)+$2SO_2(aq)+H_2O(aq) \rightarrow Ca(HSO_3)_2(aq)$+Silicon Dioxide(s)

Calcium(Weak Acid Anion)+$2SO_2(aq)+H_2O(aq) \rightarrow Ca(HSO_3)_2(aq)$+Weak Acid(s or aqueous or gas or liquid)

(2) $Ca(HSO_3)_2(aq)+Na_2SO_4(aq\ or\ s) \rightarrow 2NaHSO_3(aq)+CaSO_4(s)$ (3) $2NaHSO_3(aq) \rightarrow Na_2SO_3(aq)+H_2O(aq)+SO_2(g)$ (4) $Na_2SO_3(aq)+CO_2(g)\ 4NaHSO_3(aq)+NaHCO_3(aq\ or\ s)$ (5) Remaining $NaHSO_3(aq)$ in '(4)' may be transferred to '(3)'

Example 9: Production of Sodium Hydroxide for Air Capture and Producing Sodium Carbonate or Sodium Bicarbonate from $CO_2$ in the Air or Other $CO_2$ or $CO_2$ in the Ocean (1) Calcium(Weak Acid Anion)+$2SO_2(aq)+H_2O(aq) \rightarrow Ca(HSO_3)_2(aq)$+Weak Acid(s or aqueous or gas or liquid)

(2) $Ca(HSO_3)_2(aq)+Na_2SO_4(aq\ or\ s) \rightarrow 2NaHSO_3(aq)+CaSO_4(s)$ (3) May comprise one or more or any combination of the following:

$2NaHSO_3(aq) \rightarrow Na_2SO_3(aq)+SO_2(g)$ $2NaHSO_3(aq) \rightarrow Na_2S_2O_5(s)+Water(solvent)$ $Na_2S_2O_5(s)+Heat \rightarrow Na_2SO_3(s)+SO_2(g)$ $Na_2SO_3(s)+Water\ (Solvent) \rightarrow Na_2SO_3(aq)$ (4) $Na_2SO_3(s\ or\ aq)+Ca(OH)_2(s\ or\ aq\ or\ suspension) \rightarrow 2NaOH(aq)+CaSO_3(s)$ (5) $CaSO_3(s)+Heat \rightarrow CaO(s)+SO_2(g)$ (6) $2NaOH(aq)+CO_2(g) \rightarrow Na_2CO_3(aq)+H_2O(aq)$ Note: $CO_2(g)$ for this reaction may, if desired, comprise dilute sources, which may include, but are not limited to, air or emissions gases. NaOH(aq or s) is capable of reacting with very low concentrations of $CO_2$ and forming sodium carbonate. Alternatively, the NaOH may be added to seawater, where it will add ocean alkalinity and naturally absorb carbon dioxide from the air or ocean, increasing the ocean's capacity to sequester carbon dioxide, or react with $CO_2$, or bicarbonate, or carbonate, or anions, or any combination thereof in the ocean, or increase the pH of the ocean, or any combination thereof.

(7) One or more or any combination of the following:

$Na_2CO_3(aq) \rightarrow Na_2CO_3(s)+Water\ (solvent)$ $Na_2CO_3(aq)+CO_2(g)+H_2O(aq) \rightarrow 2NaHCO_3(aq)$ $Na_2CO_3(aq)$ or $Na_2CO_3(s)$ added to seawater or a body of water (8) $2SO_2(g)+Water(solvent) \rightarrow 2\ SO_2(aq)$ (9) $CaO(s)+H_2O\ (l\ or\ g) \rightarrow Ca(OH)_2(s\ or\ aq\ or\ suspension)$ Example 10: Decomposition of Sodium Sulfite in the Presence of Water Vapor to Sodium Hydroxide and Sulfur Dioxide (1) Calcium(Weak Acid Anion)+$2SO_2(aq)+H_2O(aq) \rightarrow Ca(HSO_3)_2(aq)$+Weak Acid(s or aqueous or gas or liquid)

(2) $Ca(HSO_3)_2(aq)+Na_2SO_4(aq$ or $s)\rightarrow 2NaHSO_3(aq)+CaSO_4(s)$
(3) $2NaHSO_3(aq)\rightarrow Na_2S_2O_5(s)+Water(solvent)$
(4) $Na_2S_2O_5(s)+Heat\rightarrow Na_2SO_3(s)+SO_2(g)$
(5) $Na_2SO_3(s)+H_2O(g)+Heat\rightarrow 2NaOH(s)+SO_2(g)$
Note: May comprise a high temperature water vapor atmosphere.
(6) $2SO_2(g)+Water$ (solvent)$\rightarrow 2\ SO_2(aq)$

Example 11: Production of Sodium Sulfite, Gypsum, and Weak Acid or Weak Acid Anion Derivative (1) Calcium(Weak Acid Anion)$+2SO_2(aq)+H_2O(aq)\rightarrow Ca(HSO_3)_2(aq)+$Weak Acid(s or aqueous or gas or liquid)
(2) $Ca(HSO_3)_2(aq)+Na_2SO_4(aq$ or $s)\rightarrow 2NaHSO_3(aq)+CaSO_4(s)$
(3) May comprise one or more or any combination of the following:
$2NaHSO_3(aq)\rightarrow Na_2SO_3(aq)+SO_2(g)$
$2NaHSO_3(aq)\rightarrow Na_2S_2O_5(s)+Water(solvent)$
$Na_2S_2O_5(s)+Heat\rightarrow Na_2SO_3(s)+SO_2(g)$
$Na_2SO_3(s)+Water$ (Solvent)$\rightarrow Na_2SO_3(aq)$
(4) $SO_2(g)+water$ (solvent)$\rightarrow SO_2(aq)$

Example 12: Production of Sodium Bisulfite or Sodium Metabisulfite and Weak Acid or Weak Acid Anion Derivative (1) Calcium(Weak Acid Anion)$+2SO_2(aq)+H_2O(aq)\rightarrow Ca(HSO_3)_2(aq)+$Weak Acid(s or aqueous or gas or liquid)
(2) $Ca(HSO_3)_2(aq)+Na_2SO_4(aq$ or $s)\rightarrow 2NaHSO_3(aq)+CaSO_4(s)$
(3) $2NaHSO_3(aq)\rightarrow Na_2S_2O_5(s)+H_2O(l$ or $g)+Water(solvent)$

Example 13: Production of Sodium Carbonate or Sodium Bicarbonate and Hydrogen Sulfide or Sulfur or Hydrogen or Sulfur Dioxide or Sulfurous Acid or Sulfuric Acid from Sodium Sulfate and Calcium Salt (1) Calcium(Weak Acid Anion)$+8SO_2(aq)+H_2O(aq)\rightarrow Ca(HSO_3)_2(aq)+$Weak Acid(s or aqueous or gas or liquid)
(2) $\rightarrow Ca(HSO_3)_2(aq)+Na_2SO_4(aq$ or $s)\rightarrow 8NaHSO_3(aq)+4CaSO_4(s)$
(3) $8NaHSO_3(aq)\rightarrow Na_2S_2O_5(s)+Water(solvent)$
(4) $4Na_2S_2O_5(s)+Heat\rightarrow 4Na_2SO_3(s)+4SO_2(g)$
(5) $4Na_2SO_3(s)+Heat\rightarrow 3Na_2SO_4(s)+Na_2S(s)$
Note: Reaction '(5)' may be exothermic.
(6) $3Na_2SO_4(s)+Na_2S(s)+Water$ (solvent)$\rightarrow 3Na_2SO_4(aq$ or $s)+Na_2S(aq)$
(7) $3Na_2SO_4(aq$ or $s)+Na_2S(aq)+CO_2(aq$ or $g)\rightarrow 3Na_2SO_4$ (aq or s)$+Na_2CO_3(aq$ or $s)+H_2S(aq$ or $g)$
(8) $3Na_2SO_4(aq$ or $s)+Na_2CO_3(aq$ or $s)+H_2S(aq$ or $g)\rightarrow 3Na_2SO_4(aq)+Na_2CO_3(aq$ or $s)+H_2S(g)$
(9) Sodium Sulfate, or Sodium Sulfide, or Sodium Carbonate, or Sodium Bicarbonate Separation. Said separation may occur, for example, before or during or after '(5)', or '(6)', or '(7)', or '(8)' and/or may comprise, including, but not limited to, one or more or any combination of the following:
Note: Sodium sulfate may be known to possess a solubility curve in water which sharply increases with temperature between 0-35° C. For example, the solubility of sodium sulfate in water may be 4.76 g/100 ml at 0° C., or may be 49.7 g/100 mL at 32.4 degrees Celsius. Sodium carbonate may be known to possess a solubility curve in water which increases with temperature between 0-35° C., although slightly less sharply than sodium sulfate. The solubility of sodium carbonate in water at 0° C. may be 7 g/100 mL, or at 15° C. may be 16.4 g/100 mL, or at 27.8° C. may be 34.07 g/100 mL, or at 34.8° C. may be 48.69 g/100 mL. Sodium bicarbonate may be known to possess a solubility curve in water which increases with temperature between 0-35° C., although not as sharply as sodium sulfate or sodium carbonate. The solubility of sodium bicarbonate in water at 0° C. may be 6.9 g/100 mL, or 8.2 g/100 ml (10° C.), or 9.6 g/100 ml (20° C.), or 10 g/100 ml (25° C.), or 11.1 g/100 ml (30° C.), or 12.7 g/100 ml (40° C.).

Option 1: $Na_2SO_4(s)$ and $Na_2S(s)$ may possess significantly different densities. For example, $Na_2SO_4(s)$ (anhydrous) may possess a density of 2.20 g/cm$^3$ and/or $Na_2S(s)$ (anhydrous) may possess a density of 1.856 g/cm$^3$. $3Na_2SO_4(s)$ and $Na_2S(s)$ may be at least partially separated by a centrifuge or other density driven separation system or method.

Option 2: Dissolve $3Na_2SO_4(s)+Na_2S(s)$ in cold water (for example 0-15° C.) or cold aqueous solution (for example −50-15° C.). For example, a cold aqueous solution may comprise, including, but not limited to, one or more or any combination of the following: ethylene glycol-water, or propylene glycol-water, or glycerol-water, or alcohol-water, or urea-water, or any combination thereof. The $3Na_2SO_4(s)+Na_2S(s)$ may comprise more $Na_2SO_4(s)$ than $Na_2S(s)$. The solubility of $Na_2SO_4(s)$ may be significantly lower in cold water or cold aqueous solution than $Na_2S(s)$, which may result in $Na_2S(s)$ dissolving in the water, while most of the $Na_2SO_4(s)$ not dissolving in the water or remaining a solid.

Option 3: Contact or mix $3Na_2SO_4(s)+Na_2S(s)$ with an organic solvent, or a mixture of water and an organic solvent, or any combination thereof. $Na_2S(s)$ may be soluble in ethanol, or methanol, or propanol, or 2-propanol, or 2-methyl-1-propanol, or benzyl alcohol, or ethylene glycol, or propylene glycol, or aqueous organic solvent solutions, or any combination thereof. $Na_2S(s)$ may have a solubility of 3.1 g/100 g in ethanol and 5.1 g/100 g in methanol. $Na_2SO_4(s)$ may be practically insoluble in most organic solvents. $3Na_2SO_4(s)+Na_2S(s)$ may be mixed with an organic solvent, which may include, but is not limited to, methanol. The $Na_2S(s)$ may dissolve, while the $3Na_2SO_4(s)$ may remain at a solid phase. The $3Na_2SO_4(s)$ may be separated from the Sodium Sulfide organic solvent solution using a solid-liquid separation. The present option may occur, for example, after step '(5)'.

Option 4: In some embodiments, the concentration of sodium sulfate may be greater than the concentration of sodium sulfide during and/or after '(6)'. The solution comprising "$3Na_2SO_4(aq)+Na_2S(aq)$ may be cooled to precipitate a portion of $3Na_2SO_4(aq)$ or may already be cool, which may prevent the dissolution of a portion of $3Na_2SO_4(s)$ during '(6)'.

Option 5: In some embodiments, the concentration of sodium sulfate may be greater than the concentration of sodium carbonate during and/or after '(7)'. At least a portion of $Na_2SO_4$ may be precipitated from the solution comprising "$3Na_2SO_4(aq)+Na_2CO_3$ (aq)+$H_2S$(aq)." It may be desirable to perform the presently described step after '(7)' and/or before or during '(8)'.

Option 6: In some embodiments, additional $CO_2$ may be added to the solution comprising $Na_2SO_4$(aq)+$Na_2CO_3$(aq) to produce sodium bicarbonate, which may result in the precipitation of at least a portion of sodium bicarbonate from solution. It may be desirable to perform the presently described step after the desorption or removal or conversion of hydrogen sulfide from solution.

Option 7: Separations, which may include, but are not limited to, one or more or any combination of the following: Distillation, or Vapor Compression Distillation, or Solventing Out, or Solvent Induced Precipitation, or Cooling Precipitation, or Cryodesalination, or Freezing Desalination, or Evaporation, or Membrane Based Process, or Reverse Osmosis, or Forward Osmosis, or Membrane Distillation, or Osmotically Assisted Reverse Osmosis, or any combination thereof.

(10) Hydrogen sulfide may be sold or transferred to an external application or may be converted in one or more or any combination of the following:

$H_2S$(g)+1.5$O_2$(g)→$SO_2$(g or aq)+$H_2O$(g or l), the $SO_2$ $H_2S$(g) to elemental sulfur $H_2S$(g) to hydrogen and sulfur or sulfur dioxide or sulfuric acid $H_2S$(g) input to the Claus Process $H_2S$(g) to reduced metal species, such as reduced iron or iron sulfide $H_2S$(g) to reduced metal species, such as reduced iron or iron sulfide, then produce hydrogen using the reduced metal species $H_2S$(g) to sulfuric acid Heat from conversion or combustion of $H_2S$(g) to $SO_2$(g or aq) or Sulfur or sulfuric acid may be employed to provide heat to one or more or any combination of reactions or separations, which may include, but are not limited to, one or more or any combination of the following: "4$Na_2S_2O_5$(s)+Heat→4$Na_2SO_3$(s)+4$SO_2$(g)", or distillation of organic solvent, or distillation of water, or supplemental heat for "4$Na_2SO_3$(s)+Heat→3 $Na_2SO_4$(s)+$Na_2S$(s)", or supplemental heat for "$CaSO_3$(s)+Heat→$CaO$(s)+$SO_2$(g)".

(11) 8$SO_2$(g)+water (solvent)→8$SO_2$(aq)

Example 14: At Some Temperature, Some Embodiments May Comprise Decomposition of Sodium Sulfite to Sodium Oxide and Sulfur Dioxide (1) Calcium(Weak Acid Anion)+2$SO_2$(aq)+$H_2O$(aq)→Ca(HSO_3)_2(aq)+Weak Acid(s or aqueous or gas or liquid)

(2) Ca(HSO_3)_2(aq)+$Na_2SO_4$(aq or s)→2$NaHSO_3$(aq)+$CaSO_4$(s)

(3) 2$NaHSO_3$(aq)→$Na_2S_2O_5$(s)+$H_2O$(l or g)+Water(solvent)

(4) $Na_2S_2O_5$(s)+Heat→$Na_2SO_3$(s)+$SO_2$(g)

(5) $Na_2SO_3$(s)+Heat→$Na_2O$(s)+$SO_2$(g)

Example 15: Decomposition of Sodium Sulfite to Sodium Sulfate and Sodium Sulfide and Production of Sodium Hydroxide (1) Calcium(Weak Acid Anion)+8$SO_2$(aq)+$H_2O$(aq)→4Ca(HSO_3)_2(aq)+Weak Acid(s or aqueous or gas or liquid)

(2) →Ca(HSO_3)_2(aq)+4$Na_2SO_4$(aq or s)→8$NaHSO_3$(aq)+4$CaSO_4$(s)

(3) 8$NaHSO_3$(aq)→4$Na_2S_2O_5$(s)+4$H_2O$(l or g)+Water (solvent)

(4) 4$Na_2S_2O_5$(s)+Heat→4$Na_2SO_3$(s)+4$SO_2$(g)

(5) 4$Na_2SO_3$(s)+Heat→3$Na_2SO_4$(s)+$Na_2S$(s)

(6) 3$Na_2SO_4$(s)+$Na_2S$(s)+Water (solvent)→3$Na_2SO_4$(aq)+$Na_2S$(aq)

(7) 3$Na_2SO_4$(aq)+$Na_2S$(aq)+Ca(OH)_2 (aq or s or both)→3$Na_2SO_4$(aq)+2$Na_0H$(aq)+CaS(s)

(8) Separate 3$Na_2SO_4$(aq)+2$Na_0H$(aq), which may comprise:
3$Na_2SO_4$(aq)+2$Na_0H$(aq)→2$Na_0H$(aq)+3$Na_2SO_4$(s)

(9) CaS(s)+$H_2O$(aq or l)+$SO_2$(aq or g)→$CaSO_3$(s)+$H_2S$ (g or aq)

(10) Comprises one or more or any combination of the following:

$H_2S$(g)+1.5$O_2$(g)→$SO_2$(g or aq)+$H_2O$(g or l)

$H_2S$(g) to elemental sulfur $H_2S$(g) to hydrogen and sulfur or sulfur dioxide or sulfuric acid $H_2S$(g) to reduced metal species, such as reduced iron or iron sulfide $H_2S$(g) to sulfuric acid

(11) $CaSO_3$(s)+Heat→CaO(s)+$SO_2$(g)

(12) $SO_2$(g)+Water (solvent)→$SO_2$(aq)

(13) CaO(s)+$H_2O$→Ca(OH)_2+Heat

Example 16: Production of Hydrogen Sulfide or Sulfur or Hydrogen or Sulfur Dioxide or Sulfurous Acid or Sulfuric Acid from Sodium Sulfate and Calcium Salt (1) Calcium(Weak Acid Anion)+8$SO_2$(aq)+$H_2O$(aq)→4Ca(HSO_3)_2(aq)+Weak Acid(s or aqueous or gas or liquid)

(2) →Ca(HSO_3)_2(aq)+4$Na_2SO_4$(aq or s)→8$NaHSO_3$(aq)+4$CaSO_4$(s)

(3) 8$NaHSO_3$(aq)→4$Na_2S_2O_5$(s)+Water(solvent)

(4) 4$Na_2S_2O_5$(s)+Heat→4$Na_2SO_3$(s)+4$SO_2$(g)

(5) 4$Na_2SO_3$(s)+Elevated Temperature→3$Na_2SO_4$(s)+$Na_2S$(s)

(6) 3$Na_2SO_4$(s)+$Na_2S$(s)+Water (Solvent)→3$Na_2SO_4$(aq)+$Na_2S$(aq)

(7) 3$Na_2SO_4$(aq)+$Na_2S$(aq)+$SO_2$(aq or g)→3$Na_2SO_4$(aq)+$Na_2SO_3$(aq)+$H_2S$(aq or g)

(8) 3$Na_2SO_4$(aq)+$Na_2SO_3$(aq)+$H_2S$(aq or g)→3$Na_2SO_4$(aq)+$Na_2SO_3$(aq)+$H_2S$(g)

Note: "3$Na_2SO_4$(aq)+$Na_2SO_3$(aq)" may comprise the solution transferred to '(2)' and/or '(2)' $Na_2SO_3$(aq) may be present during '(2)'

(9) Comprises one or more or any combination of the following:

$H_2S$(g)+1.5$O_2$(g)→$SO_2$(g or aq)+$H_2O$(g or l)

$H_2S$(g) to elemental sulfur $H_2S$(g) to hydrogen and sulfur or sulfur dioxide or sulfuric acid $H_2S$(g) to reduced metal species, such as reduced iron or iron sulfide $H_2S(g)$ to reduced metal species, such as reduced iron or iron sulfide, then produce hydrogen using the reduced metal species $H_2S(g)$ to sulfuric acid

(10) $4SO_2(g)+water\ (solvent) \rightarrow 4SO_2(aq)$

Example 17: Production of Sodium Carbonate and Gypsum (1) Calcium(Weak Acid Anion)+$8SO_2(aq)$+$H_2O(aq)$ $\rightarrow 4Ca(HSO_3)_2(aq)$+Weak Acid(s or aqueous or gas or liquid)

(2) $\rightarrow Ca(HSO_3)_2(aq)+4Na_2SO_4(aq\ \ or\ \ s) \rightarrow 8NaHSO_3(aq)+4CaSO_4(s)$ (3) $8NaHSO_3(aq) \rightarrow 4\ Na_2S_2O_5(s)+Water(solvent)$ (4) $4Na_2S_2O_5(s)+Heat \rightarrow Na_2SO_3(s)+4SO_2(g)$ (5) $4Na_2SO_3(s)+Elevated\ Temperature \rightarrow 3Na_2SO_4(s)+Na_2S(s)$ Note: Reaction '(5)' may be exothermic.

(6) $3Na_2SO_4(s)+Na_2S(s)+Methanol\ (solvent) \rightarrow 3Na_2SO_4(s)+Na_2S(dissolved)$ Note: Alternatively, in some embodiments, after solid-liquid separation of $3Na_2SO_4(s)$, $Na_2S(dissolved)$ may be removed or recovered by distillation of the solvent and crystallization of $Na_2S(s)$. The $Na_2S(s)$ may be transferred to an environment with sufficient water and carbon dioxide present for the reaction of $Na_2S$ with $CO_2$ and $H_2O$ to form $Na_2CO_3$ and $H_2S$.

(7) $Na_2S(dissolved)+CO_2(g)+H_2O(dissolved) \rightarrow 4Na_2CO_3(s)+H_2S(dissolved\ or\ g)$ Note: In some embodiments, just enough $H_2O$ may be added to enable the production of $Na_2CO_3(s)$.

Note: In some embodiments, water may be present in the methanol or organic solvent solution or inorganic solvent solution or methanol solution in both '(6)' and '(7)'.

Note: $Na_2CO_3(s)$ may be separated using a solid-liquid separation.

Note: $H_2S$ may be at least partially stripped or desorbed or removed during our after '(7)' to, for example, produce $H_2S$ and/or regenerate the organic solvent or methanol for '(6)'.

Note: $Na_2CO_3(s)$ may be slightly soluble in methanol and a portion of $Na_2CO_3(dissolved)$ may remaining in the organic solvent solution as a residual.

(8) Hydrogen sulfide may be sold or transferred to an external application or may be converted in one or more or any combination of the following:

$H_2S(g)+1.5O_2(g) \rightarrow SO_2(g\ or\ aq)+H_2O(g\ or\ l)$, the $SO_2$ $H_2S(g)$ to elemental sulfur $H_2S(g)$ to hydrogen and sulfur or sulfur dioxide or sulfuric acid $H_2S(g)$ input to the Claus Process $H_2S(g)$ to reduced metal species, such as reduced iron or iron sulfide $H_2S(g)$ to reduced metal species, such as reduced iron or iron sulfide, then produce hydrogen using the reduced metal species $H_2S(g)$ to sulfuric acid Heat from conversion or combustion of $H_2S(g)$ to $SO_2(g\ or\ aq)$ or Sulfur or sulfuric acid may be employed to provide heat to one or more or any combination of reactions or separations, which may include, but are not limited to, one or more or any combination of the following: "$4Na_2S_2O_5(s)+Heat \rightarrow 4Na_2SO_3(s)+4SO_2(g)$", or distillation of organic solvent, or distillation of water, or supplemental heat for "$4Na_2SO_3(s)+Heat \rightarrow 3\ Na_2SO_4(s)+Na_2S(s)$", or supplemental heat for "$CaSO_3(s)+Heat \rightarrow CaO(s)+SO_2(g)$".

(9) $8SO_2(g)+water\ (solvent) \rightarrow 8SO_2(aq)$

Note: In some embodiments, the weight percent of water in organic solvent, or methanol, or ethanol, or inorganic solvent, or ammonia, or any combination thereof may be less than, or greater than, or equal to one or more or any combination of the following: 0.01%, or 0.1%, or 0.5%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 25%, or 30%, or 35%, or 40%, or 45%, or 50%, or 55%, or 60%, or 65%, or 70%, or 75%, or 80%, or 85%, or 90%, or 95%, or 99%.

Example 18: Production of Sodium Carbonate and Gypsum (1) Calcium(Weak Acid Anion)+$8SO_2(aq)$+$H_2O(aq)$ $\rightarrow 4Ca(HSO_3)_2(aq)$+Weak Acid(s or aqueous or gas or liquid)

(2) $\rightarrow Ca(HSO_3)_2(aq)+4Na_2SO_4(aq\ \ or\ \ s) \rightarrow 8NaHSO_3(aq)+4CaSO_4(s)$ (3) $8NaHSO_3(aq) \rightarrow 4\ Na_2S_2O_5(s)+Water(solvent)$ (4) $4Na_2S_2O_5(s)+Heat \rightarrow 4\ Na_2SO_3(s)+4SO_2(g)$ (5) $4Na_2SO_3(s)+Elevated\ Temperature \rightarrow 3Na_2SO_4(s)+Na_2S(s)$ Note: Reaction '(5)' may be exothermic.

(6) $3Na_2SO_4(s)+Na_2S(s)+Water\ (Solvent) \rightarrow 3Na_2SO_4(s\ or\ aq)+Na_2S(aq)$ (7) $3Na_2SO_4(aq)+Na_2S(aq)+CaCO_3(s\ or\ aq) \rightarrow 3Na_2SO_4(aq)+Na_2CO_3(aq)+CaS(s)$ Note: CaS(s) may be separated from the solution using solid-liquid separation. $3Na_2SO_4(aq)+Na_2CO_3(aq)$ may be separated during or after separation of CaS(s).

(8) $CaS(s)+H_2O(l\ or\ aq\ or\ g)+CO_2(aq\ or\ g) \rightarrow CaCO_3(s\ or\ aq)+H_2S(g\ or\ aq)$ (9) Hydrogen sulfide may be sold or transferred to an external application or may be converted in one or more or any combination of the following:

$H_2S(g)+1.5O_2(g) \rightarrow SO_2(g\ or\ aq)+H_2O(g\ or\ l)$, the $SO_2$ $H_2S(g)$ to elemental sulfur $H_2S(g)$ to hydrogen and sulfur or sulfur dioxide or sulfuric acid $H_2S(g)$ input to the Claus Process $H_2S(g)$ to reduced metal species, such as reduced iron or iron sulfide $H_2S(g)$ to reduced metal species, such as reduced iron or iron sulfide, then produce hydrogen using the reduced metal species $H_2S(g)$ to sulfuric acid Heat from conversion or combustion of $H_2S(g)$ to $SO_2(g\ or\ aq)$ or Sulfur or sulfuric acid may be employed to provide heat to one or more or any combination of reactions or separations, which may include, but are not limited to, one or more or any combination of the following: "$4Na_2S_2O_5(s)+Heat \rightarrow 4Na_2SO_3(s)+4SO_2(g)$", or distillation of organic solvent, or distillation of water, or supplemental heat for "$4Na_2SO_3(s)+Heat \rightarrow 3\ Na_2SO_4(s)+Na_2S(s)$", or supplemental heat for "$CaSO_3(s)+Heat \rightarrow CaO(s)+SO_2(g)$".

(10) $8SO_2(g)+water\ (solvent) \rightarrow 8SO_2(aq)$

Example 19: Production of Sodium Carbonate and Gypsum (1) Calcium(Weak Acid Anion)+8SO$_2$(aq)+H$_2$O(aq) →4Ca(HSO$_3$)$_2$(aq)+Weak Acid(s or aqueous or gas or liquid)
(2) →Ca(HSO$_3$)$_2$(aq)+4Na$_2$SO$_4$(aq or s)→8NaHSO$_3$(aq)+4CaSO$_4$(s)
(3) 8NaHSO$_3$(aq)→4Na$_2$S$_2$O$_5$(s)+Water(solvent)
(4) 4Na$_2$S$_2$O$_5$(s)+Heat→4Na$_2$SO$_3$(s)+4SO$_2$(g)
(5) 4Na$_2$SO$_3$(s)+Elevated Temperature→3Na$_2$SO$_4$(s)+Na$_2$S(s) Note: Reaction '(5)' may be exothermic.
(6) 3Na$_2$SO$_4$(s)+Na$_2$S(s)+Methanol (solvent)→3Na$_2$SO$_4$(s)+Na$_2$S(dissolved)
Note: In some embodiments, after solid-liquid separation of 3Na$_2$SO$_4$(s), Na$_2$S(dissolved) may be removed or recovered by distillation of the solvent and crystallization of Na$_2$S(s). The Na$_2$S(s) may be transferred to an environment with sufficient water and carbon dioxide present for the reaction of Na$_2$S with CO$_2$ and H$_2$O to form Na$_2$CO$_3$ and H$_2$S.
(7) Na$_2$S(dissolved) 4Na$_2$S(s)+Methanol(Solvent)
(8) Na$_2$S(s or aq)+H$_2$O(l or aq or g)+CO$_2$(aq or g) 4Na$_2$CO$_3$(s or aq)+H$_2$S(g or aq)
(9) Hydrogen sulfide may be sold or transferred to an external application or may be converted in one or more or any combination of the following:
H$_2$S(g)+1.5O$_2$(g)→SO$_2$(g or aq)+H$_2$O(g or l), the SO$_2$
H$_2$S(g) to elemental sulfur
H$_2$S(g) to hydrogen and sulfur or sulfur dioxide or sulfuric acid
H$_2$S(g) input to the Claus Process
H$_2$S(g) to reduced metal species, such as reduced iron or iron sulfide
H$_2$S(g) to reduced metal species, such as reduced iron or iron sulfide, then produce hydrogen using the reduced metal species
H$_2$S(g) to sulfuric acid
Heat from conversion or combustion of H$_2$S(g) to SO$_2$(g or aq) or Sulfur or sulfuric acid may be employed to provide heat to one or more or any combination of reactions or separations, which may include, but are not limited to, one or more or any combination of the following: "4Na$_2$S$_2$O$_5$(s)+Heat→4Na$_2$SO$_3$(s)+4SO$_2$(g)", or distillation of organic solvent, or distillation of water, or supplemental heat for "4Na$_2$SO$_3$(s)+Heat→3 Na$_2$SO$_4$(s)+Na$_2$S(s)", or supplemental heat for "CaSO$_3$(s)+Heat-→CaO(s)+SO$_2$(g)".
(10) 8SO$_2$(g)+water (solvent)→8SO$_2$(aq)

Example 20: Production of Sodium Carbonate and Gypsum (1) Calcium(Weak Acid Anion)+8SO$_2$(aq)+H$_2$O(aq) →4Ca(HSO$_3$)$_2$(aq)+Weak Acid(s or aqueous or gas or liquid)
(2) →Ca(HSO$_3$)$_2$(aq)+4Na$_2$SO$_4$(aq or s)→8NaHSO$_3$(aq)+4CaSO$_4$(s)
(3) 8NaHSO$_3$(aq)→4Na$_2$S$_2$O$_5$(s)+Water(solvent)
(4) 4Na$_2$S$_2$O$_5$(s)+Heat→4Na$_2$SO$_3$(s)+4SO$_2$(g)
(5) 4Na$_2$SO$_3$(s)+Elevated Temperature→3Na$_2$SO$_4$(s)+Na$_2$S(s)
Note: Reaction '(5)' may be exothermic.
(6) 3Na$_2$SO$_4$(s)+Na$_2$S(s)+Methanol (solvent)→3Na$_2$SO$_4$(s)+Na$_2$S(dissolved)
Note: In some embodiments, after solid-liquid separation of 3Na$_2$SO$_4$(s), Na$_2$S(dissolved) may be removed or recovered by distillation of the solvent and crystallization of Na$_2$S(s). The Na$_2$S(s) may be transferred to an environment with sufficient water and carbon dioxide present for the reaction of Na$_2$S with CO$_2$ and H$_2$O to form Na$_2$CO$_3$ and H$_2$S.
(7) Na$_2$S(dissolved) 4Na$_2$S(s)+Methanol(Solvent)
(8) Na$_2$S(s or aq)+Water(solvent)+CaCO$_3$(aq or s) 4Na$_2$CO$_3$(s or aq)+CaS(s)
(9) CaS(s)+H$_2$O(g or l or aq)+CO$_2$(g or aq)→CaCO$_3$(aq or s)+H$_2$S(g or aq)
(10) Hydrogen sulfide may be sold or transferred to an external application or may be converted in one or more or any combination of the following:
H$_2$S(g)+1.5O$_2$(g)→SO$_2$(g or aq)+H$_2$O(g or l), the SO$_2$
H$_2$S(g) to elemental sulfur
H$_2$S(g) to hydrogen and sulfur or sulfur dioxide or sulfuric acid
H$_2$S(g) input to the Claus Process
H$_2$S(g) to reduced metal species, such as reduced iron or iron sulfide
H$_2$S(g) to reduced metal species, such as reduced iron or iron sulfide, then produce hydrogen using the reduced metal species
H$_2$S(g) to sulfuric acid
Heat from conversion or combustion of H$_2$S(g) to SO$_2$(g or aq) or Sulfur or sulfuric acid may be employed to provide heat to one or more or any combination of reactions or separations, which may include, but are not limited to, one or more or any combination of the following: "4Na$_2$S$_2$O$_5$(s)+Heat→4Na$_2$SO$_3$(s)+4SO$_2$(g)", or distillation of organic solvent, or distillation of water, or supplemental heat for "4Na$_2$SO$_3$(s)+Heat→3 Na$_2$SO$_4$(s)+Na$_2$S(s)", or supplemental heat for "CaSO$_3$(s)+Heat-→CaO(s)+SO$_2$(g)".
(10) 8SO$_2$(g)+water (solvent)→8SO$_2$(aq)

Example 21: Production of Sodium Hydroxide and Gypsum (1) Calcium(Weak Acid Anion)+8SO$_2$(aq)+H$_2$O(aq) →4Ca(HSO$_3$)$_2$(aq)+Weak Acid(s or aqueous or gas or liquid)
(2) →Ca(HSO$_3$)$_2$(aq)+4Na$_2$SO$_4$(aq or s)→8NaHSO$_3$(aq)+4CaSO$_4$(s)
(3) 8NaHSO$_3$(aq)→4Na$_2$S$_2$O$_5$(s)+Water(solvent)
(4) 4Na$_2$S$_2$O$_5$(s)+Heat→4 Na$_2$SO$_3$(s)+4SO$_2$(g)
(5) 4Na$_2$SO$_3$(s)+Elevated Temperature→3Na$_2$SO$_4$(s)+Na$_2$S(s)
Note: Reaction '(5)' may be exothermic.
(6) 3Na$_2$SO$_4$(s)+Na$_2$S(s)+Methanol (solvent)→3Na$_2$SO$_4$(s)+Na$_2$S(dissolved)
Note: In some embodiments, after solid-liquid separation of 3Na$_2$SO$_4$(s), Na$_2$S(dissolved) may be removed or recovered by distillation of the solvent and crystallization of Na$_2$S(s). The Na$_2$S(s) may be transferred to an environment with sufficient water and carbon dioxide present for the reaction of Na$_2$S with CO$_2$ and H$_2$O to form Na$_2$CO$_3$ and H$_2$S.
(7) Na$_2$S(dissolved)→Na$_2$S(s)+Methanol(Solvent)
(8) Na$_2$S(s or aq)+Ca(OH)$_2$(aq or s)→2Na$_0$H(s or aq)+CaS(s)

(9) $CaS(s)+H_2O$(g or l or aq)$+SO_2$(g or aq)$\rightarrow CaSO_3(s)+H_2S$(g or aq)
(10) $CaSO_3(s)$+Heat$\rightarrow CaO(s)+SO_2(g)$
(11) $CaO(s)+H_2O$(l or g)$\rightarrow Ca(OH)_2$(s or aq)
(12) Hydrogen sulfide may be sold or transferred to an external application or may be converted in one or more or any combination of the following:
$H_2S(g)+1.5O_2(g)\rightarrow SO_2$(g or aq)$+H_2O$(g or l), the $SO_2$
$H_2S(g)$ to elemental sulfur
$H_2S(g)$ to hydrogen and sulfur or sulfur dioxide or sulfuric acid
$H_2S(g)$ input to the Claus Process
$H_2S(g)$ to reduced metal species, such as reduced iron or iron sulfide
$H_2S(g)$ to reduced metal species, such as reduced iron or iron sulfide, then produce hydrogen using the reduced metal species
$H_2S(g)$ to sulfuric acid
Heat from conversion or combustion of $H_2S(g)$ to $SO_2$(g or aq) or Sulfur or sulfuric acid may be employed to provide heat to one or more or any combination of reactions or separations, which may include, but are not limited to, one or more or any combination of the following: "$4Na_2S_2O_5(s)$+Heat$\rightarrow 4Na_2SO_3(s)+4SO_2(g)$", or distillation of organic solvent, or distillation of water, or supplemental heat for "$4Na_2SO_3(s)$+Heat$\rightarrow 3\ Na_2SO_4(s)+Na_2S(s)$", or supplemental heat for "$CaSO_3(s)$+Heat$\rightarrow CaO(s)+SO_2(g)$".
(13) $8SO_2(g)$+water (solvent)$\rightarrow 8SO_2(aq)$ Example 22: Production of Sodium Hydroxide and Gypsum (1) Calcium(Weak Acid Anion)$+8SO_2(aq)+H_2O(aq)\rightarrow 4Ca(HSO_3)_2(aq)$+Weak Acid(s or aqueous or gas or liquid)
(2) $\rightarrow Ca(HSO_3)_2(aq)+4Na_2SO_4$(aq or s)$\rightarrow 8NaHSO_3(aq)+4CaSO_4(s)$
(3) $8NaHSO_3(aq)\rightarrow 4Na_2S_2O_5(s)$+Water(solvent)
(4) $4Na_2S_2O_5(s)$+Heat$\rightarrow 4Na_2SO_3(s)+4SO_2(g)$
(5) $4Na_2SO_3(s)$+Elevated Temperature$\rightarrow 3Na_2SO_4(s)+Na_2S(s)$
Note: Reaction '(5)' may be exothermic.
(6) $3Na_2SO_4(s)+Na_2S(s)$+Methanol (solvent)$\rightarrow 3Na_2SO_4(s)+Na_2S$(dissolved)
Note: In some embodiments, after solid-liquid separation of $3Na_2SO_4(s)$, $Na_2S$(dissolved) may be removed or recovered by distillation of the solvent and crystallization of $Na_2S(s)$. The $Na_2S(s)$ may be transferred to an environment with sufficient water and carbon dioxide present for the reaction of $Na_2S$ with $CO_2$ and $H_2O$ to form $Na_2CO_3$ and $H_2S$.
(7) $Na_2S$(dissolved)$\rightarrow Na_2S(s)$+Methanol(Solvent)
(8) $Na_2S$(s or aq)$+Ca(OH)_2$(aq or s)$\rightarrow 2Na_0H$(s or aq)$+CaS(s)$
(9) $CaS(s)+H_2O$(g or l or aq)$+CO_2$(g or aq)$\rightarrow CaCO_3(s)+H_2S$(g or aq)
(10) $CaCO_3(s)$+Heat$\rightarrow CaO(s)+CO_2(g)$
Note: '(10)' may be conducted in a manner wherein $CO_2(g)$ produced is captured.
(11) $CaO(s)+H_2O$(l or g)$\rightarrow Ca(OH)_2$(s or aq)
(12) Hydrogen sulfide may be sold or transferred to an external application or may be converted in one or more or any combination of the following:
$H_2S(g)+1.5O_2(g)\rightarrow SO_2$(g or aq)$+H_2O$(g or l), the $SO_2$
$H_2S(g)$ to elemental sulfur
$H_2S(g)$ to hydrogen and sulfur or sulfur dioxide or sulfuric acid
$H_2S(g)$ input to the Claus Process
$H_2S(g)$ to reduced metal species, such as reduced iron or iron sulfide
$H_2S(g)$ to reduced metal species, such as reduced iron or iron sulfide, then produce hydrogen using the reduced metal species
$H_2S(g)$ to sulfuric acid
Heat from conversion or combustion of $H_2S(g)$ to $SO_2$(g or aq) or Sulfur or sulfuric acid may be employed to provide heat to one or more or any combination of reactions or separations, which may include, but are not limited to, one or more or any combination of the following: "$4Na_2S_2O_5(s)$+Heat$\rightarrow 4Na_2SO_3(s)+4SO_2(g)$", or distillation of organic solvent, or distillation of water, or supplemental heat for "$4Na_2SO_3(s)$+Heat$\rightarrow 3\ Na_2SO_4(s)+Na_2S(s)$", or supplemental heat for "$CaSO_3(s)$+Heat$\rightarrow CaO(s)+SO_2(g)$".
(13) $8SO_2(g)$+water (solvent)$\rightarrow 8SO_2(aq)$ Example 23: Production of Sodium Bicarbonate or Sodium Carbonate and Gypsum with Ammonia Intermediate (1) May comprise any combination of the following:
$Na_2SO_4(s)$+Water$\rightarrow Na_2SO_4(aq)$
$2\ NH_4HCO_3(s)$+Water$\rightarrow 2\ NH_4HCO_3(aq)$
$Na_2SO_4$(s or aq)$+2\ NH_4HCO_3(aq)\rightarrow (NH_4)_2SO_4(aq)+2NaHCO_3(s)$
$Na_2SO_4$(s or aq)$+2\ (NH_4)_2CO_3(aq)\rightarrow (NH_4)_2SO_4(aq)+Na_2CO_3(s)$
(2) Calcium(Weak Acid Anion)$+2\ SO_2$(g or aq)$+H_2O(aq)\rightarrow Ca(HSO_3)_2(aq)$+Weak Acid(s or aqueous or gas or liquid)
(3) $Ca(HSO_3)_2(aq)+(NH_4)_2SO_4$(aq or s)$\rightarrow 2\ NH_4HSO_3(aq)+CaSO_4(s)$
(4) $4\ NH_4HSO_3(aq)$+Heat $2\ (NH_4)_2SO_3(aq)+2SO_2(g)$
(5) $2\ (NH_4)_2SO_3(aq)+CO_2$(g or aq)$+H_2O(aq)\rightarrow NH_4HSO_3(aq)+2\ NH_4HCO_3(s)$
Or
(1) May comprise any combination of the following:
$Na_2SO_4(s)$+Water$\rightarrow Na_2SO_4(aq)$
$2\ NH_4HCO_3(s)$+Water$\rightarrow 2\ NH_4HCO_3(aq)$
$Na_2SO_4$(s or aq)$+2\ NH_4HCO_3(aq)\rightarrow (NH_4)_2SO_4(aq)+2NaHCO_3(s)$
$Na_2SO_4$(s or aq)$+2\ (NH_4)_2CO_3(aq)\rightarrow (NH_4)_2SO_4(aq)+Na_2CO_3(s)$
(2) Calcium(Weak Acid Anion)$+_2SO_2$(g or aq)$+H_2O(aq)\rightarrow Ca(HSO_3)_2(aq)$+Weak Acid(s or aqueous or gas or liquid)
(3) $Ca(HSO_3)_2(aq)+(NH_4)_2SO_4$(aq or s)$\rightarrow 2\ NH_4HSO_3(aq)+CaSO_4(s)$
(4) $2\ NH_4HSO_3(aq)+2\ NH_4HSO_3$(s or aq)+Heat$\rightarrow 2\ (NH_4)_2SO_3(aq)+2SO_2(g)$
(5) $2\ (NH_4)_2SO_3(aq)+2CO_2$(g or aq)$+2H_2O(aq)\rightarrow 2\ NH_4HSO_3(aq)+2\ NH_4HCO_3(s)$
(6) $2\ NH_4HSO_3(aq)\rightarrow 2\ NH_4HSO_3(s)$+Water
Or
(1) May comprise any combination of the following:
$Na_2SO_4(s)$+Water$\rightarrow Na_2SO_4(aq)$
$2\ NH_4HCO_3(s)$+Water$\rightarrow 2\ NH_4HCO_3(aq)$
$2\ NH_4HCO_3(aq)$+Heat$\rightarrow (NH_4)_2CO_3(aq)+CO_2+H_2O$
$2\ NH_4HCO_3$(s or aq)+Heat$\rightarrow (NH_4)_2CO_3$(s or aq)$+CO_2+H_2O$ $Na_2SO_4$(s or aq)+2 $NH_4HCO_3$(aq)→$(NH_4)_2SO_4$(aq)+ 2$NaHCO_3$(s)

$Na_2SO_4$(s or aq)+$(NH_4)_2CO_3$(aq)→$(NH_4)_2SO_4$(aq)+ $Na_2CO_3$(s)

(2) Calcium(Weak Acid Anion)+$_2SO_2$(g or aq)+$H_2O$(aq) →$Ca(HSO_3)_2$(aq)+Weak Acid(s or aqueous or gas or liquid)

(3) $Ca(HSO_3)_2$(aq)+$(NH_4)_2SO_4$(aq or s)→2$NH_4HSO_3$(aq)+$CaSO_4$(s)

(4) 2 $NH_4HSO_3$(aq)+$(NH_4)_2SO_3$(s)+Heat→2$(NH_4)_2SO_3$(aq)+$SO_2$(g)

(5) 2 $(NH_4)_2SO_3$(aq)+2$CO_2$(g or aq)+2$H_2O$(aq) →2$NH_4HSO_3$(aq)+2 $NH_4HCO_3$(s)

(6) 2 $NH_4HSO_3$(aq)→$(NH_4)_2SO_3$(s)+$SO_2$(g)+Water (7) 2 $NH_4HCO_3$(s or aq)+Heat→$(NH_4)_2CO_3$(s or aq)+ $CO_2$+$H_2O$ Note: '(7)' may be desirable in embodiments producing sodium carbonate.

Note: $CO_2$ produced by '(7)' may be recirculated comprise a portion of the $CO_2$ input '(5)'.

Or (1) May comprise any combination of the following:
$Na_2SO_4$(s)+Water→$Na_2SO_4$(aq)
2 $NH_4HCO_3$(s)+Water→2$NH_4HCO_3$(aq)
2 $NH_4HCO_3$(aq)+Heat→$(NH_4)_2CO_3$(aq)+$CO_2$+$H_2O$
2 $NH_4HCO_3$(s or aq)+Heat→$(NH_4)_2CO_3$(s or aq)+ $CO_2$+$H_2O$
$Na_2SO_4$(s or aq)+2 $NH_4HCO_3$(aq)→$(NH_4)_2SO_4$(aq)+ 2$NaHCO_3$(s)
$Na_2SO_4$(s or aq)+$(NH_4)_2CO_3$(aq)→$(NH_4)_2SO_4$(aq)+ $Na_2CO_3$(s)

Note: In some embodiments, $Na_2CO_3$ or 2$NaHCO_3$ may be precipitated or may be separated from $(NH_4)_2SO_4$(aq) by utilizing the significant difference in solubility between $Na_2CO_3$ or 2 $NaHCO_3$ and $(NH_4)_2SO_4$(aq). In some embodiments, $Na_2CO_3$ or 2$NaHCO_3$ may be precipitated or may be separated by one, or more, or any combination of the following: cooling precipitation, or distillation, or solventing out, or cryodesalination, or evaporation, or mechanical vapor compression distillation, or solubility properties, or by supersaturation, or forward osmosis, or membrane based process, or reverse osmosis, or membrane distillation, or zero liquid discharge processes, or crystallization.

(2) Calcium(Weak Acid Anion)+$_2SO_2$(g or aq)+$H_2O$(aq)+ Water→$Ca(HSO_3)_2$(aq)+Weak Acid(s or aqueous or gas or liquid)

(3) $Ca(HSO_3)_2$(aq)+$(NH_4)_2SO_4$(aq or s)→2$NH_4HSO_3$(aq)+$CaSO_4$(s)

Note: In some embodiments, '(2)' and '(3)' may be combined into a single process or a single step or may otherwise be combined. For example, Calcium(Weak Acid Anion) and/or 2$SO_2$ and/or $H_2O$ may be added to or mixed with $(NH_4)_2SO_4$(aq) to form, for example, 2 $NH_4HSO_3$(aq)+$CaSO_4$(s) and/or Weak Acid(s or aqueous or gas or liquid). Said Weak Acid(s or aqueous or gas or liquid) may comprise, including, but not limited to, one or more or any combination of the following: carbon dioxide, or carbonic acid, or carbonate, or bicarbonate, or sesquicarbonate, or carbamate, or hydrogen sulfide, or sulfurous acid, or silicic acid, or orthosilicic acid, or silicon acid derivatives, or silicon minerals, or silicon acids, or aluminates, or ferrates, or other weak acids described herein.

(4) 2 $NH_4HSO_3$(aq)+Heat→$(NH_4)_2SO_3$(aq)+$SO_2$(g)+ $H_2O$(aq)

Note: A portion of water may be removed or distillated from '2 $(NH_4)_2SO_3$(aq)' before '(5)'. It may be desirable for the concentration of '2 $(NH_4)_2SO_3$(aq)' to be sufficiently high such that at least a portion of 2 $NH_4HCO_3$(s) may precipitate during '(5)' or upon cooling the solution during or after '(5)'.

(5) $(NH_4)_2SO_3$(aq)+$(NH_4)_2SO_3$(s or aq)+2$CO_2$(g or aq)+ 2$H_2O$(aq)→2 $NH_4HSO_3$(aq)+2 $NH_4HCO_3$(s)

(6) 2 $NH_4HSO_3$(aq)→$(NH_4)_2SO_3$(s)+$SO_2$(g)+Water

Note: $(NH_4)_2SO_3$(s) may be transferred to '(5)' and may comprise a portion of $(NH_4)_2SO_3$(s) in '(5)'.

(7) 2 $NH_4HCO_3$(s or aq)+Heat→$(NH_4)_2CO_3$(s or aq)+ $CO_2$+$H_2O$

Note: '(7)' may be desirable in embodiments producing sodium carbonate.

Note: $CO_2$ produced by '(7)' may be recirculated comprise a portion of the $CO_2$ input '(5)'.

Example 24: Production of Ammonia and Gypsum from Ammonium Sulfate (1) Calcium(Weak Acid Anion)+$_2SO_2$(g or aq)+$H_2O$(aq) →$Ca(HSO_3)_2$(aq)+Weak Acid(s or aqueous or gas or liquid)

(2) $Ca(HSO_3)_2$(aq)+$(NH_4)_2SO_4$(aq or s)→2$NH_4HSO_3$(aq)+$CaSO_4$(s)

(3) 2 $NH_4HSO_3$(aq)+$(NH_4)_2SO_3$(s)+Heat→2$(NH_4)_2SO_3$(aq)+$SO_2$(g)

(4) 2 $(NH_4)_2SO_3$(aq)+2$CO_2$(g or aq)+2$H_2O$(aq) →2$NH_4HSO_3$(aq)+2 $NH_4HCO_3$(s) (5) 2 $NH_4HSO_3$(aq)→$(NH_4)_2SO_3$(s)+$SO_2$(g)+Water (6) 2 $NH_4HCO_3$(s)+Heat→$NH_3$(g)+$CO_2$(g)+$H_2O$(g or l)

Example 25: Producing Sodium Bicarbonate and Gypsum or Magnesium Sulfate with Ammonia Intermediate (1) May comprise any combination of the following:
$Na_2SO_4$(s)+Water→$Na_2SO_4$(aq)
2 $NH_4HCO_3$(s)+Water→2$NH_4HCO_3$(aq)
2 $NH_4HCO_3$(aq)+Heat→$(NH_4)_2CO_3$(aq)+$CO_2$+$H_2O$
2 $NH_4HCO_3$(s or aq)+Heat→$(NH_4)_2CO_3$(s or aq)+ $CO_2$+$H_2O$
$Na_2SO_4$(s or aq)+2 $NH_4HCO_3$(aq)→$(NH_4)_2SO_4$(aq)+ 2$NaHCO_3$(s)
$Na_2SO_4$(s or aq)+$(NH_4)_2CO_3$(aq)→$(NH_4)_2SO_4$(aq)+ $Na_2CO_3$(s)

Note: In some embodiments, $Na_2CO_3$ or 2$NaHCO_3$ may be precipitated or may be separated from $(NH_4)_2SO_4$(aq) by utilizing the significant difference in solubility between $Na_2CO_3$ or 2$NaHCO_3$ and $(NH_4)_2SO_4$(aq). In some embodiments, $Na_2CO_3$ or 2$NaHCO_3$ may be precipitated or may be separated by one, or more, or any combination of the following: cooling precipitation, or distillation, or solventing out, or cryodesalination, or evaporation, or mechanical vapor compression distillation, or solubility properties, or by supersaturation, or forward osmosis, or membrane based process, or reverse osmosis, or membrane distillation, or zero liquid discharge processes, or crystallization.

Note: Ammonium bicarbonate may be decomposed into ammonium carbonate and carbon dioxide. The ammonium carbonate may be reacted with sodium sulfate to form sodium carbonate and ammonium sulfate. Carbon dioxide formed may be transferred to and/or employed in one or more process steps or reactions which require carbon dioxide.

(2) Calcium(Weak Acid Anion)+2SO$_2$(g or aq)+H$_2$O(aq)+Water→Ca(HSO$_3$)$_2$(aq)+Weak Acid(s or aqueous or gas or liquid)

(3) Ca(HSO$_3$)$_2$(aq)+(NH$_4$)$_2$SO$_4$(aq or s)→2NH$_4$HSO$_3$(aq)+CaSO$_4$(s)

Note: In some embodiments, '(2)' and '(3)' may be combined into a single process or a single step or may otherwise be combined. For example, Calcium(Weak Acid Anion) and/or 2SO$_2$ and/or H$_2$O may be added to or mixed with (NH$_4$)$_2$SO$_4$(aq) to form, for example, 2 NH$_4$HSO$_3$(aq)+CaSO$_4$(s) and/or Weak Acid(s or aqueous or gas or liquid). Said Weak Acid(s or aqueous or gas or liquid) may comprise, including, but not limited to, one or more or any combination of the following: carbon dioxide, or carbonic acid, or carbonate, or bicarbonate, or sesquicarbonate, or carbamate, or hydrogen sulfide, or sulfurous acid, or silicic acid, or orthosilicic acid, or silicon acid derivatives, or silicon minerals, or silicon acids, or aluminates, or ferrates, or other weak acids described herein.

(4) 2 NH$_4$HSO$_3$(aq)+Heat→(NH$_4$)$_2$SO$_3$(aq)+SO$_2$(g)+H$_2$O(aq)

Note: A portion of water may be removed or distillated from '2 (NH$_4$)$_2$SO$_3$(aq)' before '(5)'. It may be desirable for the concentration of '2 (NH$_4$)$_2$SO$_3$(aq)' to be sufficiently high such that at least a portion of 2 NH$_4$HCO$_3$(s) may precipitate during '(5)' or upon cooling the solution during or after (5) (NH$_4$)$_2$SO$_3$(aq)+(NH$_4$)$_2$SO$_3$(s or aq)+2CO$_2$(g or aq)+2H$_2$O(aq) 2 NH$_4$HSO$_3$(aq)+2 NH$_4$HCO$_3$(s)

(6) 2 NH$_4$HSO$_3$(aq)→(NH$_4$)$_2$SO$_3$(s)+SO$_2$(g)+Water

Note: In some embodiments, residual aqueous ammonia-carbon dioxide may be present in the solution comprising NH$_4$HSO$_3$(aq). A portion of ammonia-carbon dioxide may decompose into carbon dioxide gas, which may be transferred or recirculated to reactions employing carbon dioxide within the process, or to other applications, or any combination thereof.

Example 26: Production of Sodium Hydroxide and Weak Acid or Weak Acid Anion Derivative (1) One or more or any combination of the following:
MgCO$_3$+SO$_2$(aq)→MgSO$_3$(aq)+CO$_2$(g)
MgS+SO$_2$(aq)+H$_2$O(aq)→MgSO$_3$(aq)+H$_2$S(g)
MgCa(CO$_3$)$_2$(s)+SO$_2$(aq)→MgSO$_3$(aq)+CaSO$_3$(s)+CO$_2$(g)
MgCa(WA)(s)+SO$_2$(aq)→MgSO$_3$(aq)+CaSO$_3$(s)+WA(s)
MgCa(WA)(s)+SO$_2$(aq)→MgSO$_3$(aq)+Ca(WA)(s)+WA(s)
Magnesium Silicate(s)+SO$_2$(aq)+H$_2$O(aq)→MgSO$_3$(aq)+Silicon Dioxide(s)
Magnesium(Weak Acid Anion)+SO$_2$(aq)+H$_2$O(aq)→MgSO$_3$(aq)+Weak Acid(s or aqueous or gas or liquid)

Note: In some embodiments, MgSO$_3$(aq) may be separated from at least a portion of water to form, for example, MgSO$_3$(s). For example, a portion of MgSO$_3$(aq) may be precipitated as MgSO$_3$(s) by cooling precipitation. For example, in some embodiments, MgSO$_3$(aq) may be cooled to precipitate at least a portion of MgSO$_3$(s), then the MgSO$_3$(s) may be separated from the solution using a solid-liquid separation, then the remaining solution may be heated and/or the MgSO$_3$(aq) concentrated using reverse osmosis, or other membrane based process, or electrodialysis. For example, in some embodiments, MgSO$_3$(aq) may be cooled to precipitate at least a portion of MgSO$_3$(s), then the MgSO$_3$(s) may be separated from the solution using a solid-liquid separation, then the remaining solution may be mixed with new MgSO$_3$(aq), and/or heated, and/or the MgSO$_3$(aq) solution may be concentrated using reverse osmosis, or other membrane based process, or electrodialysis. In some embodiments, the concentrated and/or heated MgSO$_3$(aq) solution may be cooled to precipitate MgSO$_3$(s) and the MgSO$_3$(s) may be separated by a solid-liquid separation. In some embodiments, MgSO$_3$ may be separated from, for example, water by other separation systems and/or methods described herein, or known in the art, or any combination thereof Note: The magnesium—'WA' input may comprise a mixture of calcium and magnesium, or calcium and magnesium carbonate, or calcium and magnesium sulfide, or calcium and magnesium silicate, or any combination thereof.

(2) MgSO$_3$(aq or s)+Na$_2$SO$_4$(aq or s) 4Na$_2$SO$_3$(aq or s)+MgSO$_4$(aq or s)

Note: It may be desirable to separate Na$_2$SO$_3$(aq or s) from MgSO$_4$(aq or s). Separating Na$_2$SO$_3$(aq or s) from MgSO$_4$(aq or s) may comprise utilizing the difference in solubility properties between Na$_2$SO$_3$(aq or s) from MgSO$_4$(aq or s), or concentration, or electrical properties, or electrodialysis, or ion exchange, or water removal, or any combination thereof. In some embodiments, Na$_2$SO$_3$(aq or s) from MgSO$_4$(aq or s) may be separated by solventing out or selective precipitation of a salt by the addition and/or dissolution of a solvent, such as an organic or inorganic solvent, which may result in the selective or relative greater precipitation of one salt relative to the other salt. In some embodiments, said organic or inorganic solvent may be regenerated or recovered by, for example, distillation, or other separation system or method described herein, or other separation system or method known in the art, or any combination thereof. In some embodiments, separating Na$_2$SO$_3$(aq or s) from MgSO$_4$(aq or s) may comprise including, but not limited to, one or more or any combination of the following: precipitation, or cooling induced precipitation, or concentration induced precipitation, or distillation, or crystallization, or cryodesalination, or extraction, or membrane based process, or reverse osmosis, or other separation systems or methods described herein, or other separation systems or methods known in the art.

Note: The solubility of magnesium sulfite decreases significantly in liquid or supercritical water in a temperature between 140-220 degrees Celsius. In some embodiments, a solution of Na$_2$SO$_3$(aq)+MgSO$_4$(aq) may be heated above 140 degrees Celsius to facilitate the precipitation of MgSO$_4$(aq) as MgSO$_4$(s).

Note: It may be desirable to add MgSO$_3$, or Na$_2$SO$_4$, or any combination thereof as a solid to, for example, maximize the concentration of the solution and/or minimize water removal requirements or water removal energy consumption.

(4) Na$_2$SO$_3$(s or aq)+Ca(OH)$_2$(s or aq or suspension)→2NaOH(aq)+CaSO$_3$(s)

(5) CaSO$_3$(s)+Heat→CaO(s)+SO$_2$(g)

(6) One or more or any combination of the following:
2NaOH(aq)→2NaOH(s)+Water(solvent)
2NaOH(aq)

2NaOH(aq) or 2NaOH(s) added to seawater or body of water (7) $SO_2(g)+Water(solvent)\rightarrow SO_2(aq)$ (8) $CaO(s)+H_2O$ (l or g)$\rightarrow Ca(OH)_2$(s or aq or suspension)

Example 27: Production of Sodium Carbonate or Sodium Bicarbonate and Weak Acid or Weak Acid Anion Derivative (1) One or more or any combination of the following:
$MgCO_3+SO_2(aq)+\rightarrow MgSO_3(aq)+CO_2(g)$
$MgS+SO_2(aq)+H_2O(aq)\rightarrow MgSO_3(aq)+H_2S(g)$
$MgCa(CO_3)_2(s)+SO_2(aq)\rightarrow MgSO_3(aq)+CaSO_3(s)+CO_2(g)$
$MgCa(WA)(s)+SO_2(aq)\rightarrow MgSO_3(aq)+CaSO_3(s)+WA(s)$
$MgCa(WA)(s)+SO_2(aq)\rightarrow MgSO_3(aq)+Ca(WA)(s)+WA(s)$
Magnesium Silicate(s)$+SO_2$(aq)$+H_2O$(aq)$\rightarrow MgSO_3$(aq)+Silicon Dioxide(s)
Magnesium(Weak Acid Anion)$+SO_2$(aq)$+H_2O$(aq)$\rightarrow MgSO_3$(aq)+Weak Acid(s or aqueous or gas or liquid)

Note: In some embodiments, $MgSO_3$(aq) may be separated from at least a portion of water to form, for example, $MgSO_3$(s). For example, a portion of $MgSO_3$(aq) may be precipitated as $MgSO_3$(s) by cooling precipitation. For example, in some embodiments, $MgSO_3$(aq) may be cooled to precipitate at least a portion of $MgSO_3$(s), then the $MgSO_3$(s) may be separated from the solution using a solid-liquid separation, then the remaining solution may be heated and/or the $MgSO_3$(aq) concentrated using reverse osmosis, or other membrane based process, or electrodialysis. For example, in some embodiments, $MgSO_3$(aq) may be cooled to precipitate at least a portion of $MgSO_3$(s), then the $MgSO_3$(s) may be separated from the solution using a solid-liquid separation, then the remaining solution may be mixed with new $MgSO_3$(aq), and/or heated, and/or the $MgSO_3$(aq) solution may be concentrated using reverse osmosis, or other membrane based process, or electrodialysis. In some embodiments, the concentrated and/or heated $MgSO_3$(aq) solution may be cooled to precipitate $MgSO_3$(s) and the $MgSO_3$(s) may be separated by a solid-liquid separation. In some embodiments, $MgSO_3$ may be separated from, for example, water by other separation systems and/or methods described herein, or known in the art, or any combination thereof.

Note: The magnesium—'WA' input may comprise a mixture of calcium and magnesium, or calcium and magnesium carbonate, or calcium and magnesium sulfide, or calcium and magnesium silicate, or any combination thereof.

(2) $MgSO_3$(aq or s)$+Na_2SO_4$(aq or s)$\rightarrow Na_2SO_3$(aq or s)$+MgSO_4$(aq or s)

Note: It may be desirable to separate $Na_2SO_3$(aq or s) from $MgSO_4$(aq or s). Separating $Na_2SO_3$(aq or s) from $MgSO_4$(aq or s) may comprise utilizing the difference in solubility properties between $Na_2SO_3$(aq or s) from $MgSO_4$(aq or s), or concentration, or electrical properties, or electrodialysis, or ion exchange, or water removal, or any combination thereof. Separating $Na_2SO_3$(aq or s) from $MgSO_4$(aq or s) may comprise including, but not limited to, one or more or any combination of the following: precipitation, or cooling induced precipitation, or concentration induced precipitation, or distillation, or crystallization, or cryodesalination, or extraction, or membrane based process, or reverse osmosis, or electrodialysis, or electrodialysis reversal, or other separation systems or methods described herein, or other separation systems or methods known in the art.

Note: In some embodiments, it may be desirable to concentrate magnesium sulfite with electrodialysis, or electrodialysis reversal instead of, or in addition to, reverse osmosis. In some embodiments, it may be desirable to separate water from magnesium sulfite using electrodialysis, or electrodialysis reversal instead of, or in addition to, reverse osmosis.

Note: The solubility of magnesium sulfite decreases significantly in liquid or supercritical water in a temperature between 140-220 degrees Celsius. In some embodiments, a solution of $Na_2SO_3$(aq)+$MgSO_4$(aq) may be heated above 140 degrees Celsius to facilitate the precipitation of $MgSO_4$(aq) as $MgSO_4$(s).

Note: It may be desirable to add $MgSO_3$, or $Na_2SO_4$, or any combination thereof as a solid to, for example, maximize the concentration of the solution and/or minimize water removal requirements or water removal energy consumption.

(3) $Na_2SO_3$(aq or s)+$Na_2SO_3$(s)+$CO_2+_2H_2O_2NaHSO_3$(aq or s)+$2NaHCO_3$(aq or s)

Note: $2NaHCO_3$(aq or s) may be separated from $NaHSO_3$ (aq or s) by precipitation, or concentrating, or solubility properties, or cooling precipitation, or water removal systems or methods described herein, or separation systems or methods described herein, or water removal systems or methods described in the art, or separation systems or methods described in the art, or any combination thereof.

(4) $2NaHSO_3$(aq)$\rightarrow Na_2S_2O5$(s)+Water(solvent)

Note: $NaHSO_3$(aq) may generally exist at an aqueous phase. Upon precipitation or crystallization, $NaHSO_3$(aq) precipitates or crystalizes as $Na_2S_2O5$(s). $Na_2S_2O5$(s) may be considered anhydrous.

(5) $Na_2S_2O5$(s)+Heat$\rightarrow Na_2SO_3$(s)+$SO_2$(g)

(6) $SO_2$(g)+Water(solvent) $4SO_2$(aq)

Example 28: Production of Sodium Hydroxide and Weak Acid or Weak Acid Anion Derivative (1) One or more or any combination of the following:
$MgCO_3+SO_2(aq)\rightarrow MgSO_3(aq)+CO_2(g)$
$MgS+SO_2(aq)+H_2O(aq)\rightarrow MgSO_3(aq)+H_2S(g)$
$MgCa(CO_3)_2(s)+SO_2(aq)\rightarrow MgSO_3(aq)+CaSO_3(s)+CO_2(g)$
$MgCa(WA)(s)+SO_2(aq)\rightarrow MgSO_3(aq)+CaSO_3(s)+WA(s)$
$MgCa(WA)(s)+SO_2(aq)\rightarrow MgSO_3(aq)+Ca(WA)(s)+WA(s)$
Magnesium Silicate(s)$+SO_2$(aq)$+H_2O$(aq)$\rightarrow MgSO_3$(aq)+Silicon Dioxide(s)
Magnesium(Weak Acid Anion)$+SO_2$(aq)$+H_2O$(aq)$\rightarrow MgSO_3$(aq)+Weak Acid(s or aqueous or gas or liquid)

Note: In some embodiments, $MgSO_3$(aq) may be separated from at least a portion of water to form, for example, $MgSO_3$(s). For example, a portion of $MgSO_3$(aq) may be precipitated as $MgSO_3$(s) by cooling precipitation. For example, in some embodiments, $MgSO_3$(aq) may be cooled to precipitate at least a portion of $MgSO_3$(s), then the $MgSO_3$(s) may be separated from the solution using a solid-liquid separation, then the remaining solution may be heated and/or the MgSO$_3$(aq) concentrated using reverse osmosis, or other membrane based process, or electrodialysis. For example, in some embodiments, MgSO$_3$(aq) may be cooled to precipitate at least a portion of MgSO$_3$(s), then the MgSO$_3$(s) may be separated from the solution using a solid-liquid separation, then the remaining solution may be mixed with new MgSO$_3$(aq), and/or heated, and/or the MgSO$_3$(aq) solution may be concentrated using reverse osmosis, or other membrane based process, or electrodialysis. In some embodiments, the concentrated and/or heated MgSO$_3$(aq) solution may be cooled to precipitate MgSO$_3$(s) and the MgSO$_3$(s) may be separated by a solid-liquid separation. In some embodiments, MgSO$_3$ may be separated from, for example, water by other separation systems and/or methods described herein, or known in the art, or any combination thereof.

Note: The magnesium—'WA' input may comprise a mixture of calcium and magnesium, or calcium and magnesium carbonate, or calcium and magnesium sulfide, or calcium and magnesium silicate, or any combination thereof.

(2) MgSO$_3$(aq or s)+Na$_2$SO$_4$(aq or s) 4Na$_2$SO$_3$(aq or s)+MgSO$_4$(aq or s)

Note: It may be desirable to separate Na$_2$SO$_3$(aq or s) from MgSO$_4$(aq or s). Separating Na$_2$SO$_3$(aq or s) from MgSO$_4$(aq or s) may comprise utilizing the difference in solubility properties between Na$_2$SO$_3$(aq or s) from MgSO$_4$(aq or s), or concentration, or electrical properties, or electrodialysis, or ion exchange, or water removal, or any combination thereof. In some embodiments, Na$_2$SO$_3$(aq or s) from MgSO$_4$(aq or s) may be separated by solventing out or selective precipitation of a salt by the addition and/or dissolution of a solvent, such as an organic or inorganic solvent, which may result in the selective or relative greater precipitation of one salt relative to the other salt. In some embodiments, said organic or inorganic solvent may be regenerated or recovered by, for example, distillation, or other separation system or method described herein, or other separation system or method known in the art, or any combination thereof. In some embodiments, separating Na$_2$SO$_3$(aq or s) from MgSO$_4$(aq or s) may comprise including, but not limited to, one or more or any combination of the following: precipitation, or cooling induced precipitation, or concentration induced precipitation, or distillation, or crystallization, or cryodesalination, or extraction, or membrane based process, or reverse osmosis, or other separation systems or methods described herein, or other separation systems or methods known in the art.

Note: The solubility of magnesium sulfite decreases significantly in liquid or supercritical water in a temperature between 140-220 degrees Celsius. In some embodiments, a solution of Na$_2$SO$_3$(aq)+MgSO$_4$(aq) may be heated above 140 degrees Celsius to facilitate the precipitation of MgSO$_4$(aq) as MgSO$_4$(s).

Note: It may be desirable to add MgSO$_3$, or Na$_2$SO$_4$, or any combination thereof as a solid to, for example, maximize the concentration of the solution and/or minimize water removal requirements or water removal energy consumption.

(4) Na$_2$SO$_3$(s or aq)+Mg(OH)$_2$(s or aq or suspension)→2NaOH(aq)+MgSO$_3$(aq or s)

Note: MgSO$_3$(aq) may be separated into MgSO$_3$(s) using systems or methods described herein, or separating systems and methods described in the art, or any combination thereof.

Note: 2NaOH(aq) may be transformed into a concentrated solution comprising 2NaOH(aq) or into a solid comprising NaOH(s). Said separation may comprise systems or methods described herein, or separating systems and methods described in the art, or any combination thereof. At least a portion of MgSO$_3$ may be separated from NaOH during said transforming.

(5) MgSO$_3$(s)+Heat→MgO(s)+SO$_2$(g)

(6) One or more or any combination of the following:
2NaOH(aq)→2NaOH(s)+Water(solvent)
2NaOH(aq)
2NaOH(aq) or 2NaOH(s) added to seawater or body of water (7) SO$_2$(g)+Water(solvent) 4SO$_2$(aq)

(8) MgO(s)+H$_2$O (l or g)→Mg(OH)$_2$(s or aq or suspension)

Example 29: Production of Sodium Hydroxide and Weak Acid or Weak Acid Anion Derivative (1) Calcium(Weak Acid Anion)+2SO$_2$(aq)+H$_2$O(aq)→Ca(HSO$_3$)$_2$(aq)+Weak Acid(s or aqueous or gas or liquid)

(2) Ca(HSO$_3$)$_2$(aq)+Na$_2$SO$_4$(aq or s)→2NaHSO$_3$(aq)+CaSO$_4$(s)

(3) 2NaHSO$_3$(aq)→Na$_2$S$_2$O5(s)+Water(solvent)

Note: NaHSO$_3$(aq) may generally exist at an aqueous phase. Upon precipitation or crystallization, NaHSO$_3$(aq) precipitates or crystalizes as Na$_2$S$_2$O5(s). Na$_2$S$_2$O5(s) may be considered anhydrous.

(4) Na$_2$S$_2$O5(s)+Heat→Na$_2$SO$_3$(s)+SO$_2$(g)

(5) Na$_2$SO$_3$(s or aq)+Mg(OH)$_2$(s or aq or suspension)→2NaOH(aq)+MgSO$_3$(s or aq)

Note: MgSO$_3$(aq) may be separated into MgSO$_3$(s) using systems or methods described herein, or separating systems and methods described in the art, or any combination thereof. Note: 2NaOH(aq) may be transformed into a concentrated solution comprising 2NaOH(aq) or into a solid comprising NaOH(s). Said separation may comprise systems or methods described herein, or separating systems and methods described in the art, or any combination thereof. At least a portion of MgSO$_3$ may be separated from NaOH during said transforming.

(6) MgSO$_3$(s)+Heat→MgO(s)+SO$_2$(g)

(7) One or more or any combination of the following:
2NaOH(aq)→2NaOH(s)+Water(solvent)
2NaOH(aq)
2NaOH(aq) or 2NaOH(s) added to seawater or body of water (8) 2SO$_2$(g)+Water(solvent)→2 SO$_2$(aq)

(9) MgO(s)+H$_2$O (l or g)→Mg(OH)$_2$(s or aq or suspension)

Note: Calcium may be provided as an example alkaline earth. Alkaline earths in addition to or instead of calcium may be employed where calcium is provided as an example.

Note: Magnesium may be provided as an example alkaline earth. Alkaline earths in addition to or instead of magnesium may be employed where magnesium is provided as an example.

Note: In some embodiments, the reaction of magnesium oxide with water may generate heat. Said heat may be employed where useful within the process, or outside the process, or any combination thereof.

Example Sodium Bicarbonate and/or Sodium Carbonate Production with Ammonia Intermediate Step-by-Step Descriptions (1) Sodium sulfate, or potassium sulfate, or an alkali sulfate, may be mixed with ammonium bicarbonate, or ammonium carbonate, or ammonium carbamate, or any combination thereof, which may result in the formation of sodium bicarbonate, or sodium carbonate, or any combination thereof and/or ammonium sulfate. Sodium sulfate may be mixed with ammonium bicarbonate, which may result in the formation of sodium bicarbonate and ammonium sulfate. In some embodiments, the reaction of ammonium bicarbonate with sodium sulfate may be conducted at an aqueous state, wherein ammonium bicarbonate may be dissolved in water and/or sodium sulfate may be dissolved in water. In some embodiments, it may be desirable for '(1)' to be conducted in multiple steps or stages. For example, in some embodiments, sodium sulfate and ammonium bicarbonate may be mixed in a solution at a temperature where sodium sulfate is more soluble in water, such as at a temperature greater than 10° C., or 15° C., or 20° C., or 25° C., or 30° C., or 35° C., or 40° C., to, for example, facilitate the reaction and/or prevent the precipitation of sodium sulfate and/or promote the dissolution of sodium sulfate (if, for example, sodium sulfate is added at a solid phase). For example, in some embodiments, after the mixing of sodium sulfate and ammonium bicarbonate, in some embodiments, the combined solution may be cooled to facilitate the precipitation of at least a portion of sodium bicarbonate, while, for example, ammonium sulfate may remain dissolved. In some embodiments, the '(1)' may be a continuous process, which may involve, for example, mixing of sodium sulfate and ammonium bicarbonate and precipitation of sodium bicarbonate due to, for example, supersaturation or the resulting formation of sodium bicarbonate exceeding the solubility limits of sodium bicarbonate in the solution. In some embodiments, it may be desirable to remove or separate sodium bicarbonate from ammonium sulfate. For example, in some embodiments, temperature and/or concentration induced precipitation may separate the sodium bicarbonate from the aqueous ammonium sulfate or ammonium sulfate. For example, in some embodiments, separation may include, but is not limited to, one or more or any combination of the following: precipitation, or cooling induced precipitation, or concentration induced precipitation, or distillation, or reverse osmosis, or membrane distillation, or membrane based process, or forward osmosis, or crystallization, or cryodesalination, or extraction, or other separation systems or methods described herein, or other separation systems or methods known in the art. In some embodiments, sodium bicarbonate solid may be separated from an aqueous solution using a solid-liquid separation process. Sodium bicarbonate may comprise a valuable byproduct from the process, and/or may be, for example, further processed, or converted to sodium carbonate, or transferred, or sold, or employed in other systems or processes. The ammonium sulfate, which may exit the process as an aqueous solution, as a solid, or any combination thereof, may be transferred to '(3)'.

(2) Calcium—weak acid salt, or magnesium—weak acid salt, or alkaline-earth weak acid salt may be mixed with sulfur dioxide, or aqueous sulfur dioxide, or sulfurous acid, or water, or any combination thereof, which may result in the formation of calcium bisulfite, or magnesium bisulfite, or alkaline earth bisulfite, or any combination thereof and/or a weak acid or weak acid derivative. Calcium—weak acid salt may be mixed with sulfur dioxide, or aqueous sulfur dioxide, or sulfurous acid, or water, or any combination thereof, which may result in the formation of calcium bisulfite and/or a weak acid or weak acid derivative. Said weak acid may comprise a gas, such as carbon dioxide gas or hydrogen sulfide gas. Said weak acid may comprise a solid, such as silicon dioxide, or iron oxide, or aluminum oxide, or manganese oxide, or transition metal oxide, or zinc oxide. In some embodiments, said weak acid or weak acid derivative may comprise a byproduct and may be removed from the process. In some embodiments, said weak acid or weak acid derivative may be employed elsewhere in the process. For example, if said weak acid or weak acid derivative comprises carbon dioxide, said carbon dioxide may be employed as a portion of the input carbon dioxide employed in the production of ammonium carbonate, or ammonium bicarbonate, or ammonium carbamate, or any combination thereof within the process. In some embodiments, said a solid weak acid or weak acid derivative may be separated from the bisulfite aqueous solution by a solid-liquid separation process. Calcium bisulfite aqueous solution may be transferred to '(3)'.

(3) Calcium bisulfite, which may comprise an aqueous solution, may be mixed with ammonium sulfate, which may comprise an aqueous solution, or solid, or any combination thereof, which may result in the formation of calcium sulfate and ammonium bisulfite. Calcium sulfate may form as a precipitated due to its low solubility in water and/or due to calcium sulfate possessing a solubility in water significantly lower than ammonium bisulfite. The solubility of calcium sulfate in water may be about 0.26 g/100 ml and the solubility of ammonium bisulfite in water may be greater than 100 g/100 mL. Calcium sulfate or gypsum may be separated from the aqueous solution or the aqueous ammonium bisulfite solution by a solid-liquid separation system and/or method. Calcium sulfate or gypsum may comprise a product or output. The aqueous ammonium bisulfite solution may be transferred to '(4)'.

(4) Ammonium bisulfite or an aqueous solution comprising ammonium bisulfite may be heated, or depressurized, or may have its pressure reduced, or may have its temperature increased, or may have its pressure increased, or may have its temperature reduced, or any combination thereof, which may result in the desorption of sulfur dioxide and/or the formation of aqueous ammonium sulfite.

Note: It may be desirable for the concentration of aqueous ammonium sulfite to be sufficiently high to enable in the precipitation of at least a portion of ammonium bicarbonate in '(5)'. In some embodiments, a portion of concentrating or distillation may be desired.

(5) Ammonium sulfite, which may comprise an aqueous solution comprising ammonium sulfite, may be contacted with or reacted with carbon dioxide, which may result in the formation of ammonium bisulfite and ammonium bicarbonate.

Note: In some embodiments, at least a portion of ammonium bicarbonate may be separated from the ammonium bisulfite. For example, in some embodiments, ammonium bicarbonate may be separated from ammonium bisulfite by precipitation. For example, in some embodiments, ammonium bicarbonate may be separated from ammonium bisulfite by electrodialysis. For example, in some embodiments, separation may include, but is not limited to, one or more or any combination of the following: precipitation, or cooling induced precipitation, or concentration induced precipitation, or distillation, or crystallization, or cryodesalination, or extraction, or reverse osmosis, or membrane based process, or membrane distillation, or other separation systems or methods described herein, or other separation systems or methods known in the art. In some embodiments, ammonium bicarbonate solid may be separated from an aqueous solution using a solid-liquid separation process.

Note: It may be desirable for the partial pressure of carbon dioxide added to be sufficient to enable the formation of ammonium bicarbonate and/or sufficient or desirable absorption kinetics and/or sufficient or desirable reaction kinetics. For example, it may be desirable for the partial pressure of $CO_2(g)$ reactant to be greater than or equal to one or more or any combination of the following: 0.01 Bar, or 0.05 bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar. For example, it may be desirable for the concentration of $CO_2(g)$ reactant to be greater than or equal to one or more or any combination of the following: 1%, or 5%, or 10%, or 20%, or 30%, or 40%, or 50%, or 60%, or 70%, or 80%, or 90%, or 95%.

(6) An aqueous ammonium bisulfite solution may be transformed into ammonium sulfite, or sulfur dioxide, or water, or any combination thereof. In some embodiments, the resulting ammonium sulfite may comprise a concentrated aqueous solution, or a solid, or any combination thereof. In some embodiments, residual ammonium bicarbonate or ammonium carbonate or ammonium—carbon dioxide may be present in solution. In some embodiments, residual ammonium bicarbonate or ammonium carbonate or ammonium—carbon dioxide may decompose and/or otherwise form carbon dioxide gas. Said carbon dioxide gas may be recirculated and/or employed in '(5)'.

Or (1) Sodium sulfate, or potassium sulfate, or an alkali sulfate, may be mixed with ammonium bicarbonate, or ammonium carbonate, or ammonium carbamate, or any combination thereof, which may result in the formation of sodium bicarbonate, or sodium carbonate, or any combination thereof and/or ammonium sulfate. Sodium sulfate may be mixed with ammonium carbonate, which may result in the formation of sodium carbonate and ammonium sulfate. In some embodiments, the reaction of ammonium carbonate with sodium sulfate may be conducted at an aqueous state, wherein ammonium carbonate may be dissolved in water and/or sodium sulfate may be dissolved in water. In some embodiments, it may be desirable for '(1)' to be conducted in multiple steps or stages. For example, in some embodiments, sodium sulfate and ammonium carbonate may be mixed in a solution at a temperature where sodium sulfate is more soluble in water, such as at a temperature greater than 10° C., or 15° C., or 20° C., or 25° C., or 30° C., or 35° C., or 40° C., to, for example, facilitate the reaction and/or prevent the precipitation of sodium sulfate and/or promote the dissolution of sodium sulfate (if, for example, sodium sulfate is added at a solid phase). For example, in some embodiments, after the mixing of sodium sulfate and ammonium carbonate, in some embodiments, the combined solution may be cooled to facilitate the precipitation of at least a portion of sodium carbonate, while, for example, ammonium sulfate may remain dissolved. In some embodiments, the '(1)' may be a continuous process, which may involve, for example, mixing of sodium sulfate and ammonium carbonate and precipitation of sodium carbonate due to, for example, supersaturation or the resulting formation of sodium bicarbonate exceeding the solubility limits of sodium carbonate in the solution. In some embodiments, it may be desirable to remove or separate sodium carbonate from ammonium sulfate. For example, in some embodiments, temperature and/or concentration induced precipitation may separate the sodium bicarbonate from the aqueous ammonium sulfate or ammonium sulfate. For example, in some embodiments, separation may include, but is not limited to, one or more or any combination of the following: precipitation, or cooling induced precipitation, or concentration induced precipitation, or distillation, or crystallization, or cryodesalination, or extraction, or other separation systems or methods described herein, or other separation systems or methods known in the art. In some embodiments, sodium carbonate solid may be separated from an aqueous solution using a solid-liquid separation process. Sodium carbonate may comprise a valuable byproduct from the process, and/or may be, for example, further processed, or transferred, or sold, or employed in other systems or processes. The ammonium sulfate, which may exit the process as an aqueous solution, as a solid, or any combination thereof, may be transferred to '(3)'.

(2) Calcium—weak acid salt, or magnesium—weak acid salt, or alkaline-earth weak acid salt may be mixed with sulfur dioxide, or aqueous sulfur dioxide, or sulfurous acid, or water, or any combination thereof, which may result in the formation of calcium bisulfite, or magnesium bisulfite, or alkaline earth bisulfite, or any combination thereof and/or a weak acid or weak acid derivative. Calcium—weak acid salt may be mixed with sulfur dioxide, or aqueous sulfur dioxide, or sulfurous acid, or water, or any combination thereof, which may result in the formation of calcium bisulfite and/or a weak acid or weak acid derivative. Said weak acid may comprise a gas, such as carbon dioxide gas or hydrogen sulfide gas. Said weak acid may comprise a solid, such as silicon dioxide, or iron oxide, or aluminum oxide, or manganese oxide, or transition metal oxide, or zinc oxide. In some embodiments, said weak acid or weak acid derivative may comprise a byproduct and may be removed from the process. In some embodiments, said weak acid or weak acid derivative may be employed elsewhere in the process. For example, if said weak acid or weak acid derivative comprises carbon dioxide, said carbon dioxide may be employed as a portion of the input carbon dioxide employed in the production of ammonium carbonate, or ammonium bicarbonate, or ammonium carbamate, or any combination thereof within the process. In some embodiments, said a solid weak acid or weak acid derivative may be separated from the bisulfite aqueous solution by a solid-liquid separation process. Calcium bisulfite aqueous solution may be transferred to '(3)'.

(3) Calcium bisulfite, which may comprise an aqueous solution, may be mixed with ammonium sulfate, which may comprise an aqueous solution, or solid, or any combination thereof, which may result in the formation of calcium sulfate and ammonium bisulfite. Calcium sulfate may form as a precipitated due to its low solubility in water and/or due to calcium sulfate possessing a solubility in water significantly lower than ammonium bisulfite. The solubility of calcium sulfate in water may be about 0.26 g/100 ml and the solubility of ammonium bisulfite in water may be greater than 100 g/100 mL. Calcium sulfate or gypsum may be separated from the aqueous solution or the aqueous ammonium bisulfite solution by a solid-liquid separation system and/or method. Calcium sulfate or gypsum may comprise a product or output. The aqueous ammonium bisulfite solution may be transferred to '(4)'.

(4) Ammonium bisulfite or an aqueous solution comprising ammonium bisulfite may be heated, or depressurized, or may have its pressure reduced, or may have its temperature increased, or may have its pressure increased, or may have its temperature reduced, or any combination thereof, which may result in the desorption of sulfur dioxide and/or the formation of aqueous ammonium sulfite.

Note: It may be desirable for the concentration of aqueous ammonium sulfite to be sufficiently high to enable in the precipitation of at least a portion of ammonium bicarbonate in '(5)'. In some embodiments, a portion of concentrating or distillation may be desired.

(5) Ammonium sulfite, which may comprise an aqueous solution comprising ammonium sulfite, may be contacted with or reacted with carbon dioxide, which may result in the formation of ammonium bisulfite and ammonium bicarbonate.

Note: In some embodiments, at least a portion of ammonium bicarbonate may be separated from the ammonium bisulfite. For example, in some embodiments, ammonium bicarbonate may be separated from ammonium bisulfite by precipitation. For example, in some embodiments, ammonium bicarbonate may be separated from ammonium bisulfite by electrodialysis. For example, in some embodiments, separation may include, but is not limited to, one or more or any combination of the following: precipitation, or cooling induced precipitation, or concentration induced precipitation, or distillation, or crystallization, or cryodesalination, or extraction, or other separation systems or methods described herein, or other separation systems or methods known in the art. In some embodiments, ammonium bicarbonate solid may be separated from an aqueous solution using a solid-liquid separation process.

Note: It may be desirable for the partial pressure of carbon dioxide added to be sufficient to enable the formation of ammonium bicarbonate and/or sufficient or desirable absorption kinetics and/or sufficient or desirable reaction kinetics. For example, it may be desirable for the partial pressure of $CO_2(g)$ reactant to be greater than or equal to one or more or any combination of the following: 0.01 Bar, or 0.05 bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar. For example, it may be desirable for the concentration of $CO_2(g)$ reactant to be greater than or equal to one or more or any combination of the following: 1%, or 5%, or 10%, or 20%, or 30%, or 40%, or 50%, or 60%, or 70%, or 80%, or 90%, or 95%.

(6) An aqueous ammonium bisulfite solution may be transformed into ammonium sulfite, or sulfur dioxide, or water, or any combination thereof. In some embodiments, the resulting ammonium sulfite may comprise a concentrated aqueous solution, or a solid, or any combination thereof. In some embodiments, residual ammonium bicarbonate or ammonium carbonate or ammonium—carbon dioxide may be present in solution. In some embodiments, residual ammonium bicarbonate or ammonium carbonate or ammonium—carbon dioxide may decompose and/or otherwise form carbon dioxide gas. Said carbon dioxide gas may be recirculated and/or employed in '(5)'.

(7) Ammonium bicarbonate may be transformed into ammonium carbonate and/or carbon dioxide and/or water. Ammonium bicarbonate, which may comprise a solid, or an aqueous solution, or any combination thereof, may be decomposed into ammonium carbonate and/or carbon dioxide and/or water. In some embodiments, ammonium carbonate may be transferred to '(1)'. In some embodiments, said carbon dioxide and/or water may be transferred to '(5)'.

Example Sodium Hydroxide Production
Step-by-Step Descriptions

Example (Two Aqueous Sulfur Dioxide Reaction Steps)

(1) Calcium carbonate, or magnesium carbonate, or any combination thereof may be reacted with a solution comprising aqueous sulfur dioxide (which may be from step '(10)'), which may form a gas comprising carbon dioxide, and a solid comprising calcium sulfite, or magnesium sulfite, or any combination thereof.

Note: Solid calcium sulfite may be separated from a solution comprising water using a solid-liquid separation process, if desired.

Note: Gaseous carbon dioxide may comprise high partial pressure, or high purity carbon dioxide.

Note: In some embodiments, calcium may further comprise magnesium, or a mixture of magnesium and calcium, or magnesium. In some embodiments, magnesium sulfite may form, which may be soluble in water. After, for example, solid-liquid separation, the remaining liquid solution may comprise aqueous magnesium sulfite. In some embodiments, it may be desirable to recirculate said aqueous magnesium sulfite as the absorption solution to absorb sulfur dioxide. In some embodiments, it may be desirable for the aqueous sulfur dioxide to comprise a portion of aqueous magnesium sulfite. In some embodiments, it may be desirable to separate at least a portion of said magnesium sulfite from water or the aqueous solution using, for example, including, but not limited to, one or more or any combination of the following: cooling precipitation, or reverse osmosis, or membrane based process, or concentrating, or evaporation, or distillation, or membrane distillation, or forward osmosis, or solventing out, or addition of a soluble solvent to precipitate at least a portion of magnesium sulfite, or other separation systems and methods described herein, or other separation systems and methods described in the art.

(2) Solid calcium sulfite (which may be from step '(1)') may be reacted with a solution comprising aqueous sulfur dioxide (which may be from step '(11)'), which may form a solution comprising aqueous calcium bisulfite.

Note: '(2)' may be conducted at an elevated temperature and/or over an extended residence time. For example, the present step may be conducted at a temperature greater than 20° C., or 30° C., or 40° C., or 50° C., or 60° C., or 70° C., or 80° C., or 90° C., or 100° C., or any combination thereof. For example, the present step may be conducted over a residence time period greater than 2 minutes, or 5 minutes, or 10 minutes, or 15 minutes, or 30 minutes, or 45 minutes, or 1 hour, or 1.5 hours, or 2 hours, or 2.5 hours, or any combination thereof. For example, the present step may be conducted in the presence of mixing. In some embodiments, sulfur dioxide may be added continuously during the reaction or dissolution of calcium bisulfite. In some embodiments, the present reaction may be continuous, or semi-continuous, or cascading, or multi-stage, or multi-tank, or batch, or any combination thereof.

(3) The solution comprising aqueous calcium bisulfite (which may be from step '(2)') may be mixed with a solid or an aqueous solution comprising sodium sulfate, which may form an aqueous solution comprising sodium bisulfite and a solid comprising calcium sulfate.

Note: A solid comprising calcium sulfate may be separated form an aqueous solution comprising sodium bisulfite using a solid-liquid separation process.

(4) In some embodiments, an aqueous solution comprising sodium bisulfite (which may be from step '(3)') may be decomposed to form sulfur dioxide gas and aqueous sodium sulfite. In some embodiments, an aqueous solution comprising sodium bisulfite may be heated to desorb sulfur dioxide gas and form aqueous sodium sulfite. In some embodiments, an aqueous solution comprising sodium bisulfite (which may be from step '(3)') may be transformed into solid comprising sodium metabisulfite and a liquid comprising water. An aqueous solution comprising sodium bisulfite (which may be from step '(3)') may be transformed into solid comprising sodium metabisulfite, or a liquid comprising water, or any combination thereof. For example, an aqueous solution comprising sodium bisulfite may undergo a water removal process, or a distillation process, or a precipitation process, or a combination thereof, which may result in the formation of at least a portion of solid sodium metabisulfite and at least a portion of water.

Note: When sodium bisulfite is precipitated or otherwise removed from water, the solid form generally comprises sodium metabisulfite.

Note: In some embodiments, a solvent, such as an organic or inorganic solvent, may be added to aqueous solution comprising sodium bisulfite to solvent out, or solvent-out, or solvent dissolution induced precipitation, or adding a water soluble solvent to induce precipitation, or precipitate at least a portion of the aqueous sodium-sulfur dioxide salt or aqueous sodium bisulfite as a solid comprising sodium metabisulfite solid. Said solvent may comprise an organic solvent, or an inorganic solvent, or any combination thereof. In some embodiments, after solvent addition dissolution inducted sodium metabisulfite precipitation, the added solvent may be recovered or regenerated by distillation, or a separation system or method described herein, or separation system or method described in the art, or any combination thereof.

(5) Solid sodium metabisulfite (which may be from step '(4)') may be thermally decomposed into a solid comprising sodium sulfite and a gas comprising sulfur dioxide.

Note: In some embodiments, said gas comprising sulfur dioxide in '(5)' may comprise a relatively high partial pressure sulfur dioxide or sulfur dioxide with a partial pressure greater than 0.2 atm, or 0.3 atm, or 0.4 atm, or 0.5 atm, or 0.6 atm, or 0.7 atm, or 0.8 atm, or 0.9 atm, or 1 atm, or 1.5 atm, or 2 atm, or any combination thereof. In some embodiments, the concentration of aqueous sulfur dioxide in the resulting solution comprising aqueous sulfur dioxide may be suitable to form aqueous calcium bisulfite from at least a portion of solid calcium sulfite or calcium salt under suitable conditions with sufficient residence time.

(6) Sodium sulfite (which may be from step '(4)' or '(5)') may be mixed with a calcium oxide (which may be from step '(7)') or calcium hydroxide (which may be in part from step '(9)'), which may form a solution comprising aqueous sodium hydroxide and a solid comprising calcium sulfite. Said calcium hydroxide may comprise one or more or any combination of the following: a solid, or an aqueous solution, or a slurry, or a suspension, or milk of lime.

Note: A solid comprising calcium sulfite may be separated form a solution comprising aqueous sodium hydroxide using a solid-liquid separation process.

(7) A solid comprising calcium sulfite (which may be from step '(6)') may be thermally decomposed to form a solid comprising calcium oxide and a gas comprising sulfur dioxide.

Note: Said thermal decomposing may be conducted in a kiln or calciner.

Note: Said calcium sulfite may be dried or dehydrated before or during or both said thermal decomposing into a solid comprising calcium oxide and a gas comprising sulfur dioxide.

Note: In some embodiments, said gas comprising sulfur dioxide in '(5)' may comprise a relatively low partial pressure sulfur dioxide or sulfur dioxide with a partial pressure lower than 0.2 atm, or 0.3 atm, or 0.4 atm, or 0.5 atm, or 0.6 atm, or 0.7 atm, or 0.8 atm, or 0.9 atm, or 1 atm, or 1.5 atm, or 2 atm, or any combination thereof. In some embodiments, the concentration of aqueous sulfur dioxide in the resulting solution comprising aqueous sulfur dioxide may be suitable to form or facilitate the formation of aqueous calcium bisulfite from at least a portion of solid calcium sulfite or calcium salt under suitable conditions with sufficient residence time.

(8) A solution comprising aqueous sodium hydroxide (which may be from step '(6)') may be converted into a solid comprising sodium hydroxide and a liquid comprising water. For example, an aqueous solution comprising sodium hydroxide may undergo a water removal process, or a distillation process, or a precipitation process, or a combination thereof, which may result in the formation of at least a portion of solid sodium hydroxide and at least a portion of water. In some embodiments, the solution comprising aqueous sodium hydroxide may be a valuable product, and/or it may be desired for the sodium hydroxide to remain at an aqueous phase. In some embodiments, it may be desirable to concentrate the sodium hydroxide solution such that the concentration of sodium hydroxide is greater while remaining at an aqueous state and then selling or otherwise using the concentrated sodium hydroxide solution.

(9) Calcium oxide (which may be from step '(7)') may be reacted with water from step '(8)', forming a material comprising calcium hydroxide. Said material comprising calcium hydroxide may comprise one or more or any combination of the following: a solid, or an aqueous solution, or a slurry, or a suspension, or milk of lime. Heat generated from the reaction of calcium oxide and water may be employed in one or more other process steps, which may include, but is not limited to, one or more or any combination of the following: separation steps, or calcining steps, or heating steps, or distillation steps, or drying steps, or any combination thereof.

Note: In some embodiments, calcium oxide may be reacted directly with a solution comprising sodium sulfite, which may result in the formation of calcium sulfite solid and aqueous sodium hydroxide.

(10) A gas comprising sulfur dioxide (which may be from step '(7)') may be absorbed into a solution comprising water (which may be from step '(1)'), which may form a solution comprising aqueous sulfur dioxide.

Note: In some embodiments, said gas comprising sulfur dioxide may comprise sulfur dioxide mixed with other gases. In some embodiments, the concentration of aqueous sulfur dioxide in the resulting solution comprising aqueous sulfur dioxide may be suitable to form calcium sulfite and carbon dioxide in step '(1)'.

Note: For example, in some embodiments, it may be desirable for the concentration or partial pressure of the sulfur dioxide produced from the decomposition or calcining of calcium sulfite to be lower than the concentration or partial pressure of sulfur dioxide from the decomposition or calcining of sodium metabisulfite. For example, in some embodiments, when the $SO_2(g)$ is absorbed in '(10)', it may be desirable for the concentration of $SO_2(aq)$ in the resulting solution to be sufficiently high to form calcium sulfite and carbon dioxide in '(1)', however to be sufficiently low such that the vapor pressure of sulfur dioxide minimally contaminates the formed carbon dioxide.

(11) A gas comprising sulfur dioxide (which may be from step '(5)') may be absorbed into a solution comprising water (which may be from step '(4)'), which may form a solution comprising aqueous sulfur dioxide.

Note: In some embodiments, said gas comprising sulfur dioxide in '(11)' may comprise a relatively high partial pressure sulfur dioxide or sulfur dioxide with a partial pressure greater than 0.2 atm, or 0.3 atm, or 0.4 atm, or 0.5 atm, or 0.6 atm, or 0.7 atm, or 0.8 atm, or 0.9 atm, or 1 atm, or any combination thereof. In some embodiments, the concentration of aqueous sulfur dioxide in the resulting solution comprising aqueous sulfur dioxide may be suitable to form aqueous calcium bisulfite from at least a portion of solid calcium sulfite or calcium salt under suitable conditions with sufficient residence time.

Example (One Aqueous Sulfur Dioxide Reaction Steps)

(1) A material comprising calcium or magnesium and/or a salt comprising calcium—weak acid or magnesium—weak acid or alkaline earth—weak acid may be reacted with a solution comprising aqueous sulfur dioxide (which may be from step '(10)'), which may form a weak acid byproduct, such as a solid comprising silicon dioxide or a gas comprising carbon dioxide, and a solution comprising aqueous calcium bisulfite, or aqueous magnesium bisulfite, or any combination thereof.

Note: In some embodiments, gaseous carbon dioxide may comprise high partial pressure carbon dioxide.

Note: Gaseous carbon dioxide may form earlier in the residence time. In some embodiments, at least a portion of gaseous carbon dioxide formation may occur before most of the formation of aqueous calcium bisulfite.

Note: In some embodiments, '(1)' may be conducted in two stages. For example, some embodiments may involve a first stage wherein carbon dioxide gas may be formed, and a second stage wherein at least a portion of calcium sulfite dissolved to form aqueous calcium bisulfite.

Note: At least a portion of '(1)' may be conducted at an elevated temperature and/or over an extended residence time. For example, the present step may be conducted at a temperature greater than 20° C., or 30° C., or 40° C., or 50° C., or 60° C., or 70° C., or 80° C., or 90° C., or 100° C., or any combination thereof. For example, the present step may be conducted over a residence time period greater than 2 minutes, or 5 minutes, or 10 minutes, or 15 minutes, or 30 minutes, or 45 minutes, or 1 hour, or 1.5 hours, or 2 hours, or 2.5 hours, or any combination thereof. For example, the present step may be conducted in the presence of mixing.

(2) The solution comprising aqueous calcium bisulfite (which may be from step '(1)') may be mixed with a solid or an aqueous solution comprising sodium sulfate, which may form an aqueous solution comprising sodium bisulfite and a solid comprising calcium sulfate.

Note: A solid comprising calcium sulfate may be separated form an aqueous solution comprising sodium bisulfite using a solid-liquid separation process.

(3) In some embodiments, an aqueous solution comprising sodium bisulfite (which may be from step '(2)') may be decomposed to form sulfur dioxide gas and aqueous sodium sulfite. In some embodiments, an aqueous solution comprising sodium bisulfite may be heated to desorb sulfur dioxide gas and form aqueous sodium sulfite. In some embodiments, an aqueous solution comprising sodium bisulfite (which may be from step '(2)') may be transformed into a solid comprising sodium metabisulfite and a liquid comprising water. For example, an aqueous solution comprising sodium bisulfite may undergo a water removal process, or a distillation process, or a precipitation process, or a combination thereof, which may result in the formation of at least a portion of solid sodium metabisulfite and at least a portion of water.

Note: When sodium bisulfite is precipitated or otherwise removed from water, the solid form may generally comprise sodium metabisulfite.

(4) Solid sodium metabisulfite (which may be from step '(3)') may be thermally decomposed into a solid comprising sodium sulfite and a gas comprising sulfur dioxide.

(5) Sodium sulfite (which may be from step '(3)' or '(4)') may be mixed with calcium oxide or calcium hydroxide (which may be from step '(6)' or '(8)'), which may form a solution comprising aqueous sodium hydroxide and a solid comprising calcium sulfite. Calcium hydroxide may comprise one or more or any combination of the following: a solid, or an aqueous solution, or a slurry, or a suspension, or milk of lime.

Note: A solid comprising calcium sulfite may be separated form a solution comprising aqueous sodium hydroxide using a solid-liquid separation process.

(6) A solid comprising calcium sulfite (which may be from step '(5)') may be thermally decomposed to form a solid comprising calcium oxide and a gas comprising sulfur dioxide.

Note: Said thermal decomposing may be conducted in a kiln or calciner.

Note: Said calcium sulfite may be dried or dehydrated before or during or both said thermal decomposing into a solid comprising calcium oxide and a gas comprising sulfur dioxide.

(7) A solution comprising aqueous sodium hydroxide (which may be from step '(5)') may be converted into a solid comprising sodium hydroxide and a liquid comprising water. For example, an aqueous solution comprising sodium hydroxide may undergo a water removal process, or a distillation process, or a precipitation process, or a combination thereof, which may result in the formation of at least a portion of solid sodium hydroxide and at least a portion of water. Alternatively, or additionally, a solution comprising aqueous sodium hydroxide may comprise a valuable product, and/or may be further concentrated to produce a concentrated sodium hydroxide solution, which may comprise a valuable product.

(9) Calcium oxide (which may be from step '(6)') may be reacted with water from step '(7)', forming calcium hydroxide. Said calcium hydroxide may comprise one or more or any combination of the following: a solid, or an aqueous solution, or a slurry, or a suspension, or milk of lime. Heat generated from the reaction of calcium oxide and water to form calcium hydroxide may be employed in one or more other process steps, which may include, but is not limited to, one or more or any combination of the following: separation steps, or calcining steps, or heating steps, or distillation steps, or drying steps, or any combination thereof.

(10) A gas comprising sulfur dioxide (which may be from step '(6)' and/or step '(4)') may be absorbed into a solution comprising water (which may be from step '(3)'), which may form a solution comprising aqueous sulfur dioxide.

Figure Keys

| FIG. 1D Key | |
|---|---|
| Label | Description |
| 1 | '1' may comprise an input material comprising an alkaline earth metal salt. '1' may comprise an input material comprising a calcium salt. '1' may comprise an input material comprising a calcium - weak acid salt. '1' may comprise an input material comprising a salt of calcium and a weak acid with an acidity less than sulfurous acid. '1' may comprise an input material comprising calcium carbonate. '1' may comprise a solid. '1' may comprise limestone. '1' may comprise, including, but not limited to, one or more or a combination of the following: an alkaline-earth metal salt, a carbonate, a silicate, or silicon derivative, a carboxylic acid salt, a ferrate salt, an aluminate salt, a zincate salt, an iron derivative salt, an manganese derivative salt, a zinc derivative salt, or an aluminum derivative salt, or any combination thereof. |
| 2 | Same as '1'. |
| 3 | '3' may comprise a reaction between an input material with a solution comprising aqueous sulfur dioxide or sulfurous acid. In some embodiments, '3' may comprise a reaction between a solid material comprising calcium carbonate and sulfur dioxide or a liquid comprising aqueous sulfur dioxide to form solid calcium sulfite and gaseous carbon dioxide. In some embodiments, '3' may comprise a reaction between a material comprising calcium carbonate and a solution comprising aqueous sulfur dioxide, which may form a solid comprising calcium sulfite and an aqueous solution comprising water. In some embodiments, '3' may comprise a reaction between a material comprising calcium carbonate and a solution comprising a rich concentration of aqueous sulfur dioxide, which may form a solid comprising calcium sulfite and an aqueous solution comprising a lean concentration of aqueous sulfur dioxide. '3' may comprise a reactor or mixer or any combination thereof. '3' may be configured to allow the pressurization of gaseous carbon dioxide. '3' may be configured to enable at least a portion of carbon dioxide formed to comprise a high partial pressure, or high purity, or a combination thereof. In some embodiments, it may be desirable for the reaction to be conducted under conditions to form calcium sulfite and minimize or prevent the formation of calcium bisulfite. |
| 4 | '4' may comprise a gas comprising carbon dioxide. '4' may comprise an output. '4' may comprise a gas comprising carbon dioxide, which may undergo further treatment, or compression, or both. '4' may comprise a gas comprising a high partial pressure and/or concentration of carbon dioxide. '4' may comprise at least a portion of carbon dioxide produced from a reaction of sulfur dioxide or sulfurous acid or both with a carbonate salt. |
| 5 | Same as '4'. |
| 6 | '6' may comprise a solid-liquid mixture. '6' may comprise a mixture of a solid phase comprising at least a portion of calcium sulfite and a liquid phase comprising at least a portion of water. |
| 7 | '7' may comprise a process for solid-liquid separation. '7' may involve separating a solid comprising at least a portion of calcium sulfite from a liquid comprising water using a solid-liquid separation process. |
| 8 | '8' may comprise a material comprising at least a portion of calcium sulfite. In some embodiments, '8' may comprise at least a portion of a solid comprising |

FIG. 1D Key

| Label | Description |
|---|---|
|  | calcium sulfite. In some embodiments, '8' may comprise at least a portion of a solid comprising greater than 90 weight percent calcium sulfite. In some embodiments, '8' may comprise at least a portion of a solid comprising greater than 50 weight percent calcium sulfite. In some embodiments, '8' may comprise at least a portion of a solid comprising greater than 30 weight percent calcium sulfite. |
| 9 | '9' may comprise a reactor or mixer. '9' may comprise a solid-liquid reaction which may result in the dissolution of at least a portion of a solid phase and/or the formation of a gaseous product. '9' may comprise a reaction between a material comprising at least a portion of calcium sulfite with an aqueous sulfur dioxide solution, which may form at least a portion of dissolved or aqueous calcium bisulfite. In some embodiments, said material comprising at least a portion of calcium sulfite may further comprise residual calcium carbonate, which may react with at least a portion of the sulfur dioxide and form gaseous carbon dioxide. '9' may be conducted under conditions which may facilitate the dissolution of calcium sulfite and/or the formation of aqueous calcium bisulfite. For example, '9' may involve, including, but not limited to, high concentration of sulfur dioxide, or a concentration of aqueous sulfur dioxide entering '9' greater than 3 weight percent aqueous sulfur dioxide, or an elevated temperature, or a temperature greater than 20 degrees Celsius, or a sufficient residence time, or a residence time greater than 30 minutes, or any combination thereof. |

Sodium Bicarbonate Production

Example Inputs and Outputs

| Inputs | Outputs |
|---|---|
| $CaCO_3(s)$ or $CaSiO_3(s)$ or ½ $Ca_2SiO_4(s)$ or Ca(WA)(s) or a combination thereof | $CaSO_4$ |
| $Na_2SO_4$ | $NaHCO_3$ or $Na_2CO_3$ |
| $CO_2$ (g or l or s) | $SiO_2$ or 'WA' |
| $H_2O$ | |
| Energy (Heat and/or Electricity) | |

Example Reaction Steps (1a) $CaCO_3$ or $MgCO_3$ Input Version:

(1a1) $CaCO_3(s) + SO_2$ (aq or l or g) → $CaSO_3(s) + CO_2(g)$ (1a2) Separating $CaSO_3(s)$ from remaining liquid (if any) using, for example, a liquid-solid separation process (1a3) $CaSO_3(s) + SO_2(aq) + H_2O(l)$ → $Ca(HSO_3)_2(aq)$ Or (1b) Calcium Silicate, or Magnesium Silicate, or Other Silicate, or Other Calcium—Weak Acid, or Magnesium—Weak Acid, or a Combination Thereof Salt Input Version:

(1b1) $CaSiO_3(s) + 2SO_2(aq) + H_2O(l)$ → $Ca(HSO_3)_2(aq) + SiO_2$

Or (1b1opt2) ½ $Ca_2SiO_4(s) + 2SO_2(aq) + H_2O(l)$ → $Ca(HSO_3)_2(aq) + ½ SiO_2$ Or (1b1opt3) $Ca(WA)(s) + 2SO_2(aq) + H_2O(l)$ → $Ca(HSO_3)_2(aq) + WA$ (2) $Ca(HSO_3)_2(aq) + Na_2SO_4(aq)$ → $2NaHSO_3(aq) + CaSO_4(s)$ (3a) $2NaHSO_3(aq) + 2NaHSO_3(aq) + Heat$ → $2Na_2SO_3(aq) + 2SO_2(g)$ (4) $2Na_2SO_3(aq) + 2CO_2(g) + 2H_2O(l)$ → $2NaHSO_3(aq) + 2NaHCO_3(s)$ Note: In some embodiments, the aqueous solution may be concentrated, or cooled, or both to promote the precipitation of sodium bicarbonate. For example, in some embodiments, an aqueous solution comprising $2NaHSO_3(aq) + 2NaHCO_3(aq)$ may be concentrated using, for example, mechanical vapor compression distillation, or distillation, or desorption, and the precipitation of $2NaHCO_3(s)$ may be facilitated due to, for example, the concentrating beyond solubility limits and/or lower temperature.

(5)—in some embodiments with sodium carbonate production $NaHCO_3(s) + Heat$ → $Na_2CO_3(s) + CO_2(g) + H_2O(g$ or $l)$ Note: 'WA' or 'Weak Acid Anion' or 'Weak Acid' may comprise a weak acid or weak acid anion, which may include, but not limited to, carbon dioxide, or carbonic acid, or carbonate, or bicarbonate, or sesquicarbonate, or carbamate, or hydrogen sulfide, or sulfurous acid, or silicic acid, or orthosilicic acid, or silicon acid derivatives, or silicon minerals, or silicon acids, or aluminates, or ferrates, or any combination thereof.

Note: Concentration of $NaHSO_3$ produced from step '(4)' may be increased to match concentration of $NaHSO_3$ from step '(2)' by, for example, distillation, or membrane based process, or evaporation, or other separation process, or other concentrating process, or a combination thereof Note: In step '(3)', one of the two '$2NaHSO_3(aq)$' is from step '(2)' and the other of the two '$2NaHSO_3(aq)$' is from step '(4)'.

Note: Step '(4)' may require pure $CO_2(g)$ or high partial pressure $CO_2(g)$ or $CO_2(l)$ or $CO_2(g)$.

At least a portion of $CO_2$ input to step '(4)' may be sourced from step '(1)' if step '(1)' Or employs a carbonate input, such as, for example, step '(1a)'.

At least a portion of $CO_2$ input to step '(4)' may be sourced from step '(5)' in some embodiments employing a step '(5)'

At least a portion of $CO_2$ input to step '(4)' may be sourced from $CO_2$ captured from a combustion source, or a combustion source employed to produce heat, or emissions source, or air, or geological $CO_2$ source, or natural $CO_2$ source, or a combination thereof.

Note: Some embodiments may be designed to operate as a low temperature process, where the solutions and/or solid reagents in thermal desorption or decomposition may undergo or operate thermal desorption or decomposition at less than 150° C., or less than 200° C., or less than 250° C., or less than 300° C., or less than 350° C.

Calcium Oxide Production Example Embodiments

Example Process Steps (1) React a material comprising a silicate of calcium with aqueous sulfur dioxide or sulfurous acid, which may produce a solution comprising at least a portion dissolved calcium bisulfite and a solid phase comprising at least a portion silicon or silica or silicon dioxide or a derivative of silicon. Said material comprising a silicate of calcium may comprise an input to the process.

(2) Separate solid silicon or silica or silicon dioxide or a derivative of silicon or other solids from a liquid solution comprising aqueous calcium bisulfite. '(2)' may involve one or more or a combination of solid-liquid separation processes. Said liquid solution comprising aqueous calcium bisulfite may be transferred to step '(3)'.

(3) Desorb or separate sulfur dioxide from a solution comprising calcium bisulfite, which may produce solid calcium sulfite and liquid solution comprising water, or lean aqueous sulfur dioxide, or lean calcium sulfite, or lean calcium bisulfite, or a combination thereof. Desorption may require heat input, or depressurization, or vacuum, or vapor compression, or stripping gas, or a combination thereof. Desorbed sulfur dioxide may be transferred to step '(6)'. Solid calcium sulfite and liquid solution may be transferred to step '(4)'. In some embodiments, '(3)' and '(4)' may be conducted in the same step.

(4) Separate solid calcium sulfite from a liquid solution comprising water, or lean aqueous sulfur dioxide, or lean calcium sulfite, or lean calcium bisulfite, or a combination thereof. '(4)' may involve one or more or a combination of solid-liquid separation processes. Solid calcium sulfite may be transferred to step '(5)' and liquid solution comprising water, or lean aqueous sulfur dioxide, or lean calcium sulfite, or lean calcium bisulfite, or a combination thereof may be transferred to step '(6)'.

(5) Decompose solid calcium sulfite into calcium oxide and sulfur dioxide. Calcium oxide may comprise an output of the process. Sulfur dioxide may be transferred (6) Absorb sulfur dioxide into a liquid solution comprising water, or lean aqueous sulfur dioxide, or lean calcium sulfite, or lean calcium bisulfite, or a combination thereof to form a sulfur dioxide rich solution, or a sulfurous acid solution, or a combination thereof. It may be desirable for the concentration of sulfurous acid or sulfur dioxide in said formed liquid solution to be stoichiometrically at a molar ratio greater than or equal to 1:1 relative to the calcium input in step 1 to, for example, enable the formation of soluble calcium bisulfite. Said sulfur dioxide rich solution, or a sulfurous acid solution, or a combination thereof may be transferred to, for example, step 1.

Example Chemistry Steps (1) Calcium Silicate, or Magnesium Silicate, or Other Silicate, or cement, or concrete, or Other Calcium—Weak Acid, or Magnesium—Weak Acid, or a Combination Thereof Salt Input Version:

(1a) $CaSiO_3(s)+2H_2SO_3(aq) \rightarrow Ca(HSO_3)_2(aq)+SiO_2(s)+H_2O(l)$

Or (1b) $½ Ca_2SiO_4(s)+2SO_2(aq)+H_2O(l) \rightarrow Ca(HSO_3)_2(aq)+½ SiO_2$

Or (1c) $Ca(WA)(s)+2SO_2(aq)+H_2O(l) \rightarrow Ca(HSO_3)_2(aq)+WA$ (2) $Ca(HSO_3)_2(aq)+Heat \rightarrow CaSO_3(s)+H_2O(l)+SO_2(g)$ (3) $CaSO_3(s)+Heat \rightarrow CaO(s)+SO_2(g)$ (4) $2SO_2(g)+2H_2O(l) \rightarrow 2H_2SO_3(aq)$ Additional Description Example Chemistry

| Example Summary of Inputs and Outputs | |
|---|---|
| Inputs | Outputs |
| $CaCO_3(s)$ or $CaSiO_3(s)$ or $½ Ca_2SiO_4(s)$ or $Ca(WA)(s)$ or a combination thereof | $CaSO_4$ |
| $Na_2SO_4$ | $NaHCO_3$ or $Na_2CO_3$ |
| $CO_2$ (g or l or s) | $SiO_2$ or 'WA' |
| $H_2O$ | |
| Energy (Heat and/or Electricity) | |

Summary of Example Reactions (1a) $CaCO_3$ or $MgCO_3$ Input Version:

(1a1opt1) $CaCO_3(s)+SO_2$ (aq or l or g)$\rightarrow CaSO_3(s)+CO_2(g)$ (1a2) Separating $CaSO_3(s)$ from remaining liquid (if any) using, for example, a liquid-solid separation process (1a3) $CaSO_3(s)+SO_2(aq)+H_2O(l) \rightarrow Ca(HSO_3)_2(aq)$ Or (1a1opt2) $CaCO_3(s)+2SO_2$ (aq or l or g)$+H_2O(l) \rightarrow Ca(HSO_3)_2$ (aq)$+CO_2(g)$ And/Or (1b) Calcium Silicate, or Magnesium Silicate, or Other Silicate, or Other Calcium—Weak Acid, or Magnesium—Weak Acid, or a Combination Thereof Salt Input Version:

(1b1) $CaSiO_3(s)+2SO_2(aq)+H_2O(l) \rightarrow Ca(HSO_3)_2(aq)+SiO_2$

Or (1b1opt2) $½ Ca_2SiO_4(s)+2SO_2(aq)+H_2O(l) \rightarrow Ca(HSO_3)_2$ (aq)$+½ SiO_2$ Or (1b1 opt3) $Ca(WA)(s)+2SO_2(aq)+H_2O(l) \rightarrow Ca(HSO_3)_2$ (aq)$+WA$ (2) $Ca(HSO_3)_2(aq)+Na_2SO_4(aq) \rightarrow 2NaHSO_3(aq)+CaSO_4(s)$ (3optA) $2NaHSO_3(aq)+2NaHSO_3$(aq or s)$+Heat \rightarrow 2Na_2SO_3(aq)+2SO_2(g)+2H_2O(l)$ (4optA) $2Na_2SO_3(aq)+2CO_2(g)+2H_2O(l) \rightarrow 2NaHSO_3(aq)+2NaHCO_3(s)$ (5optA) $2SO_2(g)+2H_2O(l) \rightarrow 2H_2SO_3(aq)$ (6optA)—in some embodiments with sodium carbonate production $NaHCO_3(s)+Heat \rightarrow Na_2CO_3(s)+CO_2(g)+H_2O(g$ or $l)$ And/Or (3optB) 2NaHSO$_3$(aq)+Separation 4Na$_2$S$_2$O$_5$(s)+H$_2$O (g or 1)

Note: A portion of CO$_2$ may be generated from the decomposition of residual sodium bicarbonate. May be desirable to decompose the residual sodium bicarbonate at a lower temperature than the sodium bisulfite. May be desirable to precipitate residual sodium bicarbonate or sodium carbonate by concentrating and/or cooling precipitation before or while separating or concentrating the sodium bisulfite solution.

(4optB) Na$_2$S$_2$O$_5$(s)+Na$_2$S$_2$O$_5$(s)+Heat→2Na$_2$SO$_3$(s)+2SO$_2$(g)

Note: A portion of CO$_2$ may be generated from, for example, the decomposition of residual sodium bicarbonate. May be desirable to decompose the residual sodium bicarbonate at a lower temperature than the sodium bisulfite.

(5optB) 2Na$_2$SO$_3$(aq)+2CO$_2$(g)+2H$_2$O(l)→2NaHSO$_3$(aq)+2NaHCO$_3$(s)

(6optB) 2NaHSO$_3$(aq)+Separation→Na$_2$S$_2$O$_5$(s)+H$_2$O (g or 1)

Note: In some embodiments, a portion of CO$_2$ may be generated from the decomposition of residual sodium bicarbonate, if any. In some embodiments, it may be desirable to decompose the residual sodium bicarbonate at a lower temperature than the sodium bisulfite. May be conducted in the same step as (3optB). For example, before or during or after one or more separation processes, 2NaHSO$_3$(aq) in (6optB) may be mixed with 2NaHSO$_3$(aq) in (3optB) to form a combined solution and said combined solution may undergo one or more separation processes to form 4 NaHSO$_3$(s).

(7optB) 2SO$_2$(g)+2H$_2$O(l)→2H$_2$SO$_3$(aq)

(8optB)—in some embodiments with sodium carbonate production NaHCO$_3$(s)+Heat→Na$_2$CO$_3$(s)+CO$_2$(g)+H$_2$O(g or 1)

Note: 'H$_2$SO$_3$(aq)' or '2SO$_2$(aq)+H$_2$O(l)' may be employed interchangeably.

Detailed Description of Each Reaction $$CaCO_3(s)+SO_2(aq\ or\ l\ or\ g) \Rightarrow CaSO_3(s)+CO_2(g)$$
$$\Delta H=-24.67\ kJ/mol \qquad \text{Reaction 1a1op1:}$$

Description: The present reaction may involve reacting calcium carbonate with sulfur dioxide or sulfurous acid to produce calcium sulfite and carbon dioxide. Calcium carbonate may comprise limestone. Calcium carbonate may comprise magnesium carbonate instead of or in addition to calcium carbonate. Sulfur dioxide or sulfurous acid may be a gas or a liquid or a solution or an aqueous solution. It may be desirable to conduct the present reaction to facilitate the formation of carbon dioxide with minimal gaseous impurities, or at a high partial pressure, or both. For example, the present reaction may be conducted with a dilute solution of sulfur dioxide to minimize sulfur dioxide vapor.

Conditions: In some embodiments, the present reaction may be conducted at ambient temperature or may be cooled or both to, for example, minimize the vapor pressure of sulfur dioxide. It may be desirable to conduct the present reaction in a low diatomic oxygen environment or low diatomic oxygen atmosphere to, for example, prevent oxidation of sulfur dioxide or calcium sulfite to sulfuric acid or sulfate and/or to increase the purity of carbon dioxide produced. It may be desirable to conduct the present reaction under conditions to minimize the formation of calcium bisulfite or dissolved calcium bisulfite to, for example, enable calcium sulfite to be separated from liquid as a solid using a solid-liquid separation process and transferred to subsequent steps. For example, a CO$_2$ desorption step or the present step may possess relatively fast kinetics and may be conducted at a relatively low temperature and low concentration of sulfur dioxide. For example, a CO$_2$ desorption step or the present step may be conducted using a lower concentration of sulfur dioxide or sulfurous acid, which may be produced by recovering harder to separate, or less valuable, or lower concentration sources of sulfur dioxide or may be produced by smaller size, or less complex, or lower energy consumption, or lower cost equipment. For example, subsequent steps involving the formation of dissolved calcium bisulfite may possess relatively slower kinetics and may benefit from being conducted with a higher sulfurous acid concentration and/or at higher temperatures. For example, it may be desirable to conduct subsequent steps involving the formation of dissolved calcium bisulfite with a higher concentration of sulfurous acid or with the formation of higher concentration of calcium bisulfite to accelerate the reaction kinetics in subsequent steps and/or minimize or reduce water removal or water separation energy consumption in subsequent steps.

$$CaSO_3(s)+SO_2(aq\ or\ l\ or\ g)+H_2O(l) \Rightarrow Ca(HSO_3)_2(aq) \qquad \text{Reaction 1a3:}$$

Description: The present reaction may involve reacting calcium sulfite with a sulfurous acid solution to produce an aqueous solution of calcium bisulfite. The present reaction may be conducted under conditions to accelerate reaction rate or accelerate the formation of dissolve calcium bicarbonate. For example, the present reaction may be conducted with excess sulfur dioxide or excess sulfurous acid, or the present reaction may be conducted wherein the molar ratio of sulfurous acid to calcium sulfite(s) is greater than 1. For example, the present reaction may be conducted at temperatures at or above room temperature. For example, the present reaction may be conducted such that heat generated by the reaction remains at least a portion in the reaction, which may enable at least a portion of adiabatic temperature rise, which may facilitate reaction kinetics. For example, the present reaction may be conducted with mild heating or heat recovery to, for example, accelerate reaction kinetics. For example, the present reaction may be conducted such that product solution comprising calcium bisulfite, which may have experienced at least a portion of adiabatic temperature rise, is heat exchanged with at least a portion of the input reactants, which may raise the reaction temperature or enable higher temperature reaction operation, or operating at a reaction temperature above room temperature with less or minimal external heating or without the need for external heating. In some embodiments, heat may be recovered from the present reaction and/or employed in other steps of the present invention or for other applications. In some embodiments, it may be desirable to maximize the concentration of dissolved calcium bisulfite or reach near maximum feasible concentration of dissolved calcium bisulfite or both to, for example, minimize water removal or water separation which may be required in later steps. For example, it may be desirable for dissolve calcium bisulfite concentration in the product solution following the present reaction step to be greater than one or more of the following: 2.5 wt %, or 5 wt %, or 7.5 wt %, or 10 wt %, or 12.5 wt %, or 15 wt %, or 17.5 wt %, or 20 wt %, or 22.5 wt %, or 25 wt %, or 27.5 wt %, or 30 wt %.

CaCO$_3$(s)+2SO$_2$(aq or l or g)+H$_2$O(l) $\Rightarrow$ Ca(HSO$_3$)$_2$(aq)+CO$_2$(g)

CaSiO$_3$(s)+2SO$_2$(aq or l or g)+H$_2$O(l) $\Rightarrow$ Ca(HSO$_3$)$_2$ (aq)+SiO$_2$(s)

And/or

½Ca$_2$SiO$_4$(s)+2SO$_2$(aq or l or g)+H$_2$O(l) $\Rightarrow$ Ca(HSO$_3$)$_2$(aq)+½SiO$_2$(s)

And/or

Ca(WA)(s)+2SO$_2$(aq or l or g)+H$_2$O(l) $\Rightarrow$ Ca(HSO$_3$)$_2$ (aq)+WA(s)     Reaction 1a1op2:

Description: The present reaction may involve reacting a calcium or alkali metal—weak acid salt with sulfur dioxide or sulfurous acid or aqueous sulfurous acid or excess aqueous sulfurous acid to produce dissolved calcium bisulfite and weak acid. The weak acid produce may comprise a solid, which may be separated from the liquid aqueous calcium bisulfite solution by means of, for example, a solid-liquid separation process. The weak acid produced may comprise a gas, which may be separated from the liquid aqueous calcium bisulfite solution by means of, for example, removal of headspace gases, or depressurization, or vacuum, or heat, or a gas-liquid separation process, and/or may be further separated from residual sulfur dioxide gas. The weak acid produced may comprise a solid, which may be separated from the liquid aqueous calcium bisulfite solution by means of, for example, a solid-liquid separation process. For example, the present reaction may involve reacting a calcium silicate material with a sulfurous acid solution to form a solution comprising calcium bisulfite and a solid comprising a silicate or derivative of silicon. It may be desirable to separate said solid comprising a silicate or derivative of silicon from said solution comprising calcium bisulfite by means of a solid-liquid separation process. It may be desirable to react the calcium silicate material with sulfurous acid at a molar ratio equal to or greater than the sulfur to calcium molar ratio in calcium bisulfite.

Example Mass, Heat, and Power Flows (FIG. 3)

| Example Mass, Heat, and Power Flows for an Example Embodiment of FIG. 3 |
|---|
| ID | Description |
|---|---|
| 1 | 1 mole CaSiO$_3$; or 691.4 kg of CaSiO$_3$ per metric ton of sodium bicarbonate produced |
| 2 | A mixing or reacting process. May employ thermal management, such as cooling or heating. May require some electricity or other power for, for example, pumping or mixing. |
| 3 | 1 mole Ca(HSO$_3$)$_2$(aq) and/or 1 mole SiO$_2$(s); or 1203.7 kg of Ca(HSO$_3$)$_2$(aq) per metric ton of sodium bicarbonate produced and/or 357.6 kg of SiO$_2$(s) per metric ton of sodium bicarbonate produced<br>Solvent: 100 moles of H$_2$O; or 10,714.3 kg of H$_2$O per metric ton of sodium bicarbonate produced |
| 4 | A solid-liquid separation process. May require some thermal management, such as cooling or heating. May require some electricity or other power for, for example, pumping or mixing. |
| 5 | 1 mole SiO$_2$(s); or 357.6 kg of SiO$_2$(s) per metric ton of sodium bicarbonate produced<br>Note: May comprise other materials instead of or in addition to silicon dioxide. |
| 6 | 1 mole Ca(HSO$_3$)$_2$(aq); or 1203.7 kg of Ca(HSO$_3$)$_2$(aq) per metric ton of sodium bicarbonate produced<br>Solvent: 100 moles of H$_2$O; 10,714.3 kg of H$_2$O per metric ton of sodium bicarbonate produced |
| 7 | 1 mole Na$_2$SO$_4$(s); or 845.18 kg of Na$_2$SO$_4$(s) per metric ton of sodium bicarbonate produced |
| 8 | A mixing or reacting process. May employ thermal management, such as cooling or heating. May require some electricity or other power for, for example, pumping or mixing. |
| 9 | 2 moles NaHSO$_3$(aq) and/or 1 mole CaSO$_4$(s); or 1,238.02 kg of NaHSO$_3$(aq) per metric ton of sodium bicarbonate produced and/or 810.31 kg of CaSO$_4$(s) per metric ton of sodium bicarbonate produced<br>Solvent: 100 moles of H$_2$O; 10,713.6 kg of H$_2$O per metric ton of sodium bicarbonate produced |
| 10 | A solid-liquid separation process. May require some thermal management, such as cooling or heating. May require some electricity or other power for, for example, pumping or mixing. |
| 11 | 1 mole CaSO$_4$(s); or 810.31 kg of CaSO$_4$(s) per metric ton of sodium bicarbonate produced |
| 12 | 2 moles NaHSO$_3$(aq); or 1,238.02 kg of NaHSO$_3$(aq) per metric ton of sodium bicarbonate produced<br>Solvent: 100 moles of H$_2$O; 10,713.6 kg of H$_2$O per metric ton of sodium bicarbonate produced |
| 13 | '13' may comprise a process for distillation, or a water removal, or a drying, or a separation, or a crystallization or a combination thereof. For the present example, '13' may employ mechanical vapor compression distillation employing electricity as the energy input to power the process.<br>Separation may require the removal of 100 moles of H$_2$O (solvent) and 1 mole H$_2$O (part of sodium bisulfite dissolved, although practically part of the solvent due to properties of sodium bisulfite and sodium metabisulfite), which means 101 moles of H$_2$O needs to be removed or distilled; or about 10,820.7 kg of H$_2$O per metric ton of sodium bicarbonate produced.<br>Estimated Mechanical Vapor Compression (MVC) Distillation for 'ZLD' Energy Consumption: 15 kWh per m$^3$ of water<br>To remove 101 moles of H$_2$O using MVC: 0.0273 kWh |

| | Example Mass, Heat, and Power Flows for an Example Embodiment of FIG. 3 |
|---|---|
| ID | Description |
| | To remove 10,820.7 kg of H$_2$O using MVC: 162.31 kWh
Note: Residual sulfur dioxide may be separated or may vaporize during distillation. If desired, residual sulfur dioxide may be condensed with the separated water. Condensing the sulfur dioxide with the separated water or condensing water may be desirable as the water may be transferred to a sulfur dioxide absorption step. |
| 14 | 101 moles of H$_2$O; or 10,820.7 kg of H$_2$O per metric ton of sodium bicarbonate produced |
| 15 | May comprise sulfur dioxide. It is important to note residual or excess sulfur dioxide may be condensed with or within the water, which may comprise '14'. |
| 16 | 1 mole Na$_2$S$_2$O$_5$(s); or 1,130.88 kg of Na$_2$S$_2$O$_5$(s) per metric ton of sodium bicarbonate produced |
| 17 | '17' may comprise a calcination, or a thermal decomposition, or a desorption, or decomposition, or a combination thereof process. For the present example, '17' may employ a calciner employing heat as an energy input. Heat may be sourced from combustion or electricity or heat pump or steam or waste heat or thermal storage or solar thermal or other energy source, or a combination thereof.
Enthalpy of Decomposition of 2 Na$_2$S$_2$O$_5$(s) to 2 Na$_2$SO$_3$ and 2 SO$_2$(g) is: 87 kJ/mol SO$_2$ produced at greater than or equal to about 150° C.
To thermally decompose 2 moles of Na$_2$S$_2$O$_5$(s) to 2 moles of 2 Na$_2$SO$_3$ and 2 moles of SO$_2$(g) is: 174 kJ heat
To thermally decompose 2,261.9 kg of Na$_2$S$_2$O$_5$(s) to 1,500 kg of 2 Na2SO$_3$ and 761.9 kg of SO$_2$(g) is: 1.036 GJ heat |
| 18 | 2 moles SO$_2$(g); or 761.9 kg of SO$_2$(g) per metric ton of sodium bicarbonate produced |
| 19 | '19' may comprise an absorption process. '19' may comprise a process for dissolving sulfur dioxide in water. '19' may comprise a process for producing sulfurous acid from sulfur dioxide and a solution comprising water. May require some thermal management, such as cooling or heating. May require some electricity or other power for, for example, pumping or mixing. |
| 20 | 2 moles of SO$_2$(aq), 1 mole of H$_2$O; or 761.9 kg of SO$_2$ and 107.1 kg of H$_2$O per metric ton of sodium bicarbonate produced
Solvent: 100 moles of H$_2$O; or 10,713.6 kg of H$_2$O per metric ton of sodium bicarbonate produced
Note: Reactants may be dissolved in solvent. SO$_2$ is provided in the present example in a molar ratio to calcium based on the molar ratio in calcium bisulfite. In some embodiments, SO$_2$ may be in excess of or greater than the molar ratio of sulfur to calcium in calcium bisulfite. In some embodiments, SO$_2$ may be in less than the molar ratio of sulfur to calcium in calcium bisulfite. |
| 21 | 2 moles Na$_2$SO$_3$(s); or 1,500 kg of Na$_2$SO$_3$(s) per metric ton of sodium bicarbonate produced |
| 22 | '22' may comprise a mixing and/or dissolution process. '22' may comprise a process for dissolving sodium sulfite in water to form an aqueous sodium sulfite solution. |
| 23 | 2 moles Na$_2$SO$_3$(aq); or 1,500 kg of Na$_2$SO$_3$(aq) per metric ton of sodium bicarbonate produced
Solvent: 56 moles of H$_2$O; 5,999.6 kg of H$_2$O per metric ton of sodium bicarbonate produced |
| 24 | 2 moles CO$_2$(g); or 523.77 kg of CO$_2$(g) per metric ton of sodium bicarbonate produced |
| 25 | '25' may comprise a gas-liquid contactor. '25' may comprise a gas-liquid contactor, or an absorber, or a reactor, or a precipitator, or a combination thereof process. May require some thermal management, such as cooling or heating. May require some electricity or other power for, for example, pumping or mixing. |
| 26 | 2 moles NaHCO$_3$(s and/or aq), 2 moles NaHSO$_3$(aq); or 1,000 kg of NaHCO$_3$(s and/or aq) and 1,239.2 kg of NaHSO$_3$(aq) per metric ton of sodium bicarbonate produced
Solvent: 54 moles of H$_2$O; or 5,785 kg of H$_2$O per metric ton of sodium bicarbonate produced |
| 27 | '27' may comprise a solid-liquid separation process. May require some thermal management, such as cooling or heating. May require some electricity or other power for, for example, pumping or mixing. |
| 28 | 0.935 mole NaHCO$_3$(s); or 467.5 kg of NaHCO$_3$(s) per metric ton of sodium bicarbonate produced in total
Note: Based on solubility per 100 g water. Actual results may vary. |
| 29 | 1.064 moles NaHCO$_3$(aq), 2 moles NaHSO$_3$(aq); or 532.5 kg of NaHCO$_3$(s and/or aq) and 1,239.2 kg of NaHSO$_3$(aq) per metric ton of sodium bicarbonate produced
Solvent: 54 moles of H$_2$O; or 5,785 kg of H$_2$O per metric ton of sodium bicarbonate produced |
| 30 | '30' may comprise a process for distillation, or a water removal, or a drying, or a separation, or a crystallization, or cooling crystallization, or heating concentrating, or cooling concentration, or a combination thereof. For the present example, '30' may employ mechanical vapor compression distillation employing electricity as the energy input to power the process. '30' may involve precipitating or crystallizing remaining or residual sodium bicarbonate or sodium carbonate or both before precipitating or crystallizing remaining or residual sodium bisulfite or sodium metabisulfite.
Separation may require the removal of 54 moles of H$_2$O (solvent) and 1 mole H$_2$O (part of sodium bisulfite dissolved, although practically part of the solvent due to properties of sodium bisulfite and sodium metabisulfite), which means 55 moles of |

Example Mass, Heat, and Power Flows for an Example Embodiment of FIG. 3

| ID | Description |
|---|---|
| | $H_2O$ needs to be removed or distilled; or about _ kg of $H_2O$ per metric ton of sodium bicarbonate produced.<br>Estimated Mechanical Vapor Compression (MVC) Distillation for 'ZLD' Energy Consumption: 15 kWh per m$^3$ of water<br>To remove 55 moles of $H_2O$ using MVC: 0.01485 kWh<br>To remove 5,892.5 kg of $H_2O$ using MVC: 88.39 kWh |
| 31 | 55 moles $H_2O$; or 5,892.5 kg of $H_2O$ per metric ton of sodium bicarbonate produced total.<br>Makeup water comprising, for example 1 mole of $H_2O$ per every 55 moles of water, may be added to, for example, makeup for water lost in the sodium bicarbonate product. Some $H_2O$ in the sodium bicarbonate product may be recovered if sodium bicarbonate is converted to sodium carbonate and/or water in subsequent treatment or processing. |
| 32 | 1.064 moles $NaHCO_3(s)$; or 532.5 kg of $NaHCO_3(s)$ per metric ton of sodium bicarbonate produced total |
| 33 | 1 mole $Na_2S_2O_5(s)$; or 1,130.88 kg of $Na_2S_2O_5(s)$ per metric ton of sodium bicarbonate produced total |

Example Heat Input Requirements (FIG. 3)

Summary of Example Heat and Power Requirements FIG. 3

| | |
|---|---|
| Heat | 1.036 GJ heat per metric ton of sodium bicarbonate produced, heat may be at a temperature greater than or equal to 150° C. Heat may be supplied to, for example, 13. |
| Electricity | 250.7 kWh per metric ton of sodium bicarbonate produced, assumes process for dewatering or removing water comprises a mechanical vapor compression distillation process or similar electricity powered process. |

Example $CO_2$ Balance (FIG. 3)

Example $CO_2$ Net Balance from Example Heat, and Power Flows FIG. 3 (Assumes Heat is from Natural Gas and Power is Electricity and Electricity is USA Grid Electricity with Average USA Electricity Carbon Intensity)

| | | |
|---|---|---|
| $CO_2$ Emissions per Metric Ton of Sodium Bicarbonate (Direct and Indirect Emissions) | Heat (Natural Gas Combustion) | 0.05116 metric tons $CO_2$ |
| | Electric Power (based on USA average electric grid carbon intensity of 450 kg $CO_2$ per MWh) | 0.11282 metric tons $CO_2$ |
| Net $CO_2$ Consumption | $CO_2$ Consumed in Produced Sodium Bicarbonate Output | −0.52381 metric tons $CO_2$ |
| Net $CO_2$ Balance (Negative Values are Good) | | −0.35983 metric tons $CO_2$ |

Example $CO_2$ Net Balance from Example Heat, and Power Flows FIG. 3 (Assumes Heat is from Natural Gas and Power is Electricity and Electricity is $CO_2$ Emissions Free)

| | | |
|---|---|---|
| $CO_2$ Emissions per Metric Ton of Sodium Bicarbonate (Direct and Indirect Emissions) | Heat (Natural Gas Combustion) | 0.05116 metric tons $CO_2$ |
| | Electric Power (based on hydropower or renewables or nuclear sourced electricity) | 0 metric tons $CO_2$ |
| Net $CO_2$ Consumption | $CO_2$ Consumed in Produced Sodium Bicarbonate Output | −0.52381 metric tons $CO_2$ |
| Net $CO_2$ Balance (Negative Values are Good) | | −0.47265 metric tons $CO_2$ |

| Example $CO_2$ Net Balance from Example Heat, and Power Flows FIG. 3 (Assumes Heat is from Electricity and Power is from Electricity and Electricity is $CO_2$ Emissions Free) | | |
| --- | --- | --- |
| $CO_2$ Emissions per Metric Ton of Sodium Bicarbonate (Direct and Indirect Emissions) | Heat (based on hydropower or renewables or nuclear sourced electricity) | 0 metric tons $CO_2$ |
| | Electric Power (based on hydropower or renewables or nuclear sourced electricity) | 0 metric tons $CO_2$ |
| Net $CO_2$ Consumption | $CO_2$ Consumed in Produced Sodium Bicarbonate Output | −0.52381 metric tons $CO_2$ |
| Net $CO_2$ Balance (Negative Values are Good) | | −0.52381 metric tons $CO_2$ |

Example Cost of Inputs, Value of Outputs, and Operating Profit (FIG. 3)

| Example Inputs and Cost of Inputs (FIG. 3) | | |
| --- | --- | --- |
| Input | Cost per Standard Unit of Measure | Cost per Metric Ton of Sodium Bicarbonate Produced |
| Calcium Silicate or Magnesium Silicate or Zinc Silicate or Iron Silicate or other similar composition or a combination thereof | Free (if concrete waste) $10-80 per metric ton if co-located to silicate ore mineral resource | Free (if concrete waste) |
| Sodium Sulfate | $80 per metric ton | $67.61 |
| Carbon Dioxide | Free (if co-located with $CO_2$ source requiring offtake) $10-35 per metric ton on commodity market ($20 for simplicity) (Note: May be paid to offtake and convert $CO_2$ - not included to ensure conservative estimate) | $10.48 |
| Water | $0.40 per metric ton | $0.04 |
| Heat (Natural Gas Combustion) | $3.00 per MMBtu | $2.95 |
| Electricity | $0.06 per kWh | $15.04 |
| Total Cost of Inputs per Metric Ton Sodium Bicarbonate Produced | | $96.12 |

| Example Outputs and Value of Outputs (FIG. 3) | | |
|---|---|---|
| Output | Value per Standard Unit of Measure | Value per Metric Ton of Sodium Bicarbonate Produced |
| Silicon Dioxide | None | None |
| Calcium Sulfate | $120 per metric ton (high purity because it is precipitated gypsum) | $97.24 |
| Sodium Bicarbonate | $200 per metric ton | $200 |
| Total Value of Outputs per Metric Ton Sodium Bicarbonate Produced | | $297.24 |

| Inputs Cost, Value of Outputs, and Net Operating Profit (FIG. 3) | |
|---|---|
| Inputs Cost | $96.12 |
| Value of Outputs | $297.24 |
| Net Profit per Metric Ton of Sodium Bicarbonate Produced | $201.12 |

Example Mass, Heat, and Power Flows (FIG. 4)

| Example Mass, Heat, and Power Flows for an Example Embodiment of FIG. 4 | |
|---|---|
| ID | Description |
| 1 | 1 mole $CaCO_3$; or 595.7 kg of $CaCO_3$ per metric ton of sodium bicarbonate produced |
| 2 | A mixing or reacting process. May employ thermal management, such as cooling or heating. May require some electricity or other power for, for example, pumping or mixing. |
| 3 | 1 mole $Ca(HSO_3)_2(aq)$ and/or 1 mole $CO_2(g)$; or 1203.7 kg of $Ca(HSO_3)_2(aq)$ per metric ton of sodium bicarbonate produced and/or 261.9 kg of $CO_2(g)$ per metric ton of sodium bicarbonate produced<br>Solvent: 100 moles of $H_2O$; or 10,714.3 kg of $H_2O$ per metric ton of sodium bicarbonate produced |
| 4 | A solid-liquid separation process. May require some thermal management, such as cooling or heating. May require some electricity or other power for, for example, pumping or mixing. |
| 5 | Residual solids. Residual solids may include, but is not limited to, impurities, silicon dioxide, or unreacted reagents, or a combination thereof. |
| 6 | 1 mole $Ca(HSO_3)_2(aq)$; or 1203.7 kg of $Ca(HSO_3)_2(aq)$ per metric ton of sodium bicarbonate produced<br>Solvent: 100 moles of $H_2O$; 10,714.3 kg of $H_2O$ per metric ton of sodium bicarbonate produced |
| 7 | 1 mole $Na_2SO_4(s)$; or 845.18 kg of $Na_2SO_4(s)$ per metric ton of sodium bicarbonate produced |
| 8 | A mixing or reacting process. May employ thermal management, such as cooling or heating. May require some electricity or other power for, for example, pumping or mixing. |
| 9 | 2 moles $NaHSO_3(aq)$ and/or 1 mole $CaSO_4(s)$; or 1,238.02 kg of $NaHSO_3(aq)$ per metric ton of sodium bicarbonate produced and/or 810.31 kg of $CaSO_4(s)$ per metric ton of sodium bicarbonate produced<br>Solvent: 100 moles of $H_2O$; 10,713.6 kg of $H_2O$ per metric ton of sodium bicarbonate produced |
| 10 | A solid-liquid separation process. May require some thermal management, such as cooling or heating. May require some electricity or other power for, for example, pumping or mixing. |
| 11 | 1 mole $CaSO_4(s)$; or 810.31 kg of $CaSO_4(s)$ per metric ton of sodium bicarbonate produced |
| 12 | 2 moles $NaHSO_3(aq)$; or 1,238.02 kg of $NaHSO_3(aq)$ per metric ton of sodium bicarbonate produced<br>Solvent: 100 moles of $H_2O$; 10,713.6 kg of $H_2O$ per metric ton of sodium bicarbonate produced |
| 13 | '13' may comprise a process for distillation, or a water removal, or a drying, or a separation, or a crystallization or a combination thereof. For the present example, '13' may employ mechanical vapor compression distillation employing electricity as the energy input to power the process.<br>Separation may require the removal of 100 moles of $H_2O$ (solvent) and 1 mole $H_2O$ (part of sodium bisulfite dissolved, although practically part of the solvent due to properties of sodium bisulfite and sodium metabisulfite), which means 101 moles of $H_2O$ needs to be removed or distilled; or about 10,820.7 kg of $H_2O$ per metric ton of sodium bicarbonate produced.<br>Estimated Mechanical Vapor Compression (MVC) Distillation for 'ZLD' Energy Consumption: 15 kWh per $m^3$ of water<br>To remove 101 moles of $H_2O$ using MVC: 0.0273 kWh<br>To remove 10,820.7 kg of $H_2O$ using MVC: 162.31 kWh<br>Note: Residual sulfur dioxide may be separated or may vaporize during distillation. If desired, residual sulfur dioxide may be condensed with the separated water. Condensing the sulfur dioxide with the separated water or condensing water may be desirable as the water may be transferred to a sulfur dioxide absorption step. |
| 14 | 101 moles of $H_2O$; or 10,820.7 kg of $H_2O$ per metric ton of sodium bicarbonate produced |
| 15 | May comprise sulfur dioxide. It is important to note residual or excess sulfur dioxide may be condensed with or within the water, which may comprise '14'. |

| Example Mass, Heat, and Power Flows for an Example Embodiment of FIG. 4 |
| --- |
| ID Description |

16. 1 mole $Na_2S_2O_5(s)$; or 1,130.88 kg of $Na_2S_2O_5(s)$ per metric ton of sodium bicarbonate produced
17. '17' may comprise a calcination, or a thermal decomposition, or a desorption, or decomposition, or a combination thereof process. For the present example, '17' may employ a calciner employing heat as an energy input. Heat may be sourced from combustion or electricity or heat pump or steam or waste heat or thermal storage or solar thermal or other energy source, or a combination thereof.
    Enthalpy of Decomposition of 2 $Na_2S_2O_5(s)$ to 2 $Na_2SO_3$ and 2 $SO_2(g)$ is: 87 kJ/mol $SO_2$ produced at greater than or equal to about 150° C.
    To thermally decompose 2 moles of $Na_2S_2O_5(s)$ to 2 moles of 2 $Na_2SO_3$ and 2 moles of $SO_2(g)$ is: 174 kJ heat
    To thermally decompose 2,261.9 kg of $Na_2S_2O_5(s)$ to 1,500 kg of 2 $Na_2SO_3$ and 761.9 kg of $SO_2(g)$ is: 1.036 GJ heat
18. 2 moles $SO_2(g)$; or 761.9 kg of $SO_2(g)$ per metric ton of sodium bicarbonate produced
19. '19' may comprise an absorption process. '19' may comprise a process for dissolving sulfur dioxide in water. '19' may comprise a process for producing sulfurous acid from sulfur dioxide and a solution comprising water. May require some thermal management, such as cooling or heating. May require some electricity or other power for, for example, pumping or mixing.
20. 2 moles of $SO_2(aq)$, 1 mole of $H_2O$; or 761.9 kg of SO2 and 107.1 kg of $H_2O$ per metric ton of sodium bicarbonate produced
    Solvent: 100 moles of $H_2O$; or 10,713.6 kg of $H_2O$ per metric ton of sodium bicarbonate produced
    Note: Reactants may be dissolved in solvent. $SO_2$ is provided in the present example in a molar ratio to calcium based on the molar ratio in calcium bisulfite. In some embodiments, $SO_2$ may be in excess of or greater than the molar ratio of sulfur to calcium in calcium bisulfite. In some embodiments, $SO_2$ may be in less than the molar ratio of sulfur to calcium in calcium bisulfite.
21. 2 moles $Na_2SO_3(s)$; or 1,500 kg of $Na_2SO_3(s)$ per metric ton of sodium bicarbonate produced
22. '22' may comprise a mixing and/or dissolution process. '22' may comprise a process for dissolving sodium sulfite in water to form an aqueous sodium sulfite solution.
23. 2 moles $Na_2SO_3(aq)$; or 1,500 kg of $Na_2SO_3(aq)$ per metric ton of sodium bicarbonate produced
    Solvent: 56 moles of $H_2O$; 5,999.6 kg of $H_2O$ per metric ton of sodium bicarbonate produced
24. 1 mole $CO_2(g)$; or 261.9 kg of $CO_2(g)$ per metric ton of sodium bicarbonate produced
25. '25' may comprise a gas-liquid contactor. '25' may comprise a gas-liquid contactor, or an absorber, or a reactor, or a precipitator, or a combination thereof process. May require some thermal management, such as cooling or heating. May require some electricity or other power for, for example, pumping or mixing.
26. 2 moles $NaHCO_3$(s and/or aq), 2 moles $NaHSO_3(aq)$; or 1,000 kg of $NaHCO_3$(s and/or aq) and 1,239.2 kg of $NaHSO_3(aq)$ per metric ton of sodium bicarbonate produced
    Solvent: 54 moles of $H_2O$; or 5,785 kg of $H_2O$ per metric ton of sodium bicarbonate produced
27. '27' may comprise a solid-liquid separation process. May require some thermal management, such as cooling or heating. May require some electricity or other power for, for example, pumping or mixing.
28. 0.935 mole $NaHCO_3(s)$; or 467.5 kg of $NaHCO_3(s)$ per metric ton of sodium bicarbonate produced in total
    Note: Based on solubility per 100 g water. Actual results may vary.
29. 1.064 moles $NaHCO_3(aq)$, 2 moles $NaHSO_3(aq)$; or 532.5 kg of $NaHCO_3$(s and/or aq) and 1,239.2 kg of $NaHSO_3(aq)$ per metric ton of sodium bicarbonate produced
    Solvent: 54 moles of $H_2O$; or 5,785 kg of $H_2O$ per metric ton of sodium bicarbonate produced
30. '30' may comprise a process for distillation, or a water removal, or a drying, or a separation, or a crystallization, or cooling crystallization, or heating concentrating, or cooling concentration, or a combination thereof. For the present example, '30' may employ mechanical vapor compression distillation employing electricity as the energy input to power the process. '30' may involve precipitating or crystalizing remaining or residual sodium bicarbonate or sodium carbonate or both before precipitating or crystalizing remaining or residual sodium bisulfite or sodium metabisulfite.
    Separation may require the removal of 54 moles of $H_2O$ (solvent) and 1 mole $H_2O$ (part of sodium bisulfite dissolved, although practically part of the solvent due to properties of sodium bisulfite and sodium metabisulfite), which means 55 moles of $H_2O$ needs to be removed or distilled; or about _ kg of $H_2O$ per metric ton of sodium bicarbonate produced.
    Estimated Mechanical Vapor Compression (MVC) Distillation for 'ZLD' Energy Consumption: 15 kWh per $m^3$ of water
    To remove 55 moles of $H_2O$ using MVC: 0.01485 kWh
    To remove 5,892.5 kg of $H_2O$ using MVC: 88.39 kWh
31. 55 moles $H_2O$; or 5,892.5 kg of $H_2O$ per metric ton of sodium bicarbonate produced total.
    Makeup water comprising, for example 1 mole of $H_2O$ per every 55 moles of water, may be added to, for example, makeup for water lost in the sodium bicarbonate

| Example Mass, Heat, and Power Flows for an Example Embodiment of FIG. 4 |
|---|
| ID Description |
| product. Some $H_2O$ in the sodium bicarbonate product may be recovered if sodium bicarbonate is converted to sodium carbonate and/or water in subsequent treatment or processing. |
| 32  1.064 moles $NaHCO_3$(s); or 532.5 kg of $NaHCO_3$(s) per metric ton of sodium bicarbonate produced total |
| 33  1 mole $Na_2S_2O_5$(s); or 1,130.88 kg of $Na_2S_2O_5$(s) per metric ton of sodium bicarbonate produced total |
| 34  1 mole $CO_2$(g); or 261.9 kg of $CO_2$(g) per metric ton of sodium bicarbonate produced |

Example Heat Input Requirements (FIG. 4)

| Summary of Example Heat and Power Requirements FIG. 4 | |
|---|---|
| Heat | 1.036 GJ heat per metric ton of sodium bicarbonate produced, heat may be at a temperature greater than or equal to 150° C. Heat may be supplied to, for example, 13. |
| Electricity | 250.7 kWh per metric ton of sodium bicarbonate produced, assumes process for dewatering or removing water comprises a mechanical vapor compression distillation process or similar electricity powered process. |

Example CO2 Balance (FIG. 4)

| Example $CO_2$ Net Balance from Example Heat, and Power Flows FIG. 4 (Assumes Heat is from Natural Gas and Power is Electricity and Electricity is USA Grid Electricity with Average USA Electricity Carbon Intensity) | | |
|---|---|---|
| $CO_2$ Emissions per Metric Ton of Sodium Bicarbonate (Direct and Indirect Emissions) | Heat (Natural Gas Combustion) | 0.05116 metric tons $CO_2$ |
|  | Electric Power (based on USA average electric grid carbon intensity of 450 kg $CO_2$ per MWh) | 0.11282 metric tons $CO_2$ |
|  | High Purity $CO_2$ produced by Sulfurous Acid + Carbonate Reaction (transferred to sodium bicarbonate production step in FIG. 4) | 0.2619 metric tons $CO_2$ |
| Net $CO_2$ Consumption | $CO_2$ Consumed in Produced Sodium Bicarbonate Output | −0.52381 metric tons $CO_2$ |
| Net $CO_2$ Balance (Negative Values are Good) |  | −0.09793 metric tons $CO_2$ |

| Example $CO_2$ Net Balance from Example Heat, and Power Flows FIG. 4 (Assumes Heat is from Natural Gas and Power is Electricity and Electricity is $CO_2$ Emissions Free) | | |
|---|---|---|
| $CO_2$ Emissions per Metric Ton of Sodium Bicarbonate (Direct and Indirect Emissions) | Heat (Natural Gas Combustion) | 0.05116 metric tons $CO_2$ |
|  | Electric Power (based on hydropower or renewables or nuclear sourced electricity) | 0 metric tons $CO_2$ |
|  | High Purity $CO_2$ produced by Sulfurous Acid + Carbonate Reaction (transferred to sodium bicarbonate production step in FIG. 4) | 0.2619 metric tons $CO_2$ |

Example CO₂ Net Balance from Example Heat, and Power Flows
FIG. 4 (Assumes Heat is from Natural Gas and Power is Electricity
and Electricity is CO₂ Emissions Free)

| | | |
|---|---|---|
| Net $CO_2$ Consumption | $CO_2$ Consumed in Produced Sodium Bicarbonate Output | −0.52381 metric tons $CO_2$ |
| Net $CO_2$ Balance (Negative Values are Good) | | −0.21075 metric tons $CO_2$ |

Example CO₂ Net Balance from Example Heat, and Power Flows
FIG. 4 (Assumes Heat is from Electricity and Power is from Electricity
and Electricity is CO₂ Emissions Free)

| | | |
|---|---|---|
| $CO_2$ Emissions per Metric Ton of Sodium Bicarbonate (Direct and Indirect Emissions) | Heat (based on hydropower or renewables or nuclear sourced electricity) | 0 metric tons $CO_2$ |
| | Electric Power (based on hydropower or renewables or nuclear sourced electricity) | 0 metric tons $CO_2$ |
| | High Purity $CO_2$ produced by Sulfurous Acid + Carbonate Reaction (transferred to sodium bicarbonate production step in FIG. 4) | 0.2619 metric tons $CO_2$ |
| Net $CO_2$ Consumption | $CO_2$ Consumed in Produced Sodium Bicarbonate Output | −0.52381 metric tons $CO_2$ |
| Net $CO_2$ Balance (Negative Values are Good) | | −0.26191 metric tons $CO_2$ |

Example Cost of Inputs, Value of Outputs, and Operating Profit (FIG. 4)

Example Inputs and Cost of Inputs (FIG. 4)

| Input | Cost per Standard Unit of Measure | Cost per Metric Ton of Sodium Bicarbonate Produced |
|---|---|---|
| Calcium Carbonate or Magnesium Carbonate or Limestone or a Combination Thereof | Crushed limestone: $30-$38 per metric ton | $20.25 |
| Sodium Sulfate | $80 per metric ton | $67.61 |
| Carbon Dioxide | Free (if co-located with $CO_2$ source requiring offtake) $10-35 per metric ton on commodity market ($20 for simplicity) (Note: May be paid to offtake and convert $CO_2$ - not included to ensure conservative estimate) | $5.24 |
| Water | $0.40 per metric ton | $0.04 |
| Heat (Natural Gas Combustion) | $3.00 per MMBtu | $2.95 |
| Electricity | $0.06 per kWh | $15.04 |
| Total Cost of Inputs per Metric Ton Sodium Bicarbonate Produced | | $111.13 |

| Example Outputs and Value of Outputs (FIG. 4) | | |
|---|---|---|
| Output | Value per Standard Unit of Measure | Value per Metric Ton of Sodium Bicarbonate Produced |
| Silicon Dioxide | None | None |
| Calcium Sulfate | $120 per metric ton (high purity because it is precipitated gypsum) | $97.24 |
| Sodium Bicarbonate | $200 per metric ton | $200 |
| Total Value of Outputs per Metric Ton Sodium Bicarbonate Produced | | $297.24 |

| Inputs Cost, Value of Outputs, and Net Operating Profit (FIG. 4) | |
|---|---|
| Inputs Cost | $111.13 |
| Value of Outputs | $297.24 |
| Net Profit per Metric Ton of Sodium Bicarbonate Produced | $186.11 |

Example Mass, Heat, and Power Flows (FIG. 5)

| Example Mass, Heat, and Power Flows for an Example Embodiment of FIG. 5 | |
|---|---|
| ID | Description |
| 1 | 1 mole $CaCO_3$, or 595.7 kg of $CaCO_3$ per metric ton of sodium bicarbonate produced |
| 2 | A mixing or reacting process. May employ thermal management, such as cooling or heating. May require some electricity or other power for, for example, pumping or mixing. |
| 3 | 1 mole $Ca(HSO_3)_2(aq)$ and/or 1 mole $SiO_2(s)$; or 1203.7 kg of $Ca(HSO_3)_2(aq)$ per metric ton of sodium bicarbonate produced and/or 357.6 kg of $SiO_2(s)$ per metric ton of sodium bicarbonate produced<br>Solvent: 100 moles of $H_2O$; or 10,714.3 kg of $H_2O$ per metric ton of sodium bicarbonate produced |
| 4 | A solid-liquid separation process. May require some thermal management, such as cooling or heating. May require some electricity or other power for, for example, pumping or mixing. |
| 5 | Residual solids. Residual solids may include, but is not limited to, impurities, silicon dioxide, or unreacted reagents, or a combination thereof. |
| 6 | 1 mole $Ca(HSO_3)_2(aq)$; or 1203.7 kg of $Ca(HSO_3)_2(aq)$ per metric ton of sodium bicarbonate produced<br>Solvent: 100 moles of $H_2O$; 10,714.3 kg of $H_2O$ per metric ton of sodium bicarbonate produced |
| 7 | 1 mole $Na_2SO_4(s)$; or 845.18 kg of $Na_2SO_4(s)$ per metric ton of sodium bicarbonate produced |
| 8 | A mixing or reacting process. May employ thermal management, such as cooling or heating. May require some electricity or other power for, for example, pumping or mixing. |
| 9 | 2 moles $NaHSO_3(aq)$ and/or 1 mole $CaSO_4(s)$; or 1,238.02 kg of $NaHSO_3(aq)$ per metric ton of sodium bicarbonate produced and/or 810.31 kg of $CaSO_4(s)$ per metric ton of sodium bicarbonate produced<br>Solvent: 100 moles of $H_2O$; 10,713.6 kg of $H_2O$ per metric ton of sodium bicarbonate produced |
| 10 | A solid-liquid separation process. May require some thermal management, such as cooling or heating. May require some electricity or other power for, for example, pumping or mixing. |
| 11 | 1 mole $CaSO_4(s)$; or 810.31 kg of $CaSO_4(s)$ per metric ton of sodium bicarbonate produced |
| 12 | 2 moles $NaHSO_3(aq)$; or 1,238.02 kg of $NaHSO_3(aq)$ per metric ton of sodium bicarbonate produced<br>Solvent: 100 moles of $H_2O$; 10,713.6 kg of $H_2O$ per metric ton of sodium bicarbonate produced |
| 13 | '13' may comprise a process for distillation, or a water removal, or a drying, or a separation, or a crystallization or a combination thereof. For the present example, '13' may employ mechanical vapor compression distillation employing electricity as the energy input to power the process.<br>Separation may require the removal of 100 moles of $H_2O$ (solvent) and 1 mole $H_2O$ (part of sodium bisulfite dissolved, although practically part of the solvent due to properties of sodium bisulfite and sodium metabisulfite), which means 101 moles of $H_2O$ needs to be removed or distilled; or about 10,820.7 kg of $H_2O$ per metric ton of sodium bicarbonate produced.<br>Estimated Mechanical Vapor Compression (MVC) Distillation for 'ZLD' Energy Consumption: 15 kWh per $m^3$ of water<br>To remove 101 moles of $H_2O$ using MVC: 0.0273 kWh<br>To remove 10,820.7 kg of $H_2O$ using MVC: 162.31 kWh<br>Note: Residual sulfur dioxide may be separated or may vaporize during distillation. If desired, residual sulfur dioxide may be condensed with the separated water. Condensing the sulfur dioxide with the separated water or condensing water may be desirable as the water may be transferred to a sulfur dioxide absorption step. |
| 14 | 101 moles of $H_2O$; or 10,820.7 kg of $H_2O$ per metric ton of sodium bicarbonate produced |
| 15 | May comprise sulfur dioxide. It is important to note residual or excess sulfur dioxide may be condensed with or within the water, which may comprise '14'. |

Example Mass, Heat, and Power Flows for an Example Embodiment of FIG. 5

| ID | Description |
|---|---|
| 16 | 1 mole $Na_2S_2O_5(s)$; or 1,130.88 kg of $Na_2S_2O_5(s)$ per metric ton of sodium bicarbonate produced |
| 17 | '17' may comprise a calcination, or a thermal decomposition, or a desorption, or decomposition, or a combination thereof process. For the present example, '17' may employ a calciner employing heat as an energy input. Heat may be sourced from combustion or electricity or heat pump or steam or waste heat or thermal storage or solar thermal or other energy source, or a combination thereof.<br>Enthalpy of Decomposition of 2 $Na_2S_2O_5(s)$ to 2 $Na_2SO_3$ and 2 $SO_2(g)$ is: 87 kJ/mol $SO_2$ produced at greater than or equal to about 150° C.<br>To thermally decompose 2 moles of $Na_2S_2O_5(s)$ to 2 moles of 2 $Na_2SO_3$ and 2 moles of $SO_2(g)$ is: 174 kJ heat<br>To thermally decompose 2,261.9 kg of $Na_2S_2O_5(s)$ to 1,500 kg of 2 $Na_2SO_3$ and 761.9 kg of $SO_2(g)$ is: 1.036 GJ heat |
| 18 | 2 moles $SO_2(g)$; or 761.9 kg of $SO_2(g)$ per metric ton of sodium bicarbonate produced |
| 19 | '19' may comprise an absorption process. '19' may comprise a process for dissolving sulfur dioxide in water. '19' may comprise a process for producing sulfurous acid from sulfur dioxide and a solution comprising water. May require some thermal management, such as cooling or heating. May require some electricity or other power for, for example, pumping or mixing. |
| 20 | 2 moles of $SO_2(aq)$, 1 mole of $H_2O$; or 761.9 kg of $SO_2$ and 107.1 kg of $H_2O$ per metric ton of sodium bicarbonate produced<br>Solvent: 100 moles of $H_2O$; or 10,713.6 kg of $H_2O$ per metric ton of sodium bicarbonate produced<br>Note: Reactants may be dissolved in solvent. $SO_2$ is provided in the present example in a molar ratio to calcium based on the molar ratio in calcium bisulfite. In some embodiments, $SO_2$ may be in excess of or greater than the molar ratio of sulfur to calcium in calcium bisulfite. In some embodiments, $SO_2$ may be in less than the molar ratio of sulfur to calcium in calcium bisulfite. |
| 21 | 2 moles $Na_2SO_3(s)$; or 1,500 kg of $Na_2SO_3(s)$ per metric ton of sodium bicarbonate produced |
| 22 | '22' may comprise a mixing and/or dissolution process. '22' may comprise a process for dissolving sodium sulfite in water to form an aqueous sodium sulfite solution. |
| 23 | 2 moles $Na_2SO_3(aq)$; or 1,500 kg of $Na_2SO_3(aq)$ per metric ton of sodium bicarbonate produced<br>Solvent: 56 moles of $H_2O$; 5,999.6 kg of $H_2O$ per metric ton of sodium bicarbonate produced |
| 24 | 2 moles $CO_2(g)$; or 523.77 kg of $CO_2(g)$ per metric ton of sodium bicarbonate produced |
| 25 | '25' may comprise a gas-liquid contactor. '25' may comprise a gas-liquid contactor, or an absorber, or a reactor, or a precipitator, or a combination thereof process. May require some thermal management, such as cooling or heating. May require some electricity or other power for, for example, pumping or mixing. |
| 26 | 2 moles $NaHCO_3$(s and/or aq), 2 moles $NaHSO_3(aq)$; or 1,000 kg of $NaHCO_3$(s and/or aq) and 1,239.2 kg of $NaHSO_3(aq)$ per metric ton of sodium bicarbonate produced<br>Solvent: 54 moles of $H_2O$; or 5,785 kg of $H_2O$ per metric ton of sodium bicarbonate produced |
| 27 | '27' may comprise a solid-liquid separation process. May require some thermal management, such as cooling or heating. May require some electricity or other power for, for example, pumping or mixing. |
| 28 | 0.935 mole $NaHCO_3(s)$; or 467.5 kg of $NaHCO_3(s)$ per metric ton of sodium bicarbonate produced in total<br>Note: Based on solubility per 100 g water. Actual results may vary. |
| 29 | 1.064 moles $NaHCO_3(aq)$, 2 moles $NaHSO_3(aq)$; or 532.5 kg of $NaHCO_3$(s and/or aq) and 1,239.2 kg of $NaHSO_3(aq)$ per metric ton of sodium bicarbonate produced<br>Solvent: 54 moles of $H_2O$; or 5,785 kg of $H_2O$ per metric ton of sodium bicarbonate produced |
| 30 | '30' may comprise a process for distillation, or a water removal, or a drying, or a separation, or a crystallization, or cooling crystallization, or heating concentrating, or cooling concentration, or a combination thereof. For the present example, '30' may employ mechanical vapor compression distillation employing electricity as the energy input to power the process. '30' may involve precipitating or crystalizing remaining or residual sodium bicarbonate or sodium carbonate or both before precipitating or crystalizing remaining or residual sodium bisulfite or sodium metabisulfite.<br>Separation may require the removal of 54 moles of $H_2O$ (solvent) and 1 mole $H_2O$ (part of sodium bisulfite dissolved, although practically part of the solvent due to properties of sodium bisulfite and sodium metabisulfite), which means 55 moles of $H_2O$ needs to be removed or distilled; or about 5892.5 kg of $H_2O$ per metric ton of sodium bicarbonate produced.<br>Estimated Mechanical Vapor Compression (MVC) Distillation for 'ZLD' Energy Consumption: 15 kWh per m$^3$ of water<br>To remove 55 moles of $H_2O$ using MVC: 0.01485 kWh<br>To remove 5,892.5 kg of $H_2O$ using MVC: 88.39 kWh |
| 31 | 55 moles $H_2O$; or 5,892.5 kg of $H_2O$ per metric ton of sodium bicarbonate produced total. |

Example Mass, Heat, and Power Flows for an Example Embodiment of FIG. 5

ID Description

Makeup water comprising, for example 1 mole of $H_2O$ per every 55 moles of water, may be added to, for example, makeup for water lost in the sodium bicarbonate product. Some $H_2O$ in the sodium bicarbonate product may be recovered if sodium bicarbonate is converted to sodium carbonate and/or water in subsequent treatment or processing.

32 1.064 moles $NaHCO_3(s)$; or 532.5 kg of $NaHCO_3(s)$ per metric ton of sodium bicarbonate produced total 33 1 mole $Na_2S_2O_5(s)$; or 1,130.88 kg of $Na_2S_2O_5(s)$ per metric ton of sodium bicarbonate produced total 35 1 mole $CO_2(g)$; or 261.9 kg of $CO_2(g)$ per metric ton of sodium bicarbonate produced

Example Heat Input Requirements (FIG. 5)

| Summary of Example Heat and Power Requirements FIG. 5 | |
| --- | --- |
| Heat | 1.036 GJ heat per metric ton of sodium bicarbonate produced, heat may be at a temperature greater than or equal to 150° C. |
| Electricity | Heat may be supplied to, for example, 13.250.7 kWh per metric ton of sodium bicarbonate produced, assumes process for dewatering or removing water comprises a mechanical vapor compression distillation process or similar electricity powered process. |

Example CO2 Balance (FIG. 5)

Example $CO_2$ Net Balance from Example Heat, and Power Flows FIG. 5 (Assumes Heat is from Natural Gas and Power is Electricity and Electricity is USA Grid Electricity with Average USA Electricity Carbon Intensity)

| $CO_2$ Emissions per Metric Ton of Sodium Bicarbonate (Direct and Indirect Emissions) | Heat (Natural Gas Combustion) | 0.05116 metric tons $CO_2$ |
| --- | --- | --- |
| | Electric Power (based on USA average electric grid carbon intensity of 450 kg $CO_2$ per MWh) | 0.11282 metric tons $CO_2$ |
| | High Purity $CO_2$ produced by Sulfurous Acid + Carbonate Reaction (transferred to $CO_2$ utilization, or conversion, or sequestration in FIG. 5) | 0 |
| Net $CO_2$ Consumption | $CO_2$ Consumed in Produced Sodium Bicarbonate Output | −0.52381 metric tons $CO_2$ |
| Net $CO_2$ Balance (Negative Values are Good) | | −0.35983 metric tons $CO_2$ |

Example $CO_2$ Net Balance from Example Heat, and Power Flows FIG. 5 (Assumes Heat is from Natural Gas and Power is Electricity and Electricity is $CO_2$ Emissions Free)

| $CO_2$ Emissions per Metric Ton of Sodium Bicarbonate (Direct and Indirect Emissions) | Heat (Natural Gas Combustion) | 0.05116 metric tons $CO_2$ |
| --- | --- | --- |
| | Electric Power (based on hydropower or renewables or nuclear sourced electricity) | 0 metric tons $CO_2$ |
| | High Purity $CO_2$ produced by Sulfurous Acid + Carbonate Reaction (transferred to $CO_2$ utilization, or conversion, or sequestration in FIG. 5) | 0 |

Example $CO_2$ Net Balance from Example Heat, and Power Flows FIG. 5 (Assumes Heat is from Natural Gas and Power is Electricity and Electricity is $CO_2$ Emissions Free)

| | | |
|---|---|---|
| Net $CO_2$ Consumption | $CO_2$ Consumed in Produced Sodium Bicarbonate Output | −0.52381 metric tons $CO_2$ |
| Net $CO_2$ Balance (Negative Values are Good) | | −0.47265 metric tons $CO_2$ |

Example $CO_2$ Net Balance from Example Heat, and Power Flows FIG. 5 (Assumes Heat is from Electricity and Power is from Electricity and Electricity is $CO_2$ Emissions Free)

| | | |
|---|---|---|
| $CO_2$ Emissions per Metric Ton of Sodium Bicarbonate (Direct and Indirect Emissions) | Heat (based on hydropower or renewables or nuclear sourced electricity) | 0 metric tons $CO_2$ |
| | Electric Power (based on hydropower or renewables or nuclear sourced electricity) | 0 metric tons $CO_2$ |
| | High Purity $CO_2$ produced by Sulfurous Acid + Carbonate Reaction (transferred to $CO_2$ utilization, or conversion, or sequestration in FIG. 5) | 0 |
| Net $CO_2$ Consumption | $CO_2$ Consumed in Produced Sodium Bicarbonate Output | −0.52381 metric tons $CO_2$ |
| Net $CO_2$ Balance (Negative Values are Good) | | −0.52381 metric tons $CO_2$ |

Example Cost of Inputs, Value of Outputs, and Operating Profit (FIG. 5) 30

Example Inputs and Cost of Inputs (FIG. 5)

| Input | Cost per Standard Unit of Measure | Cost per Metric Ton of Sodium Bicarbonate Produced |
|---|---|---|
| Calcium Carbonate or Magnesium Carbonate or Limestone or a Combination Thereof | Crushed limestone: $30-$38 per metric ton | $20.25 |
| Sodium Sulfate | $80 per metric ton | $67.61 |
| Carbon Dioxide | Free ($CO_2$ Emissions or $CO_2$ Emissions Gas Mixture) | $0.00 |
| Water | $0.40 per metric ton | $0.04 |
| Heat (Natural Gas Combustion) | $3.00 per MMBtu | $2.95 |
| Electricity | $0.06 per kWh | $15.04 |
| Total Cost of Inputs per Metric Ton Sodium Bicarbonate Produced | | $105.89 |

| Example Outputs and Value of Outputs (FIG. 5) | | |
|---|---|---|
| Output | Value per Standard Unit of Measure | Value per Metric Ton of Sodium Bicarbonate Produced |
| High Purity $CO_2$ | $10-35 per ton ($20 for simplicity) | $5.24 |
| Calcium Sulfate | $120 per metric ton (high purity because it is precipitated gypsum) | $97.24 |
| Sodium Bicarbonate | $200 per metric ton | $200 |
| Total Value of Outputs per Metric Ton Sodium Bicarbonate Produced | | $302.48 |

| Inputs Cost, Value of Outputs, and Net Operating Profit (FIG. 5) | |
|---|---|
| Inputs Cost | $111.13 |
| Value of Outputs | $302.48 |
| Net Profit per Metric Ton of Sodium Bicarbonate Produced | $191.35 |

Example Figure Keys

| FIG. 3 Key | |
|---|---|
| ID | Description |
| 1 | An input material comprising a salt of silicate, or carbonate, or bicarbonate, or a salt of a weaker acid than sulfurous acid, or a salt an acid with a higher pKa than sulfurous acid, or a combination thereof. An input material comprising calcium silicate, or magnesium silicate, or calcium carbonate, or magnesium carbonate, or a calcium salt comprising silicon, or a magnesium salt comprising silicon, or a calcium - weak acid anion salt, or a magnesium - weak acid anion salt, or an alkaline earth - weak acid anion salt, or a mineral thereof, or a derivative thereof, or a combination thereof. |
| 2 | '2' may comprise a process for mixing or reacting or both an input material (such as, for example, '1') with sulfurous acid or a solution comprising dissolved sulfur dioxide. '2' may involve mixing sulfurous acid with a calcium or magnesium - weak acid salt. '2' may involve mixing sulfurous acid with a calcium or magnesium - weak acid salt to form calcium or magnesium sulfite or bisulfite. In the present embodiment, it may be desirable for the molar ratio of sulfur in the sulfurous acid reactant to the calcium and/or magnesium in the input material reactant to be about the same or greater than the molar ratio of sulfur to calcium or magnesium in dissolved calcium bisulfite or magnesium bisulfite. Sulfurous acid reactant in excess of the molar ratio than the molar ratio of sulfur to calcium or magnesium in dissolved calcium bisulfite or magnesium bisulfite may comprise 'excess' sulfurous acid. In some embodiments, 'excess' sulfurous acid may be desirable in '2' to, for example, improve reaction kinetics or otherwise facilitate the reaction to form calcium bisulfite and/or magnesium bisulfite. '2' may form dissolved calcium bisulfite and/or magnesium bisulfite and a weak acid product. Said weak acid product may comprise a solid, or a liquid, or a gas, or a combination thereof, which may be separated from the calcium bisulfite and/or magnesium bisulfite within '2' or in a separate step. For example, said weak acid product may comprise a solid comprising silicon dioxide or a silicon derivative. |
| 3 | '3' may comprise the products from '2'. '3' may involve transferring the products from '2' to a separation step. For example, in some embodiments, the products from '2' may comprise a solid-liquid slurry comprising an aqueous liquid phase solution of calcium bisulfite and/or magnesium bisulfite and a solid phase comprising silicon dioxide or a silicon derivative or a combination thereof. In some embodiments, the products from '2' may comprise at least a portion residual sulfurous acid or residual excess sulfurous acid, which may, if desired, remain at a liquid phase with the liquid solution comprising calcium bisulfite and/or magnesium bisulfite in '3'. |
| 4 | '4' may comprise a phase separation process. For example, '4' may comprise a process designed to separate at least a portion of the aqueous liquid phase solution comprising calcium bisulfite and/or magnesium bisulfite from at least a portion of the weak acid product in '3'. For example, '4' may comprise a solid-liquid separation process. For example, '4' may comprise a process designed to separate at least a portion of the aqueous liquid phase solution comprising calcium bisulfite and/or magnesium bisulfite from at least a portion of a solid weak acid product comprising silicon dioxide or a derivative of silicon. |
| 5 | '5' may comprise separated weak acid product. '5' may comprise separated solid phase weak acid product comprising silicon dioxide or a derivative of silicon. '5' may comprise an output. '5' may undergo further separation, treatment, or use, or a combination thereof. |
| 6 | '6' may comprise separated aqueous liquid phase solution comprising calcium bisulfite and/or magnesium bisulfite. '6' may comprise separated aqueous liquid phase solution comprising calcium bisulfite and/or magnesium bisulfite transferred from a solid-liquid separation process to a reaction with sodium sulfate. |
| 7 | '7' may comprise an input material comprising sodium sulfate. '7' may be at a solid phase, a liquid phase, or both. |
| 8 | '8' may comprise a process for mixing or reacting or both an input material, such as '7', with a separated aqueous liquid phase solution comprising calcium bisulfite and/or or magnesium bisulfite, such as '6'. Aqueous solution comprising calcium bisulfite or magnesium bisulfite may react with sodium sulfate to form an aqueous solution comprising sodium bisulfite and a solid phase comprising calcium sulfate or |

FIG. 3 Key

| ID | Description |
|---|---|
|  | magnesium sulfate. Residual dissolved calcium sulfate or magnesium sulfate may remain present in the aqueous solution comprising sodium bisulfite, although it is important to note the appreciably lower solubility of calcium sulfate or magnesium sulfate in water than sodium bisulfite. |
| 9 | '9' may comprise the products from '8'. '9' may involve transferring the products from '8' to a separation step. For example, in some embodiments, the products from '8' may comprise a solid-liquid slurry comprising an aqueous liquid phase solution of sodium bisulfite and a solid phase comprising calcium sulfate or magnesium sulfate. In some embodiments, the products from '8' may comprise at least a portion residual sulfurous acid or residual excess sulfurous acid, which may, if desired, remain at a liquid phase with the liquid solution comprising sodium bisulfite in '9'. |
| 10 | '10' may comprise a phase separation process. For example, '10' may comprise a process designed to separate at least a portion of the aqueous liquid phase solution comprising sodium bisulfite from at least a portion of the solid calcium sulfate or magnesium sulfate in '9'. For example, '10' may comprise a solid-liquid separation process. For example, '10' may comprise a process designed to separate at least a portion of the aqueous liquid phase solution comprising sodium sulfite from at least a portion of a solid comprising calcium sulfate or magnesium sulfate. |
| 11 | '11' may comprise a separated solid phase. '11' may comprise separated calcium sulfate, or magnesium sulfate, or both. '11' may comprise an output. It is important to note the separated calcium sulfate, or magnesium sulfate, or both may be of sufficiently high purity for commercial uses of gypsum. For some applications, '11' may be in an appropriate form of use or sale. For some applications, '11' may require additional treatment, or dehydration, or drying, or refining, or pulverizing, or a combination thereof. |
| 12 | '12' may comprise separated aqueous liquid phase solution comprising sodium bisulfite. '12' may comprise separated aqueous liquid phase solution comprising sodium bisulfite transferred from a solid-liquid separation process to a distillation, or a water removal, or a drying, or a separation, or a crystallization or a combination thereof step. |
| 13 | '13' may comprise a process for distillation, or a water removal, or a drying, or a separation, or a crystallization or a combination thereof. '13' may comprise a process employed to separate a salt solution into at least a portion water and at least a portion solid salt. '13' may comprise one or more or a combination of separation processes described herein. '13' may comprise, for example, MVC, or MED, or MSF, or membrane-based process, or a combination thereof. '13' may comprise a process for separating an aqueous solution comprising sodium bisulfite, such as '12', into at least a portion of water and at least a portion of solid sodium metabisulfite. '13' may comprise a process for separating an aqueous solution comprising sodium bisulfite, such as '12', into at least a portion of water, at least a portion of solid sodium metabisulfite, and at least a portion of residual sulfur dioxide. Said at least a portion of residual sulfur dioxide may comprise dissolved sulfur dioxide or sulfurous acid in the at least a portion of water, or may comprise gas phase sulfur dioxide, or may comprise liquid phase sulfur dioxide, or may comprise a combination thereof. |
| 14 | '14' may comprise water. '14' may comprise water and residual dissolved sulfur dioxide. '14' may comprise water transferred from a water removal or water separation process to an absorption process. |
| 15 | '15' may comprise at least a portion of gaseous sulfur dioxide. In embodiments employing excess sulfur dioxide and/or embodiments employing thermal or gas-liquid phase transition separation for water removal, gaseous sulfur dioxide may be produced during a water removal step, such as '14'. |
| 16 | '16' may comprise a separated solid. '16' may comprise solid sodium metabisulfite separated from water. '16' may comprise solid sodium metabisulfite separated from a solution comprising sodium bisulfite. '16' may comprise a solid comprising sodium metabisulfite, or sodium sulfite, or a combination thereof. '16' may comprise a solid transferred from a separation process or water removal process to a calcination or a thermal decomposition or a thermal desorption process. |
| 17 | '17' may comprise a calcination, or a thermal decomposition, or a desorption, or decomposition, or a combination thereof process. '17' may involve thermally decomposing or calcining sodium metabisulfite into solid sodium sulfite and gaseous sulfur dioxide. '17' may employ one or more processes described herein, or known in the art, or a combination thereof for calcination, or a thermal decomposition, or a desorption, or decomposition, or a combination thereof. |
| 18 | '18' may comprise gaseous sulfur dioxide produced from a process for calcination, or a thermal decomposition, or a desorption, or decomposition, or a combination thereof. '18' may comprise gaseous sulfur dioxide transferred to a sulfur dioxide absorption process or a process for producing sulfurous acid. |
| 19 | '19' may comprise an absorption process. '19' may comprise a process for dissolving sulfur dioxide in water. '19' may comprise a process for producing sulfurous acid from sulfur dioxide and a solution comprising water. '19' may comprise a process for producing concentrated or 'rich' sulfurous acid from sulfur dioxide and a solution comprising water. |

FIG. 3 Key

| ID | Description |
|----|-------------|
| 20 | '20' may comprise a solution comprising sulfur dioxide. '20' may comprise an aqueous sulfurous acid solution, or a concentrated sulfurous acid solution, or a combination thereof. '20' may comprise an aqueous sulfurous acid solution transferred from a sulfur dioxide absorption step to a sulfurous acid reaction step. |
| 21 | '21' may comprise a solid comprising at least a portion of sodium sulfite. '21' may comprise sodium sulfite transferred from a calcination step to a dissolution step. |
| 22 | '22' may comprise a mixing and/or dissolution process. '22' may comprise a process for dissolving sodium sulfite in water to form an aqueous sodium sulfite solution. |
| 23 | '23' may comprise a solution comprising sodium sulfite. '23' may comprise an aqueous sodium sulfite solution or a solution comprising dissolved sodium sulfite. '23' may comprise an aqueous sodium sulfite solution transferred from a dissolution step to an absorber, or gas-liquid contactor, or reactor, or a precipitator, or a combination thereof process. |
| 24 | '24' may comprise carbon dioxide. '24' may comprise input carbon dioxide. '24' may comprise a gas stream comprising carbon dioxide. '24' may comprise carbon dioxide in a pure gas stream, for example, a gas stream with greater than 93% carbon dioxide. '24' may comprise carbon dioxide in a mixture with other gases, which may include, but is not limited to, one or more or a combination of the following: flue gas, carbon dioxide in a gas mixture with air, air, biogas, stripped carbon dioxide, stripping gas comprising carbon dioxide, sour gas, natural gas, or other gas mixture comprising carbon dioxide. '24' may comprise carbon dioxide transferred to an absorber or reactor or both, wherein, for example, carbon dioxide may be reacted or absorbed. |
| 25 | '25' may comprise a gas-liquid contactor. '25' may comprise a gas-liquid contactor, or an absorber, or a reactor, or a precipitator, or a combination thereof process. '25' may comprise a process for reacting carbon dioxide with a solution comprising sodium sulfite to form sodium bicarbonate and sodium bisulfite. '25' may comprise a process for reacting carbon dioxide with a solution comprising sodium sulfite to form sodium bicarbonate, or sodium carbonate, or a combination thereof and sodium bisulfite. In some embodiments, '25' may be heated or allowed to increase in temperature during absorption to minimize sodium bicarbonate or sodium carbonate precipitation during absorption, then the solution may be cooled to produce sodium bicarbonate or sodium carbonate precipitate. Alternatively, or additionally, in some embodiments, '25' may be cooled to facilitate the precipitation of sodium bicarbonate or sodium carbonate. Alternatively, or additionally, in some embodiments, '25' may be cooled to facilitate the precipitation of sodium bicarbonate or sodium carbonate during the absorption of carbon dioxide. |
| 26 | '26' may comprise products of a reaction. '26' may comprise a solid-liquid mixture comprising sodium bicarbonate solid and an aqueous solution comprising sodium bisulfite. '26' may undergo further cooling to facilitate the precipitation of sodium bicarbonate, or sodium carbonate, or both. '26' may comprise solid-liquid mixture transferred from an absorber or reactor step to a solid-liquid separation step. |
| 27 | '27' may comprise a solid-liquid separation process. '27' may comprise a process for separating at least a portion of solid phase sodium bicarbonate, or sodium carbonate, or a combination thereof from at least a portion of liquid phase solution comprising aqueous sodium bisulfite. |
| 28 | '28' may comprise a solid separated by a solid-liquid separation process. '28' may comprise a solid comprising sodium bicarbonate, or sodium carbonate, or a combination thereof. In some embodiments, said sodium bicarbonate, or sodium carbonate, or a combination thereof may be transferred or used in an application. In some embodiments, said sodium bicarbonate, or sodium carbonate, or a combination thereof may undergo further treatment in some embodiments. For example, in some embodiments, said sodium bicarbonate, or sodium carbonate, or a combination thereof may undergo drying, or calcining, or further purification, or a combination thereof before use in one or more applications. |
| 29 | '29' may comprise a liquid solution separated from a solid following a solid-liquid separation process. '29' may comprise an aqueous solution comprising sodium bisulfite. '29' may comprise residual sodium bicarbonate, or sodium carbonate, or a combination thereof. '29' may comprise an aqueous solution comprising sodium bisulfite and residual dissolved sodium bicarbonate, or sodium carbonate, or a combination thereof. '29' may be transferred from a solid-liquid separation process to a process for distillation, or a water removal, or a drying, or a separation, or a crystallization or a combination thereof. |
| 30 | '30' may comprise a process for distillation, or a water removal, or a drying, or a separation, or a crystallization or a combination thereof. '30' may comprise a process for separating a solution comprising sodium bisulfite and/or residual sodium bicarbonate, or sodium carbonate, or a combination thereof into liquid, or solid sodium bicarbonate, or solid sodium carbonate, or solid sodium metabisulfite, or solid sodium sulfite, or a combination thereof. In some embodiments, '30' may involve removing or distilling at least a portion of water with subsequent or simultaneous precipitation of lower solubility salts, such as residual sodium bicarbonate, or residual sodium carbonate, or a combination thereof. In some embodiments, '30' may involve removing or distilling at least a portion of water with subsequent or simultaneous precipitation of sodium metabisulfite, or sodium sulfite, or a combination thereof. In some embodiments, a portion of carbon dioxide, or sulfur dioxide, or a combination thereof may be produced in '30'. |

FIG. 3 Key

| ID | Description |
|---|---|
| 31 | '31' may comprise at least a portion of water separated during a solid-liquid separation process. '31' may comprise water transferred from a process for distillation, or a water removal, or a drying, or a separation, or a crystallization or a combination thereof to a dissolution process. |
| 32 | '32' may comprise a solid comprising sodium bicarbonate, or sodium carbonate, or a combination thereof. In some embodiments, said sodium bicarbonate, or sodium carbonate, or a combination thereof may be transferred or used in an application. In some embodiments, said sodium bicarbonate, or sodium carbonate, or a combination thereof may undergo further treatment in some embodiments. For example, in some embodiments, said sodium bicarbonate, or sodium carbonate, or a combination thereof may undergo drying, or calcining, or further purification, or a combination thereof before use in one or more applications. |
| 33 | '33' may comprise a solid comprising sodium metabisulfite, or sodium sulfite, or a combination thereof. '33' may comprise a solid transferred from a separation process or water removal process to a calcination or a thermal decomposition or a thermal desorption process. |

FIG. 4 Key

| ID | Description |
|---|---|
| 1 | An input material comprising a salt of carbonate, or silicate, or bicarbonate, or a salt of a weaker acid than sulfurous acid, or a salt an acid with a higher pKa than sulfurous acid, or a combination thereof. An input material comprising calcium carbonate, or magnesium carbonate, or calcium silicate, or magnesium silicate, or a calcium salt comprising carbon, or a magnesium salt comprising carbon, or a calcium - weak acid anion salt, or a magnesium - weak acid anion salt, or an alkaline earth - weak acid anion salt, or a mineral thereof, or a derivative thereof, or a combination thereof. |
| 2 | '2' may comprise a process for mixing or reacting or both an input material (such as, for example, '1') with sulfurous acid or a solution comprising dissolved sulfur dioxide. '2' may involve mixing sulfurous acid with a calcium or magnesium - weak acid salt. '2' may involve mixing sulfurous acid with a calcium or magnesium - weak acid salt to form calcium or magnesium sulfite or bisulfite. In the present embodiment, it may be desirable for the molar ratio of sulfur in the sulfurous acid reactant to the calcium and/or magnesium in the input material reactant to be about the same or greater than the molar ratio of sulfur to calcium or magnesium in dissolved calcium bisulfite or magnesium bisulfite. Sulfurous acid reactant in excess of the molar ratio than the molar ratio of sulfur to calcium or magnesium in dissolved calcium bisulfite or magnesium bisulfite may comprise 'excess' sulfurous acid. In some embodiments, 'excess' sulfurous acid may be desirable in '2' to, for example, improve reaction kinetics or otherwise facilitate the reaction to form calcium bisulfite and/or magnesium bisulfite. '2' may form dissolved calcium bisulfite and/or magnesium bisulfite and a weak acid product. Said weak acid product may comprise a solid, or a liquid, or a gas, or a combination thereof, which may be separated from the calcium bisulfite and/or magnesium bisulfite within '2' or in a separate step. For example, said weak acid product may comprise gaseous carbon dioxide, which may be employed as a valuable byproduct or employed internally or a combination thereof. |
| 3 | '3' may comprise the liquid and/or solid products from '2'. '3' may involve transferring the products from '2' to a separation step. For example, in some embodiments, the products from '2' may comprise a solid-liquid slurry comprising an aqueous liquid phase solution of calcium bisulfite and/or magnesium bisulfite and a solid phase comprising one or more or a combination of the following: unreacted material, or silicon dioxide, or a silicon derivative, or a combination thereof. In some embodiments, the products from '2' may comprise at least a portion residual sulfurous acid or residual excess sulfurous acid, which may, if desired, remain at a liquid phase with the liquid solution comprising calcium bisulfite and/or magnesium bisulfite. |
| 4 | '4' may comprise a phase separation process. For example, '4' may comprise a process designed to separate at least a portion of the aqueous liquid phase solution comprising calcium bisulfite and/or magnesium bisulfite from solid phase material. For example, '4' may comprise a solid-liquid separation process. For example, '4' may comprise a process designed to separate at least a portion of the aqueous liquid phase solution comprising calcium bisulfite and/or magnesium bisulfite from at least a portion of a solid phase comprising, for example, one or more or a combination of the following: unreacted material, or silicon dioxide, or a silicon derivative, or a combination thereof. |
| 5 | '5' may comprise separated solid phase. For example, '5' may comprise a solid phase comprising, for example, including, but not limited to, one or more or a combination of the following: unreacted material, or silicon dioxide, or a silicon derivative, or a combination thereof. '5' may comprise an output. '5' may undergo further separation, treatment, or use, or a combination thereof. |
| 6 | '6' may comprise separated aqueous liquid phase solution comprising calcium bisulfite and/or magnesium bisulfite. '6' may comprise separated aqueous liquid |

-continued

FIG. 4 Key

| ID | Description |
|---|---|
| | phase solution comprising calcium bisulfite and/or magnesium bisulfite transferred from a solid-liquid separation process to a reaction with sodium sulfate. |
| 7 | '7' may comprise an input material comprising sodium sulfate. '7' may be at a solid phase, a liquid phase, or both. |
| 8 | '8' may comprise a process for mixing or reacting or both an input material, such as '7', with a separated aqueous liquid phase solution comprising calcium bisulfite and/or magnesium bisulfite, such as '6'. Aqueous solution comprising calcium bisulfite or magnesium bisulfite may react with sodium sulfate to form an aqueous solution comprising sodium bisulfite and a solid phase comprising calcium sulfate or magnesium sulfate. Residual dissolved calcium sulfate or magnesium sulfate may remain present in the aqueous solution comprising sodium bisulfite, although it is important to note the appreciably lower solubility of calcium sulfate or magnesium sulfate in water than sodium bisulfite. |
| 9 | '9' may comprise the products from '8'. '9' may involve transferring the products from '8' to a separation step. For example, in some embodiments, the products from '8' may comprise a solid-liquid slurry comprising an aqueous liquid phase solution of sodium bisulfite and a solid phase comprising calcium sulfate or magnesium sulfate. In some embodiments, the products from '8' may comprise at least a portion residual sulfurous acid or residual excess sulfurous acid, which may, if desired, remain at a liquid phase with the liquid solution comprising sodium bisulfite in '9'. |
| 10 | '10' may comprise a phase separation process. For example, '10' may comprise a process designed to separate at least a portion of the aqueous liquid phase solution comprising sodium bisulfite from at least a portion of the solid calcium sulfate or magnesium sulfate in '9'. For example, '10' may comprise a solid-liquid separation process. For example, '10' may comprise a process designed to separate at least a portion of the aqueous liquid phase solution comprising sodium sulfite from at least a portion of a solid comprising calcium sulfate or magnesium sulfate. |
| 11 | '11' may comprise a separated solid phase. '11' may comprise separated calcium sulfate, or magnesium sulfate, or both. '11' may comprise an output. It is important to note the separated calcium sulfate, or magnesium sulfate, or both may be of sufficiently high purity for commercial uses of gypsum. For some applications, '11' may be in an appropriate form of use or sale. For some applications, '11' may require additional treatment, or dehydration, or drying, or refining, or pulverizing, or a combination thereof. |
| 12 | '12' may comprise separated aqueous liquid phase solution comprising sodium bisulfite. '12' may comprise separated aqueous liquid phase solution comprising sodium bisulfite transferred from a solid-liquid separation process to a distillation, or a water removal, or a drying, or a separation, or a crystallization or a combination thereof step. |
| 13 | '13' may comprise a process for distillation, or a water removal, or a drying, or a separation, or a crystallization or a combination thereof. '13' may comprise a process employed to separate a salt solution into at least a portion water and at least a portion solid salt. '13' may comprise one or more or a combination of separation processes described herein. '13' may comprise, for example, MVC, or MED, or MSF, or membrane-based process, or a combination thereof. '13' may comprise a process for separating an aqueous solution comprising sodium bisulfite, such as '12', into at least a portion of water and at least a portion of solid sodium metabisulfite. '13' may comprise a process for separating an aqueous solution comprising sodium bisulfite, such as '12', into at least a portion of water, at least a portion of solid sodium metabisulfite, and at least a portion of residual sulfur dioxide. Said at least a portion of residual sulfur dioxide may comprise dissolved sulfur dioxide or sulfurous acid in the at least a portion of water, or may comprise gas phase sulfur dioxide, or may comprise liquid phase sulfur dioxide, or may comprise a combination thereof. |
| 14 | '14' may comprise water. '14' may comprise water and residual dissolved sulfur dioxide. '14' may comprise water transferred from a water removal or water separation process to an absorption process. |
| 15 | '15' may comprise at least a portion of gaseous sulfur dioxide. In embodiments employing excess sulfur dioxide and/or embodiments employing thermal or gas-liquid phase transition separation for water removal, gaseous sulfur dioxide may be produced during a water removal step, such as '14'. |
| 16 | '16' may comprise a separated solid. '16' may comprise solid sodium metabisulfite separated from water. '16' may comprise solid sodium metabisulfite separated from a solution comprising sodium bisulfite. '16' may comprise a solid comprising sodium metabisulfite, or sodium sulfite, or a combination thereof. '16' may comprise a solid transferred from a separation process or water removal process to a calcination or a thermal decomposition or a thermal desorption process. |
| 17 | '17' may comprise a calcination, or a thermal decomposition, or a desorption, or decomposition, or a combination thereof process. '17' may involve thermally decomposing or calcining sodium metabisulfite into solid sodium sulfite and gaseous sulfur dioxide. '17' may employ one or more processes described herein, or known in the art, or a combination thereof for calcination, or a thermal decomposition, or a desorption, or decomposition, or a combination thereof. |

-continued

FIG. 4 Key

| ID | Description |
|----|-------------|
| 18 | '18' may comprise gaseous sulfur dioxide produced from a process for calcination, or a thermal decomposition, or a desorption, or decomposition, or a combination thereof. '18' may comprise gaseous sulfur dioxide transferred to a sulfur dioxide absorption process or a process for producing sulfurous acid. |
| 19 | '19' may comprise an absorption process. '19' may comprise a process for dissolving sulfur dioxide in water. '19' may comprise a process for producing sulfurous acid from sulfur dioxide and a solution comprising water. '19' may comprise a process for producing concentrated or 'rich' sulfurous acid from sulfur dioxide and a solution comprising water. |
| 20 | '20' may comprise a solution comprising sulfur dioxide. '20' may comprise an aqueous sulfurous acid solution, or a concentrated sulfurous acid solution, or a combination thereof. '20' may comprise an aqueous sulfurous acid solution transferred from a sulfur dioxide absorption step to a sulfurous acid reaction step. |
| 21 | '21' may comprise a solid comprising at least a portion of sodium sulfite. '21' may comprise sodium sulfite transferred from a calcination step to a dissolution step. |
| 22 | '22' may comprise a mixing and/or dissolution process. '22' may comprise a process for dissolving sodium sulfite in water to form an aqueous sodium sulfite solution. |
| 23 | '23' may comprise a solution comprising sodium sulfite. '23' may comprise an aqueous sodium sulfite solution or a solution comprising dissolved sodium sulfite. '23' may comprise an aqueous sodium sulfite solution transferred from a dissolution step to an absorber, or gas-liquid contactor, or reactor, or a precipitator, or a combination thereof process. |
| 24 | '24' may comprise carbon dioxide. '24' may comprise input carbon dioxide. '24' may comprise a gas stream comprising carbon dioxide. '24' may comprise carbon dioxide in a pure gas stream, for example, a gas stream with greater than 93% carbon dioxide. '24' may comprise carbon dioxide in a mixture with other gases, which may include, but is not limited to, one or more or a combination of the following: flue gas, carbon dioxide in a gas mixture with air, air, biogas, stripped carbon dioxide, stripping gas comprising carbon dioxide, sour gas, natural gas, or other gas mixture comprising carbon dioxide. '24' may comprise carbon dioxide transferred to an absorber or reactor or both, wherein, for example, carbon dioxide may be reacted or absorbed. |
| 25 | '25' may comprise a gas-liquid contactor. '25' may comprise a gas-liquid contactor, or an absorber, or a reactor, or a precipitator, or a combination thereof process. '25' may comprise a process for reacting carbon dioxide with a solution comprising sodium sulfite to form sodium bicarbonate and sodium bisulfite. '25' may comprise a process for reacting carbon dioxide with a solution comprising sodium sulfite to form sodium bicarbonate, or sodium carbonate, or a combination thereof and sodium bisulfite. In some embodiments, '25' may be heated or allowed to increase in temperature during absorption to minimize sodium bicarbonate or sodium carbonate precipitation during absorption, then the solution may be cooled to produce sodium bicarbonate or sodium carbonate precipitate. Alternatively, or additionally, in some embodiments, '25' may be cooled to facilitate the precipitation of sodium bicarbonate or sodium carbonate. Alternatively, or additionally, in some embodiments, '25' may be cooled to facilitate the precipitation of sodium bicarbonate or sodium carbonate during the absorption of carbon dioxide. |
| 26 | '26' may comprise products of a reaction. '26' may comprise a solid-liquid mixture comprising sodium bicarbonate solid and an aqueous solution comprising sodium bisulfite. '26' may undergo further cooling to facilitate the precipitation of sodium bicarbonate, or sodium carbonate, or both. '26' may comprise solid-liquid mixture transferred from an absorber or reactor step to a solid-liquid separation step. |
| 27 | '27' may comprise a solid-liquid separation process. '27' may comprise a process for separating at least a portion of solid phase sodium bicarbonate, or sodium carbonate, or a combination thereof from at least a portion of liquid phase solution comprising aqueous sodium bisulfite. |
| 28 | '28' may comprise a solid separated by a solid-liquid separation process. '28' may comprise a solid comprising sodium bicarbonate, or sodium carbonate, or a combination thereof. In some embodiments, said sodium bicarbonate, or sodium carbonate, or a combination thereof may be transferred or used in an application. In some embodiments, said sodium bicarbonate, or sodium carbonate, or a combination thereof may undergo further treatment in some embodiments. For example, in some embodiments, said sodium bicarbonate, or sodium carbonate, or a combination thereof may undergo drying, or calcining, or further purification, or a combination thereof before use in one or more applications. |
| 29 | '29' may comprise a liquid solution separated from a solid following a solid-liquid separation process. '29' may comprise an aqueous solution comprising sodium bisulfite. '29' may comprise residual sodium bicarbonate, or sodium carbonate, or a combination thereof. '29' may comprise an aqueous solution comprising sodium bisulfite and residual dissolved sodium bicarbonate, or sodium carbonate, or a combination thereof. '29' may be transferred from a solid-liquid separation process to a process for distillation, or a water removal, or a drying, or a separation, or a crystallization or a combination thereof. |
| 30 | '30' may comprise a process for distillation, or a water removal, or a drying, or a separation, or a crystallization or a combination thereof. '30' may comprise a process for separating a solution comprising sodium bisulfite and/or residual sodium bicarbonate, or sodium carbonate, or a combination thereof into liquid, or solid |

FIG. 4 Key

| ID | Description |
|---|---|
| | sodium bicarbonate, or solid sodium carbonate, or solid sodium metabisulfite, or solid sodium sulfite, or a combination thereof. In some embodiments, '30' may involve removing or distilling at least a portion of water with subsequent or simultaneous precipitation of lower solubility salts, such as residual sodium bicarbonate, or residual sodium carbonate, or a combination thereof. In some embodiments, '30' may involve removing or distilling at least a portion of water with subsequent or simultaneous precipitation of sodium metabisulfite, or sodium sulfite, or a combination thereof. In some embodiments, a portion of carbon dioxide, or sulfur dioxide, or a combination thereof may be produced in '30'. |
| 31 | '31' may comprise at least a portion of water separated during a solid-liquid separation process. '31' may comprise water transferred from a process for distillation, or a water removal, or a drying, or a separation, or a crystallization or a combination thereof to a dissolution process. |
| 32 | '32' may comprise a solid comprising sodium bicarbonate, or sodium carbonate, or a combination thereof. In some embodiments, said sodium bicarbonate, or sodium carbonate, or a combination thereof may be transferred or used in an application. In some embodiments, said sodium bicarbonate, or sodium carbonate, or a combination thereof may undergo further treatment in some embodiments. For example, in some embodiments, said sodium bicarbonate, or sodium carbonate, or a combination thereof may undergo drying, or calcining, or further purification, or a combination thereof before use in one or more applications. |
| 33 | '33' may comprise a solid comprising sodium metabisulfite, or sodium sulfite, or a combination thereof. '33' may comprise a solid transferred from a separation process or water removal process to a calcination or a thermal decomposition or a thermal desorption process. |
| 34 | '34' may comprise gaseous carbon dioxide. '34' may comprise gaseous carbon dioxide produced from the reaction of sulfurous acid with a carbonate or bicarbonate salt in '2'. '34' may comprise high concentration, or high purity, or high partial pressure carbon dioxide. '34' may be reacted with at least a portion sodium sulfite to produce sodium bicarbonate and/or sodium bisulfite. |

FIG. 5 Key

| ID | Description |
|---|---|
| 1 | An input material comprising a salt of carbonate, or silicate, or bicarbonate, or a salt of a weaker acid than sulfurous acid, or a salt an acid with a higher pKa than sulfurous acid, or a combination thereof. An input material comprising calcium carbonate, or magnesium carbonate, or calcium silicate, or magnesium silicate, or a calcium salt comprising carbon, or a magnesium salt comprising carbon, or a mineral thereof, or a derivative thereof, or a calcium - weak acid anion salt, or a magnesium - weak acid anion salt, or an alkaline earth - weak acid anion salt, or a combination thereof. |
| 2 | '2' may comprise a process for mixing or reacting or both an input material (such as, for example, '1') with sulfurous acid or a solution comprising dissolved sulfur dioxide. '2' may involve mixing sulfurous acid with a calcium or magnesium - weak acid salt. '2' may involve mixing sulfurous acid with a calcium or magnesium - weak acid salt to form calcium or magnesium sulfite or bisulfite. In the present embodiment, it may be desirable for the molar ratio of sulfur in the sulfurous acid reactant to the calcium and/or magnesium in the input material reactant to be about the same or greater than the molar ratio of sulfur to calcium or magnesium in dissolved calcium bisulfite or magnesium bisulfite. Sulfurous acid reactant in excess of the molar ratio than the molar ratio of sulfur to calcium or magnesium in dissolved calcium bisulfite or magnesium bisulfite may comprise 'excess' sulfurous acid. In some embodiments, 'excess' sulfurous acid may be desirable in '2' to, for example, improve reaction kinetics or otherwise facilitate the reaction to form calcium bisulfite and/or magnesium bisulfite. '2' may form dissolved calcium bisulfite and/or magnesium bisulfite and a weak acid product. Said weak acid product may comprise a solid, or a liquid, or a gas, or a combination thereof, which may be separated from the calcium bisulfite and/or magnesium bisulfite within '2' or in a separate step. For example, said weak acid product may comprise gaseous carbon dioxide, which may be employed as a valuable byproduct or employed internally or a combination thereof. |
| 3 | '3' may comprise the liquid and/or solid products from '2'. '3' may involve transferring the products from '2' to a separation step. For example, in some embodiments, the products from '2' may comprise a solid-liquid slurry comprising an aqueous liquid phase solution of calcium bisulfite and/or magnesium bisulfite and a solid phase comprising one or more or a combination of the following: unreacted material, or silicon dioxide, or a silicon derivative, or a combination thereof. In some embodiments, the products from '2' may comprise at least a portion residual sulfurous acid or residual excess sulfurous acid, which may, if desired, remain at a liquid phase with the liquid solution comprising calcium bisulfite and/or magnesium bisulfite. |
| 4 | '4' may comprise a phase separation process. For example, '4' may comprise a process designed to separate at least a portion of the aqueous liquid phase solution |

-continued

FIG. 5 Key

| ID | Description |
|---|---|
| | comprising calcium bisulfite and/or magnesium bisulfite from solid phase material. For example, '4' may comprise a solid-liquid separation process. For example, '4' may comprise a process designed to separate at least a portion of the aqueous liquid phase solution comprising calcium bisulfite and/or magnesium bisulfite from at least a portion of a solid phase comprising, for example, one or more or a combination of the following: unreacted material, or silicon dioxide, or a silicon derivative, or a combination thereof. |
| 5 | '5' may comprise separated solid phase. For example, '5' may comprise a solid phase comprising, for example, including, but not limited to, one or more or a combination of the following: unreacted material, or silicon dioxide, or a silicon derivative, or a combination thereof. '5' may comprise an output. '5' may undergo further separation, treatment, or use, or a combination thereof. |
| 6 | '6' may comprise separated aqueous liquid phase solution comprising calcium bisulfite and/or magnesium bisulfite. '6' may comprise separated aqueous liquid phase solution comprising calcium bisulfite and/or magnesium bisulfite transferred from a solid-liquid separation process to a reaction with sodium sulfate. |
| 7 | '7' may comprise an input material comprising sodium sulfate. '7' may be at a solid phase, a liquid phase, or both. |
| 8 | '8' may comprise a process for mixing or reacting or both an input material, such as '7', with a separated aqueous liquid phase solution comprising calcium bisulfite and/or magnesium bisulfite, such as '6'. Aqueous solution comprising calcium bisulfite or magnesium bisulfite may react with sodium sulfate to form an aqueous solution comprising sodium bisulfite and a solid phase comprising calcium sulfate or magnesium sulfate. Residual dissolved calcium sulfate or magnesium sulfate may remain present in the aqueous solution comprising sodium bisulfite, although it is important to note the appreciably lower solubility of calcium sulfate or magnesium sulfate in water than sodium bisulfite. |
| 9 | '9' may comprise the products from '8'. '9' may involve transferring the products from '8' to a separation step. For example, in some embodiments, the products from '8' may comprise a solid-liquid slurry comprising an aqueous liquid phase solution of sodium bisulfite and a solid phase comprising calcium sulfate or magnesium sulfate. In some embodiments, the products from '8' may comprise at least a portion residual sulfurous acid or residual excess sulfurous acid, which may, if desired, remain at a liquid phase with the liquid solution comprising sodium bisulfite in '9'. |
| 10 | '10' may comprise a phase separation process. For example, '10' may comprise a process designed to separate at least a portion of the aqueous liquid phase solution comprising sodium bisulfite from at least a portion of the solid calcium sulfate or magnesium sulfate in '9'. For example, '10' may comprise a solid-liquid separation process. For example, '10' may comprise a process designed to separate at least a portion of the aqueous liquid phase solution comprising sodium sulfite from at least a portion of a solid comprising calcium sulfate or magnesium sulfate. |
| 11 | '11' may comprise a separated solid phase. '11' may comprise separated calcium sulfate, or magnesium sulfate, or both. '11' may comprise an output. It is important to note the separated calcium sulfate, or magnesium sulfate, or both may be of sufficiently high purity for commercial uses of gypsum. For some applications, '11' may be in an appropriate form of use or sale. For some applications, '11' may require additional treatment, or dehydration, or drying, or refining, or pulverizing, or a combination thereof. |
| 12 | '12' may comprise separated aqueous liquid phase solution comprising sodium bisulfite. '12' may comprise separated aqueous liquid phase solution comprising sodium bisulfite transferred from a solid-liquid separation process to a distillation, or a water removal, or a drying, or a separation, or a crystallization or a combination thereof step. |
| 13 | '13' may comprise a process for distillation, or a water removal, or a drying, or a separation, or a crystallization or a combination thereof. '13' may comprise a process employed to separate a salt solution into at least a portion water and at least a portion solid salt. '13' may comprise one or more or a combination of separation processes described herein. '13' may comprise, for example, MVC, or MED, or MSF, or membrane-based process, or a combination thereof. '13' may comprise a process for separating an aqueous solution comprising sodium bisulfite, such as '12', into at least a portion of water and at least a portion of solid sodium metabisulfite. '13' may comprise a process for separating an aqueous solution comprising sodium bisulfite, such as '12', into at least a portion of water, at least a portion of solid sodium metabisulfite, and at least a portion of residual sulfur dioxide. Said at least a portion of residual sulfur dioxide may comprise dissolved sulfur dioxide or sulfurous acid in the at least a portion of water, or may comprise gas phase sulfur dioxide, or may comprise liquid phase sulfur dioxide, or may comprise a combination thereof. |
| 14 | '14' may comprise water. '14' may comprise water and residual dissolved sulfur dioxide. '14' may comprise water transferred from a water removal or water separation process to an absorption process. |
| 15 | '15' may comprise at least a portion of gaseous sulfur dioxide. In embodiments employing excess sulfur dioxide and/or embodiments employing thermal or gas-liquid phase transition separation for water removal, gaseous sulfur dioxide may be produced during a water removal step, such as '14'. |

FIG. 5 Key

| ID | Description |
|---|---|
| 16 | '16' may comprise a separated solid. '16' may comprise solid sodium metabisulfite separated from water. '16' may comprise solid sodium metabisulfite separated from a solution comprising sodium bisulfite. '16' may comprise a solid comprising sodium metabisulfite, or sodium sulfite, or a combination thereof. '16' may comprise a solid transferred from a separation process or water removal process to a calcination or a thermal decomposition or a thermal desorption process. |
| 17 | '17' may comprise a calcination, or a thermal decomposition, or a desorption, or decomposition, or a combination thereof process. '17' may involve thermally decomposing or calcining sodium metabisulfite into solid sodium sulfite and gaseous sulfur dioxide. '17' may employ one or more processes described herein, or known in the art, or a combination thereof for calcination, or a thermal decomposition, or a desorption, or decomposition, or a combination thereof. |
| 18 | '18' may comprise gaseous sulfur dioxide produced from a process for calcination, or a thermal decomposition, or a desorption, or decomposition, or a combination thereof. '18' may comprise gaseous sulfur dioxide transferred to a sulfur dioxide absorption process or a process for producing sulfurous acid. |
| 19 | '19' may comprise an absorption process. '19' may comprise a process for dissolving sulfur dioxide in water. '19' may comprise a process for producing sulfurous acid from sulfur dioxide and a solution comprising water. '19' may comprise a process for producing concentrated or 'rich' sulfurous acid from sulfur dioxide and a solution comprising water. |
| 20 | '20' may comprise a solution comprising sulfur dioxide. '20' may comprise an aqueous sulfurous acid solution, or a concentrated sulfurous acid solution, or a combination thereof. '20' may comprise an aqueous sulfurous acid solution transferred from a sulfur dioxide absorption step to a sulfurous acid reaction step. |
| 21 | '21' may comprise a solid comprising at least a portion of sodium sulfite. '21' may comprise sodium sulfite transferred from a calcination step to a dissolution step. |
| 22 | '22' may comprise a mixing and/or dissolution process. '22' may comprise a process for dissolving sodium sulfite in water to form an aqueous sodium sulfite solution. |
| 23 | '23' may comprise a solution comprising sodium sulfite. '23' may comprise an aqueous sodium sulfite solution or a solution comprising dissolved sodium sulfite. '23' may comprise an aqueous sodium sulfite solution transferred from a dissolution step to an absorber, or gas-liquid contactor, or reactor, or a precipitator, or a combination thereof process. |
| 24 | '24' may comprise carbon dioxide. '24' may comprise input carbon dioxide. '24' may comprise a gas stream comprising carbon dioxide. '24' may comprise carbon dioxide in a pure gas stream, for example, a gas stream with greater than 93% carbon dioxide. '24' may comprise carbon dioxide in a mixture with other gases, which may include, but is not limited to, one or more or a combination of the following: flue gas, carbon dioxide in a gas mixture with air, air, biogas, stripped carbon dioxide, stripping gas comprising carbon dioxide, sour gas, natural gas, or other gas mixture comprising carbon dioxide. '24' may comprise carbon dioxide transferred to an absorber or reactor or both, wherein, for example, carbon dioxide may be reacted or absorbed. |
| 25 | '25' may comprise a gas-liquid contactor. '25' may comprise a gas-liquid contactor, or an absorber, or a reactor, or a precipitator, or a combination thereof process. '25' may comprise a process for reacting carbon dioxide with a solution comprising sodium sulfite to form sodium bicarbonate and sodium bisulfite. '25' may comprise a process for reacting carbon dioxide with a solution comprising sodium sulfite to form sodium bicarbonate, or sodium carbonate, or a combination thereof and sodium bisulfite. In some embodiments, '25' may be heated or allowed to increase in temperature during absorption to minimize sodium bicarbonate or sodium carbonate precipitation during absorption, then the solution may be cooled to produce sodium bicarbonate or sodium carbonate precipitate. Alternatively, or additionally, in some embodiments, '25' may be cooled to facilitate the precipitation of sodium bicarbonate or sodium carbonate. Alternatively, or additionally, in some embodiments, '25' may be cooled to facilitate the precipitation of sodium bicarbonate or sodium carbonate during the absorption of carbon dioxide. |
| 26 | '26' may comprise products of a reaction. '26' may comprise a solid-liquid mixture comprising sodium bicarbonate solid and an aqueous solution comprising sodium bisulfite. '26' may undergo further cooling to facilitate the precipitation of sodium bicarbonate, or sodium carbonate, or both. '26' may comprise solid-liquid mixture transferred from an absorber or reactor step to a solid-liquid separation step. |
| 27 | '27' may comprise a solid-liquid separation process. '27' may comprise a process for separating at least a portion of solid phase sodium bicarbonate, or sodium carbonate, or a combination thereof from at least a portion of liquid phase solution comprising aqueous sodium bisulfite. |
| 28 | '28' may comprise a solid separated by a solid-liquid separation process. '28' may comprise a solid comprising sodium bicarbonate, or sodium carbonate, or a combination thereof. In some embodiments, said sodium bicarbonate, or sodium carbonate, or a combination thereof may be transferred or used in an application. In some embodiments, said sodium bicarbonate, or sodium carbonate, or a combination thereof may undergo further treatment in some embodiments. For example, in some embodiments, said sodium bicarbonate, or sodium carbonate, or a combination thereof may undergo drying, or calcining, or further purification, or a combination thereof before use in one or more applications. |

FIG. 5 Key

| ID | Description |
|---|---|
| 29 | '29' may comprise a liquid solution separated from a solid following a solid-liquid separation process. '29' may comprise an aqueous solution comprising sodium bisulfite. '29' may comprise residual sodium bicarbonate, or sodium carbonate, or a combination thereof. '29' may comprise an aqueous solution comprising sodium bisulfite and residual dissolved sodium bicarbonate, or sodium carbonate, or a combination thereof. '29' may be transferred from a solid-liquid separation process to a process for distillation, or a water removal, or a drying, or a separation, or a crystallization or a combination thereof. |
| 30 | '30' may comprise a process for distillation, or a water removal, or a drying, or a separation, or a crystallization or a combination thereof. '30' may comprise a process for separating a solution comprising sodium bisulfite and/or residual sodium bicarbonate, or sodium carbonate, or a combination thereof into liquid, or solid sodium bicarbonate, or solid sodium carbonate, or solid sodium metabisulfite, or solid sodium sulfite, or a combination thereof. In some embodiments, '30' may involve removing or distilling at least a portion of water with subsequent or simultaneous precipitation of lower solubility salts, such as residual sodium bicarbonate, or residual sodium carbonate, or a combination thereof. In some embodiments, '30' may involve removing or distilling at least a portion of water with subsequent or simultaneous precipitation of sodium metabisulfite, or sodium sulfite, or a combination thereof. In some embodiments, a portion of carbon dioxide, or sulfur dioxide, or a combination thereof may be produced in '30'. |
| 31 | '31' may comprise at least a portion of water separated during a solid-liquid separation process. '31' may comprise water transferred from a process for distillation, or a water removal, or a drying, or a separation, or a crystallization or a combination thereof to a dissolution process. |
| 32 | '32' may comprise a solid comprising sodium bicarbonate, or sodium carbonate, or a combination thereof. In some embodiments, said sodium bicarbonate, or sodium carbonate, or a combination thereof may be transferred or used in an application. In some embodiments, said sodium bicarbonate, or sodium carbonate, or a combination thereof may undergo further treatment in some embodiments. For example, in some embodiments, said sodium bicarbonate, or sodium carbonate, or a combination thereof may undergo drying, or calcining, or further purification, or a combination thereof before use in one or more applications. |
| 33 | '33' may comprise a solid comprising sodium metabisulfite, or sodium sulfite, or a combination thereof. '33' may comprise a solid transferred from a separation process or water removal process to a calcination or a thermal decomposition or a thermal desorption process. |
| 35 | '35' may comprise gaseous carbon dioxide. '35' may comprise gaseous carbon dioxide produced from the reaction of sulfurous acid with a carbonate or bicarbonate salt in '2'. '35' may comprise high concentration, or high purity, or high partial pressure carbon dioxide. '35' may undergo further separation, or treatment, or compression, or phase change into a supercritical fluid, or phase change into a liquid, or a combination thereof. '35' may comprise a valuable byproduct. |

DESCRIPTION OF AN EXAMPLE EMBODIMENT (1) Use reaction of Calcium Bisulfite with Sodium Sulfate to produce Calcium Sulfate (Gypsum) and Sodium Bisulfite (aqueous).
(2) Decompose Sodium Bisulfite (Sodium Metabisulfite) into Sodium Sulfite.
(3) Absorb $CO_2$ into Sodium Sulfite solution to produce Sodium Bicarbonate (at least a portion of which may be precipitated or otherwise separated) and Sodium Bisulfite (aqueous). Recirculate a portion of the remaining Sodium Bisulfite aqueous solution to step 2 (above)

Notes

Note: 'WA' may comprise a weak acid, which may include, but not limited to, silicic acid, or orthosilicic acid, or silicon acid derivatives, or silicon minerals, or silicon acids, or aluminates, or ferrates, or a combination thereof.

Note: Calcium or magnesium—weak acid input may comprise, for example, including, but not limited to, one or more or a combination of the following: carbonates, or bicarbonates, or silicates, or silicate derivatives, or minerals, or concrete, or cement, or waste concrete, or waste cement, or steel slag, or fly ash, or ash, or limestone, or rock.

Note: Concentration of $NaHSO_3$ produced from one step may be increased to match concentration of $NaHSO_3$ from another step by, for example, distillation, or membrane based process, or evaporation, or other separation process, or other concentrating process, or a combination thereof.

Note: A portion $SO_2$ may desorb during some concentrating processes

Note: CO2 may desorb during some concentration processes

Water produced from some separation processes may employed to absorb SO2 in to form H2SO3 or aqueous sulfurous acid or sulfurous acid.

Note: In some embodiments, higher partial pressure $CO_2$, or higher concentration $CO_2$, or pure $CO_2(g)$, or high partial pressure $CO_2(g)$, or $CO_2(l)$, or $CO_2(g)$, may be employed to facilitate formation of bicarbonate salts. For example, in some embodiments, one or more or a combination of the following may be employed:

At least a portion of $CO_2$ input may be sourced from a reaction of calcium carbonate with sulfurous acid At least a portion of $CO_2$ input may be sources from $CO_2$ sources produced within the process, or other $CO_2$ sources, or a combination thereof At least a portion of $CO_2$ input may be sourced from $CO_2$ captured from a combustion source, or a combustion source employed to produce heat, or emissions source, or air, or geological $CO_2$ source, or natural $CO_2$ source, or a combination thereof.

Note: $CO_2$ sources include, but are not limited to, one or more or any combination of the following: Air, or combustion, or emissions gases, or refinery gases, or Power Plant (Natural gas, coal, oil, petcoke, biofuel, municipal waste), Cement production, chemical production, Waste Water Treatment, Landfill gas, Air, Metal production/refining (such as Iron, Steel, Aluminum, etc.), Glass production, Oil refineries, LNG liquification, HVAC, Transportation vehicles (ships, boats, cars, buses, trains, trucks, airplanes), Natural Gas, Biogas, Alcohol fermentation, Volcanic Activity, Decomposing leaves/biomass, Septic tank, Respiration, Manufacturing facilities, Fertilizer production, or Geothermal processes where CO2(g)

Additional Notes

Note: Some embodiments may be designed to operate as a low temperature process, where the solutions and/or solid reagents in thermal desorption or decomposition may undergo or operate thermal desorption or decomposition at less than 150° C., or less than 200° C., or less than 250° C., or less than 300° C., or less than 350° C.

Note: In some embodiments, at least a portion of heat may be supplied by a heat pump, or a refrigeration cycle, or a combination thereof. A heat pump may comprise, including, but not limited to, a mechanical, or absorption, or a combination thereof process. A heat pump may be powered by, including, but not limited to, electricity, or heat, or photons, or chemical reaction, or radiation, or mechanical work, or pneumatic process, or hydraulic process, or expansion, or compression, or evaporation, or absorption, or vapor pressure differences, or osmotic pressure differences, or temperature differences, or pressure differences, or a combination thereof.

Note: Heat greater than or equal to 150° C. can be supplied by heat pumps known in the art. Heat pumps may reduce the total energy consumption required to supply heat.

Note: In some embodiments, at least a portion of $CO_2$ may be supplied by a gas stream comprising $CO_2$ and at least one other gas. For example, said gas stream may comprise, including, but not limited to, one or more or a combination of the following: air, flue gas, waste gases, sour gas, or fermentation gases, purge gases, or a combination thereof.

For example, $Na_2SO_3$(aq) or sodium sulfite may be contacted with a gas mixture comprising $CO_2$, such as flue gas, and absorb $CO_2$ from said gas to form, for example, at least a portion of $Na_2CO_3$(aq), or $NaHCO_3$, or a combination thereof. In some embodiments, a subsequent step may involve further reacting with higher partial pressure $CO_2$ to enable, for example, maximum conversion efficiency to $NaHCO_3$.

It may be desirable to contact $Na_2SO_3$ and/or $NaHSO_3$ and/or other sulfites and/or bisulfites exclusively with gases or fluids comprising low, or minimal, or practically no presence of oxygen to, for example, prevent the formation of sulfates and/or bisulfates.

Note: In some embodiments, sulfides and/or hydrogen sulfide may comprise a weak acid or weak acid anion.

Note: Sources of low cost sodium sulfate may possess a higher purity or require less treatment to produce high purity sodium sulfite than common sources of sodium chloride, such as sodium chloride brines. The use of relatively high purity sodium sulfate input may result in lower pre-treatment or purification costs, especially compared to some sodium chloride input sources.

Note: Sodium sulfate may be employed in the reaction with calcium bisulfite because calcium sulfate is minimally soluble or practically insoluble in water, especially relative to sodium bisulfite reaction product. The bulk of calcium sulfate may be separated by, for example, one or more processes for solid-liquid separation.

Additional Notes

Note: Dehydrating sodium bicarbonate or sodium carbonate can be energy intensive and may be unnecessary in embodiments where the end application of sodium bicarbonate or sodium carbonate can employ wet or hydrates sodium bicarbonate or sodium carbonate. For example, in embodiments producing sodium bicarbonate or sodium carbonate for applications which are or may be conducted at an aqueous or wet state, it may be desirable to allow the sodium bicarbonate to remain at a hydrated state. Applications which are or may be conducted at an aqueous or wet state may include, but are not limited to, one or more or a combination of the following: water treatment, or water processing, or waste water treatment, or pH balancing, or alkalinization, or sulfur dioxide scrubbing, or nitrogen oxide scrubbing, or acid scrubbing, or addition to ocean water or other water body to increase alkalinity or enable effective $CO_2$ sequestration.

Note: Advantageously, unlike sodium bicarbonate or sodium carbonate, sodium bisulfite precipitates or solidifies or crystalizes at a non-hydrated state. Sodium bisulfite is not known to exist in a solid form. The solid form of sodium bisulfite may be sodium metabisulfite, which comprises sodium bisulfite without the water molecule. When a solution comprising sodium bisulfite undergoes precipitation or crystallization, the solid salt which forms may comprise sodium metabisulfite. Advantageously, calcining sodium metabisulfite or 'precipitated sodium bisulfite' to, for example, sodium sulfite, may not require dehydrating sodium metabisulfite, which may enable lower energy consumption. For comparison, decomposing wet sodium bicarbonate to sodium carbonate at a hydrated state and carbon dioxide requires 0.92 GJ per ton of sodium carbonate product, while decomposing wet sodium bicarbonate to sodium carbonate at a de-hydrated state requires 3.7 GJ per ton of sodium carbonate.

Note: Separations for recovering water, or concentrating, or crystalizing, or precipitating, or separating, or a combination thereof may include, but are not limited to, one or more or a combination of the following: mechanical vapor compression (MVC), or mechanical vapor recompression, or multi-effect distillation (MED), or multi-stage flash distillation (MSF), or vapor compression (VC) distillation, or vacuum vapor compression (VVC), or membrane distillation, or evaporation, or distillation, or forward osmosis, or reverse osmosis, or nanofiltration, or hot nanofiltration, or hot reverse osmosis, or hot concentrating followed by cooling precipitation, or hot concentrating followed by cooling precipitation and solid-liquid separation, or heating precipitation, centrifuge, settling, or filter, or rotary filter, or calcining, or desorption, or absorption, or coalescing, or decanting, or aggregation, or coagulation, or frothing, or density based methods, or surface tension based methods, or foaming separation, emulsification, or de-emulsification, or flocculation, solventing out, or salting out, or cooling precipitation, or heating, or cryodesalination, or freeze desalination, or zero liquid discharge processes, or crystallization processes, or electrodialysis reversal (EDR), or electrodialysis process.

Additional Notes

Note: Technologies for transforming salt brines into water and crystalized salt, which may be considered 'zero-liquid discharge' technologies, generally require 15 to 40 kWh per m$^3$ of water recovered.

The process in FIG. 4 may be the same as the process in FIG. 3, except FIG. 4 may involve a process employing a calcium carbonate or magnesium carbonate input. FIG. 4 may involve producing $CO_2$(g) in the production of calcium sulfite or calcium bisulfite or both. The produced $CO_2$(g) may be reacted in a later step to produce sodium bicarbonate or sodium carbonate or both. In some embodiments, the produced $CO_2$ may be reacted or absorbed or both in a concentrated or almost pure or pure form. In some embodiments, the produced $CO_2$ may be mixed with a $CO_2$ gas mixture, such as flue gas, increasing the concentration of said $CO_2$ gas mixture before employing the $CO_2$ gas mixture to produce sodium bicarbonate, or sodium carbonate, or a combination thereof.

Note: Advantageously, some embodiments of the present invention may produce sodium bicarbonate or sodium carbonate without requiring the presence of ammonia or an ammonia catalyst.

Note: Some embodiments may employ an inert gas, such as nitrogen or argon, or a gas other than diatomic oxygen, such as $CO_2$, or a combination thereof in the headspace to prevent, for example, oxidation of or reaction of oxygen with sulfite, metabisulfite, bisulfite, sulfur dioxide, sulfurous acid, or a combination thereof.

Additional Notes

Note: Potassium or other alkali or alkali salts may be employed instead of or in addition to sodium. Alternatively, or additionally, ammonia, or ammonium, or amine, or a combination thereof may be employed instead of or in addition to sodium. Alternatively, or additionally, zinc may be employed instead of or in addition to sodium. Zinc can form sulfites and/or metabisulfites.

Note: Magnesium or other alkaline earth or alkaline earth salts may be employed instead of or in addition to calcium. Alternatively, or additionally, zinc or other metal cation may be employed instead of or in addition to sodium. Zinc can form sulfites and/or metabisulfites.

Note: Concrete waste is produced in excess of 600 million tons annually in the USA alone, which is more than twice the amount of generated municipal solid waste.

Note: At least a portion of sulfur dioxide may be lost in one or more or a combination of steps. Alternatively, or additionally, sulfur dioxide may be exit the process as a, for example, a residual, in one or more outputs. Sulfur dioxide or 'make-up sulfur dioxide' may be added to the process. In some embodiments, sulfur dioxide may be stored on site and added as desired or needed to the process. In some embodiments, elemental sulfur, or hydrogen sulfide, or a salt comprising sulfur, or sulfide salt, or sulfite salt, or sulfate salt, or a combination thereof may be a source of sulfur dioxide or sulfurous acid, by, for example, including, but not limited to, one or more or a combination thereof: combustion, or acid-base reaction, or reaction with an acid, or carbothermic reduction, or thermal or decomposition, or electrolysis, or electrodialysis, or electrochemical reaction.

Additional Notes

Note: At least a portion of residual calcium sulfate may be removed. For example, a portion of residual dissolved calcium sulfate may precipitate and may be removed by, for example, including, but not limited to, solid-liquid separation, or removal of calcium sulfate scaling, or a combination thereof.

Note: One or more or a combination of steps in one or more embodiments may require heating and/or cooling. For example, a reaction of sulfurous acid with a calcium—weak acid or magnesium—weak acid may require or may be facilitated by cooling or heating. For example, a reaction of sodium sulfate with aqueous calcium bisulfite or magnesium bisulfite may require or may be facilitated by cooling or heating. Alternatively, or additionally, heat or heating or cooling or a combination thereof may be recovered from one or more or a combination of reaction steps. In some embodiments, heat or heating or cooling or a combination thereof may be recovered and said recovered heat or heating or cooling or a combination thereof may be transferred or employed in one or more other steps, or in the same step, or in other applications.

Note: Losses may occur during the process. Makeup streams of one or more or a combination of reagents may be added.

Note: Contaminants may exist or accumulate in the process. If desired, one or more contaminants may be at least partially removed periodically, or continuously, or as desired, or a combination thereof.

Additional Notes

Note: List of example Silicate Minerals which may be employed may include, but are not limited to, silicate minerals or minerals described in the following reference:

Daval, D. Carbon dioxide sequestration through silicate degradation and carbon mineralisation: promises and uncertainties. npj Mater Degrad 2, 11 (2018).

Note: 80-100% lower emissions than virgin concrete or virgin calcium oxide. Exact same product.

Note: Some embodiments may employ waste concrete, or steel slag, or fly ash, or olivine, or any combination thereof as an input.

Note: If non-calcium of non-magnesium metals dissolve or react with $SO_2$ or sulfurous acid, said metals or metal salts may be separated before or after separation of calcium sulfite or magnesium sulfite or both. If said non-calcium of non-magnesium metal salts are still dissolved, said non-calcium of non-magnesium salts may be separated by precipitation, or systems and/or methods for zero liquid discharge, or a combination thereof.

Additional Notes

Note: In some embodiments, steam may be employed as a stripping or carrier gas. Steam can be condensed after decomposition of one or more reagents. If steam is employed, it must be contacted at a temperature greater than the decomposition temperature of calcium hydroxide. Contact calcium oxide with steam to form calcium hydroxide may enable the reaction of calcium oxide and water to generate higher temperature and/or higher quality heat, which may be employed within one or more reaction steps or may be employed in a different application.

Note: Kiln with cryogenic separation of $SO_2$ from the flue gas or off gases. The separated $SO_2$ may be employed in one or more or any combination of reaction steps.

Note: React calcium oxide or calcium hydroxide or both with sodium sulfite or sodium sulfite to produce precipitated calcium sulfate (precipitated, clean gypsum, which can be sold) or precipitate calcium sulfide and sodium hydroxide solution.

Note: Sodium hydroxide solution may be crystallized from solution and sold.

Note: Sodium hydroxide solution may be sold

Note: Sodium hydroxide solution may be added to the ocean to increase ocean alkalinity and permanently remove CO2 from the atmosphere (two moles of CO2 for each mole of original calcium oxide)

Note: Sodium hydroxide solution may be reacted with flue gas and other $CO_2$ emissions, and then sold as sodium carbonate or bicarbonate Note: Sodium hydroxide solution may be reacted with CO2 in the air, producing Sodium carbonate. Sodium carbonate may be sold as a valuable product, or added to the ocean to increase ocean alkalinity and permanently remove more CO2 from the atmosphere/ocean, or a combination thereof.

Note: Thermally decompose Calcium sulfite in an electric kilns

Note: Thermally decompose calcium sulfite in a natural gas, or coal, or waste incinerator, or biofuel, or biomass, or electricity, or oil, or petcoke, or fossil fuel, or charcoal, or solar thermal, or thermal, or any combination thereof powered kiln.

Note: Thermally decompose calcium sulfite using a hydrogen fuels system. If hydrogen is used for heat, there will be no CO2 emissions in the end to end process. Also, green hydrogen can be produced from solar energy and stored, eliminating the challenge of solar intermittency. Alternatively or additionally, hydrogen may be blue hydrogen, or hydrogen from natural gas, where the carbon or CO2 is removed from the natural gas to produce hydrogen before hydrogen is burned. Alternatively, a process may employ a combination of blue hydrogen (during the night) and solar electricity (during the day).

Additional Notes

Note: Recovery heat form hydrating calcium oxide to calcium hydroxide to provide heat or steam or both for applications requiring heat (e.g. separating SO2 from calcium bisulfite solution may require heat)

Note: Remaining flue gas after most or all SO2 is removed or recovered may comprise at least a portion CO2.

Note: Flue gas CO2 may be concentrated with pressure swing absorption or pressure swing adsorption or gas membrane or both, then the flue gas with higher concentrations of CO2 may be employed as a feedstock for the production of sodium bicarbonate or sodium carbonate.

Note: CO2 may be cryogenically separated from this remaining flue gas.

Note: Convert calcium silicate from the Pidgeon process May employ calcium, or magnesium, or alkaline earth, or a combination thereof. Calcium or magnesium or alkaline earth may be substituted.

Note: $H_2SO_3(aq)$' or '$2SO_2(aq)+H_2O(1)$' or $SO_2(aq)$' may be used interchangeably.

Note: The weight percent concentration of $SO_2$ in one or more aqueous sulfurous acid solutions may be greater than or equal to one or more or a combination of the following: 0.001%, or 0.1%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35%, or 36%, or 37%, or 38%, or 39%, or 40%, or 41%, or 42%, or 43%, or 44%, or 45%, or 46%, or 47%, or 48%, or 49%, or 50%, or 51%, or 52%, or 53%, or 54%, or 55%, or 56%, or 57%, or 58%, or 59%, or 60%, or 61%, or 62%, or 63%, or 64%, or 65%, or 66%, or 67%, or 68%, or 69%, or 70%, or 71%, or 72%, or 73%, or 74%, or 75%, or 76%, or 77%, or 78%, or 79%, or 80%, or 81%, or 82%, or 83%, or 84%, or 85%, or 86%, or 87%, or 88%, or 89%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.9%, or less than or equal to 100%.

Additional Notes

Note: The volume % concentration of 02 in the headspace gases may be less than or equal to one or more or a combination of the following: 0.001%, or 0.1%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35%, or 36%, or 37%, or 38%, or 39%, or 40%, or 41%, or 42%, or 43%, or 44%, or 45%, or 46%, or 47%, or 48%, or 49%, or 50%, or 51%, or 52%, or 53%, or 54%, or 55%, or 56%, or 57%, or 58%, or 59%, or 60%, or 61%, or 62%, or 63%, or 64%, or 65%, or 66%, or 67%, or 68%, or 69%, or 70%, or 71%, or 72%, or 73%, or 74%, or 75%, or 76%, or 77%, or 78%, or 79%, or 80%, or 81%, or 82%, or 83%, or 84%, or 85%, or 86%, or 87%, or 88%, or 89%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.9%, or less than or equal to 100%.

Note: 'WA' may comprise a weak acid, which may include, but not limited to, silicic acid, or orthosilicic acid, or silicon acid derivatives, or silicon minerals, or silicon acids, or aluminates, or ferrates, or a combination thereof.

Note: Some embodiments may involve reacting calcium silicate or a material comprising silicon directly with sulfur dioxide, or liquid sulfur dioxide, or sulfur dioxide in an non-aqueous solution, or any combination thereof.

Note: In some embodiments, contaminants or impurities may dissolve in a solution comprising sulfur dioxide, or due to the presence of sulfuric acid, or a combination thereof. Contaminants or impurities may include, but are not limited to, one or more or a combination of the following: iron, or aluminum, or alkali metals, or transition metals, or other non-bisulfate soluble salts, or non-alkaline earth bisulfate salts, or a combination thereof. In some embodiments, dissolved contaminants may be present after solid-liquid separation, and/or after calcium sulfite precipitation. In some embodiments, at least a portion of contaminants may be separated periodically or continuously. Contaminants may be separated by, including, but not limited to, precipitation, or membrane based process, or cooling, or heating, or crystallization, or cryodesalination, or a separation process described herein, or a separation process in the art, or a combination thereof.

Note: 'Calcium' may also refer to magnesium and/or other alkaline earth metals.

Note: $NaHSO_3$(aq) may generally exist at an aqueous phase. Upon precipitation or crystallization, $NaHSO_3$ (aq) precipitates or crystalizes as $Na_2S_2O5$(s). $Na_2S_2O5$(s) may be considered anhydrous.

Additional Notes

Note: In some embodiments, sulfur dioxide may be sourced from the roasting of sulfide ores, which generally may produce sulfur dioxide. In some embodiments, sulfur dioxide may be sourced from the combustion of sulfur, or hydrogen sulfide, or fuels, or any combination thereof.

Note: In some embodiments, it may be desirable for the partial pressure of $CO_2$(g) reactant to be greater than or equal to one or more or any combination of the following: 0.01 Bar, or 0.05 bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar. For example, it may be desirable for the concentration of $CO_2$(g) reactant to be greater than or equal to one or more or any combination of the following: 1%, or 5%, or 10%, or 20%, or 30%, or 40%, or 50%, or 60%, or 70%, or 80%, or 90%, or 95%. In some embodiments, it may be desirable for the partial pressure of $CO_2$(g) reactant to facilitate or enable the formation of bicarbonate to be greater than or equal to one or more or any combination of the following: 0.01 Bar, or 0.05 bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar. For example, it may be desirable for the concentration of $CO_2$(g) reactant to facilitate or enable the formation of bicarbonate to be greater than or equal to one or more or any combination of the following: 1%, or 5%, or 10%, or 20%, or 30%, or 40%, or 50%, or 60%, or 70%, or 80%, or 90%, or 95%.

Note: In some embodiments, magnesium sulfite may form an aqueous solution comprising aqueous magnesium sulfite. In some embodiments, magnesium sulfite may be separated from at least a portion of calcium sulfite, or calcium carbonate, or magnesium carbonate, or other practically insoluble materials. Calcium sulfite is practically insoluble in water, with a solubility of 0.043 grams per liter at 18° C. Magnesium sulfite is soluble in water, with a solubility of 5.2 grams per liter at 25° C. The reaction of a material comprising calcium and magnesium with aqueous sulfur dioxide may result in the formation of at least a portion of a solid phase comprising calcium and at least a portion of an aqueous phase comprising magnesium sulfite.

Note: Recovering magnesium sulfite from an aqueous solution comprising magnesium sulfite may be conducted using one or more or a combination of methods from separating a dissolved salt from an aqueous solution. Some properties of aqueous magnesium sulfite may enable simple, or low energy, or high throughput, or a combination thereof separation of solid magnesium sulfite from a solution comprising aqueous magnesium sulfite. For example, the solubility of magnesium sulfite increases with temperature—according to Solubilities of magnesium sulfite hydrates by Sohnel, et al, the solubility of magnesium sulfite or magnesium sulfite hexahydrate is 11.04 grams per liter at 43.0° C., or 14.19 grams per liter at 51.4° C., or 19.30 grams per liter at 61.4° C., or 28.87 grams per liter at 71.5° C., or 40.17 grams per liter at 79.0° C., or 53.73 grams per liter at 84.1° C., or 71.21 grams per liter at 88.0° C., or 95.19 grams per liter at 94.0° C. In some embodiments, the reaction of aqueous sulfur dioxide with a material comprising calcium and/or magnesium may be conducted at an elevated temperature, such as, for example, greater than room temperature, or greater than ambient air temperature, or greater than 25° C., or greater than 35° C., or greater than 45° C., or greater than 55° C., or greater than 65° C., or greater than 75° C., or greater than 85° C., or greater than 95° C., or greater than 100° C., or less than the boiling point of the solution at the pressure of the reactor, or greater than 105° C. By conducting at an elevated temperature, the concentration of magnesium sulfite in the aqueous magnesium sulfite may be greater, or the rate of reaction may be greater, or a combination thereof.

Additional Notes

Regardless of the temperature of the reaction of aqueous sulfur dioxide with a material comprising calcium and/or magnesium, it may be desirable to concentrate the aqueous magnesium sulfite before or during the precipitation of aqueous magnesium sulfite. It may be desirable for at least a portion of said solution to be concentrated. It may be desirable for at least a portion of said solution to be concentrated using distillation. It may be desirable for at least a portion of said solution to be concentrated using a membrane based process at an elevated temperature. It may be desirable for at least a portion of said solution to be concentrated using forward osmosis at an elevated temperature. It may be desirable for at least a portion of said solution to be concentrated using a reverse osmosis at an elevated temperature. It may be desirable for at least a portion of said solution to be heated before or during concentrating. It may be desirable for at least a portion of said solution to be heated before or during concentrating, to, for example, enable greater solubility of aqueous magnesium sulfite. It may be desirable for said aqueous magnesium sulfite to be treated to prevent scaling during concentrating, or to remove at least a portion of non-magnesium sulfite impurities, or a combination thereof. It may be desirable for at least a portion of said solution to be concentrated using a membrane-based process. For example, said aqueous magnesium sulfite solution may comprise a feed solution to a reverse osmosis process, wherein the reverse osmosis process separates said aqueous magnesium sulfite solution into a permeate comprising water and a concentrate comprising a greater concentration of aqueous magnesium sulfite. Said permeate comprising water may be transferred to a countercurrent heat exchanger for heat recovery and/or to a sulfur dioxide absorption process and/or to another step within the process requiring water or water solvent. It may be desirable for the reverse osmosis process to concentrate magnesium sulfite and/or other salts to a concentration lower than their solubility limits at the temperature of the solution to prevent or minimize membrane scaling. It may be desirable for the solution to be at an elevation temperature during the reverse osmosis process due to the greater solubility limit of magnesium sulfite with higher temperature and/or to prevent scaling or precipitation during reverse osmosis concentrating. Said concentrate comprising aqueous magnesium sulfite may be cooled to precipitate at least a portion of magnesium sulfite solid, due to, for example, the lesser solubility of magnesium sulfite in water with decreasing temperature, and/or said magnesium sulfite solid may be separated using a solid-liquid separation process. The remaining solution after separating magnesium sulfite solid using a solid-liquid separation process may comprise residual dissolved magnesium sulfite and/or dissolved non-magnesium sulfite salts or chemicals, and/or may undergo further treatment. For example, said remaining solution after separating magnesium sulfite solid using a solid-liquid separate process may be heated and/or transferred or mixed with additional new aqueous magnesium sulfite solution and/or may comprise at portion the feed solution to the reverse osmosis process. For example, said remaining solution after separating magnesium sulfite solid using a solid-liquid separate process may undergo further reverse osmosis steps. For example, said remaining solution after separating magnesium sulfite solid using a solid-liquid separate process may be heated and/or transferred to another membrane-based process. For example, said remaining solution after separating magnesium sulfite solid using a solid-liquid separate process may be distilled and/or crystalized, which may further separate water from dissolved chemicals and/or separate magnesium sulfite from other salts or chemicals. For example, said remaining solution after separating magnesium sulfite solid using a solid-liquid separate process may be mixed with solution transferred to a sulfur dioxide absorption process. For example, said remaining solution after separating magnesium sulfite solid using a solid-liquid separate process may be further treated with, including, but not limited to, one or more or a combination of the following: ion exchange, or resins, or filters, or chemical treatments, or chemical reactions, or membrane based process, or distillation, or multi-effect distillation, or mechanical vapor recompression distillation, or mechanical vapor compression distillation, or multi-stage flash distillation, or membrane distillation, or cooling, or heating, or freezing, or crydesalination, or solventing-out, or solvent induced precipitation, or salting-out, or other treatment. One or more solutions comprising water may be transferred to a sulfur dioxide absorption step, or mixed with a solution transferred to a sulfur dioxide absorption step, or a combination thereof.

Additional Notes

In some embodiments, the material comprising magnesium and calcium may further comprise impurities. In some embodiments, the material comprising magnesium carbonate and calcium carbonate may further comprise impurities. For example, the material comprising magnesium carbonate and calcium carbonate may further comprise magnesium sulfate, or calcium sulfate, or sodium salts, or potassium salts, or iron salts, or manganese salts, or silicon chemicals, or silicon salts, or aluminum salts, or zinc salts, or other salts. Additionally, the aqueous solution comprising magnesium sulfite may be exposed to diatomic oxygen or inadvertently exposed to diatomic oxygen, which may result in a portion of the magnesium sulfite converting to magnesium sulfate. In some embodiments, impurities in the solution comprising aqueous magnesium sulfite may comprise dissolved salts or other chemicals other than magnesium sulfite. In some embodiments, although certain chemicals may be classified as 'impurities', some 'impurities' may comprise valuable products. For example, impurities comprising calcium sulfate and/or magnesium sulfate may be separated and may comprise valuable products. In some embodiments, at least a portion of impurities may be separated from an aqueous solution comprising magnesium sulfite before, or during, or after magnesium sulfite concentrating and/or precipitation of magnesium sulfite. In some embodiments, potential impurities may be practically insoluble in the aqueous magnesium sulfite solution. For example, iron sulfite, or manganese sulfite may be practically insoluble in water if the formation of bisulfite salts is avoided or minimized by employing stoichiometric concentrations of aqueous sulfur dioxide, and/or minimizing residence time. Calcium sulfite solid may comprise other chemicals than calcium sulfite, which may include, but are not limited to, non-calcium sulfite salts described herein.

Calcium sulfite produced from a reaction with aqueous sulfur dioxide may comprise wet calcium sulfite. Wet calcium sulfite may be physically wetted, as in wet calcium sulfite may contain water on the surface of the solid or embedded within the solid. Wet calcium sulfite may comprise hydrated calcium sulfite, which contains a chemically reacted hydrate or wherein water is reacted or part of the calcium sulfite solid. Dry calcium sulfite may comprise calcium sulfite solid which has minimal or no water on its surface or is not physically wetted. Dry calcium sulfite may comprise calcium sulfite solid which is anhydrous. In some embodiments, dry calcium sulfite may comprise calcium sulfite solid may comprise calcium sulfite solid which is partially hydrated, which means it may comprise hydrates of calcium sulfite, although is less hydrated than the potential full hydrate capacity of the calcium sulfite. Transforming wet calcium sulfite to dry calcium sulfite may require energy. Transforming wet calcium sulfite to dry calcium sulfite may comprise 'drying'. Some embodiments may involve employing wet calcium sulfite as an input to a calcining process to produce calcium oxide. Employing wet calcium sulfite as an input to a calcining process to produce calcium oxide may require more energy than employing dry calcium sulfite. Additionally, the amount and/or quality of energy required to calcine wet calcium sulfite may greater than if the wet calcium sulfite is dried into dry calcium sulfite before calcining. One or more or a combination of systems and methods may be employed to dry or dehydrate calcium sulfite. For example, calcium sulfite may be dried by heating the wet calcium sulfite to liberate water as a liquid or a vapor or both and separating said liberated water. If heating is employed, it may be desirable for the temperature of the heat employed to be less than the temperature of calcining calcium sulfite, or for the energy consumed to provide said heat to be less expensive or less carbon emission intensive than the energy consumed to calcine calcium sulfite, or a combination thereof. For example, said heat may be provided by, including, but not limited to, solar thermal, or heat pump, or waste heat, or steam, or low pressure steam, or stored heat, or process heat, or geothermal heat, or nuclear heat, or co-gen heat, or any combination thereof. For example, calcium sulfite may be dried by a carrier gas or stripping gas. For example, calcium sulfite may be dried by a recirculating carrier gas. For example, said recirculating carrier gas may comprise a gas or gas mixture with a diatomic oxygen concentration lower than 1 percent, or 2 percent, or 3 percent, or 4 percent, or 5 percent, or 6 percent, or 7 percent, or 8 percent, or 9 percent, or 10 percent, or 11 percent, or 12 percent, or 13 percent, or 14 percent, or 15 percent, or 16 percent, or 17 percent, or 18 percent, or 19 percent, or 20 percent, or 21 percent, or 22 percent, or any combination thereof by volume. For example, calcium sulfite may be dried by a recirculating carrier gas, wherein at least a portion of water vapor in the recirculating carrier gas is removed by a regenerable liquid desiccant. For example, calcium sulfite may be dried by a recirculating carrier gas, wherein at least a portion of water vapor in the recirculating carrier gas is removed by a regenerable liquid desiccant, which may include, but is not limited to, a glycol liquid desiccant, or glycol dehydration system, or a salt brine, or lithium bromide, or calcium chloride, or a liquid-liquid phase transition liquid desiccant, or a liquid desiccant regenerated by heat, or a liquid desiccant regenerated by vaporization of water, or a liquid desiccant regenerated by freezing desalination, or a liquid desiccant regenerated by a liquid-liquid phase transition into a water-rich phase and a water-lean phase, or a combination thereof. For example, calcium sulfite may be dried by a recirculating carrier gas, wherein at least a portion of water vapor in the recirculating carrier gas is removed by a regenerable solid desiccant, which may include, but is not limited to, an adsorbent, or gypsum, or silicate, or silica gel, or calcium oxide-calcium hydroxide, or a combination thereof. For example, calcium sulfite may be dried by a liquid desiccant, or a solid desiccant, or a combination thereof. For example, calcium sulfite may be dried by a recirculating carrier gas, wherein at least a portion of water vapor in the recirculating carrier gas is removed by a non-regenerated desiccant, which may comprise a solid or a liquid. For example, a non-regenerated desiccant may comprise a material which reacts with water to form a product, which may be removed from the process as a valuable product, or is disposed. For example, an example non-regenerated solid desiccant may comprise calcium oxide reacted with water or water vapor to form calcium hydroxide. For example, in some embodiments, calcium oxide produced by the process may be reacted with water vapor in said carrier gas, removing at least a portion of said water vapor while forming calcium hydroxide. Said calcium hydroxide may comprise a valuable product, or may be further reacted with water, or may be converted into other derivatives of calcium hydroxide. In some embodiments, at least a portion of heat generated from forming calcium hydroxide, from, for example, calcium oxide, may be employed to power at least a portion of the energy required to dry the wet calcium sulfite solid.

Additional Notes

Magnesium sulfite solid produced in one or more steps of the process may comprise wet magnesium sulfite. Wet magnesium sulfite may be physically wetted, as in wet magnesium sulfite may contain water on the surface of the solid or embedded within the solid. Wet magnesium sulfite may comprise hydrated magnesium sulfite solid, which contains a chemically reacted hydrate or wherein water is reacted or part of the magnesium sulfite solid. Dry magnesium sulfite may comprise magnesium sulfite solid which has minimal or no water on its surface or is not physically wetted. Dry magnesium sulfite may comprise magnesium sulfite solid which is anhydrous. In some embodiments, dry magnesium sulfite may comprise magnesium sulfite solid and/or may comprise magnesium sulfite solid which is partially hydrated, which means it may comprise hydrates of magnesium sulfite, although is less hydrated than the potential full hydrate capacity of the magnesium sulfite. Transforming wet magnesium sulfite into dry magnesium sulfite may require energy. Transforming wet magnesium sulfite to dry magnesium sulfite may comprise 'drying'. Some embodiments may involve employing wet magnesium sulfite as an input to a calcining process to produce magnesium oxide. Employing wet magnesium sulfite as an input to a calcining process to produce magnesium oxide may require more energy than employing dry magnesium sulfite. Additionally, the amount and/or quality of energy required to calcine wet magnesium sulfite may greater than if the wet magnesium sulfite is dried into dry magnesium sulfite before calcining. One or more or a combination of systems and methods may be employed to dry or dehydrate magnesium sulfite. For example, magnesium sulfite may be dried by heating the wet magnesium sulfite to liberate water as a liquid or a vapor or both and separating said liberated water. If heating is employed, it may be desirable for the temperature of the heat employed to be less than the temperature of calcining magnesium sulfite, or for the energy consumed to provide said heat to be less expensive or less carbon emission intensive than the energy consumed to calcine magnesium sulfite, or a combination thereof. For example, said heat may be provided by, including, but not limited to, solar thermal, or heat pump, or waste heat, or steam, or low pressure steam, or stored heat, or process heat, or geothermal heat, or nuclear heat, or co-gen heat, or any combination thereof. For example, magnesium sulfite may be dried by a carrier gas or stripping gas. For example, magnesium sulfite may be dried by a recirculating carrier gas. For example, said recirculating carrier gas may comprise a gas or gas mixture with a diatomic oxygen concentration less than 2 percent by volume. For example, magnesium sulfite may be dried by a recirculating carrier gas, wherein at least a portion of water vapor in the recirculating carrier gas is removed by a regenerable liquid desiccant. For example, magnesium sulfite may be dried by a recirculating carrier gas, wherein at least a portion of water vapor in the recirculating carrier gas is removed by a regenerable liquid desiccant, which may include, but is not limited to, a glycol liquid desiccant, or glycol dehydration system, or a salt brine, or lithium bromide, or calcium chloride, or a liquid-liquid phase transition liquid desiccant, or a liquid desiccant regenerated by heat, or a liquid desiccant regenerated by vaporization of water, or a liquid desiccant regenerated by freezing desalination, or a liquid desiccant regenerated by a liquid-liquid phase transition into a water-rich phase and a water-lean phase, or a combination thereof. For example, magnesium sulfite may be dried by a recirculating carrier gas, wherein at least a portion of water vapor in the recirculating carrier gas is removed by a regenerable solid desiccant, which may include, but is not limited to, an adsorbent, or gypsum, or silicate, or silica gel, or calcium oxide-calcium hydroxide, or an acid, or a combination thereof. For example, magnesium sulfite may be dried by a liquid desiccant, or a solid desiccant, or a combination thereof. For example, magnesium sulfite may be dried by a recirculating carrier gas, wherein at least a portion of water vapor in the recirculating carrier gas is removed by a non-regenerated solid desiccant. For example, a non-regenerated solid desiccant may comprise a material which reacts with water to form a product, which may be removed from the process as a valuable product, or may be disposed, or both. For example, an example non-regenerated solid desiccant may comprise calcium oxide reacted with water or water vapor to form calcium hydroxide. For example, in some embodiments, calcium oxide produced by the process may be reacted with water vapor in said carrier gas, removing at least a portion of said water vapor while forming calcium hydroxide. Said calcium hydroxide may comprise a valuable product, or may be further reacted with water, or may be converted into other derivatives of calcium hydroxide. In some embodiments, at least a portion of heat generated from forming calcium hydroxide, from, for example, calcium oxide, may be employed to power at least a portion of the energy required to dry the wet magnesium sulfite solid.

Notes

Note: Excess water may be removed from system. Similarly, water may be added to the system if desired. Water removal may be conducted by for example, including, but not limited to, one or more or a combination of the following: forward osmosis, decanter, separatory funnel, coalescer, centrifuge, filter, switchable solvent, cyclone, semi-permeable membrane, nanofiltration, organic solvent nanofiltration, reverse osmosis, ultrafiltration, microfiltration, hot nanofiltration, hot ultrafiltration, distillation, membrane distillation, flash distillation, multi-effect distillation, mechanical vapor compression distillation, or hybrid systems.

Note: Sodium Bicarbonate may be decomposed to form Sodium Carbonate, Sodium hydroxide, Sodium Sesquicarbonate, or a combination thereof, or other sodium-carbon dioxide or sodium bicarbonate derivative chemicals.

Note: Separation devices, or systems, or methods, or any combination thereof may include, but are not limited to, one or more or a combination of the following: decanter, separatory funnel, coalescer, centrifuge, filter, switchable solvent, cyclone, semi-permeable membrane, nanofiltration, organic solvent nanofiltration, reverse osmosis, ultrafiltration, microfiltration, hot nanofiltration, hot ultrafiltration, distillation, membrane distillation, flash distillation, multi-effect distillation, mechanical vapor compression distillation, or hybrid systems Note: The temperature of recovered heat or ambient heat source may be increased using a heat pump or a refrigeration cycle, if, for example, higher temperature heat is required for one or more process steps or one or more applications. For example, if recovered heat is in the form of steam, said steam may be compressed to a greater pressure, which may enable said steam to condense at a higher temperature and/or supply higher temperature heat.

Additional Notes

Note: Heat sources may include, but are not limited to, one or more or a combination of the following: flare gas heat, or combustion, or biofuel, or fossil fuel, or slaking lime, or natural gas combustion, nuclear heat, Waste Heat, Ambient Temperature Changes, or ambient heat, Diurnal Temperature Variation, Thermocline liquid body, thermocline solid body, thermocline gaseous body, Thermocline of a water body, halocline, heat pump, solar thermal, solar thermal pond, light, electricity, steam, combustion, compression, pressure increase, geothermal, radiative heat, condensation, exothermic dissolution, exothermic precipitation, exothermic formation of more liquid phases, exothermic formation of less liquid phases, exothermic phase change, or other heat sources described herein, or other heat sources known in the art.

Note: Systems and methods described herein may be batch, semi-batch, or continuous, or a combination thereof.

Note: Other metals or metal ions or cations which may be present or may be employed, may include, but are not limited to, one or more or a combination of the following: iron, lead, copper, cobalt, nickel, manganese, chromium, silver, scandium, vanadium, titanium, aluminum, magnesium, calcium, sodium, potassium, Yttrium, Zirconium, Niobium, Molybdenum Technetium, Ruthenium, Rhodium, Palladium, Silver, Cadmium, Hafnium, Tantalum, Tungsten, Rhenium, Osmium, Iridium, Platinum, Gold, Mercury, Rutherfordium, Dubnium, Seaborgium, Bohrium, Hassium, Meitnerium, Ununnilium, Unununium, or Ununbium.

Note: Reactions or systems and methods, steps, or a combination thereof herein may comprise a batch, semi-batch, semi-continuous, continuous stirred reactor (CSTR), continuous, or a combination thereof.

Note: Depending on the operating conditions, phases of inputs, concentrations, or a combination thereof, heating or cooling or separating or any combination thereof may be required in one or more or a combination of the steps or parts of one or more or a combination of embodiments.

Additional Notes

Note: Some embodiments may employ equipment comprising materials compatible with one or more or a combination of the following: $SO_2$, $CO_2$, or $H_2O$, or sulfur, or sulfur derivatives or one or more of the fuels (if any) employed in heating and/or their combustion products. It may be desirable for said materials to be compatible at temperature ranges of operation.

Note: In some embodiments, it may be desirable for the $CaCO_3$ or $SO_2$ or $CaSO_3$ or CaO or a combination thereof in an oxygen-free or very low oxygen environment. An oxygen-free or very low oxygen environment may, for example, prevent the oxidation of $SO_2$ or $CaSO_3$ or other $SO_3$ salt into a $SO_4$ salt.

Note: The present invention may be employed to regenerate CaO from $CaCO_3$ or similar carbonate or bicarbonate molecules in a $CO_2$ capture process. For example, the present invention may be employed in a device to capture $CO_2$ from the air.

Note: The SO2 may be substituted with nitric acid (HNO3). Ca(NO3)2 (which may be a resulting byproduct) can be thermally decomposed in a similar manner to CaSO3 to form CaO and NOx or O2 or NO2 or NO or a combination thereof. NOx, NO2, or NO may be converted back into nitric acid through reaction with water in, for example, the NOx+O2 and NOx+H$_2$O reaction steps of the Ostwald process, regenerating the nitric acid in the present embodiment. Advantageously, Ca(NO3)2 does not oxidize in the presence of O2, which may enable the process to operate in an environment with the presence of O2, if desired.

Note: The carrier gas may comprise a reactive gas if desired. For example, steam may be employed as a carrier gas. Advantageously, steam may condense following calcination and the heat generated may be recoverable and the heat generated may exceed initial heat input to generate steam due to, for example, the exothermic dissolution of $SO_2$ in the condensed steam (water) and/or the exothermic reaction of $H_2O$ with CaO to produce calcium hydroxide.

Note: Excess water may be removed from system. Similarly, water may be added to the system if desired. Water removal may be conducted by for example, including, but not limited to, one or more or a combination of the following: forward osmosis, decanter, separatory funnel, coalescer, centrifuge, filter, switchable solvent, cyclone, semi-permeable membrane, nanofiltration, organic solvent nanofiltration, reverse osmosis, ultrafiltration, microfiltration, hot nanofiltration, hot ultrafiltration, distillation, membrane distillation, flash distillation, multi-effect distillation, mechanical vapor compression distillation, or hybrid systems.

Additional Notes

Note: Sodium bicarbonate may be thermally decomposed into at least a portion carbon dioxide to, for example, produce sodium carbonate or sodium sesquicarbonate. Said carbon dioxide may be recycled internally, for example, to a carbon dioxide absorption step. Said carbon dioxide, may improve absorption characteristics including, but not limited to, one or more or a combination of the following: absorption rate, maximum carbon dioxide loading, absorption capacity, solution carrying capacity, sodium bicarbonate recovery yield, sodium bicarbonate recovery rate, or sodium bicarbonate recovery rate per a unit volume or mass of solution. Said carbon dioxide may increase the concentration of carbon dioxide in one or more or a combination of parts of the system, for example, which may be related, including, but not limited to, one or more or a combination of the following: carbon dioxide solutions, carbon dioxide gases, carbon dioxide absorption, bicarbonate salts, salts.

Note: Solutions may be passed or cycled or recycled or recirculated through a step more than once. Said 'passed or cycled or recycled or recirculated' may be conducted before, for example, proceeding to a next step. Said solutions may comprise, for example, absorption solutions or solutions undergoing precipitation or distillation solutions or solution undergoing treatment or concentrating with a membrane based process.

Note: One or more or a combination of the embodiments described herein may be employed as a net carbon dioxide emission negative method for permanently or semi-permanently sequestering carbon dioxide. For example, the sodium bicarbonate, or sodium sesquicarbonate, or sodium carbonate or sodium hydroxide or a combination thereof produced by one or more embodiments may be dissolved in the ocean. Adding net carbon dioxide emission negative sodium bicarbonate, or sodium sesquicarbonate, or sodium carbonate or a combination thereof to the ocean may have multiple benefits, which may include, but are not limited to, one or more or a combination of the following: permanent or semi-permanent sequestration of carbon dioxide in the ocean; increasing the pH of ocean water; increasing the concentration of carbonate ions in the ocean; buffering ocean acidification, restoring coral reefs; restoring marine life; local rejuvenation of marine life; local rejuvenation of coral; rejuvenation of coral.

Note: Cooling and/or heating may be conducted at additional or different temperatures and/or at additional or different locations than described herein.

Note: One or more or a combination of embodiments of the present invention may comprise a retrofit to pre-existing processes for producing sodium bicarbonate or sodium carbonate or sodium hydroxide, or other alkali hydroxide, or carbonate, or bicarbonate salts.

Additional Notes

Note: One or more or a combination of embodiments of the present invention may require solid handling or solid transfer or solid storage. Solid transfer may include, but is not limited to, conveyor belts, screw conveyors, bucket elevators, belt conveyors, pneumatic conveyors, or a combination thereof. Solid storage or transport or a combination thereof may include, but is not limited to, bin, or silo, hopper cars, bulk sacks, or other solids shipping containers, or a combination thereof.

Note: Temperatures in one or more parts of one or more embodiments may include, but are not limited to, greater than, equal to, or less than one or more or a combination of the following in degrees Celsius: −50, −40, −30, −20, −10, 0, 5, 10, 15, 20, 25, 30 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1150, 1200, 1250, 1300, 1350, 1400, 1450, 1500, 1600, 1700, 1800, 1900, 2000, 2250, 2500, 2750, 3000

Note: Sodium may be provided as an example alkali. Other alkali metal salts or cations may be employed instead of or in addition to sodium. For example, potassium or lithium or rubidium or cesium or a combination thereof may be employed. For example, alkali-like cations or salts, such as ammonia or ammonium, may be employed.

Note: Ammonia may be provided as an example weak base or alkali-like cation derivative. Other weak bases or weak base gases may be employed instead of or in addition to ammonia. For example, said other weak bases may include, but are not limited to, one or more or a combination of the following: amines, ammonia derivatives, imines, azines, $CO_2$ capture absorbent cations, $CO_2$ capture absorbents, or a combination thereof, or other weak bases, or other weak gases.

Note: $CO_2$ sources may include, but are not limited to, one or more or a combination of the following: Power Plant (Natural gas, coal, oil, petcoke, biofuel, municipal waste), Cement production, chemical production, Waste Water Treatment, Landfill gas, Air, Metal production/refining (such as Iron, Steel, Aluminum, etc.), Glass production, Oil refineries, LNG liquification, HVAC, Transportation vehicles (ships, boats, cars, buses, trains, trucks, airplanes), Natural Gas, Biogas, Alcohol fermentation, Volcanic Activity, Decomposing leaves/biomass, Septic tank, Respiration, Manufacturing facilities, Fertilizer production, or Geothermal processes where $CO_2(g)$ releases from a well or wells.

Additional Notes

Note: Input $CO_2$ vol % concentration may be greater than or equal to one or more or a combination of the following volume percent concentrations: 0%, or 0.001%, or 0.1%, or 0.5%, or 1%, or 1.5%, or 2%, or 2.5%, or 3%, or 3.5%, or 4%, or 4.5%, 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 20%, or 30%, or 40%, or 50%, or 60%, or 70%, or 80%, or 90%, or 100%.

Note: A gas stream comprising $CO_2$ may be concentrated to a greater concentration of $CO_2$ or a greater partial pressure of $CO_2$ before being absorbed or reacted in one or more or a combination of embodiments of the present invention. Said concentrating may be conducted using including, but not limited to, one or more or a combination of the following: gas membrane, or absorption/desorption $CO_2$ capture, or adsorption/desorption $CO_2$ capture, or recirculated $CO_2$, or desorption $CO_2$, or $CO_2$ from one or more or a combination of higher concentration $CO_2$ sources, or condensation of non-$CO_2$ gas, or cooling, or heating, or deposition, or deposition/sublimination, or cryogenic separation, or compression, or pressurization, electrochemical process, or ion exchange, or electrodialysis, or fuel cell, or a combination thereof.

Note: A gas stream comprising $SO_2$ may be concentrated to a greater concentration of $SO_2$ or a greater partial pressure of $SO_2$ before being absorbed or reacted in one or more or a combination of embodiments of the present invention. Said concentrating may be conducted using including, but not limited to, one or more or a combination of the following: gas membrane, or membrane based process, or absorption/desorption $SO_2$ capture, or adsorption/desorption $SO_2$ capture, or recirculated $SO_2$, or desorption $SO_2$, or $SO_2$ from one or more or a combination of higher concentration $SO_2$ sources, or condensation of non-$SO_2$ gas, or cooling, or heating, or deposition, or deposition/sublimination, or cryogenic separation, or compression, or pressurization, electrochemical process, or ion exchange, or electrodialysis, or fuel cell, or a combination thereof.

Note: Absorption of a gas into a solution containing ammonia and/or absorption of ammonia into a solution may result in the formation of a residual or remaining gas stream comprising residual ammonia. Said residual or remaining gas stream may comprise, for example, remaining unabsorbed gases or inert gases. One or more or a combination of embodiments herein may employ an ammonia recovery or ammonia abatement cycle or system. Alternately or additionally, ammonia may be removed to ultra-low concentrations (e.g. single or double digit PPM concentrations) using hydrochloric acid (which may be produced by some embodiments herein), and/or ammonia or hydrochloric acid or both may be recovered from the resulting ammonium chloride using one or more or a combination of embodiments herein.

Additional Notes

Note: Ammonia losses may occur within one or more or a combination of embodiments described herein. Makeup ammonia may be provided, for example, as needed or as desired.

Note: $SO_2$ losses may occur within one or more or a combination of embodiments described herein. Makeup $SO_2$ may be provided, for example, as needed or as desired.

Note: Losses may occur within one or more or a combination of embodiments described herein. Makeup reagents may be provided, for example, as needed or as desired.

Note: In some embodiments, ammonia may form at elevated temperatures. In some embodiments, if oxygen is present, some ammonia may undergo combustion. Ammonia combustion products, even at residual or low concentrations, may be present in one or more gases or liquids or solids or a combination thereof in one or more or a combination of embodiments. Said ammonia combustion products may comprise, including, but not limited to, nitrogen oxides, or nitrogen, or nitric acid, or a derivative thereof, or a combination thereof. Systems and methods for detecting, treating, removing, economically using, recovering, or a combination thereof said ammonia combustion products may be employed.

Note: Filling, or reacting, or emptying, or a combination thereof may be conducted simultaneously if desired.

Notes

Note: Example alkalis may include, but are not limited to, one or more or any combination of the following: lithium (Li), or sodium (Na), or potassium (K), or rubidium (Rb), or cesium (Cs)

Note: Example alkaline earths may include, but are not limited to, one or more or any combination of the following: beryllium (Be), or magnesium (Mg), or calcium (Ca), or strontium (Sr), or barium (Ba), or radium (Ra).

Note: Calcium may comprise an example alkaline earth. Other alkaline earths may be employed in addition to or instead of calcium where calcium is described herein. For example, in some embodiments, calcium may comprise mixtures of calcium and magnesium, or calcium may instead comprise magnesium.

Additional Notes

Note: Sodium may comprise an example alkali. Other alkalis may be employed in addition to or instead of sodium where sodium is described herein. For example, in some embodiments, Sodium may comprise mixtures of sodium and potassium, or sodium and lithium, or potassium, or lithium, or any combination thereof.

Note: An alkaline earth cation—weak acid anion salt may include, but is not limited to, alkaline earth cation salts with one or more or any combination of the following anions: carbonate, or bicarbonate, or sulfite, or sulfide, or silicate, or ferrate, or aluminate, or ferrite, or a silicate, or silicon derivative, or a carboxylic acid salt, or a ferrate salt, or an aluminate salt, or a zincate salt, or an iron derivative salt, or a manganese derivative salt, or a zinc derivative salt, or an aluminum derivative salt, or transition metal oxide anion, or metal oxide anion, or organic acid, or carboxylic acid, or phosphor acid, or anion of an acid weaker than sulfuric acid, or anion of an acid weaker than nitric acid, or an anion of an acid weaker than sulfurous acid.

Note: Heat produced from the reaction of calcium oxide with water to form calcium hydroxide may be utilized. For example, said heat may be employed within separation steps, or distillation steps, or drying steps, or calcining steps, or decomposition steps, or gas liberating steps, or any combination thereof within the invention. For example, said heat may be utilized in an external application.

Note: Heat produced from the combustion or conversion of hydrogen sulfide, or the production of sulfuric acid, or exothermic reactions comprising sulfur chemicals, or any combination thereof may be utilized. For example, said heat may be employed within separation steps, or distillation steps, or drying steps, or calcining steps, or decomposition steps, or gas liberating steps, or any combination thereof within the invention. For example, said heat may be utilized in an external application.

Note: In some embodiments, sodium sulfate may be produced by the reaction of sodium chloride with sulfuric acid or sulfur dioxide or oxygen or any combination thereof, which may produce hydrochloric acid and sodium sulfate.

$2NaCl + H_2SO_4 \rightarrow 2HCl + Na_2SO_4$ $4NaCl + 2SO_2 + O_2 + 2H_2O \rightarrow 4HCl + 2Na_2SO_4$ Note: Sodium sulfate may be produced by mining of sodium sulfate deposits or extraction of sodium sulfate from natural resources.

Additional Notes

Note: In some embodiments, sodium hydroxide, or sodium carbonate, or sodium sesquicarbonate, or sodium bicarbonate, or any combination thereof may be added to an ocean or sea to, for example, including, but not limited to, one or more or any combination of the following: increase the pH, or increase the local pH, or provide a high quality mechanism to permanently absorb carbon dioxide from the air, or to increase the local pH to improve health of marine ecosystems and corals, or improve biomass production, or improve productivity of a fishery, or facilitate tourism, or grow a local economy, or to improve the health of the ocean, or the prevent or combat algae blooms or cyanobacteria blooms, or any combination thereof.

Note: Sodium sulfate may be a byproduct in the production of, including, but not limited to, lithium carbonate, or chelating agents, or resorcinol, or ascorbic acid, or silica pigments, or nitric acid, or phenol, or any combination thereof.

Note: The present invention may comprise a process for recycling sodium or sodium carbonate in the production of lithium or lithium carbonate.

Note: In some embodiments, sodium sulfate may be added directly to the aqueous calcium bisulfite as solid sodium sulfate Note: In some embodiments, sodium sulfate may be dissolved in at least a portion of the water and the resulting aqueous solution comprising aqueous sodium sulfate is mixed with an aqueous solution comprising calcium bisulfite Note: A portion of gaseous sulfur dioxide may form during the formation of sodium metabisulfite from aqueous sodium bisulfite. For example, excess aqueous sulfur dioxide may be present in the aqueous sodium bisulfite solution and a portion of said aqueous sulfur dioxide may desorb during the formation of sodium metabisulfite solid. For example, a portion of bisulfite may decompose to form gaseous sulfur dioxide during the formation of sodium metabisulfite.

Note: Forming sodium metabisulfite from an aqueous solution comprising sodium bisulfite may involve, including, but not limited to, one or more or a combination of the following: removing water, or precipitation, or crystallization, or cryodesalination, or freezing desalination, or distillation, or membrane based process, or forward osmosis, or reverse osmosis, or multi effect distillation, or mechanical vapor compression distillation, or multistage flash distillation, or membrane distillation, or heat recovery distillation, or zero liquid discharge Additional Notes Note: Use raw minerals of sodium sulfate as the input material, rather than processed sodium sulfate, because the price of these materials are practically free. These minerals are listed below:
https://en.m.wikipedia.org/wiki/Mirabilite
https://en.m.wikipedia.org/wiki/Thenardite Note: Alternatively, "Sodium sulfate is produced on a very large scale as a by-product of several important industrial processes. In many cases, disposal of this material is difficult.". In some embodiments, the present invention may be co-located with a process where sodium sulfate is produced as a product, or byproduct, or waste product.

Note: Sodium sulfate is known to be a very significant waste product of the lithium production industry. In some lithium production applications, sodium hydroxide is reacted with lithium sulfate produced from a roasting process to recover lithium, which may result in the production of a sodium sulfate product. Some embodiments of the present invention may enable recycling of sodium sulfate into sodium hydroxide or sodium carbonate.

Note: Sodium hydroxide may facilitate hydrogen production.

Note: Some embodiments may involve reacting a material comprising calcium and/or magnesium with supercritical, or liquid, or gaseous, or any combination thereof sulfur dioxide to form calcium sulfite and/or magnesium sulfite, then contacting at least a portion of the formed calcium sulfite and/or magnesium sulfite with water to form at least a portion of dissolve magnesium sulfite.

Note: $MgCa(CO_3)_2(s)$ may comprise a solid comprising a mixture of calcium and magnesium salts. $MgCa(CO_3)_2(s)$ may comprise, for example, including, but not limited to, limestone or dolomite. Alternatively, or additionally, $MgCa(CO_3)_2(s)$ may comprise a portion of magnesium silicate or magnesium aluminate or magnesium ferrate. Alternatively, or additionally, $MgCa(CO_3)_2(s)$ may comprise a portion of calcium silicate or calcium aluminate or calcium ferrate.

Note: In some embodiments, a solvent other than or in addition to water may be employed. For example, an organic solvent or inorganic solvent may be present in solution. For example, a glycol, or an alcohol, or a sugar alcohol may be present. For example, an organic solvent or a solvent other than water. For example, ammonia or urea may be present in solution.

Note: Concentration of aqueous magnesium sulfite in a solution comprising aqueous magnesium sulfite may be greater than or equal to one or more or a combination of the following: 0.025 g/L, or 0.05 g/L, or 0.1 g/L, or 0.2 g/L, or 0.3 g/L, 0.4 g/L, or 0.5 g/L, or 0.6 g/L, or 0.7 g/L, or 0.8 g/L, or 0.9 g/L, or 1.0 g/L, or 1.1 g/L, or 1.2 g/L, or 1.3 g/L, or 1.4 g/L, or 1.5 g/L, or 1.6 g/L, or 1.7 g/L, or 1.8 g/L, or 1.9 g/L, or 2 g/L Additional Notes Note: 'g/L' may comprise grams of solute per liter of solution. For example, 1 g/L of magnesium sulfate may comprise a solution with 1 gram of dissolved magnesium sulfite per liter of total solution.

Note: Temperature of at least a portion of concentrating with reverse osmosis or forward osmosis or both may be greater than or equal to one or more or a combination of the following: 0° C., or 5° C., or 10° C., or 15° C., or 20° C., or 25° C., or 30° C., or 35° C., or 40° C., or 45° C., or 50° C., or 55° C., or 60° C., or 65° C., or 70° C., or 75° C., or 80° C., or 85° C., or 90° C., or 95° C., or 100° C., or 105° C., or 110° C., or 115° C.

Note: Temperature of calcining at least a portion of calcium sulfite, or magnesium sulfite, or both may be greater than or equal to one or more or a combination of the following: 500° C., or 550° C., or 600° C., or 650° C., or 700° C., or 750° C., or 775° C., or 800° C., or 825° C., or 850° C., or 875° C., or 900° C.

Note: Temperature of drying or dehydrating or both may be less than or equal to one or more or a combination of the following: 800° C., or 750° C., or 700° C., or 650° C., or 600° C., or 550° C., or 500° C., or 450° C., or 400° C., or 350° C., or 300° C., or 250° C., or 200° C., or 150° C., or 100° C.

Note: The partial pressure of captured carbon dioxide produced by one or more or a combination of embodiments may be greater than or equal to one or more or a combination of the following: 0.05 atm, or 0.1 atm, or 0.2 atm, or 0.3 atm, or 0.4 atm, or 0.5 atm, or 0.6 atm, or 0.7 atm, or 0.8 atm, or 0.9 atm, or 1 atm, or 1.1 atm, or 1.2 atm, or 1.3 atm, or 1.4 atm, or 1.5 atm, or 1.6 atm, or 1.7 atm, or 1.8 atm, or 1.9 atm, or 2.0 atm, or 2.25 atm, or 2.5 atm, or 2.75 atm, or 3 atm, or 4 atm, or 5 atm, or 6 atm, or 7 atm, or 8 atm, or 9 atm, or 10 atm, or 12.5 atm, or 15 atm, or 17.5 atm, or 20 atm, or 25 atm, or 30 atm, or 35 atm, or 40 atm, or 45 atm, or 50 atm Note: The concentration of captured carbon dioxide produced by the process may comprise a volume percent concentration of carbon dioxide which may include, but is not limited to, greater than, or equal to, one or more or a combination of the following: 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%

Additional Notes

Note: The concentration of captured carbon dioxide produced by the process may comprise a volume percent concentration of carbon dioxide which may include, greater than, or equal to, one or more or a combination of the following: 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Additional Notes

Note: 'A portion': A portion may comprise a part of a stream or material, or all of a stream or material. A portion may include, but is not limited to, less than, or greater than, or equal to, one or more or a combination of the following: 0%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Note: Calcining may involve thermally decomposing calcium sulfite and/or magnesium sulfite into calcium oxide and/or magnesium oxide. Calcining may involve thermally decomposing calcium carbonate and/or magnesium carbonate into calcium oxide and/or magnesium oxide.

Note: In some embodiments, calcium sulfite and magnesium sulfite may be calcined separately. For example, in some embodiments, calcium sulfite may be calcined in a separate kiln than magnesium sulfite. For example, in some embodiments, calcium sulfite may be calcined in the same kiln as magnesium sulfite, although in different locations within the same kiln. For example, in some embodiments, calcium sulfite may be calcined in the same kiln as magnesium sulfite, although at different times.

Note: In some embodiments, calcium sulfite and magnesium sulfite may be calcined in the same kiln. For example, a material may comprise both calcium sulfite and magnesium sulfite, and said material comprising both calcium sulfite and magnesium sulfite may be calcined. For example, a separate calcium sulfite and magnesium sulfite may be mixed and may be calcined in the same kiln as a mixture.

Note: Some embodiments may involve using an input material comprising a salt of calcium and/or magnesium and a weak acid, wherein said weak acid comprises a weak acid anion other than a carbon dioxide derivative, or other than a carbonate. For example, said weak acid anion other than a carbon dioxide derivative may comprise, including, but not limited to, one or more or a combination of the following: a sulfide, or silicon derivative, or silicate, or aluminate, or ferrate, or ferrite, or iron, or zinc, or aluminum, or manganese, or copper, or a combination thereof.

Additional Notes

Note: In some embodiments, a material comprising calcium and/or magnesium may comprise calcium silicate or magnesium silicate or both. In some embodiments, a material comprising calcium and/or magnesium may comprise, for example, including, but not limited to, cement, or concrete, or waste concrete, or steel slag, or iron slag, or slag, or a combination thereof.

Note: If non-calcium of non-magnesium metals dissolve or react with $SO_2$ or sulfurous acid, these minerals may be separated before or after separation of calcium sulfite or magnesium sulfite or both. If these non-calcium of non-magnesium metal salts are still dissolved, they may be separated by precipitation, or systems and/or methods for zero liquid discharge, or a combination thereof.

Note: Employ the calcium oxide produced by the present invention as an input to the Solvay to make reduced $CO_2$ emissions sodium carbonate and sodium bicarbonate. Calcium oxide is used in the Solvay process to remove chloride from ammonium chloride.

Note: Some embodiments may employ high temperature steam in the calcination process. In some embodiments, it may be desirable for the temperature of the steam to be greater than the decomposition temperature or decomposition temperature range of calcium hydroxide. At least a portion of the steam may be condensed after forming a mixture with sulfur dioxide. If steam is employed, it must be contacted at a temperature greater than the decomposition temperature of calcium hydroxide.

Note: Sulfur dioxide may be separated or recovered by cryogenic separation, or freezing separation, or liquification separation, or condensing separation, or deposition separation, or a combination thereof. The resulting liquid or solid or supercritical $SO_2$ may be added to water or sulfurous acid solution to form or maintain concentrated or 'excess' sulfurous acid. Alternatively or additionally, the resulting liquid or solid or supercritical $SO_2$ may be reacted with directly with the material comprising calcium and/or magnesium.

Additional Notes

Note: Thermally decompose calcium sulfite in an electric kiln

Note: Thermally decompose calcium sulfite in a natural gas or coal or both kiln.

Note: Thermally decompose calcium sulfite using a hydrogen fuels system. If hydrogen is used for heat, there may be no $CO_2$ emissions in the end to end process. Also, green hydrogen can be produced from solar energy and stored, eliminating the challenge of solar intermittency. Alternatively or additionally, hydrogen may be blue hydrogen, or hydrogen from natural gas, where the carbon or $CO_2$ is removed from the natural gas to produce hydrogen before hydrogen is burned. Alternatively, a process may employ a combination of blue hydrogen (during the night) and solar electricity (during the day).

Note: Some embodiments may employ a hydrogen powered kiln. In some embodiments, the resulting water vapor may be condensed to form sulfurous acid. In some embodiments where combustion is employed to power the calcining and said combustion forms water, it may be desirable for a portion of said water to be condensed to form at least a portion of aqueous sulfur dioxide.

Note: 'Aqueous sulfur dioxide' and 'sulfurous acid' may be employed interchangeably Note: Recovery heat form hydrating calcium oxide to calcium hydroxide to provide heat or steam or both for applications requiring heat Note: Remaining flue gas after most or all $SO_2$ is removed or recovered may comprise at least a portion $CO_2$.

Note: Flue gas or $CO_2$ from the flue gas may be employed as a $CO_2$ input or $CO_2$ source for a Solvay process to produce Sodium Bicarbonate or Sodium Carbonate. The Solvay process calcium oxide will be sourced from the present invention.

Note: Flue gas $CO_2$ may be concentrated with pressure swing absorption or pressure swing adsorption or gas membrane or both, then the flue gas with higher concentrations of $CO_2$ may be employed as a feedstock for the production of sodium bicarbonate or sodium carbonate.

Additional Notes

Note: Convert calcium silicate from the Pidgeon process to calcium oxide or recovery calcium oxide from the Pidgeon process Note: a process for enabling full conversion of calcium carbonate or calcium silicate or a combination thereof to calcium oxide: $CO_2$ production process from calcium carbonate, where the first step is to react Calcium Carbonate with equal to or less than stoichiometric amounts of sulfurous acid or with low vapor pressure sulfurous acid. The calcium sulfite solid is separated from this solution using solid-liquid separation. Then the resulting solid calcium sulfite (which may still comprise at least a portion calcium carbonate) is transferred to a step where it is dissolved in excess concentrated sulfurous acid, forming dissolve calcium bisulfate and $CO_2$ from any unreacted calcium carbonate. Remaining $CO_2$ is separated from the $SO_2$ gas atmosphere by, for example, condensation of at least a portion of $SO_2$ and/or a combination of other systems and/or methods. Any non-calcium sulfite or calcium carbonate (e.g. calcium sulfate or silica or other mostly insoluble chemicals) may remain as a solid and may be separated from the calcium bisulfite solution via liquid-solid separation.

Note: May employ calcium, or magnesium, or alkaline earth, or a combination thereof. Calcium or magnesium or alkaline earth may be substituted.

Note: In some embodiments, gas comprising sulfur dioxide may be compressed prior to or during absorption of sulfur dioxide in one or more or a combination of process steps described herein.

Note: In some embodiments, it may be desirable to avoid the formation of dissolved calcium bisulfite. In some embodiments, the formation of calcium bisulfite may be prevented by employing an organic solvent, or a non-water solvent, or both instead of or in addition to water as a solvent to absorb sulfur dioxide and/or react sulfur dioxide with calcium carbonate, or magnesium carbonate, or calcium silicate, or magnesium silicate, or a calcium-'WA' salt, or a magnesium-'WA' salt, or a combination thereof. The absence of water, or a lower concentration of water, or the presence of other solvents than water, or a combination thereof may inhibit the formation of dissolved calcium bisulfite in, for example, some embodiments where it is desired.

Note: 'WA' may comprise a weak acid. For example, 'WA' may comprise an acid with acidity less than or equal to sulfurous acid.

Additional Notes

Note: A calcium silicate, or magnesium silicate, or both may comprise at least a portion calcium carbonate in some embodiments.

Note: One or more or a combination of reagents, or process steps, or a combination thereof may be heated, or cooled, or a combination thereof.

Note: Calcium silicate may comprise a material comprising silicate. A material comprising an impure limestone comprising at a portion a silicate material. For example, a material comprising silicate may comprise clay, or silicon dioxide, or alumino-silicate, or ferrite, or a combination thereof.

Note: Calcining of calcium sulfite may be conducted in the presence of clay, or silicon dioxide, or shale, or sand, or iron ore, or bauxite, or fly ash, and or slag or other materials employed to, for example, produce or facilitate the production of cement, or cement clinker, or a combination thereof.

Note: In some embodiments, it may be desirable to operate the calcination of calcium sulfite and/or cement manufacturing inputs in the presence of diatomic oxygen. For example, in some embodiments, diatomic oxygen present in a flue gas stream, or in hot gases entering or within a kiln, or a combination thereof may react or oxidize sulfur dioxide, or calcium sulfite, or derivatives thereof to form materials or chemicals which may be facilitate the manufacturing of cement or clinker or may enable advantageous properties in the cement or clinker. For example, in some embodiments, diatomic oxygen present in a flue gas stream, or in hot gases entering or within a kiln, or a combination thereof may react or oxidize sulfur dioxide, or calcium sulfite, or derivatives thereof to form calcium sulfate and/or derivatives thereof, which may be an advantageous ingredient or component of some cement or clinker compositions. For example, in some embodiments, diatomic oxygen present in a flue gas stream, or in hot gases entering or within a kiln, or a combination thereof may react or oxidize sulfur dioxide, or calcium sulfite, or derivatives thereof to form compounds or materials comprising sulfur with superior strength, or chemical resistance, or longevity, or pressure, or compressive strength, or water resistance, or temperature resilience, or other resilience, or cost, or adhesive properties, or chemical compatibility, or a combination thereof. For example, in some embodiments, diatomic oxygen present in a flue gas stream, or in hot gases entering or within a kiln, or a combination thereof may react with or oxidize sulfur dioxide, or calcium sulfite, or derivatives thereof to form compounds or materials with superior strength, or chemical resistance, or longevity, or pressure, or compressive strength, or water resistance, or temperature resilience, or other resilience, or cost, or adhesive properties, or chemical compatibility, or a combination thereof. For example, in some embodiments, diatomic oxygen present in a flue gas stream, or in hot gases entering or within a kiln, or a combination thereof may react with or oxidize sulfur dioxide, or calcium sulfite, or derivatives thereof to produce heat, which may reduce energy requirements or increase the energy efficiency of calcining.

Note: In some embodiments, the use of calcium sulfite as an input material for the production of cement may enable cement with superior properties, which may include, but are not limited to, superior strength, or chemical resistance, or longevity, or pressure, or compressive strength, or water resistance, or temperature resilience, or other resilience, or cost, or adhesive properties, or chemical compatibility, or a combination thereof.

Additional Notes

Note: In some embodiments, calcium silicate may comprise cement manufacturing inputs. In some embodiments, cement manufacturing inputs may comprise calcium silicate. In some embodiments, cement manufacturing inputs may comprise calcium sulfite, or calcium oxide, or a combination thereof. In some embodiments, cement manufacturing inputs may comprise calcium bisulfite.

Note: Weak acids and weak acid anions may include, but are not limited to, one or more or a combination of the following: silicates, or carbonates, or aluminates, or aluminoferrites, or aluminum oxides, or zinc oxides, or iron oxides, or $Al_2O_6$, or $Al_2Fe_2O_{10}$.

Note: In some embodiments, at least a portion of the gases produced during or from the calcination of calcium sulfite may comprise water or water vapor. For example, if hydrogen, or natural gas, or ammonia, or a hydrocarbon, or other combustion, or steam, or a combination thereof is/are employed to provide heat for calcination, water vapor may be generated. In some embodiments, at least a portion of said gases produced during or from the calcination of calcium sulfite may be condensed to form an aqueous solution comprising aqueous sulfur dioxide or sulfurous acid. In some embodiments, said aqueous solution comprising aqueous sulfur dioxide or sulfurous acid may be employed as an aqueous sulfur dioxide solution or sulfurous acid solution in one or more process steps. In some embodiments, said aqueous solution comprising aqueous sulfur dioxide or sulfurous acid may undergo further concentrating, or diluting, or treating, or a combination thereof before being employed as an aqueous sulfur dioxide solution or sulfurous acid solution in one or more process steps.

Note: In some embodiments, nitrogen gas may be added to air before combustion with said air to reduce the concentration of oxygen before said air may be employed in the combustion of fuel for calcining calcium sulfite. For example, a nitrogen concentrating process may be employed. For example, an oxygen concentrating or oxygen removal process may be employed.

Additional Notes

Note: In some embodiments, at least a portion of oxygen may be removed from air before combustion with said air to reduce the concentration of oxygen before said air may be employed in the combustion of fuel for calcining calcium sulfite. For example, a nitrogen concentrating process may be employed. For example, an oxygen concentrating or oxygen removal process may be employed.

Note: In some embodiments, a portion of gases after combustion and after sulfur dioxide removal may be added to air to reduce the concentration of diatomic oxygen before said air may be employed in the combustion of fuel for calcining calcium sulfite.

Note: In some embodiments, sulfur dioxide or carbon dioxide or both may be added to air to reduce the concentration of diatomic oxygen before said air may be employed in the combustion of fuel for calcining calcium sulfite.

Note: It may be desirable to calcine the calcium sulfite under conditions where the temperature is sufficiently low to prevent produced CaO crystallites from fusing. It may be desirable to calcine calcium sulfite under conditions and temperatures where the specific surface of the calcium oxide remains intact. It may be desirable to produce CaO with non-fused crystals, or where the specific surface of the calcium oxide remains intact, or a combination thereof for applications, which may include, but are not limited to, the steel industry.

Note: It may be desirable to calcine the calcium sulfite under conditions where the temperature is sufficiently high to facilitate the production of fused CaO crystallites. It may be desirable to calcine calcium sulfite under conditions and temperatures which reduce the specific surface of the calcium oxide. It may be desirable to produce CaO with fused crystals, or where the specific surface of the calcium oxide is reduced, or a combination thereof for applications, which may include, but are not limited to, the production of aerated concrete, or sand lime bricks, or a combination thereof.

Note: Heat sources may include, but are not limited to, one or more or a combination of the following: combustion of a fuel, hydrogen, ammonia, natural gas, heavy fuel oil, pulverized coal, liquefied gas, off-gas from steel-making process, wood dust, waste oil, biomass, biofuel, electricity, heat pump, solar thermal, chemical reaction, sulfur, sulfurous fuel, sulfuric acid production, salt production, waste heat, waste gases, nuclear heat, geothermal, quicklime, hydration reaction, oxidation.

Additional Notes

Note: One or more of the present embodiments may produce strongly carbon dioxide negative or negative emissions calcium oxide Note: In some embodiments, produced calcium oxide may be reacted with carbon dioxide originating from the air or separated from the air. For example, calcium oxide may be reacted with sodium carbonate or potassium carbonate or sodium carbonate or potassium carbonate solution to produce sodium hydroxide or potassium hydroxide solution and calcium carbonate, which may be a permanent sequestration byproduct. Said sodium hydroxide or potassium hydroxide solution may then be contacted with air or $CO_2$ originating from air to produce a solution comprising sodium carbonate, or potassium carbonate, or a combination thereof.

Note: A portion of the calcium oxide produced may be converted to calcium carbonate by reaction, with, for example, carbon dioxide in the air, or carbon dioxide originating from the air, or an air capture process, or regenerating an alkali-carbonate to an alkali-oxide in an absorption loop, or regenerating an alkali-carbonate to an alkali-oxide in an absorption or separation process, or a combination thereof.

Note: A portion of the cement produced may be employed in the production of non-hydraulic cement, or cement employing at least a portion of $CO_2$ input, or a combination thereof to increase the net $CO_2$ removal or emissions reduction.

Note: Magnesium and calcium may be present in the same input material. For example, slags, or waste concrete, or minerals may comprise at least a portion of magnesium. For example, dolomite may comprise a portion of magnesium. In some embodiments, at least a portion of magnesium sulfite and/or magnesium oxide and/or magnesium hydroxide may be produced separately from calcium sulfite and/or calcium oxide and/or calcium hydroxide. For example, the separation of calcium and magnesium may be conducted by including, but not limited to, the significant difference in solubility in water between magnesium sulfite and calcium sulfite and/or the significant temperature dependent solubility of magnesium sulfite.

Additional Notes

Note: The concentration of sulfur dioxide in aqueous sulfur dioxide may be greater than or equal to one or more of the following weight percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Note: The concentration of sulfur dioxide gas in a gas comprising sulfur dioxide may be greater than or equal to one or more of the following volume percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Additional Notes

Note: The concentration of magnesium oxide in the output comprising magnesium oxide may be greater than or equal to one or more of the following weight percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Additional Notes

Note: The concentration of calcium oxide in the output comprising magnesium oxide may be greater than or equal to one or more of the following weight percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Note: The concentration of oxygen gas or diatomic oxygen in a head space or a reactor may be lower than or equal to one or more of the following volume percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Additional Notes

Note: 'H2SO3(aq)' or '2SO2(aq)+H2O(1)' may be employed interchangeably.

Note: The weight percent concentration of $SO_2$ in one or more aqueous sulfurous acid solutions or one or more solutions comprising sulfur dioxide may be greater than or equal to one or more or a combination of the following: 0.001%, or 0.1%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35%, or 36%, or 37%, or 38%, or 39%, or 40%, or 41%, or 42%, or 43%, or 44%, or 45%, or 46%, or 47%, or 48%, or 49%, or 50%, or 51%, or 52%, or 53%, or 54%, or 55%, or 56%, or 57%, or 58%, or 59%, or 60%, or 61%, or 62%, or 63%, or 64%, or 65%, or 66%, or 67%, or 68%, or 69%, or 70%, or 71%, or 72%, or 73%, or 74%, or 75%, or 76%, or 77%, or 78%, or 79%, or 80%, or 81%, or 82%, or 83%, or 84%, or 85%, or 86%, or 87%, or 88%, or 89%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.9%, or less than or equal to 100%.

Note: The volume percent concentration of $SO_2$ in one or more gases described herein may be greater than or equal to one or more or a combination of the following: 0.001%, or 0.1%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35%, or 36%, or 37%, or 38%, or 39%, or 40%, or 41%, or 42%, or 43%, or 44%, or 45%, or 46%, or 47%, or 48%, or 49%, or 50%, or 51%, or 52%, or 53%, or 54%, or 55%, or 56%, or 57%, or 58%, or 59%, or 60%, or 61%, or 62%, or 63%, or 64%, or 65%, or 66%, or 67%, or 68%, or 69%, or 70%, or 71%, or 72%, or 73%, or 74%, or 75%, or 76%, or 77%, or 78%, or 79%, or 80%, or 81%, or 82%, or 83%, or 84%, or 85%, or 86%, or 87%, or 88%, or 89%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.9%, or less than or equal to 100%.

Additional Notes

Note: 'WA' may comprise a weak acid, which may include, but not limited to, silicic acid, or orthosilicic acid, or silicon acid derivatives, or silicon minerals, or silicon acids, or aluminates, or ferrates, or a combination thereof.

Note: Some embodiments may involve reacting calcium silicate or a material comprising silicon directly with sulfur dioxide or sulfur dioxide in an non-aqueous solution or a combination thereof.

Note: In some embodiments, contaminants or impurities may dissolve in a solution comprising sulfur dioxide, or due to the presence of sulfuric acid, or a combination thereof. Contaminants or impurities may include, but are not limited to, one or more or a combination of the following: iron, or aluminum, or alkali metals, or transition metals, or other non-bisulfate soluble salts, or non-alkaline earth bisulfate salts, or a combination thereof. In some embodiments, dissolved contaminants may be present after solid-liquid separation, and/or after calcium sulfite precipitation. In some embodiments, at least a portion of contaminants may be separated periodically or continuously. Contaminants may be separated by, including, but not limited to, precipitation, or membrane based process, or cooling, or heating, or crystallization, or cryodesalination, or a separation process described herein, or a separation process in the art, or a combination thereof.

Note: 'Calcium' may also refer to magnesium and/or other alkaline earth metals.

Note: In some embodiments, one absorption column, or absorption step, or absorption process, or a combination thereof may be employed to absorb sulfur dioxide gas and form aqueous sulfur dioxide or a sulfurous acid solution. In some embodiments, more than one absorption column, or absorption step, or absorption process, or a combination thereof may be employed to absorb sulfur dioxide gas and form aqueous sulfur dioxide or a sulfurous acid solution.

Note: Calcining kilns may include, but are not limited to, one or more or a combination of the following: Shaft kilns, or Counter-current shaft kilns, or Regenerative kilns, or Annular kilns, or Rotary kilns.

Additional Notes

Note: 'WA' may comprise a weak acid, which may include, but not limited to, silicic acid, or orthosilicic acid, or silicon acid derivatives, or silicon minerals, or silicon acids, or aluminates, or ferrates, or a combination thereof.

Note: Calcium or magnesium—weak acid input may comprise, for example, including, but not limited to, one or more or a combination of the following: carbonates, or bicarbonates, or silicates, or silicate derivatives, or minerals, or concrete, or cement, or waste concrete, or waste cement, or steel slag, or fly ash, or ash, or limestone, or rock.

Note: In some embodiments, higher partial pressure $CO_2$, or higher concentration $CO_2$, or pure $CO_2(g)$, or high partial pressure $CO_2(g)$, or $CO_2(l)$, or $CO_2(g)$, may be employed to facilitate formation of bicarbonate salts. For example, in some embodiments, one or more or a combination of the following may be employed:

At least a portion of $CO_2$ input may be sourced from a reaction of calcium carbonate with sulfurous acid At least a portion of $CO_2$ input may be sources from $CO_2$ sources produced within the process, or other $CO_2$ sources, or a combination thereof At least a portion of $CO_2$ input may be sourced from $CO_2$ captured from a combustion source, or a combustion source employed to produce heat, or emissions source, or air, or geological $CO_2$ source, or natural $CO_2$ source, or a combination thereof.

Note: $CO_2$ sources include, but are not limited to,

Note: Some embodiments may be designed to operate as a low temperature process, where the solutions and/or solid reagents in thermal desorption or decomposition may undergo or operate thermal desorption or decomposition at less than 150° C., or less than 200° C., or less than 250° C., or less than 300° C., or less than 350° C.

Note: In some embodiments, at least a portion of heat may be supplied by a heat pump, or a refrigeration cycle, or a combination thereof. A heat pump may comprise, including, but not limited to, a mechanical, or thermal, or absorption, or a combination thereof process. A heat pump may be powered by, including, but not limited to, electricity, or heat, or photons, or chemical reaction, or radiation, or mechanical work, or pneumatic process, or hydraulic process, or expansion, or compression, or evaporation, or absorption, or vapor pressure differences, or osmotic pressure differences, or temperature differences, or pressure differences, or a combination thereof.

Additional Notes

Note: In some embodiments, sulfides and/or hydrogen sulfide may comprise a weak acid or weak acid anion.

Note: Separations for removing accumulating water, or removing water, or recovering water, or concentrating, or crystalizing, or precipitating, or separating, or removing, or a combination thereof may include, but are not limited to, one or more or a combination of the following: falling film evaporator, mechanical vapor compression (MVC), or mechanical vapor recompression, or multi-effect distillation (MED), or multi-stage flash distillation (MSF), or vapor compression (VC) distillation, or vacuum vapor compression (VVC), or membrane distillation, or evaporation, or distillation, or forward osmosis, or reverse osmosis, or nanofiltration, or hot nanofiltration, or hot reverse osmosis, or hot concentrating followed by cooling precipitation, or hot concentrating followed by cooling precipitation and solid-liquid separation, or heating precipitation, centrifuge, settling, or filter, or rotary filter, or calcining, or desorption, or absorption, or coalescing, or decanting, or aggregation, or coagulation, or frothing, or density based methods, or surface tension based methods, or foaming separation, emulsification, or de-emulsification, or flocculation, solventing out, or salting out, or cooling precipitation, or heating, or cryodesalination, or zero liquid discharge processes, or crystallization processes, or electrodialysis reversal (EDR), or electrodialysis process, or magnetic separation, or eddy currents, or electromagnetic induction, or filtration, or activated carbon, or ion exchange, or ion exchange membrane, or precipitation process, or cryodesalination, or cooling desalination, or cooling, or heating, or salting-out, or solventing-out, or adding a solvent to precipitate a solid and then removing the added solvent, or a combination thereof.

Note: Some embodiments may employ an inert gas, such as nitrogen or argon, or a gas other than diatomic oxygen, such as $CO_2$, or a combination thereof in the headspace to prevent, for example, oxidation of or reaction of oxygen with sulfite, metabisulfite, bisulfite, sulfur dioxide, sulfurous acid, or a combination thereof.

Additional Notes

Note: Magnesium or other alkaline earth or alkaline earth salts may be employed instead of or in addition to calcium.

Note: Concrete waste may be produced in excess of 600 million tons annually in the USA alone, which is more than twice the amount of generated municipal solid waste.

Note: At least a portion of sulfur dioxide may be lost in one or more or a combination of steps. Alternatively, or additionally, sulfur dioxide may be exit the process as a, for example, a residual, in one or more outputs. Sulfur dioxide or 'make-up sulfur dioxide' may be added to the process. In some embodiments, sulfur dioxide may be stored on site and added as desired or needed to the process. In some embodiments, elemental sulfur, or hydrogen sulfide, or a salt comprising sulfur, or sulfide salt, or sulfite salt, or sulfate salt, or a combination thereof may be a source of sulfur dioxide or sulfurous acid, by, for example, including, but not limited to, one or more or a combination thereof: combustion, or acid-base reaction, or reaction with an acid, or carbothermic reduction, or thermal or decomposition, or electrolysis, or electrodialysis, or electrochemical reaction.

Note: In some embodiments, at least a portion of calcium sulfate may be removed. For example, a portion of residual dissolved calcium sulfate may precipitate and may be removed by, for example, including, but not limited to, solid-liquid separation, or removal of calcium sulfate scaling, or a combination thereof.

Note: One or more or a combination of steps in one or more embodiments may require heating and/or cooling. For example, a reaction of sulfurous acid with a calcium—weak acid or magnesium—weak acid may require or may be facilitated by cooling or heating. Alternatively, or additionally, heat or heating or cooling or a combination thereof may be recovered from one or more or a combination of reaction steps. In some embodiments, heat or heating or cooling or a combination thereof may be recovered and said recovered heat or heating or cooling or a combination thereof may be transferred or employed in one or more other steps, or in the same step, or in other applications.

Note: Losses may occur during the process. Makeup streams of one or more or a combination of reagents may be added.

Additional Notes

Note: Contaminants may exist or accumulate in the process. If desired, one or more contaminants may be at least partially removed periodically, or continuously, or as desired, or a combination thereof.

Note: Other acid gases may be employed instead of or in addition to sulfur dioxide, which may include, but are not limited to, nitrogen oxides, or nitrogen dioxide, or nitrogen monoxide, or dinitrogen tetroxide, or nitric acid, or carbon dioxide, or carbonic acid, or hydrogen sulfuric, or sulfonic acid, or hydrosulfuric acid, or organo-sulfurous compounds, or hydrochloric acid, or hydrobromic acid, or hydroiodic acid, or hydrogen cyanide, or sulfuric acid, or perchloric acid, or nitrous acid, or hydrofluoric acid, or nitrogen derivative acids, or halogen derivative acids, or derivatives thereof, or a combination thereof.

Note: At least a portion of heat may be provided from the reaction of calcium oxide with water to form calcium hydroxide or a calcium hydroxide solution.

Note: Calcium—weak acid or magnesium—weak acid salts or 'WA' may include, but are not limited, salts of organic acids. Organic acids, or carboxylic acids, or organic acid anions, or a combination thereof may include, but are not limited to, one or more or a combination of the following: citric acid, or aconitates, or citrates, or isocitrates, or alloisocitrate, or oxalic acid, or acetic acid, or carboxylic acids, or lactic acid, or aconitic acid, or formic acid, or uric acid, or malic acid, or tartaric acid, methanoic acid, or hydroxymethanoic acid, or ethanoic acid, or 2-hydroxyethanoic acid, or oxoethanoic acid, or ethanedioic acid, or propanoic acid, or propenoic acid, or propynoic acid, or 2-hydroxypropanoic acid, or 3-hydroxypropanoic acid, or 2,3-dihydroxypropanoic acid, or 2-oxopropanoic acid, or 3-oxopropanoic acid, or 2,3-dioxopropanoic acid, or propanedioic acid, or 2-hydroxypropanedioic acid, or 2,2-dihydroxypropanedioic acid, or oxopropanedioic acid, or oxirane-2-carboxylic acid, or butanoic acid, or 2-methylpropanoic acid, or (E)-but-2-enoic acid, or (Z)-but-2-enoic acid, or 2-methylpropenoic acid, or but-3-enoic acid, or but-2-ynoic acid, or 2-hydroxybutanoic acid, or 3-hydroxybutanoic acid, or 4-hydroxybutanoic acid, or 2-oxobutanoic acid, or 3-oxobutanoic acid, or 4-oxobutanoic acid, or butanedioic acid, or 2-methylpropanedioic acid, or (E)-butenedioic acid, or (Z)-butenedioic acid, or butynedioic acid, or hydroxybutanedioic acid, or 2,3-dihydroxybutanedioic acid, or oxobutanedioic acid, or dioxobutanedioic acid, or pentanoic acid, or 3-methylbutanoic acid, or 2-methylbutanoic acid, or 2,2-dimethylpropanoic acid, or 3-hydroxypentanoic acid, or 4-hydroxypentanoic acid, or 3-hydroxy-3-methylbutanoic acid, or pentanedioic acid, or 2-oxopentanedioic acid, or 3-oxopentanedioic acid, or furan-2-carboxylic acid, or tetrahydrofuran-2-carboxylic acid, or hexanoic acid, or hexanedioic acid, or 2,3-dimethylbutanoic acid, or 3,3-dimethylbutanoic acid, or 2-hydroxypropane-1,2,3-tricarboxylic acid, or prop-1-ene-1,2,3-tricarboxylic acid, or 1-hydroxypropane-1,2,3-tricarboxylic acid, or (2E,4E)-hexa-2,4-dienoic acid, or heptanoic acid, or heptanedioic acid, or cyclohexanecarboxylic acid, or benzenecarboxylic acid, or 2-hydroxybenzoic acid, or 4-carboxybenzoic acid, or 2,2-dimethylpentanoic acid, or 2,3-dimethylpentanoic acid, or 2,4-dimethylpentanoic acid, or 3,3-dimethylpentanoic acid, or 2-ethylpentanoic acid, or 3-ethylpentanoic acid, or 2-methylhexanoic acid, or 3-methylhexanoic acid, or 2,2,3-trimethylbutanoic acid, or 2-ethyl-2-methylbutanoic acid, or 2-ethyl-3-, or methylbutanoic acid, or octanoic acid, or benzene-1,2-dicarboxylic acid, or 2-methylheptanoic acid, or 3-methylheptanoic acid, or 4-methylheptanoic acid, or 5-methylheptanoic acid, or 6-methylheptanoic acid, or 2,2-dimethylhexanoic acid, or 2,3-dimethylhexanoic acid, or 2,4-dimethylhexanoic acid, or 2,5-dimethylhexanoic acid, or 3,3-dimethylhexanoic acid, or 3,4-dimethylhexanoic acid, or 3,5-dimethylhexanoic acid, or 4,4-dimethylhexanoic acid, or 4,5-dimethylhexanoic acid, or 5,5-dimethylhexanoic acid, or 2-ethanehexanoic acid, or 3-ethanehexanoic acid, or 4-ethanehexanoic acid, or 5-ethanehexanoic acid, or 2-octenoic acid, or 3-octenoic acid, or 4-octenoic acid, or 5-octenoic acid, or 6-octenoic acid, or 7-octenoic acid, or nonanoic acid, or benzene-1,3,5-tricarboxylic acid, or (E)-3-phenylprop-2-enoic acid, or decanoic acid, or decanedioic acid, or undecanoic acid, or dodecanoic acid, or benzene-1,2,3,4,5,6-hexacarboxylic acid, or tridecanoic acid, or tetradecanoic acid, or pentadecanoic acid, or hexadecanoic acid, or heptadecanoic acid, or octadecanoic acid, or (9Z)-octadec-9-enoic acid, or (9Z,12Z)-octadeca-9,12-dienoic acid, or (9Z,12Z,15Z)-octadeca-9,12,15-trienoic acid, or (6Z,9Z,12Z)-octadeca-6,9,12-trienoic acid, or (6Z,9Z,12Z,15Z)-octadeca-6,9,12,15-tetraenoic acid, or nonadecanoic acid, or eicosanoic acid, or (5Z,8Z,11Z)-eicosa-5,8,11-trienoic acid, or (5Z,8Z,11Z,14Z)-eicosa-5,8,11,14-tetraenoic acid, or (5Z,8Z,11Z,14Z,17Z)-eicosa-5,8,11,14-pentaenoic acid, or heneicosanoic acid, or docosanoic acid, or (4Z,7Z,10Z,13Z,16Z,19Z)-docosa-4,7,10,13,16,19-hexaenoic acid, or tricosanoic acid, or tetracosanoic acid, or pentacosanoic acid, or hexacosanoic acid, or amino acids, or glutamate, or glutamic acid.

Note: Weak acids or organic acids may include, but are not limited to, one or more or a combination of the following: carboxylic acids, or sulfonic acids, or alcohols, or thiols, or enols, or phenols, or carbonic acid Additional Notes Note: Calcium citrate may be in the form of tri-calcium citrate tetrahydrate.
Note: Separated citric acid may be in the form of an aqueous solution, or citric acid monohydrate, or anhydrous citric acid, or a combination thereof.
Note: Remaining solution after removal of citric acid may be treated with activated carbon, or passed through cation or anion exchangers, or an anion exchange resin, or a cation exchanger resin, or a combination thereof.
Note: Citric acid, or other carboxylic acid, or organic acid, or a combination thereof may be separated from or recovered from including, but not limited to, one or more or a combination of the following: fermentation broth, or sugar broths, or sugars, or raw sugars, or raw agricultural feedstocks, or agricultural byproducts, or sugar refining liquids, or mold produced citric acid, or juices, or fungi produced acids, or liquids or acids produced by *Aspergillus niger*, or sucrose broth, or dextrose broth, or glucose broth, or corn steep liquor, or molasses, or hydrolyzed corn starch, or citrus fruits, or fruit juices. Said separating or recovering may involve reaction or contacting with calcium hydroxide or aqueous calcium hydroxide solution.
Note: Heat may be recovered in one or more process steps and may employed in one or more other process steps, or within the same process step, or both.
Note: Calcium citrate may be provided as an example organic acid salt of calcium.
Note: Calcium may be provided as an example alkaline earth metal or alkaline earth metal cation or alkaline earth metal cation salt.
Note: Calcium silicate may be provided as an example weak acid salt of calcium or an example reagent representing a wide array of compositions or minerals comprising calcium, magnesium, silicon, oxygen, and derivatives thereof.
Note: Calcium oxide produced may be reacted with water to produce calcium hydroxide or a solution comprising aqueous calcium hydroxide. The aqueous calcium hydroxide may be reacted with $CO_2$, such as a gas comprising $CO_2$, to produce precipitate calcium carbonate and water. For example, aqueous sodium hydroxide may be reacted with flue gas, or raw gas, or air, or gases produced from fuel combusted to power the calciner, or remaining gases after absorption of sulfur dioxide, or other gas comprising at least a portion $CO_2$, or a combination thereof. Some embodiments of the present invention may be employed to produce $CO_2$-emissions neutral or negative precipitated calcium carbonate. Some embodiments of the present invention may involve producing $CO_2$-emissions neutral or negative precipitated calcium carbonate using $CO_2$ from the air or captured from the air using the presently described process.

Additional Notes

Note: Calcium oxide produced may be reacted with water to produce calcium hydroxide or a solution comprising aqueous calcium hydroxide. The aqueous calcium hydroxide may be reacted sodium carbonate, such as an aqueous solution of sodium carbonate, to produce precipitate calcium carbonate and aqueous sodium hydroxide. The precipitated calcium carbonate may be separated from the aqueous sodium hydroxide and may comprise a valuable byproduct. The aqueous sodium hydroxide may be reacted with a gas comprising carbon dioxide to produce aqueous sodium carbonate. For example, aqueous sodium hydroxide may be reacted with flue gas, or raw gas, or air, or gases produced from fuel combusted to power the calciner, or remaining gases after absorption of sulfur dioxide, or other gas comprising at least a portion $CO_2$, or a combination thereof. Some embodiments of the present invention may be employed to produce $CO_2$-emissions neutral or negative precipitated calcium carbonate. Some embodiments of the present invention may involve producing $CO_2$-emissions neutral or negative precipitated calcium carbonate using $CO_2$ from the air or captured from the air using the presently described process. Some embodiments of the present invention may involve producing $CO_2$-emissions neutral or negative precipitated calcium carbonate using $CO_2$ from emissions sources, or air, or both using the presently described process.

Note: The weight percent concentration of one or more or a combination of reagents may include, but is not limited to, less than, or equal to, or greater than one or more or a combination of the following: 0%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Additional Notes

Note: Calcium silicate input or magnesium silicate input may comprise a slag. For example, global iron slag production is estimated to be 320 million to 384 million tons annually and steel stag is estimated to be between 190 million to 280 million tons annually. Other slags may include, but are not limited to, slags from magnesium production. Slags are generally produced when calcium oxide or magnesium oxide are added to a metal production process to remove impurities, or facilitate certain conditions or properties, or a combination thereof. The present invention may convert said slags into calcium oxide or magnesium oxide or other alkaline earth oxide. The present invention may enable a circular economy in the iron-marking, or steel-making, or other metal production industries because calcium oxide and/or magnesium oxide are used as the inputs which result in the production of slag. If iron or steel makers can recycle at least a portion of slag into calcium oxide or magnesium oxide, iron or steel makers may greatly reduce or eliminate their need to purchase calcium oxide or magnesium oxide, significantly reducing operating costs. If at least a portion of iron or steel stag is recycled into calcium oxide or magnesium oxide, iron and/or steel production lifecycle carbon dioxide emissions will be greatly reduced.

Note: Calcium sulfite and/or magnesium sulfite may comprise hydrates. For example, magnesium sulfite may form a hexahydrate, or a trihydrate, or may be anhydrous. For example, calcium sulfite may form a tetrahydrate, or a hemihydrate, or may be anhydrous. It may be desirable to dehydrate at least a portion of the hydrate of calcium sulfite, or magnesium sulfite, or both before or during calcining of a sulfite into an oxide and sulfur dioxide. It may be desirable to dehydrate at least a portion of the hydrate of calcium sulfite, or magnesium sulfite, or both before calcining of a sulfite into an oxide and sulfur dioxide. For example, magnesium sulfite hexahydrate may be heated to above 40° C., where magnesium sulfite hexahydrate may decompose or dehydrate into magnesium sulfite trihydrate. For example, calcium sulfite tetrahydrate may be heated to decompose or dehydrate into calcium sulfite hemihydrate. For example, calcium and/or magnesium hydrates may be decomposed or dehydrated into anhydrous forms. For example, calcium sulfite hydrate and/or magnesium sulfite hydrate may be heated to decompose or dehydrate into anhydrous forms. Dehydrating hydrates may require heat or other energy. It may be desirable to supply said heat or other energy for dehydrating hydrates from lower cost, or lower quality heat sources, such as, including, but not limited to, one or more or a combination of the following: waste heat, or heat from other process steps, or low quality steam, or medium quality steam, or high quality step, or combustion of one or more fuels, or solar thermal, or slacking lime, or hydrating a oxide to a hydroxide, or other heat source.

Additional Notes

Note: Systems and methods may be employed to remove impurities, or prevent or minimize accumulation of impurities, or a combination thereof. For example, input materials may comprise impurities other than desired reagents. In some instances, said impurities or contaminants may accumulate, or may result in the formation of other impurities, or a combination thereof. In some instances, impurities may dissolve in one or more solutions in the process. Impurities may be removed, or treated, or separated, by, including, but not limited to, one or more or a combination of the following: chemical reaction, or electrodialysis, or ion-exchanger, or precipitation, or cooling, or heating, or distillation, or membrane-based process, or solventing-out, or salting out.

Note: At least a portion of the weak acid product, or undissolved materials, or a combination thereof are employed as a concrete aggregate.

Note: At least a portion of the weak acid product, or undissolved materials, or a combination thereof may be disposed of or may comprise a waste product.

Note: A material comprising calcium and/or magnesium may comprise a material comprising an alkaline-earth. Alkaline-earths may include one or more or a combination of the following: beryllium (Be), or magnesium (Mg), or calcium (Ca), or strontium (Sr), or barium (Ba), or radium (Ra)

Note: In some embodiments, a material comprising calcium and/or magnesium may further comprise one or more or a combination of the following: iron oxides, or iron, or manganese oxide, or manganese, may include, but are not limited to, one or more or a combination of the following: iron (II), or iron (11,111), or iron (III), or iron (II) oxide, or iron (11,11) oxide, or iron (III) oxide, or iron, or iron sulfite, or iron sulfate, or iron sulfide, or iron, or ferrites, or ferrates, or calcium-iron salts, or magnesium iron salts, or iron silicate salts, or iron silicon salts, or iron carbon salts, or manganese salts, or manganese –3, or manganese –2, or manganese –1, or manganese 0, or manganese +1, or manganese +2, or manganese, or manganese +3, or manganese +4, or manganese +5, or manganese +6, or manganese +7, or manganese sulfite, or manganese oxide, or manganese carbonate, or manganese-iron, or calcium-manganese, or calcium-manganese salts, or magnesium-manganese, or magnesium-manganese salts, or manganese silicon, or manganese carbon, or manganese Additional Notes Note: The properties of iron and manganese may be similar. Manganese may be present in some materials which may comprise iron, such as some slags, or concretes, or minerals. In some embodiments, iron and manganese may be used interchangeably.

Note: Solutions comprising salts of metals lead, or copper, or gold, or silver, or zinc, or aluminum, or chromium, or cobalt, or manganese, or rare-earth metals, or iron, or molybdenum, or cadmium, or nickel, or silver, or cobalt, or zinc, or gold, or platinum, or platinum group metals, or a combination thereof may undergo a separations and/or refining process. For example, one or more or a combination of said metals may be separated or produced from solution or from a separated state or both by means of, for example, including, but not limited to, one or more or a combination of the following: electrolytic refining, or electrowinning, or electroextraction, or electrodeposition. For example, a solution comprising aqueous iron bisulfite, or manganese bisulfite, or iron sulfate, or manganese bisulfate, or iron chloride, or magnesium chloride may undergo electroextraction to produce manganese, iron, or a combination thereof. In some embodiments, one or more or a combination of the aforementioned metals may be separated by reaction with hydrogen sulfide or sulfur to produce a sulfide or an insoluble sulfide, then said sulfide may be converted into a form for use as in input to an electroextraction process.

Note: Separation of at least a portion of iron sulfite solid from at least a portion of calcium sulfite solid, or separation of iron from calcium or magnesium, or a combination thereof may be conducted by, including, but not limited to, one or more or a combination of the following: density based separation, or floatation and sinking separation using a dense liquid, or separation using a dense liquid, or separation using a liquid with a lower density than iron sulfite and a greater density than calcium sulfite, or magnetic separation, or magnetic separation of iron from calcium, or oxidation of iron, or reaction of solution comprising dissolved iron with hydrogen sulfide to produce iron sulfide solid precipitate, or reaction of solution comprising calcium with sulfuric acid to form calcium sulfate precipitate, or frothing, or floatation, or solid separation, or centrifuge, or grinding, or pulverization, or reaction of iron sulfite and calcium sulfite solids with sulfuric acid to form dissolved or aqueous iron sulfate and calcium sulfate solid, or reaction of a mixture of calcium oxide and iron oxide with water to form calcium hydroxide dissolved or aqueous and iron oxide solid, or precipitation of iron sulfite before calcium sulfite, or precipitation of calcium sulfite before iron sulfite, or electrodialysis, or electrodialysis reversal, or ion exchange, or iron exchange resin, or iron reaction, or double-salt reaction, or precipitation reaction, or temperature driven precipitation, or concentration driven precipitation Additional Notes Note: Oxygen or 'oxide' or 'hydroxide' or a combination thereof may be considered weak acids or 'weak acid anions' or a combination thereof.

Note: Desorption of sulfur dioxide form a solution comprising bisulfite may be conducted by, for example, including, but not limited to, one or more or a combination of the following: thermal desorption, or steam stripping, or a combination thereof. A solution comprising bisulfite may include, but is not limited to, a solution comprising one or more or a combination of the following: alkaline earth bisulfite, or magnesium bisulfite, or calcium bisulfite, or iron bisulfite, or manganese bisulfite, or zinc bisulfite, or sulfur dioxide, or water, or sulfurous acid.

Note: Separations may include, but are not limited to, one or more or a combination of the following: Separation by density, or Separation by magnetism, or Separation by frothing or surface tension, or Separation by residual solubility differences, or Separation by oxidation, or Separation by ion exchange, or Separation by reaction with an alkali hydroxide solution, or Separation by reaction with hydrogen sulfide, or Separation by reaction with aqueous sulfuric acid, or Separation by density using a high density liquid with a density less than at least one salt and a density greater than one salt, or Separation by density using a high density liquid with a density less than iron sulfite and a density greater than calcium sulfite, or Separation by density using a centrifuge, or Separation by a magnetic field using a mixing and an externally applied magnetic field, or Separation by reaction with and/or dissolution in water, or Grinding or pulverization, or Separation by froth flotation, or Other solid-solid separation method, or Other method for separating iron from calcium, or Other separation method Additional Notes Note: In some embodiments, remaining solution after separating magnesium sulfite solid using a solid-liquid separate process may be further treated with, including, but not limited to, one or more or a combination of the following: ion exchange, or resins, or filters, or chemical treatments, or chemical reactions, or membrane based process, or distillation, or cooling, or heating, or freezing, or cryodesalination, or solventing-out, or solvent induced precipitation, or salting-out, or other treatment. One or more solutions comprising water may be transferred to a sulfur dioxide absorption step, or mixed with a solution transferred to a sulfur dioxide absorption step, or a combination thereof.

Example Embodiments Sodium Hydroxide Production Using Calcium or Magnesium Input and Sulfur Dioxide Intermediate 1. A process comprising:
reacting a material comprising calcium carbonate with a solution comprising aqueous sulfur dioxide to form a gas comprising carbon dioxide and a solid comprising calcium sulfite;
reacting the solid comprising calcium sulfite with water and sulfur dioxide to form a solution comprising aqueous calcium bisulfite;
reacting the solution comprising aqueous calcium bisulfite with sodium sulfate to form an aqueous solution comprising sodium bisulfite and a solid comprising calcium sulfate;
decomposing said aqueous sodium bisulfite to form sodium sulfite and sulfur dioxide gas;
reacting said sodium sulfite with calcium hydroxide to form an aqueous solution comprising sodium hydroxide and a solid comprising calcium sulfite;
decomposing said calcium sulfite to form calcium oxide and sulfur dioxide;
2. The process of example embodiment 1 further comprising reacting calcium oxide with water to form calcium hydroxide.
3. The process of example embodiment 1 wherein said decomposing of an aqueous solution comprising sodium bisulfite comprises desorbing sulfur dioxide gas from said aqueous solution to form aqueous sodium sulfite.
4. The process of example embodiment 1 wherein said decomposing of an aqueous solution comprising sodium bisulfite comprises:
Removing water from said aqueous sodium bisulfite to form sodium metabisulfite solid; and
Thermally decomposing said sodium metabisulfite to form solid sodium sulfite and sulfur dioxide.
5. The process of example embodiment 1 further comprising capturing at least a portion of the carbon dioxide.
6. The process of example embodiment 5 wherein the captured carbon dioxide comprises a concentration greater than 70 percent or a partial pressure greater than 0.7 Bar.
7. The process of example embodiment 1 further comprising absorbing the sulfur dioxide formed from the decomposition of calcium sulfite into an aqueous solution to form aqueous sulfurous acid.
8. The process of example embodiment 7 further comprising reacting aqueous sulfurous acid with calcium carbonate to form a gas comprising carbon dioxide and a solid comprising calcium sulfite.
9. The process of example embodiment 1 further comprising absorbing the sulfur dioxide formed from the decomposition of sodium bisulfite into an aqueous solution to form aqueous sulfurous acid.
10. The process of example embodiment 9 further comprising reacting said aqueous sulfurous acid with calcium sulfite to form a solution comprising aqueous calcium bisulfite.
11. The process of example embodiment 1 further comprising absorbing the sulfur dioxide formed from the decomposition of sodium bisulfite into an aqueous solution in the presence of calcium sulfite to form a solution comprising aqueous calcium bisulfite.
12. The process of example embodiment 1 wherein said calcium hydroxide comprises milk of lime.
13. The process of example embodiment 2 wherein the reaction of calcium oxide and water produces heat; and
wherein at least a portion of said heat is employed to dry a calcium sulfite before a calcination.
14. The process of example embodiment 1 wherein the reaction of calcium oxide and water produces heat; and
wherein at least a portion of said heat is employed in decomposing said sodium bisulfite to sodium sulfite and sulfur dioxide.
15. The process of example embodiment 1 wherein said material comprising calcium carbonate further comprises magnesium; and
wherein said reacting a material comprising calcium carbonate with a solution comprising aqueous sulfur dioxide to form a gas comprising carbon dioxide and a solid comprising calcium sulfite solid further comprises forming a solution comprising aqueous magnesium sulfite.
16. The process of example embodiment 15 further comprising:
cooling the solution comprising aqueous magnesium sulfite to precipitate at least a portion of magnesium sulfite;
removing at least a portion of precipitated magnesium sulfite from the solution comprising aqueous magnesium sulfite to form a second solution comprising less magnesium sulfite;
heating said second solution;
mixing said second heated solution with a third solution comprising magnesium sulfite to form a fourth solution; and
separating said fourth solution at a higher temperature using reverse osmosis to form a retentate comprising concentrated aqueous magnesium sulfite and a permeate comprising water.
17. The process of example embodiment 1 wherein the partial pressure of sulfur dioxide gas formed from the decomposing of calcium sulfite is lower than the partial pressure of sulfur dioxide gas formed from the decomposing of sodium bisulfite.
18. A process comprising:
reacting a material comprising alkaline earth cation-weak acid anion with sulfur dioxide and an aqueous solution to form a weak acid derivative and an aqueous solution comprising alkaline earth bisulfite;
separating said weak acid derivative from said aqueous solution comprising alkaline earth bisulfite;
reacting aqueous alkaline earth bisulfite with sodium sulfate to form an aqueous solution comprising sodium bisulfite and a solid comprising an alkaline earth sulfate;
separating said solid comprising an alkaline earth sulfate from said aqueous solution comprising sodium bisulfite;

decomposing the aqueous solution comprising sodium bisulfite to form sodium sulfite and sulfur dioxide gas;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing said solid comprising calcium sulfite to form calcium oxide and sulfur dioxide gas;

reacting the calcium oxide with water to form calcium hydroxide.

19. The process of example embodiment 18 wherein the alkaline earth cation comprises one or more or any combination of the following cations: beryllium (Be), or magnesium (Mg), or calcium (Ca), or strontium (Sr), or barium (Ba), or radium (Ra).

20. The process of example embodiment 18 wherein said weak acid derivative comprises a derivative of an acid with an acid strength lower than or less acidic than sulfurous acid.

21. The process of example embodiment 18 wherein said weak acid derivative comprises carbon dioxide, or hydrogen sulfide, or silicon dioxide, or iron oxide, or manganese oxide, or aluminum oxide, or any mixture thereof.

22. The process of example embodiment 18 wherein said decomposing of an aqueous solution comprising sodium bisulfite comprises desorbing sulfur dioxide gas from said aqueous solution to form aqueous sodium sulfite.

23. The process of example embodiment 18 wherein said decomposing of an aqueous solution comprising sodium bisulfite comprises:

Removing water from said aqueous sodium bisulfite to form sodium metabisulfite solid; and Thermally decomposing said sodium metabisulfite to form solid sodium sulfite and sulfur dioxide.

24. The process of example embodiment 18 wherein said sulfur dioxide and an aqueous solution comprises reacting sulfur dioxide gas with an aqueous solution in the presence of alkaline earth sulfite to facilitate the formation of aqueous alkaline earth bisulfite.

25. The process of example embodiment 18 further comprising absorbing at least a portion of sulfur dioxide gas into an aqueous solution to form aqueous sulfurous acid. 26. A process comprising:

reacting a material comprising magnesium-weak acid with a solution comprising aqueous sulfur dioxide to form a weak acid derivative and an aqueous solution comprising magnesium sulfite;

separating said weak acid derivative from said aqueous solution comprising magnesium sulfite;

reacting magnesium sulfite with sodium sulfate to form sodium sulfite and magnesium sulfate;

separating at least a portion of said sodium sulfite from said magnesium sulfate;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing calcium sulfite to form calcium oxide and sulfur dioxide; and reacting calcium oxide with water to form calcium hydroxide.

27. The process of example embodiment 26 further comprising separating the aqueous solution comprising magnesium sulfite to form water and a magnesium sulfite solid.

28. The process of example embodiment 26 further comprising:

cooling the aqueous solution comprising magnesium sulfite to precipitate at least a portion of magnesium sulfite;

separating at least a portion of precipitated magnesium sulfite to form a second solution comprising less magnesium sulfite;

heating said second solution comprising less magnesium sulfite; and separating said heated second solution at a higher temperature using reverse osmosis to form a retentate comprising concentrated aqueous magnesium sulfite and a permeate comprising water.

29. The process of example embodiment 26 further comprising:

precipitating a portion of magnesium sulfite from a first solution comprising concentrated aqueous magnesium sulfite by cooling;

separating magnesium sulfite solid precipitate from the remaining solution comprising a second solution comprising aqueous magnesium sulfite;

heating said second solution comprising aqueous magnesium sulfite to a higher temperature;

mixing said second solution comprising aqueous magnesium sulfite at a higher temperature with a third solution comprising magnesium sulfite to form a fourth solution; and separating said fourth solution at a higher temperature using reverse osmosis into a retentate comprising a first solution comprising concentrated aqueous magnesium sulfite and a permeate comprising water.

30. A process comprising:

reacting a material comprising alkaline earth cation-weak acid anion with sulfur dioxide and an aqueous solution to form a weak acid derivative and an aqueous solution comprising alkaline earth bisulfite;

separating said weak acid derivative from said aqueous solution comprising alkaline earth bisulfite;

reacting the aqueous solution comprising alkaline earth bisulfite with sodium sulfate to form an aqueous solution comprising sodium bisulfite and a solid comprising an alkaline earth sulfate;

separating said solid comprising the alkaline earth sulfate from said aqueous solution comprising sodium bisulfite;

decomposing said aqueous solution comprising sodium bisulfite to form sodium sulfite and sulfur dioxide gas;

reacting said sodium sulfite with alkaline earth hydroxide to form sodium hydroxide and an alkaline earth sulfite;

separating said alkaline earth sulfite from said aqueous solution comprising sodium hydroxide;

decomposing alkaline earth sulfite to form alkaline earth oxide and sulfur dioxide; and reacting alkaline earth oxide with water to form alkaline earth hydroxide.

1. A process for producing sodium hydroxide and gypsum from a material comprising calcium wherein the process comprises:

reacting a material comprising calcium carbonate with a solution comprising aqueous sulfur dioxide to form a gas comprising carbon dioxide and a solid comprising calcium sulfite;

reacting the solid comprising calcium sulfite with water and sulfur dioxide to form a solution comprising aqueous calcium bisulfite;

reacting the aqueous solution comprising aqueous calcium bisulfite with sodium sulfate to form aqueous sodium bisulfite and a solid comprising calcium sulfate;

separating sodium metabisulfite from said aqueous solution comprising sodium bisulfite;

decomposing said sodium metabisulfite to form sodium sulfite and sulfur dioxide gas;

reacting said sodium sulfite with calcium hydroxide to form an aqueous solution comprising sodium hydroxide and a solid comprising calcium sulfite;

decomposing said calcium sulfite to form calcium oxide and sulfur dioxide;

reacting calcium oxide with water to form calcium hydroxide.

2. The process of example embodiment 1 wherein the carbon dioxide formed from the reaction of calcium carbonate with aqueous sulfur dioxide may comprise captured carbon dioxide.

3. The process of example embodiment 2 wherein the carbon dioxide formed comprises a concentration greater than 70 percent or a partial pressure greater than 0.7 Bar.

4. The process of example embodiment 1 wherein the sulfur dioxide formed from the decomposition of calcium sulfite is absorbed into an aqueous solution to form aqueous sulfurous acid.

5. The process of example embodiment 4 wherein said formed aqueous sulfur dioxide is reacted with calcium carbonate to form a gas comprising carbon dioxide and a solid comprising calcium sulfite.

6. The process of example embodiment 1 wherein the sulfur dioxide formed from the decomposition of sodium metabisulfite is absorbed into an aqueous solution to form aqueous sulfurous acid.

7. The process of example embodiment 6 wherein said formed aqueous sulfur dioxide is reacted with calcium sulfite to form a solution comprising aqueous calcium bisulfite.

8. The process of example embodiment 1 wherein the sulfur dioxide formed from the decomposition of sodium metabisulfite is absorbed into an aqueous solution in the presence of calcium sulfite to form a solution comprising aqueous calcium bisulfite.

9. The process of example embodiment 1 wherein said calcium hydroxide comprise milk of lime.

10. The process of example embodiment 1 wherein the reaction of calcium oxide and water produces heat; and
wherein at least a portion of said heat is employed to dry calcium sulfite before calcination.

11. The process of example embodiment 1 wherein the reaction of calcium oxide and water produces heat; and wherein at least a portion of said heat is employed to facilitate the decomposition of sodium metabisulfite to sodium sulfite and sulfur dioxide.

12. The process of example embodiment 1 wherein said separating sodium metabisulfite from said aqueous solution comprising sodium bisulfite comprises removing water, or precipitation of sodium metabisulfite, or distillation, or cooling, or freeze desalination, or solvent addition precipitation.

13. The process of example embodiment 1 wherein said calcium carbonate further comprises magnesium; and
wherein said reaction of calcium carbonate with aqueous sulfur dioxide to form calcium sulfite solid further comprises forming a solution comprising aqueous magnesium sulfite.

14. The process of example embodiment 13 wherein magnesium sulfite solid is separated from said aqueous magnesium sulfite by cooling precipitation.

15. The process of example embodiment 13 comprising:
Precipitating a portion of magnesium sulfite from a first solution comprising concentrated aqueous magnesium sulfite by cooling; and Separating magnesium sulfite solid precipitate from the remaining solution comprising a second solution comprising aqueous magnesium sulfite; and Heating said second solution comprising aqueous magnesium sulfite to a higher temperature; and Mixing said second solution comprising aqueous magnesium sulfite at a higher temperature with a third solution comprising magnesium sulfite introduced from the process to form a fourth solution; and Separating said fourth solution at a higher temperature using reverse osmosis into a retentate comprising a first solution comprising concentrated aqueous magnesium sulfite and a permeate comprising water.

16. The process of example embodiment 1 wherein the partial pressure of sulfur dioxide gas formed from the decomposing of calcium sulfite is lower than 0.3 atm.

17. The process of example embodiment 1 wherein the partial pressure of sulfur dioxide gas formed from the decomposing of sodium metabisulfite is greater than 1 atm.

18. A process for producing sodium hydroxide and gypsum from a material comprising alkaline earth wherein the process comprises:

reacting a material comprising alkaline earth cation-weak acid anion with sulfur dioxide and an aqueous solution to form a weak acid derivative and an aqueous solution comprising alkaline earth bisulfite;

separating said weak acid derivative from said aqueous solution comprising alkaline earth bisulfite;

reacting aqueous alkaline earth bisulfite with sodium sulfate to form aqueous solution comprising sodium bisulfite and a solid comprising an alkaline earth sulfate;

separating said solid comprising an alkaline earth sulfate from said aqueous solution comprising sodium bisulfite;

removing water from said aqueous solution comprising sodium bisulfite to form sodium metabisulfite;

decomposing sodium metabisulfite to form sodium sulfite and sulfur dioxide gas;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing calcium sulfite to form calcium oxide and sulfur dioxide;

reacting calcium oxide with water to form calcium hydroxide.

19. The process of example embodiment 18 wherein the alkaline earth comprises one or more or any combination of the following: beryllium (Be), or magnesium (Mg), or calcium (Ca), or strontium (Sr), or barium (Ba), or radium (Ra).

20. The process of example embodiment 18 wherein said weak acid derivative comprises a derivative of an acid with an acid strength lower than or less acidic than sulfurous acid.

21. The process of example embodiment 18 wherein said weak acid derivative comprises a gas selected from carbon dioxide, or hydrogen sulfide, or a mixture thereof.

22. The process of example embodiment 18 wherein said weak acid derivative comprises silicon dioxide, or iron oxide, or manganese oxide, or aluminum oxide, or a mixture thereof.

23. The process of example embodiment 18 wherein said sulfur dioxide and an aqueous solution comprises aqueous sulfur dioxide.

24. The process of example embodiment 18 wherein said sulfur dioxide and an aqueous solution comprises reacting sulfur dioxide gas with an aqueous solution in the presence of alkaline earth sulfite to facilitate the formation of aqueous alkaline earth bisulfite.

25. The process of example embodiment 18 further comprising absorbing sulfur dioxide from the decomposition of calcium sulfite and decomposition of sodium metabisulfite into an aqueous solution to form aqueous sulfurous acid.

26. A process for producing sodium hydroxide and magnesium sulfate from a material comprising magnesium wherein the process comprises:
   reacting a material comprising magnesium-weak acid with a solution comprising aqueous sulfur dioxide to form a weak acid derivative and an aqueous solution comprising magnesium sulfite;
   separating said weak acid derivative from said aqueous solution comprising magnesium sulfite;
   reacting magnesium sulfite with sodium sulfate to form sodium sulfite and magnesium sulfate;
   separating at least a portion of said sodium sulfite from said magnesium sulfate;
   reacting said sodium sulfite with calcium hydroxide to form an aqueous solution comprising sodium hydroxide and a solid comprising calcium sulfite;
   separating said solid comprising calcium sulfite from said aqueous solution comprising sodium hydroxide;
   decomposing calcium sulfite to form calcium oxide and sulfur dioxide;
   reacting calcium oxide with water to form calcium hydroxide.

27. The process of example embodiment 26 further comprising separating the aqueous magnesium sulfite into water and magnesium sulfite solid.

28. The process of example embodiment 27 comprising:
   Precipitating a portion of magnesium sulfite from a first solution comprising concentrated aqueous magnesium sulfite by cooling; and
   Separating magnesium sulfite solid precipitate from the remaining solution comprising a second solution comprising aqueous magnesium sulfite; and
   Mixing said second solution comprising aqueous magnesium sulfite with a third solution comprising magnesium sulfite introduced from the process to form a fourth solution; and
   Heating said fourth solution to a higher temperature; and
   Separating said fourth solution at a higher temperature using reverse osmosis into a retentate comprising a first solution comprising concentrated aqueous magnesium sulfite and a permeate comprising water.

29. The process of example embodiment 27 comprising:
   Precipitating a portion of magnesium sulfite from a first solution comprising concentrated aqueous magnesium sulfite by cooling; and
   Separating magnesium sulfite solid precipitate from the remaining solution comprising a second solution comprising aqueous magnesium sulfite; and
   Heating said second solution comprising aqueous magnesium sulfite to a higher temperature; and
   Mixing said second solution comprising aqueous magnesium sulfite at a higher temperature with a third solution comprising magnesium sulfite introduced from the process to form a fourth solution; and
   Separating said fourth solution at a higher temperature using reverse osmosis into a retentate comprising a first solution comprising concentrated aqueous magnesium sulfite and a permeate comprising water.

30. A process for producing sodium hydroxide and gypsum from a material comprising alkaline earth wherein the process comprises:
   reacting a material comprising alkaline earth cation-weak acid anion with sulfur dioxide and an aqueous solution to form a weak acid derivative and an aqueous solution comprising alkaline earth bisulfite;
   separating said weak acid derivative from said aqueous solution comprising alkaline earth bisulfite;
   reacting aqueous alkaline earth bisulfite with sodium sulfate to form aqueous solution comprising sodium bisulfite and a solid comprising an alkaline earth sulfate;
   separating said solid comprising an alkaline earth sulfate from said aqueous solution comprising sodium bisulfite;
   removing water from said aqueous solution comprising sodium bisulfite to form sodium metabisulfite;
   decomposing sodium metabisulfite to form sodium sulfite and sulfur dioxide gas;
   reacting said sodium sulfite with alkaline earth hydroxide to form sodium hydroxide and an alkaline earth sulfite;
   separating said alkaline earth sulfite from said aqueous solution comprising sodium hydroxide;
   decomposing alkaline earth sulfite to form alkaline earth oxide and sulfur dioxide;
   reacting alkaline earth oxide with water to form alkaline earth hydroxide.

Additional Example Embodiments

1. A process for producing sodium hydroxide and gypsum from a material comprising calcium wherein the process comprises:
   reacting a material comprising calcium carbonate with a solution comprising aqueous sulfur dioxide to form a gas comprising $CO_2$ and a solid comprising calcium sulfite;
   separating said solid comprising calcium sulfite;
   reacting the calcium sulfite solid with a solution comprising aqueous sulfur dioxide to form aqueous calcium bisulfite;
   reacting aqueous calcium bisulfite with sodium sulfate to form aqueous sodium bisulfite and a solid comprising calcium sulfate;
   separating said solid comprising calcium sulfate from said aqueous solution comprising sodium bisulfite;
   removing water from said aqueous solution comprising sodium bisulfite to form sodium metabisulfite;
   decomposing said sodium metabisulfite to form sodium sulfite and sulfur dioxide gas;
   reacting said sodium sulfite with calcium hydroxide to form an aqueous solution comprising sodium hydroxide and a solid comprising calcium sulfite;
   separating said solid comprising calcium sulfite from said aqueous solution comprising sodium hydroxide;
   decomposing calcium sulfite to form calcium oxide and sulfur dioxide;
   reacting calcium oxide with water to form calcium hydroxide.

1. A process for producing sodium hydroxide from a material comprising alkaline earth wherein the process comprises:
   reacting a material comprising alkaline earth cation-weak acid anion with a solution comprising aqueous sulfur dioxide to form a weak acid derivative and a solid comprising alkaline earth sulfite;
   separating said solid comprising alkaline earth sulfite and said weak acid derivative;

reacting the alkaline earth sulfite with a solution comprising aqueous sulfur dioxide to form aqueous alkaline earth bisulfite;

reacting aqueous alkaline earth bisulfite with sodium sulfate to form aqueous sodium bisulfite and a solid comprising alkaline earth sulfate;

separating said solid comprising alkaline earth sulfate from said aqueous solution comprising sodium bisulfite;

removing water from said aqueous solution comprising sodium bisulfite to form sodium metabisulfite;

decomposing said sodium metabisulfite to form sodium sulfite and sulfur dioxide gas;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing calcium sulfite to form calcium oxide and sulfur dioxide;

reacting calcium oxide with water to form calcium hydroxide.

1. A process for producing sodium hydroxide and gypsum from a material comprising alkaline earth wherein the process comprises:

reacting a material comprising alkaline earth cation-weak acid anion with a solution comprising aqueous sulfur dioxide to form a weak acid derivative and an aqueous solution comprising alkaline earth sulfite;

separating said weak acid derivative from said aqueous solution comprising alkaline earth sulfite;

reacting aqueous alkaline earth sulfite with sodium sulfate to form aqueous sodium sulfite and a solid comprising an alkaline earth sulfate;

separating said solid comprising an alkaline earth sulfate from said aqueous solution comprising sodium sulfite;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing calcium sulfite to form calcium oxide and sulfur dioxide;

reacting calcium oxide with water to form calcium hydroxide.

1. A process for producing sodium hydroxide and magnesium sulfate from a material comprising magnesium wherein the process comprises:

reacting a material comprising magnesium-weak acid with a solution comprising aqueous sulfur dioxide to form a weak acid derivative and an aqueous solution comprising magnesium sulfite;

separating said weak acid derivative from said aqueous solution comprising magnesium sulfite;

reacting aqueous magnesium sulfite with sodium sulfate to form aqueous sodium sulfite and magnesium sulfate;

separating at least a portion of said magnesium sulfate from said sodium sulfite;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing calcium sulfite to form calcium oxide and sulfur dioxide;

reacting calcium oxide with water to form calcium hydroxide.

1. A process for producing sodium hydroxide and magnesium sulfate from a material comprising magnesium wherein the process comprises:

reacting a material comprising magnesium-weak acid with a solution comprising aqueous sulfur dioxide to form a weak acid derivative and an aqueous solution comprising magnesium sulfite;

separating said weak acid derivative from said aqueous solution comprising magnesium sulfite;

reacting aqueous magnesium sulfite with sodium sulfate to form aqueous sodium sulfite and magnesium sulfate;

separating at least a portion of said sodium sulfite from said magnesium sulfate;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing calcium sulfite to form calcium oxide and sulfur dioxide;

reacting calcium oxide with water to form calcium hydroxide.

1. A process for producing sodium hydroxide and gypsum from a material comprising alkaline earth wherein the process comprises:

reacting a material comprising alkaline earth cation-weak acid anion with a solution comprising aqueous sulfur dioxide to form a weak acid derivative and an aqueous solution comprising alkaline earth bisulfite;

separating said weak acid derivative from said aqueous solution comprising alkaline earth bisulfite;

reacting aqueous alkaline earth bisulfite with sodium sulfate to form aqueous solution comprising sodium bisulfite and a solid comprising an alkaline earth sulfate;

separating said solid comprising an alkaline earth sulfate from said aqueous solution comprising sodium bisulfite;

removing water from said aqueous solution comprising sodium sulfite or sodium bisulfite to form sodium metabisulfite;

decomposing sodium metabisulfite to form sodium sulfite and sulfur dioxide gas;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing calcium sulfite to form calcium oxide and sulfur dioxide;

reacting calcium oxide with water to form calcium hydroxide.

1. A process for producing sodium hydroxide and gypsum from a material comprising alkaline earth wherein the process comprises:

reacting a material comprising alkaline earth cation-weak acid anion with a solution comprising aqueous sulfur dioxide to form a weak acid derivative and an aqueous solution comprising alkaline earth sulfite or bisulfite;

separating said weak acid derivative from said aqueous solution comprising alkaline earth sulfite or bisulfite;

reacting aqueous alkaline earth sulfite or bisulfite with sodium sulfate to form aqueous sodium sulfite or bisulfite and a solid comprising an alkaline earth sulfate;

separating said solid comprising an alkaline earth sulfate from said aqueous solution comprising sodium sulfite or sodium bisulfite;

removing water from said aqueous solution comprising sodium sulfite or sodium bisulfite to form sodium sulfite or sodium metabisulfite;

decomposing sodium metabisulfite to form sodium sulfite and sulfur dioxide gas;

reacting said sodium sulfite with calcium hydroxide to form an aqueous solution comprising sodium hydroxide and a solid comprising calcium sulfite;

separating said solid comprising calcium sulfite from said aqueous solution comprising sodium hydroxide;

decomposing calcium sulfite to form calcium oxide and sulfur dioxide;

reacting calcium oxide with water to form calcium hydroxide.

2. The process of example embodiment 1 wherein the weak acid derivative comprises carbon dioxide.

3. The process of example embodiment 1 wherein the weak acid derivative comprising silicon dioxide.

4. The process of example embodiment 1 wherein the alkaline earth comprises one or more or any combination of the following: beryllium (Be), or magnesium (Mg), or calcium (Ca), or strontium (Sr), or barium (Ba), or radium.

5. The process of example embodiment 1 wherein said water removal comprises precipitation, or crystallization, or cryo-desalination, or freezing desalination, or distillation, or membrane based process, or forward osmosis, or reverse osmosis, or multi effect distillation, or mechanical vapor compression distillation, or multistage flash distillation, or membrane distillation, or heat recovery distillation, or zero liquid discharge.

6. The process of example embodiment 1 wherein the heat from the reaction of calcium oxide with water to form calcium hydroxide is used to dry calcium sulfite before decomposing calcium sulfite.

7. The process of example embodiment 1 wherein the heat from the reaction of calcium oxide with water to form calcium hydroxide is used to facilitate the removal of water from the aqueous solution comprising sodium sulfite or sodium bisulfite.

The process of example embodiment wherein magnesium sulfite solid is separated from said aqueous magnesium sulfite by cooling precipitation.

The process of example embodiment wherein water is separated from said aqueous magnesium sulfite by reverse osmosis.

Example Embodiments Sodium Bicarbonate and/or Sodium Carbonate Production Using Calcium or Magnesium Input with an Ammonia Intermediate 1. A process for producing sodium carbonate and gypsum from a material comprising an alkaline earth wherein the process comprises:

reacting ammonium carbonate with a solution comprising aqueous sodium sulfate to form ammonium sulfate and sodium carbonate;

reacting a material comprising alkaline earth cation-weak acid anion with sulfur dioxide and an aqueous solution to form a weak acid derivative and an aqueous solution comprising alkaline earth bisulfite;

reacting the aqueous solution comprising alkaline earth bisulfite with ammonium sulfate to form aqueous ammonium bisulfite and an alkaline earth sulfate;

desorbing sulfur dioxide from said aqueous ammonium bisulfite to form ammonium sulfite and sulfur dioxide gas;

reacting said ammonium sulfite with carbon dioxide to form ammonium bisulfite and ammonium bicarbonate;

decomposing said ammonium bicarbonate to form ammonium carbonate and carbon dioxide gas.

2. The process of example embodiment 1 wherein said formed carbon dioxide gas is employed in the reaction of ammonium sulfite and carbon dioxide.

3. The process of example embodiment 1 wherein aqueous ammonium bisulfite is transformed into ammonium sulfite solid, water, and sulfur dioxide gas.

4. The process of example embodiment 3 wherein said transforming comprises thermal desorption or distillation.

5. The process of example embodiment 3 wherein said ammonium sulfite is employed in the reaction of ammonium sulfite with carbon dioxide.

6. The process of example embodiment 3 wherein residual ammonium bicarbonate is present; and wherein said residual ammonium bicarbonate is decomposed to produce carbon dioxide.

7. The process of example embodiment 6 wherein said carbon dioxide is employed in the reaction of ammonium sulfite with carbon dioxide.

8. The process of example embodiment 1 wherein the alkaline earth comprises one or more or any combination of the following: beryllium (Be), or magnesium (Mg), or calcium (Ca), or strontium (Sr), or barium (Ba), or radium (Ra).

9. The process of example embodiment 1 wherein said weak acid derivative comprises a derivative of an acid with an acid strength lower than or less acidic than sulfurous acid.

10. The process of example embodiment 1 wherein said weak acid derivative comprises a gas selected from carbon dioxide, or hydrogen sulfide, or a mixture thereof.

11. The process of example embodiment 1 wherein said weak acid derivative comprises silicon dioxide, or iron oxide, or manganese oxide, or aluminum oxide, or a mixture thereof.

12. The process of example embodiment 1 wherein said sulfur dioxide and an aqueous solution comprises aqueous sulfur dioxide.

13. The process of example embodiment 1 wherein $Na_2CO_3$ is separated from $(NH_4)_2SO_4(aq)$ using the significant solubility difference in water between $Na_2CO_3$ and $(NH_4)_2SO_4$ (aq).

14. The process of example embodiment 1 wherein the alkaline earth sulfate is separated from the aqueous ammonium bisulfite as a solid precipitate.

15. The process of example embodiment 1 wherein ammonium bicarbonate is separated from ammonium bisulfite as a solid precipitate.

16. A process for producing sodium bicarbonate and gypsum from a material comprising an alkaline earth wherein the process comprises:

reacting ammonium bicarbonate with a solution comprising aqueous sodium sulfate to form ammonium sulfate and sodium bicarbonate;

reacting a material comprising alkaline earth cation-weak acid anion with sulfur dioxide and an aqueous solution to form a weak acid derivative and an aqueous solution comprising alkaline earth bisulfite;

reacting the aqueous solution comprising alkaline earth bisulfite with ammonium sulfate to form aqueous ammonium bisulfite and an alkaline earth sulfate;

desorbing sulfur dioxide from said aqueous ammonium bisulfite to form ammonium sulfite and sulfur dioxide gas;

reacting said ammonium sulfite with carbon dioxide to form ammonium bisulfite and ammonium bicarbonate.

17. The process of example embodiment 1 wherein aqueous ammonium bisulfite is transformed into ammonium sulfite solid, water, and sulfur dioxide gas.
18. The process of example embodiment 17 wherein said transforming comprises thermal desorption or distillation.
19. The process of example embodiment 17 wherein said ammonium sulfite is employed in the reaction of ammonium sulfite with carbon dioxide.
20. The process of example embodiment 17 wherein residual ammonium bicarbonate is present; and wherein said residual ammonium bicarbonate is decomposed to produce carbon dioxide.
21. The process of example embodiment 20 wherein said carbon dioxide is employed in the reaction of ammonium sulfite with carbon dioxide.
22. The process of example embodiment 16 wherein the alkaline earth comprises one or more or any combination of the following: beryllium (Be), or magnesium (Mg), or calcium (Ca), or strontium (Sr), or barium (Ba), or radium (Ra).
23. The process of example embodiment 16 wherein said weak acid derivative comprises a derivative of an acid with an acid strength lower than or less acidic than sulfurous acid.
24. The process of example embodiment 16 wherein said weak acid derivative comprises a gas selected from carbon dioxide, or hydrogen sulfide, or a mixture thereof.
25. The process of example embodiment 16 wherein said weak acid derivative comprises silicon dioxide, or iron oxide, or manganese oxide, or aluminum oxide, or a mixture thereof.
26. The process of example embodiment 16 wherein said sulfur dioxide and an aqueous solution comprises aqueous sulfur dioxide.
27. The process of example embodiment 16 wherein $NaHCO_3$ is separated from $(NH_4)_2SO_4(aq)$ using the significant solubility difference in water between $NaHCO_3$ and $(NH_4)_2SO_4(aq)$.
28. The process of example embodiment 16 wherein the alkaline earth sulfate is separated from the aqueous ammonium bisulfite as a solid precipitate.
29. The process of example embodiment 16 wherein ammonium bicarbonate is separated from ammonium bisulfite as a solid precipitate.

Example Embodiments Sodium Bicarbonate and/or Sodium Carbonate Production Using Calcium or Magnesium Input 1. A process for producing sodium bicarbonate and gypsum from a material comprising an alkaline earth wherein the process comprises:
    reacting a material comprising alkaline earth cation—weak acid anion with sulfur dioxide and an aqueous solution to form a weak acid derivative and an aqueous solution comprising alkaline earth bisulfite;
    reacting the aqueous solution comprising alkaline earth bisulfite with sodium sulfate to form aqueous sodium bisulfite and an alkaline earth sulfate;
    separating sodium metabisulfite from said aqueous solution comprising sodium bisulfite;
    decomposing said sodium metabisulfite to form sodium sulfite and sulfur dioxide gas;
    reacting said sodium sulfite with carbon dioxide to form sodium bisulfite and sodium bicarbonate;
    decomposing said ammonium bicarbonate to form ammonium carbonate and carbon dioxide gas.

2. The process of example embodiment 1 wherein sodium bicarbonate is separated from sodium bisulfite due to the difference in solubility between sodium bicarbonate and sodium bisulfite in water.
3. The process of example embodiment 1 wherein said separating sodium metabisulfite from said aqueous solution comprising sodium bisulfite comprises precipitating sodium metabisulfite.
4. The process of example embodiment 1 wherein said separating sodium metabisulfite from said aqueous solution comprising sodium bisulfite comprises removing water using one or more or any combination of the following: multistage flash distillation, or multi-effect distillation, or mechanical vapor compression distillation, or electrodialysis, or electrodialysis reversal, or forward osmosis, or membrane distillation, or evaporation, or crystallization, or solventing out.
5. The process of example embodiment 1 wherein remaining aqueous sodium bisulfite from the reaction of sodium sulfite with carbon dioxide is separated into solid sodium metabisulfite.
6. The process of example embodiment 1 wherein residual sodium bicarbonate is present in the sodium metabisulfite; and
    Wherein said residual sodium bicarbonate decomposes into carbon dioxide.
7. The process of example embodiment 6 wherein said carbon dioxide is employed as a portion of the carbon dioxide in the reaction of sodium sulfite with carbon dioxide.
8. The process of example embodiment 1 wherein the partial pressure of sulfur dioxide gas formed from the decomposing of sodium metabisulfite is greater than 0.5 atm.
9. The process of example embodiment 1 wherein the alkaline earth comprises one or more or any combination of the following: beryllium (Be), or magnesium (Mg), or calcium (Ca), or strontium (Sr), or barium (Ba), or radium (Ra).
10. The process of example embodiment 1 wherein said weak acid derivative comprises a derivative of an acid with an acid strength lower than or less acidic than sulfurous acid.
12. The process of example embodiment 1 wherein said weak acid derivative comprises a gas selected from carbon dioxide, or hydrogen sulfide, or a mixture thereof.
13. The process of example embodiment 1 wherein said weak acid derivative comprises silicon dioxide, or iron oxide, or manganese oxide, or aluminum oxide, or a mixture thereof.
14. The process of example embodiment 1 wherein said sulfur dioxide and an aqueous solution comprises aqueous sulfur dioxide.
15. The process of example embodiment 1 wherein said sodium bicarbonate is decomposed to form sodium carbonate and carbon dioxide.
16. The process of example embodiment 15 wherein said formed carbon dioxide is employed in the reaction of sodium sulfite and carbon dioxide.
17. The process of example embodiment 11 wherein said sulfur dioxide and an aqueous solution comprises reacting sulfur dioxide gas with an aqueous solution in the presence of alkaline earth-'weak acid' to facilitate the formation of aqueous alkaline earth bisulfite.
18. The process of example embodiment 1 wherein the weak acid derivative is separated from the aqueous solution using a solid-liquid separation method.

The invention claimed is:

1. A process comprising:
reacting a material comprising alkaline earth cation—weak acid anion with sulfur dioxide and an aqueous solution to form a weak acid derivative and an aqueous solution comprising alkaline earth bisulfite;
separating said weak acid derivative from said aqueous solution comprising alkaline earth bisulfite;
reacting aqueous alkaline earth bisulfite with sodium sulfate to form an aqueous solution comprising sodium bisulfite and a solid comprising an alkaline earth sulfate;
separating said solid comprising an alkaline earth sulfate from said aqueous solution comprising sodium bisulfite;
decomposing the aqueous solution comprising sodium bisulfite to form sodium sulfite and sulfur dioxide gas;
reacting said sodium sulfite with calcium hydroxide to form an aqueous solution comprising sodium hydroxide and a solid comprising calcium sulfite;
separating said solid comprising calcium sulfite from said aqueous solution comprising sodium hydroxide;
decomposing said solid comprising calcium sulfite to form calcium oxide and sulfur dioxide gas; and
reacting the calcium oxide with water to form calcium hydroxide.

2. The process of claim 1 wherein said weak acid derivative comprises a derivative of an acid with an acid strength lower than or less acidic than sulfurous acid.

3. The process of claim 1 wherein said weak acid derivative comprises carbon dioxide, or hydrogen sulfide, or silicon dioxide, or iron oxide, or manganese oxide, or aluminum oxide, or any mixture thereof.

4. The process of claim 1 wherein said decomposing of an aqueous solution comprising sodium bisulfite comprises desorbing sulfur dioxide gas from said aqueous solution to form aqueous sodium sulfite.

5. The process of claim 1 wherein said decomposing of an aqueous solution comprising sodium bisulfite comprises:
removing water from said aqueous sodium bisulfite to form sodium metabisulfite solid; and
thermally decomposing said sodium metabisulfite to form solid sodium sulfite and sulfur dioxide.

6. The process of claim 1 which further comprises reacting sulfur dioxide gas from decomposing with an aqueous solution in the presence of alkaline earth sulfite to form alkaline earth bisulfite solution.

7. The process of claim 1 further comprising absorbing at least a portion of sulfur dioxide gas into an aqueous solution to form aqueous sulfurous acid.

* * * * *